(12) United States Patent
Miasnikov et al.

(10) Patent No.: US 10,428,354 B2
(45) Date of Patent: Oct. 1, 2019

(54) ALTERED HOST CELL PATHWAY FOR IMPROVED ETHANOL PRODUCTION

(71) Applicant: DANISCO US INC, Palo Alto, CA (US)

(72) Inventors: Andrei Miasnikov, Union City, CA (US); Jeffrey Wayne Munos, Palo Alto, CA (US)

(73) Assignee: DANISCO US INC, Palo Alto, CA (US)

( * ) Notice: Subject to any disclaimer, the term of this patent is extended or adjusted under 35 U.S.C. 154(b) by 0 days.

(21) Appl. No.: 16/245,143

(22) Filed: Jan. 10, 2019

(65) Prior Publication Data

US 2019/0127765 A1    May 2, 2019

Related U.S. Application Data

(63) Continuation of application No. 15/126,376, filed as application No. PCT/US2015/021558 on Mar. 19, 2015, now Pat. No. 10,240,168.

(60) Provisional application No. 61/971,745, filed on Mar. 28, 2014.

(51) Int. Cl.
```
C12N 9/88      (2006.01)
C12P 7/10      (2006.01)
C12P 7/06      (2006.01)
C12N 9/02      (2006.01)
C12N 9/10      (2006.01)
C12N 15/52     (2006.01)
```

(52) U.S. Cl.
CPC .............. *C12P 7/10* (2013.01); *C12N 9/0008* (2013.01); *C12N 9/1018* (2013.01); *C12N 9/1029* (2013.01); *C12N 9/88* (2013.01); *C12N 15/52* (2013.01); *C12P 7/06* (2013.01); *C12Y 102/0101* (2013.01); *C12Y 203/01008* (2013.01); *C12Y 401/02009* (2013.01); *Y02E 50/16* (2013.01); *Y02E 50/17* (2013.01)

(58) Field of Classification Search
CPC ...... C12N 9/88; C12P 7/06; C12Y 401/02009
See application file for complete search history.

(56) References Cited

U.S. PATENT DOCUMENTS

| | | |
|---|---|---|
| 7,785,858 B2 | 8/2010 | Kozlov et al. |
| 8,415,136 B1 | 4/2013 | Gardner et al. |
| 8,623,622 B2 | 1/2014 | Srience et al. |
| 2005/0153411 A1 | 7/2005 | Wahlbom et al. |
| 2009/0305363 A1 | 12/2009 | Anthony et al. |
| 2011/0275130 A1 | 11/2011 | Pronk et al. |
| 2013/0236942 A1 | 9/2013 | Gardner et al. |

FOREIGN PATENT DOCUMENTS

| | | |
|---|---|---|
| EP | 2666855 A1 | 11/2013 |
| WO | 2004/085627 A1 | 10/2004 |
| WO | 2009/056984 A1 | 5/2009 |
| WO | 2012/062767 A2 | 5/2012 |
| WO | 2013/076144 A2 | 5/2013 |
| WO | 2013/081456 A2 | 6/2013 |
| WO | 2013/102554 A1 | 7/2013 |
| WO | 2014/081803 A1 | 5/2014 |

OTHER PUBLICATIONS

Wang et al., "Cloning, Sequence, and Disruption of the *Saccharomyces diastaticus* DAR1 Gene Encoding a Glycerol-3-Phosphate Dehydrogenase," J. Bacteriol., 1994, vol. 176, No. 22, pp. 7091-7095.
Walfridsson et al., "Xylose—Metabolizing *Saccharomyces cerevisiae* Strains Overexpressing the TKL1 and TAL1 Genes Encoding the Pentose Phosphate Pathway Enzymes Transketolase and Transaldolase," Appl. Environ. Microbiol., 1995, vol. 61, No. 12, pp. 4184-4190.
Suzuki et al., "Overexpression, crystallization and preliminary X-ray analysis of xylulose-5-phosphate/fructose-6-phosphate phosphoketolase from Bifidobacterium breve," Acta Cryst. Section F, 2010, vol. 66, No. 8, pp. 941-943.
Sonderegger et al., "Metabolic engineering of a phosphoketolase pathway for pentose catabolism in *Saccharomyces cerevisiae*," Applied and Environmental Microbiology, 2004, vol. 70, No. 5, pp. 2892-2897.
PCT International Search Report and the Written Opinion of the International Searching Authority for International Application No. PCT/US2015/021558; ISA/EPO; dated Jul. 23, 2015.
Nissen et al., "Anaerobic and aerobic batch cultivations of *Saccharomyces cerevisiae* mutants impaired in glycerol synthesis," Yeast, 2000, vol. 16, pp. 463-474.
Nevoigt et al., "Engineering of Promoter Replacement Cassettes for Fine-Tuning of Gene Expression in *Saccharomyces cerevisiae*," Appl. Environ. Microbiol., 2006, vol. 72, No. 8, pp. 5266-5273.
Moraes et al., "Development of yeast strains for the efficient utilisation of starch: evaluation of constructs that express-amylase and glucoamylase separately or as bifunctional fusion proteins," Appl. Microbiol. Biotechnol., 1995, vol. 43, pp. 1067-1076.
Meile et al., "Characterization of the D-Xylulose 5-Phosphate/D-Fructose 6-Phosphate Phosphoketolase Gene (xfp) from Bifidobacterium lactis," J. Bacteriology, 2001, vol. 183, No. 9, pp. 2929-2936.

(Continued)

*Primary Examiner* — Tekchand Saidha

(57) ABSTRACT

A recombinant yeast cell, fermentation compositions, and methods of use thereof are provided. The recombinant yeast cell includes at least one heterologous nucleic acid encoding one or more polypeptide having phosphoketolase activity; phosphotransacetylase activity; and/or acetylating acetaldehyde dehydrogenase activity, wherein the cell does not include a heterologous modified xylose reductase gene, and wherein the cell is capable of increased biochemical end product production in a fermentation process when compared to a parent yeast cell.

16 Claims, 16 Drawing Sheets

Specification includes a Sequence Listing.

(56) References Cited

OTHER PUBLICATIONS

Medina et al., "Elimination of Glycerol Production in Anaerobic Cultures of a *Saccharomyces cerevisiae* Strain Engineered to Use Acetic Acid as an Electron Acceptor," Appl. Environ. Microbiol., 2010, vol. 76, No. I, pp. 190-195.

Lengeler et al., Eds., Biology of the Prokaryotes, Blackwell Science, New York, 1999, pp. 299-301.

Kozak et al., "Replacement of the *Saccharomyces cerevisiae* acetyl-CoA synthetases by alternative pathways for cytosolic acetyl-CoA synthesis," Metabolic Engineering, 2014, vol. 21, pp. 46-59.

Jeong et al., "Cloning and Characterization of a Gene Encoding Phosphoketolase in a Lactobacillus paraplantarum Isolated from Kimchi," J. Microbiol. Biotechnol., 2007, vol. 17, No. 5, pp. 822-829.

Guo et al., "Minimization of glycerol synthesis in industrial ethanol yeast without influencing its fermentation performance," Metabolic Engineering, 2011, vol. 13, pp. 49-59.

Guo et al., "Interruption of glycerol pathway in industrial alcoholic yeasts to improve the ethanol production," Appl. Microbiol. Biotechnol., 2009, vol. 82, pp. 287-292.

Guo et al., "Improving ethanol productivity by modification of glycolytic redox factor generation in glycerol-3-phosphate dehydrogenase mutants of an industrial ethanol yeast", Appl. Microbiol. Biotechnol., 2011, vol. 38, pp. 935-943.

Fleige et al., "Establishment of an alternative phosphoketolase-dependent pathway for fructose catabolism in Ralstonia eutropha H16," Appl Microbial Biotechnol., 2011, vol. 91, No. 3, pp. 769-776.

Eriksson et al., "Cloning and characterization of GPD2, a second gene encoding sn-glycerol 3-phosphate dehydrogenase (NAD+) in *Saccharomyces cerevisiae*, and its comparison with GPD1," Mol. Microbiol., 1995, vol. 17, No. 1, pp. 95-107.

Björkqvist et al., "Physiological Response to Anaerobicity of Glycerol-3-Phosphate Dehydrogenase Mutants of *Saccharomyces cerevisiae*," Appl. Environ. Microbiol., 1997, vol. 63, No. 1, pp. 128-132.

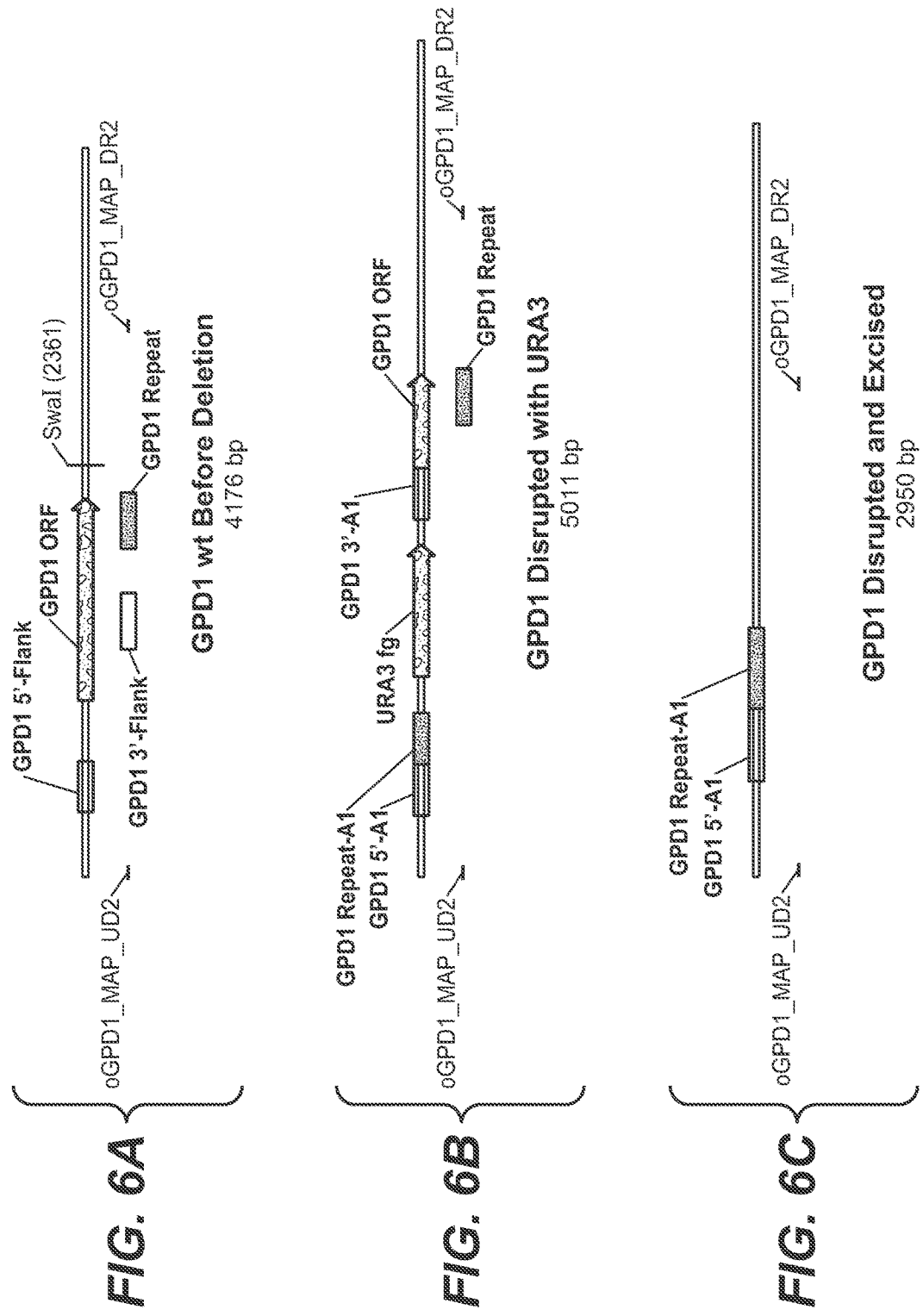

ALTERED HOST CELL PATHWAY FOR IMPROVED ETHANOL PRODUCTION

CROSS REFERENCE TO RELATED APPLICATIONS

The present application is a continuation of U.S. patent application Ser. No. 15/126,376, filed Sep. 15, 2016, which is a 371 of International Patent Application No. PCT/US2015/021558, filed Mar. 19, 2015, which claims priority to U.S. Provisional Patent Application No. 61/971,745, filed Mar. 28, 2014, and all of which are herein incorporated by reference.

FIELD OF THE INVENTION

The invention relates generally to the field of industrial microbiology. The invention relates to recombinant host cells comprising one or more heterologous polynucleotides encoding proteins having phosphoketolase, phosphotransacetylase, and acylating acetaldehyde dehydrogenase activities and that are capable of increased production of ethanol. The invention also includes methods for producing and using the same. In some embodiments, the recombinant cells further comprise one or more modifications in an endogenous gene encoding a polypeptide that converts dihydroxyacetone phosphate to sn-glycerol 3-phosphate.

BACKGROUND

Interest is growing in the use of sustainable and economical biological processes for generating materials of interest. Biological processes hold the promise of renewably using energy from the sun to make such materials. For example, energy from the sun can be stored in plant biomolecules such as the polysaccharides starch and cellulose. By fermentation of the simple sugars arising from breakdown of these polysaccharides, microbes can transfer the sun's energy into molecules of commercial interest to humans, including ethanol. Historically, large-scale polysaccharide breakdown has been accomplished by heat and chemicals, but in the past decades industrially produced starch hydrolytic enzymes have been employed to facilitate this process.

The tools of recombinant DNA technology arising in the 1980's have enabled the creation of transgenic organisms capable of expressing high levels of starch hydrolysis enzymes. In routine use today are alpha amylases, glucoamylases, and pullulanases, produced by recombinant microbes at the scale of tanker trucks per day. However, making biomolecules of interest by this process is lengthy and inherently inefficient. For example, energy is first transferred from the sun to plant polysaccharides, then from these plant polysaccharides to microbes that make starch hydrolysis enzymes, and then the enzymes thus produced are used to facilitate breakdown of additional plant polysaccharides used by yet another microbe to eventually form ethanol. Accordingly, using the same microbe that produces the material of interest to also produce the starch hydrolysis enzymes offers the opportunity for more efficient resource utilization (see for example, U.S. Pat. No. 5,422,267).

Such approaches have recently come to commercial fruition in the form of a glucoamylase-expressing yeast in the fuel ethanol industry. These approaches promise to reduce the use of expensive exogenously added enzymes. However, in this infant industry setting many unmet needs exist. One large need resides in engineering the biochemical pathways of a yeast host to support improved biochemical yield, e.g., ethanol yield.

Another need in the ethanol industry is to improve the levels of ethanol recovered in a yeast fermentation process. Glycerol produced by industrial yeast strains detracts from the potential yield of ethanol recovered. Yeast strains with partially or completely blocked glycerol biosynthesis have been described earlier, e.g., by Wang H-T et al. J. Bacteriol. 176 (22), 709 (1994); Eriksson P et al. Mol. Microbiol. 17 (1), 95, 1995; Björkqvist S et al. Appl. Environ. Microbiol. 63 (1), 128 (1997); Nissen T L et al. Yeast 16, 463 (2000); and Nevoigt E et al. Appl. Environ. Microbiol. 72 (8), 5266 (2006). All of these studies were conducted in haploid laboratory strains of the yeast *Saccharomyces cerevisiae* and are not necessarily directly applicable to industrial diploid/polyploid yeast strains. More recently, some publications report molecular engineering as an approach for industrial yeast strains with disrupted glycerol pathway. (See e.g., Guo Z-p et al. Appl. Microbiol. Biotechnol. 82, 287 (2009); Guo Z-p et al. Appl. Microbiol. Biotechnol. 38, 935 (2011); Guo Z-p et al. Metabolic Engineering 13, 49 (2011)). However, in reality, these authors work with haploid derivatives of industrial yeast, which has different properties and are not industrial yeast strains themselves. As such, a need still exists for approaches to improve ethanol yield from industrial yeast strains.

SUMMARY

The invention provided herein discloses, inter alia, recombinant cells, compositions of these cells and methods of using these cells to increase production of ethanol.

Accordingly, in one aspect, provided herein is a recombinant cell capable of increased carbon flux through a phosphoketolase utilizing pathway, In other aspects, provided herein are isolated polypeptides with phosphoketolase activity produced by any methods of screening, identifying, and/or detecting disclosed herein.

The present teachings provide recombinant yeast cells, fermentation compositions, and methods of use thereof. The recombinant yeast cells can include at least one heterologous nucleic acid encoding one or more polypeptide having phosphoketolase activity; phosphotransacetylase activity; and/or acetylating acetaldehyde dehydrogenase activity, wherein the cell does not include a heterologous modified xylose reductase gene, and wherein the cell is capable of increased biochemical end product production in a fermentation process when compared to a parent yeast cell.

In general, in one aspect a recombinant yeast cell is envisioned having at least one heterologous nucleic acid encoding one or more polypeptide having i) phosphoketolase activity; ii) phosphotransacetylase activity; and/or iii) acetylating acetaldehyde dehydrogenase activity, wherein the cell does not comprise a heterologous modified xylose reductase gene, and wherein the cell is capable of increased biochemical end product production in a fermentation process when compared to a parent yeast cell.

In one embodiment the yeast cell has a reduced NAD-dependant glycerol phosphate dehydrogenase (GPD) activity when compared to a parent yeast cell. In a related embodiment the yeast cell includes an altered pentose phosphate pathway resulting from one or more heterologously expressed nucleic acid affecting the pentose phosphate pathway.

In one embodiment the recombinant yeast cell produces a biochemical end product and the biochemical end product is ethanol and it is produced at a level at least 0.5% higher to at least 15% higher than that produced in a parent yeast cell. In alternative embodiments, the recombinant yeast produces ethanol a level higher than that produced in a parent yeast cell selected from the group consisting of at least 0.5% higher, at least 1% higher, at least 1.5% higher, at least 2% higher, at least 2.5% higher, at least 3% higher, at least 3.5% higher, at least 4% higher, at least 4.5% higher, at least 5% higher, at least 5.5% higher, at least 6% higher, at least 6.5% higher, at least 7% higher, at least 7.5% higher, at least 8% higher, at least 8.5% higher, at least 9% higher, at least 9.5% higher, at least 10% higher, at least 10.5% higher, at least 11% higher, at least 11.5% higher, at least 12% higher, at least 12.5% higher, at least 13% higher, at least 13.5% higher, at least 14% higher, at least 14.5% higher, and at least 15% higher.

In yet another embodiment the recombinant cell described herein includes a) the phosphoketolase activity is encoded by a nucleic acid comprising SEQ ID NO: 3 or having at least 80%, 85%, 90%, 95%, 98% or 99% identity to SEQ ID NO: 3; b) the phophotransacetylase activity is encoded by a nucleic acid comprising SEQ ID NO: 4 or having at least 80%, 85%, 90%, 95%, 98% or 99% identity to SEQ ID NO: 4; and/or c) the acetylating acetaldehyde dehyrogenase activity is encoded by a nucleic acid comprising SEQ ID NO: 5 or having at least 80%, 85%, 90%, 95%, 98% or 99% identity to SEQ ID NO: 5.

In other embodiments the phosphoketolase activity is encoded by a nucleic acid selected from at least one of the group consisting of a nucleic acid encoding SEQ ID NO: 56, SEQ ID NO: 54, SEQ ID NO: 48, SEQ ID NO: 3, SEQ ID NO: 44, SEQ ID NO: 60, SEQ ID NO: 62, SEQ ID NO: 64, SEQ ID NO:66, SEQ ID NO:72. In a related embodiment the phosphoketolase activity is encoded by a nucleic acid having at least 80%, 85%, 90%, 95%, 98% or 99% identity to at least one of the group consisting of SEQ ID NO: 56, SEQ ID NO: 54, SEQ ID NO: 48, SEQ ID NO: 3, SEQ ID NO: 44, SEQ ID NO: 60, SEQ ID NO: 62, SEQ ID NO: 64, SEQ ID NO:66 or SEQ ID NO:72.

In a further embodiment the acetylating acetaldehyde dehydrogenase activity is encoded by a nucleic acid selected from at least one of the group consisting of a nucleic acid encoding SEQ ID NO: 25, SEQ ID NO: 31, SEQ ID NO: 5, SEQ ID NO: 17, SEQ ID NO: 13, SEQ ID NO: 15, SEQ ID NO: 19, SEQ ID NO: 27, SEQ ID NO: 33. In a related embodiment the acetylating acetaldehyde dehydrogenase activity is encoded by a nucleic acid having at least 80%, 85%, 90%, 95%, 98% or 99% identity to at least one of the group consisting of SEQ ID NO: 25, SEQ ID NO: 31, SEQ ID NO: 5, SEQ ID NO: 17, SEQ ID NO: 13, SEQ ID NO: 15, SEQ ID NO: 19, SEQ ID NO: 27 or SEQ ID NO: 33.

In a particular embodiment the recombinant yeast cell described herein is a recombinant *Saccharomyces cerevisiae*.

In another embodiment the recombinant yeast cell described herein is useful in a fermentation process and the fermentation process can be selected from a number of types of fermentation including, for example, post-liquefaction and saccharification fermentation, simultaneous saccharification and fermentation (SSF) and granular starch hydrolyzing enzyme (GSHE) fermentation.

In another embodiment the recombinant yeast cell produces a biochemical end product selected from a group including an organic acid, an amino acid, an alcohol and ethanol. In a particular embodiment the biochemical end product is ethanol.

In another aspect disclosed herein is a fermentation composition including the recombinant yeast cell of the disclosure, glucose and xylose. In one embodiment the fermentation composition has, for example, a glucose to xylose concentration greater than 1:1. In a different embodiment the glucose to xylose concentration is greater than 5:1. In another embodiment the fermentation composition further includes glucoamylase. In a related embodiment the glucoamylase is expressed by the recombinant yeast cell. The glucoamylase can be, for example, a) encoded by a recombinant gene comprising the amino acid sequence of SEQ ID NO. 11; orb) a recombinant gene having at least 80%, 85%, 90%, 95%, 98% or 99% identity to the amino acid sequence of SEQ ID NO. 11.

In a further embodiment the fermentation composition additionally includes at least one additional recombinant gene, wherein the at least one additional recombinant gene encodes one or more of an enzyme selected from the group including, for example a dehydrogenase, a transketolase, a phosphoketolase, a transladolase, an epimerase, a phytase, a xylanase, a β-glucanase, a phosphatase, a protease, an alpha-amylase, a beta-amylase, a different glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase. In a particular embodiment the at least one additional recombinant gene encodes an alpha-amylase, a glucoamylase, a cutinase, a trehalase or combinations thereof. In a specific embodiment, the at least one additional recombinant gene encodes an alpha-amylase.

In another embodiment the fermentation composition further includes an additional yeast species.

In general, in another aspect a method of producing a desired biochemical is provided including use of the recombinant yeast cell or fermentation composition as described herein, in a fermentation process with a feedstock, wherein the desired biochemical is selected from the group consisting of ethanol, butanol, etc. arabinitol, n-butanol, isobutanol, ethanol, glycerol, methanol, ethylene glycol, 1,3-propanediol (propylene glycol), butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, tryptophan, and threonine); a gas (e.g., methane, hydrogen (H2), carbon dioxide ($CO_2$), and carbon monoxide (CO)); isoprene, isoprenoid, sesquiterpene; a ketone (e.g., acetone); an aldehyde (e.g., acetaldehyde, butryladehyde); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); 1-3 propane diol, and polyketide. In a specific embodiment the fermentation employs a feedstock selected from the group including, for example glucose, liquefied starch, granular starch, cellulose, hemicellulose or any combination thereof. In a related aspect of the methods disclosed herein the desired biochemical is ethanol.

BRIEF DESCRIPTION OF THE FIGURES

FIGS. 6A, 6B and 6C depict GPD1 chromosomal locus before disruption (FIG. 6A), after disruption with URA3 marker (FIG. 6B), and after excision of URA3 by homologous recombination (FIG. 6C).

FIG. 14A shows raw experimental data and FIG. 14B shows the same data corrected for estimated evaporation loss.

DETAILED DESCRIPTION

Figure 1:
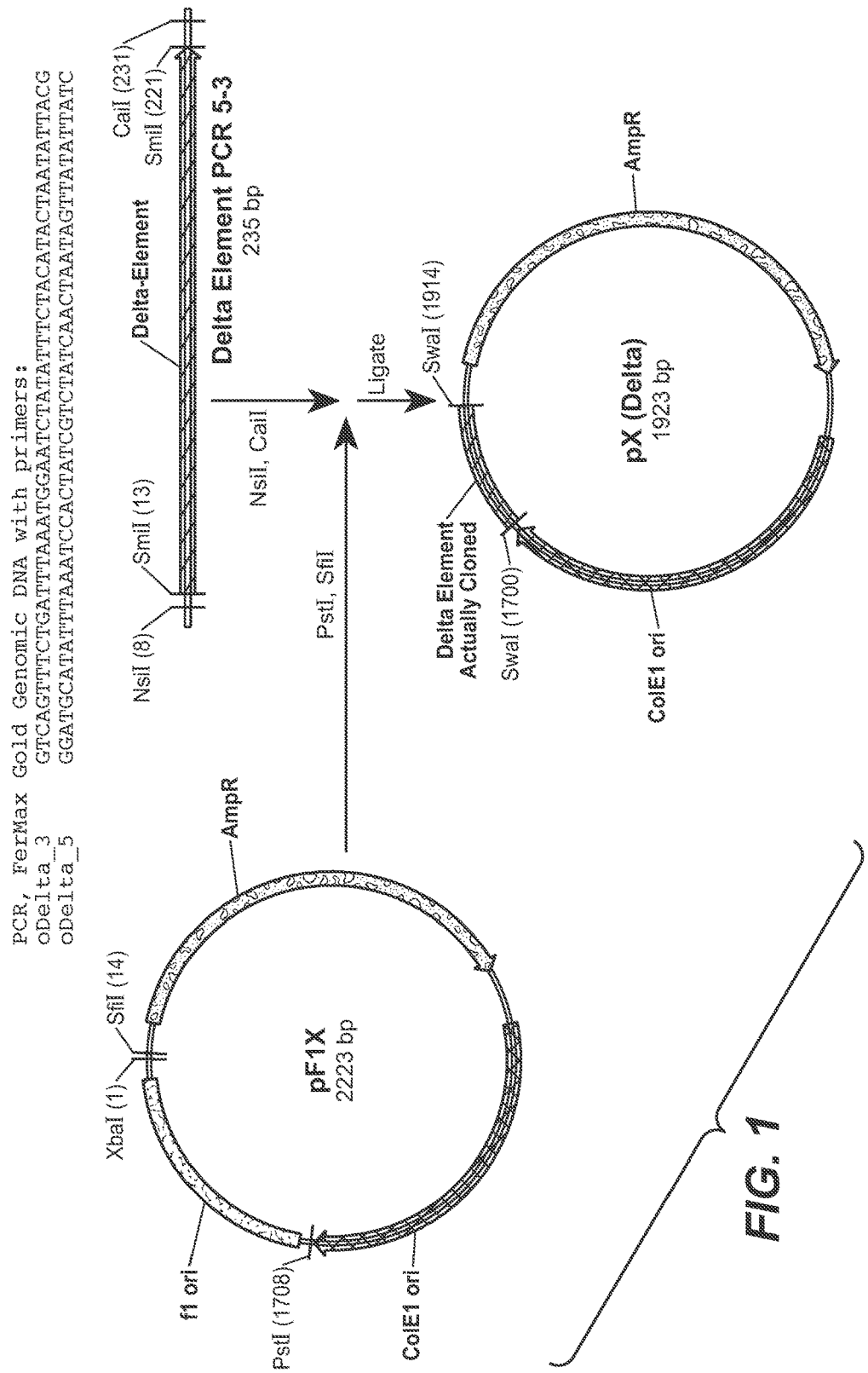
FIG. 1 depicts the construction of plasmid intermediate pX (Delta).
Figure 2:
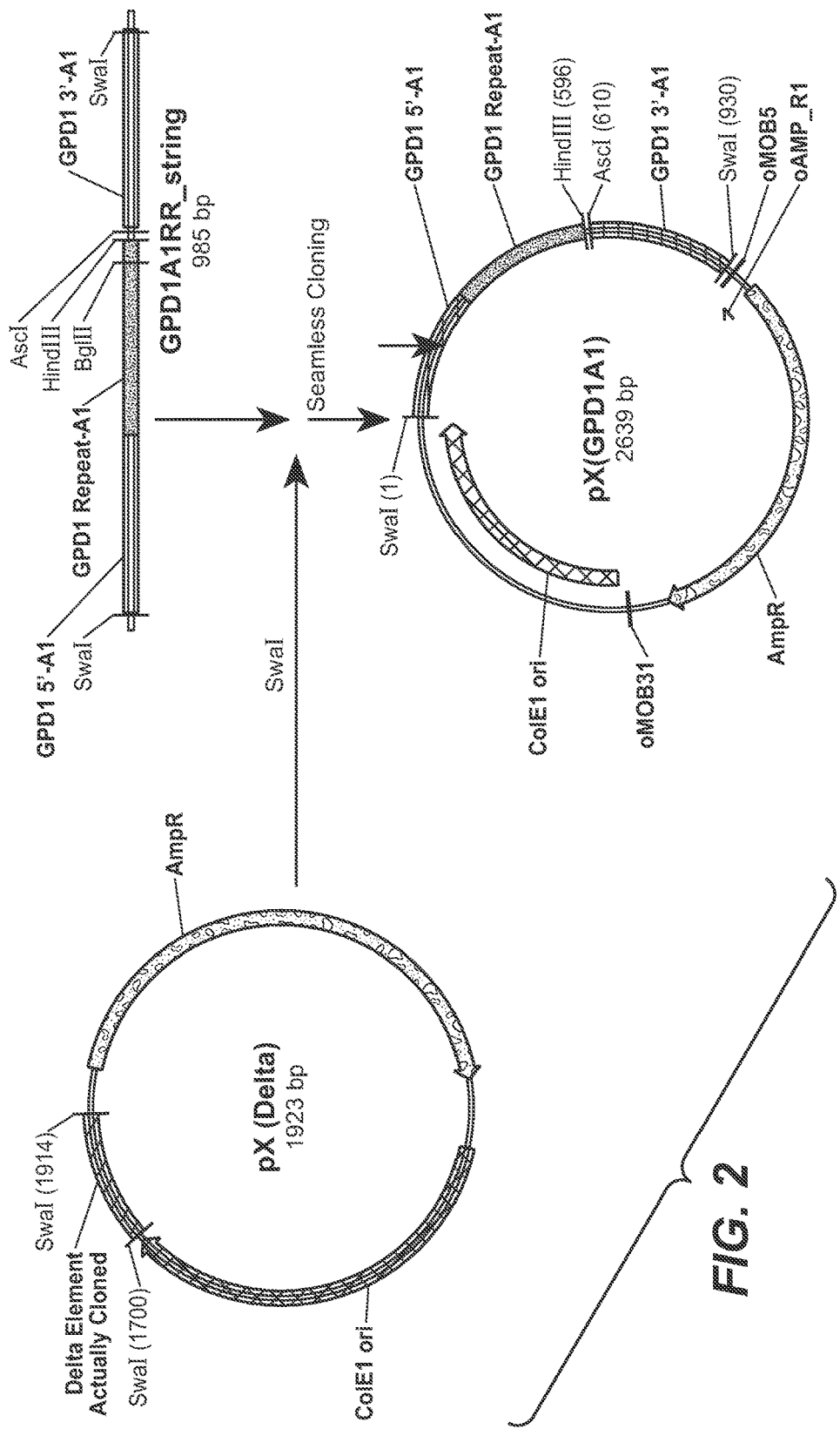
FIG. 2 depicts cloning the synthetic sequence containing GPD1 "flanking" and "repeat" sequence segments into pX (Delta).
Figure 3:
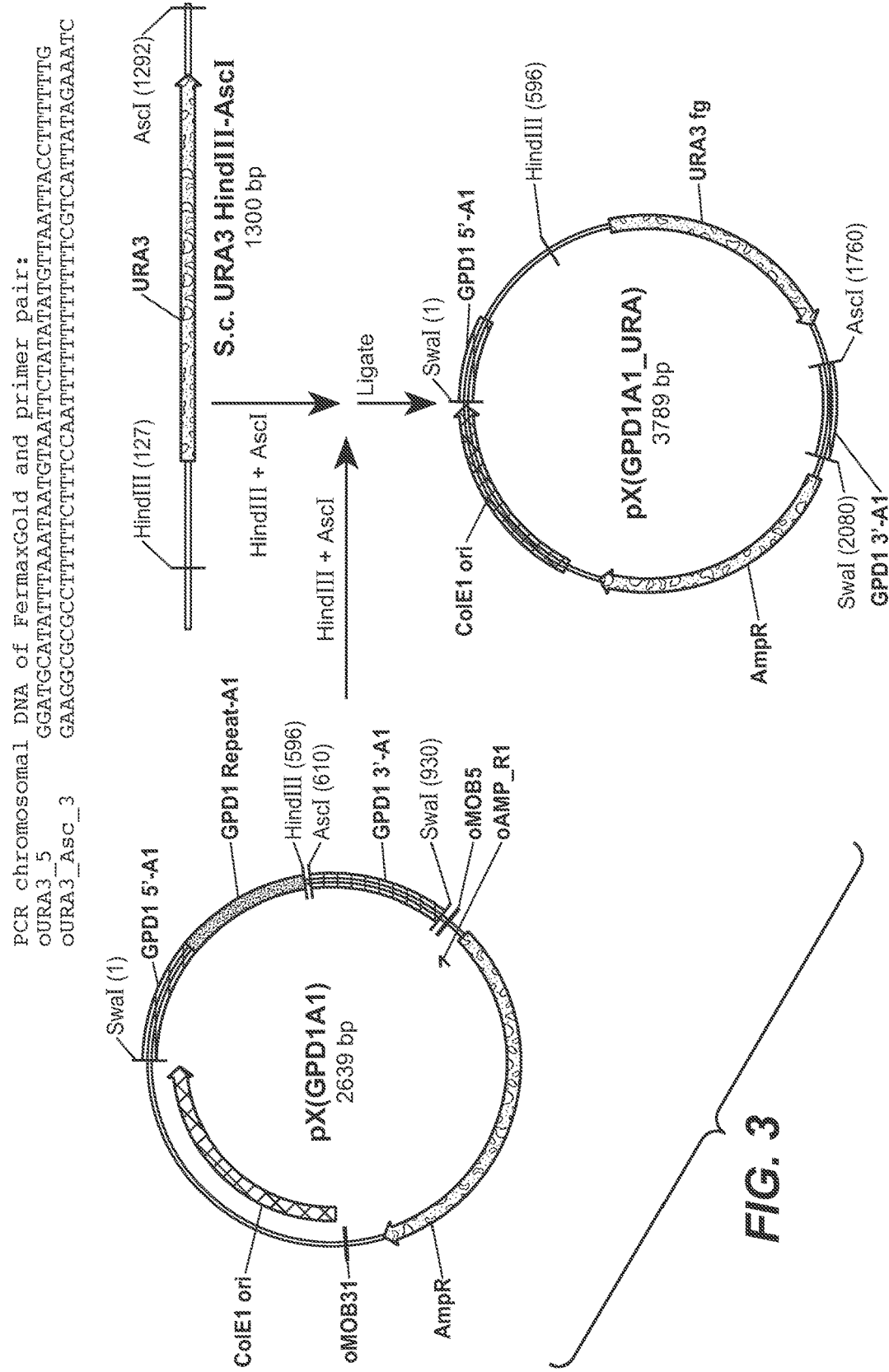
FIG. 3 depicts the final assembly of a disruption cassette for GPD1.
Figure 4:
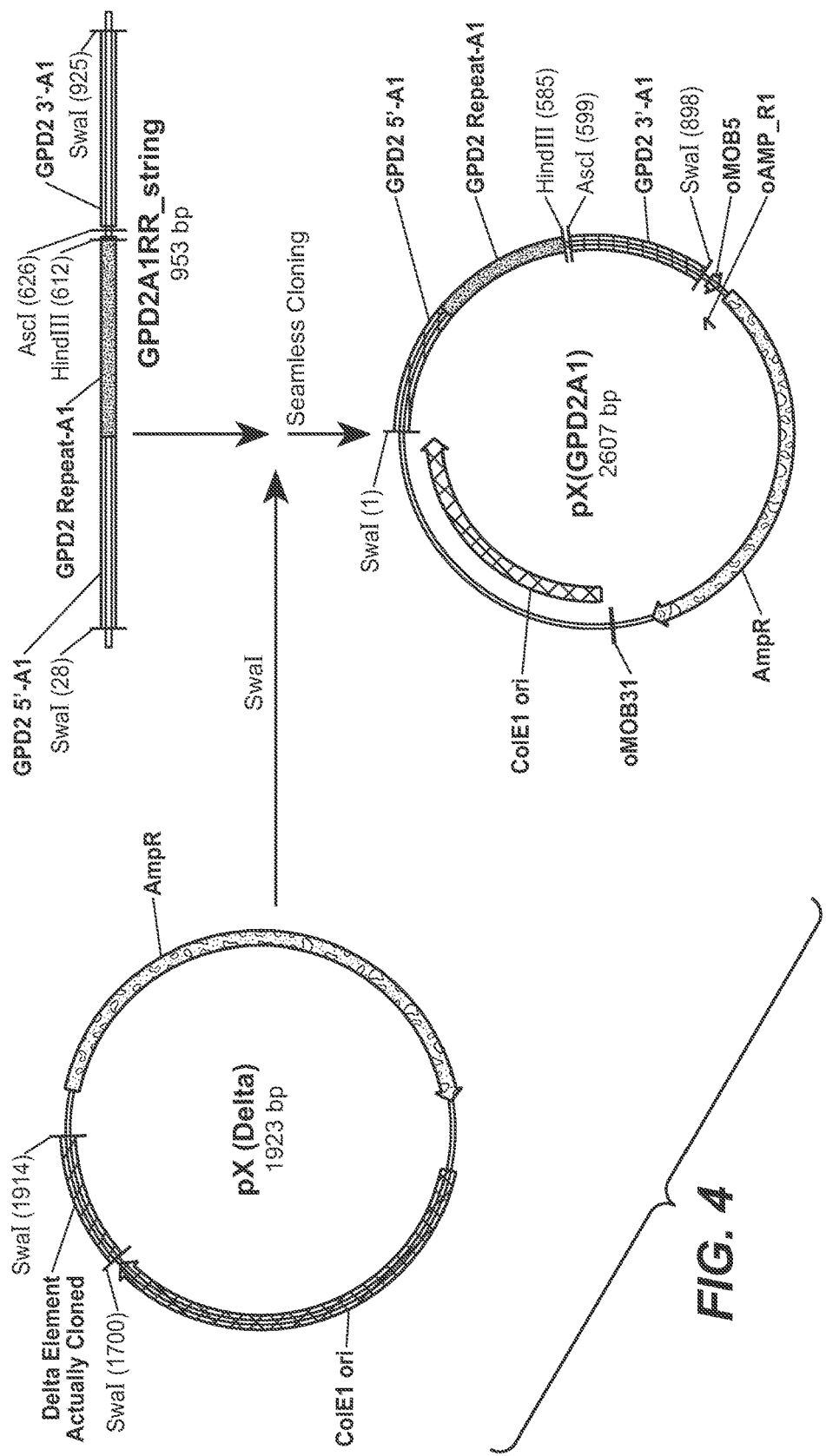
FIG. 4 depicts cloning the synthetic sequence containing GPD2 "flanking" and "repeat" sequence segments into pX (Delta).
Figure 5:
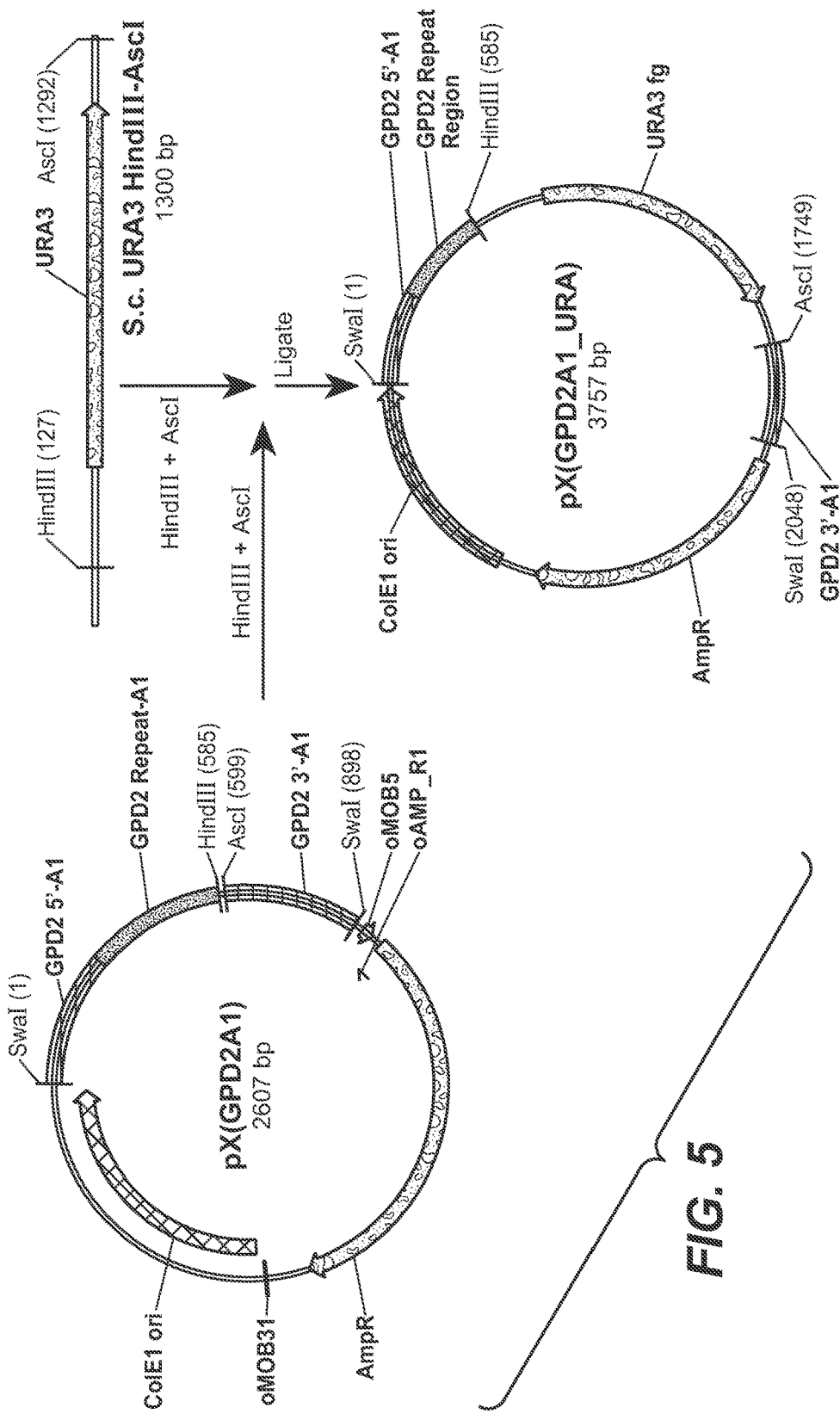
FIG. 5 depicts the final assembly of a disruption cassette for GPD2.

The practice of the present teachings will employ, unless otherwise indicated, conventional techniques of molecular biology (including recombinant techniques), microbiology, cell biology, biochemistry, and animal feed pelleting, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984; *Current Protocols in Molecular Biology* (F. M. Ausubel et al., eds., 1994); *PCR: The Polymerase Chain Reaction* (Mullis et al., eds., 1994); *Gene Transfer and Expression: A Laboratory Manual* (Kriegler, 1990), and *The Alcohol Textbook* (Ingledew et al., eds., Fifth Edition, 2009).

Unless defined otherwise herein, all technical and scientific terms used herein have the same meaning as commonly understood by one of ordinary skill in the art to which the present teachings belong. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present teachings.

Numeric ranges provided herein are inclusive of the numbers defining the range.

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

As used herein, the terms "comprises," "comprising," "includes," "including,", "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

The term "polynucleotide" is intended to encompass a singular nucleic acid as well as plural nucleic acids, and refers to a nucleic acid molecule or construct, e.g., messenger RNA (mRNA) or plasmid DNA (pDNA). A polynucleotide can contain the nucleotide sequence of the full-length cDNA sequence, or a fragment thereof, including the untranslated 5' and 3' sequences and the coding sequences. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. "Polynucleotide" embraces chemically, enzymatically, or metabolically modified forms.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

By "heterologous nucleic acid" is meant a nucleic acid sequence derived from a different organism, species or strain than the host cell. In some embodiments, the heterologous nucleic acid is not identical to a wild-type nucleic acid that is found in the same host cell in nature. For example, a nucleic acid encoded by the phosphoketolase gene from *Bifidobacterium animalis Burkholderia phytofirmans, Lactobacillus buchneri, Bifidobacterium gallicum, Bifidobacterium dentium, Bifidobacterium bifidum*, and/or *Clostridium acetobutylicum* and used to transform yeast, for example, *Saccharomyces cerevisiae* is a heterologous nucleic acid.

A polynucleotide sequence may be referred to as "isolated," in which it has been removed from its native environment. For example, a heterologous polynucleotide encoding a polypeptide or polypeptide fragment having phosphoketolase activity contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA may be comprised of one or more segments of cDNA, genomic DNA or synthetic DNA.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Endogenous gene" refers to a native gene in its natural location in the genome of an organism. A "heterologous gene" refers to a gene not normally found in the host organism, but that is introduced into the host organism by gene transfer. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. Foreign genes can comprise native genes inserted into a non-native organism, or chimeric genes. In another example, a heterologous gene can be a gene reintroduced into the source organism in a location that is different from that in the unaltered host organism.

As used herein, the term "at least one additional recombinant gene" refers to a nucleic acid encoding a protein that is integrated into the genome of the yeast, in addition to the at least one recombinant gene for hydrolyzing starch. Examples are numerous as will be appreciated by one of skill in the art, and include any of the genes mentioned herein.

The term "parent yeast" or "parent yeast cell" or "parent cell" as used herein, means a yeast, e.g., *Saccharomyces cerevisiae*, to which an alteration is made to produce a recombinant yeast cell or genetically engineered yeast cell of the present disclosure. Suitably the parent yeast may be, for example, a naturally occurring (wild-type) yeast, a laboratory strain of yeast or an industrial yeast strain. In one embodiment the parent yeast is a commercial ethanologen yeast strain suitable for use the fuel ethanol industry.

As used herein, the term "genetically engineered yeast" refers to the targeted modification of at least one nucleotide of a nucleotide sequence resulting in a sequence that does not naturally occur. Such a genetic engineering can be the targeted modification of an endogenous wild type gene, the targeted modification of an endogenous wild type non-coding region, and/or through the insertion of a different organism's gene or non-coding sequence (such different organism's gene or non-coding region itself optionally having been the subject of targeted modification) into the yeast (the use of such a different organism's genetic material aka "recombinant"). Mere genetic changes in a yeast that arise through mutagenesis and screening is not considered by themselves in the present invention to constitute a "genetically engineered yeast". Examples of genes that can constitute a genetically engineered yeast are numerous, and include any of dehydrogenases, transketolases, phosphoketolases, transladolases, epimerases, isomerases, phytases, xylanases, β-glucanases, phosphatases, proteases, amylases (alpha or beta or glucoamylases), pullulanases, isoamylases, cellulases, trehalases, lipases, pectinases, polyesterases, cutinases, oxidases, transferases, reductases, hemicellulases, mannanases, esterases, pectinases, lactases, peroxidases, laccases, and other redox enzymes. Indeed, any enzyme either secreted by the cell or intracellularly expressed can be used according to the present teachings, and non-limiting examples include a phosphoketolase from *Bifidobacterium animalis*, phosphotransacetylase from *Lactobacillus plantarum*, acetaldehyde dehydrogenase from *Salmonella enterica*, xylanase from *Trichoderma reesei* and a variant xylanase from *Trichoderma reesei*, both available from DuPont Industrial Biosciences. Alternatively, the xylanase may be the inherently thermostable xylanase described in EP1222256B1, as well as other xylanases from *Aspergillus niger, Aspergillus kawachii, Aspergillus tubigensis, Bacillus circulans, Bacillus pumilus, Bacillus subtilis, Neocallimastix patriciarum, Penicillium* species, *Streptomyces lividans, Streptomyces thermoviolaceus, Thermomonospora fusca, Trichoderma harzianum, Trichoderma reesei, Trichoderma viride* or *Fusarium*. Additional enzymes include phytases, such as for example Finase L®, a phytase from *Aspergillus* sp., available from AB Enzymes, Darmstadt, Germany; Phyzyme™ XP, a phytase from *E. Coli*, available from Danisco Animal Nutrition, and other phytases from, for example, the following organisms: *Trichoderma, Penicillium, Fusarium, Buttiauxella, Citrobacter, Enterobacter, Penicillium, Humicola, Bacillus*, and *Peniophora*. An example of a cellullase is Multifect® BGL, a cellulase (beta glucanase), available from DuPont Industrial Biosciences and other cellulases from species such as *Aspergillus, Trichoderma, Penicillium, Humicola, Bacillus, Cellulomonas, Penicillium, Thermomonospore, Clostridium*, and *Hypocrea*. The cellulases and endoglucanases described in US20060193897A1 also may be used. Amylases may be, for example, from species such as *Aspergillus, Trichoderma, Penicillium, Bacillus*, for instance, *B. subtilis, B. stearothermophilus, B. lentus, B. licheniformis, B. coagulans*, and *B. amyloliquefaciens*. Suitable fungal amylases are derived from *Aspergillus*, such as *A. oryzae* and *A. niger*. Proteases may be from *Bacillus amyloliquefaciens, Bacillus lentus, Bacillus subtilis, Bacillus licheniformis, Fusarium* and *Aspergillus* and *Trichoderma* species. In some embodiments, any of the enzymes discussed above may be used, either alone, or in combination with themselves, or others. One of skill in the art will appreciate that various engineering efforts have produced improved enzymes with properties of interest, any of which can be included in a genetically engineered yeast according to the present teachings. For example, in the context of amylases, various swapping and mutation of starch binding modules (SBM) and/or carbohydrate binding modules (CBM) (for cellulose, starch, or otherwise) have generated enzymes of interest that could be placed into the genetically engineered yeast of the present teachings (see for example, U.S. Pat. No. 8,076,109, and EP1687419B1, as well as Machovic, Cell. Mol. Life Sc. 63 (2006) 2710-2724, and Latorre-Garcia, J. biotech, 2005 (3, 019) 167-176). As another example, the *Rhizomucor pusillus* alpha-amylase can be combined with any CBM. Also, the present teachings can employ any of the enzymes disclosed in PCT/US2009/036283, Moraes et al, Appl Microbiol Biotechnol (1995) 43:1067-1076, and Li et al, Protein Expression and Purification 79 (2011) 142-148. In certain embodiments, the microorganism may be genetically modified to produce butanol. It will also be appreciated that in some embodiments the production of butanol by a microorganism, is disclosed, for example, in U.S. Pat. Nos. 7,851,188; 7,993,889; 8,178,328; and 8,206,970; and U.S. Patent Application Publication Nos. 2007/0292927; 2008/0182308; 2008/0274525; 2009/0305363; 2009/0305370; 2011/0250610; 2011/0313206; 2011/0111472; 2012/0258873; and 2013/0071898, the entire contents of each are herein incorporated by reference. In certain embodiments, the microorganism is genetically modified to comprise a butanol biosynthetic pathway or a biosynthetic pathway for a butanol isomer, such as 1-butanol, 2-butanol, or isobutanol. In certain embodiments, at least one, at least two, at least three, at least four, or at least five polypeptides catalyzing substrate to product conversions in the butanol biosynthetic pathway are encoded by heterologous polynucleotides in the microorganism. In certain embodiments, all the polypeptides catalyzing substrate to product conversions of the butanol biosynthetic pathway are encoded by heterologous polynucleotides in the microorganism. It will be appreciated that microorganisms comprising a butanol biosynthetic pathway may further comprise one or more additional genetic modifications as disclosed in U.S. Patent Application Publication No. 2013/0071898, which is herein incorporated by reference in its entirety. Biosynthetic pathways for the production of isobutanol that may be used include those as described by Donaldson et al. in U.S. Pat. Nos. 7,851,188; 7,993,388; and International Publication No. WO 2007/050671, which are incorporated herein by reference. Biosynthetic pathways for the production of 1-butanol that may be used include those described in U.S. Patent Application Publication No. 2008/0182308 and WO2007/041269, which are incorporated herein by reference. Biosynthetic pathways for the production of 2-butanol that may be used include those described by Donaldson et al. in U.S. Pat. No. 8,206,970; U.S. Patent Application Publication Nos. 2007/0292927 and 2009/0155870; International Publication Nos. WO 2007/130518 and WO 2007/130521, all of which are incorporated herein by reference. In some embodiments, the present teachings also contemplate the incorporation of a trehalase into a yeast to generate the genetically modified organism, either alone or with other enzymes of interest. Exemplary trehalases can be found in U.S. Pat. No. 5,312,909 and EP0451896B1.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. A polypeptide may be derived from a natural biological source or produced by recombinant technology, but is not necessarily translated from a designated nucleic acid sequence. It may be generated in any manner, including by chemical synthesis.

As used herein, the term "variant" refers to a polypeptide differing from a specifically recited polypeptide of the invention by amino acid insertions, deletions, mutations, and substitutions, created using, e.g., recombinant DNA techniques, such as mutagenesis. Guidance in determining which amino acid residues may be replaced, added, or deleted without abolishing activities of interest, may be found by comparing the sequence of the particular polypeptide with that of homologous polypeptides, e.g., yeast or bacterial, and minimizing the number of amino acid sequence changes made in regions of high homology (conserved regions) or by replacing amino acids with consensus sequences. By "heterologous polypeptide" is meant a polypeptide encoded by a nucleic acid sequence derived from a different organism, species, or strain than the host cell. In some embodiments, a heterologous polypeptide is not identical to a wild-type polypeptide that is found in the same host cell in nature.

As used herein, the terms "phosphoketolase", "phosphoketolase enzyme" or "phosphoketolase polypeptide" are used interchangeably and refer to a polypeptide that converts xylulose 5-phosphate to glyceraldehyde 3-phosphate and acetyl phosphate and/or converts fructose 6-phosphate to erythrose 4-phosphate and acetyl phosphate. Generally, phosphoketolases act upon ketoses. In certain embodiments, the phosphoketolase polypeptide catalyzes the conversion of xylulose 5-phosphate to glyceraldehyde 3-phosphate and acetyl phosphate. In other embodiments, the phosphoketolase polypeptide catalyzes the conversion of fructose 6-phosphate to erythrose 4-phosphate and acetyl phosphate. In other embodiments, the phosphoketolase polypeptide catalyzes the conversion of sedoheptulose-7-phosphate to a product (e.g., ribose-5-phosphate) and acetyl phosphate.

As used herein, the term "mass yield" refers to the mass of the product produced by the recombinant cells divided by the mass of the glucose consumed by the recombinant cells expressed as a percentage.

By "specific productivity," it is meant the mass of the product produced by the recombinant cell divided by the product of the time for production, the cell density, and the volume of the culture.

By "titer," it is meant the mass of the product produced by the recombinant cells divided by the volume of the culture.

As used herein, the term "cell productivity index (CPI)" refers to the mass of the product produced by the recombinant cells divided by the mass of the recombinant cells produced in the culture.

As used herein, the term "an additional yeast species" refers to the existence of another yeast, or more, that is grown to scale along with the genetically engineered yeast and comprises the active dry yeast formulation. Such an additional yeast can itself be a genetically engineered yeast, but need not be.

As used herein, the term "Percent sequence identity" means that a variant has at least a certain percentage of amino acid residues identical to a reference sequence when aligned using the CLUSTAL W algorithm with default parameters. See Thompson et al. (1994) Nucleic Acids Res. 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

Deletions are counted as non-identical residues, compared to a reference sequence. Deletions occurring at either terminus are included. For example, a variant with five amino acid deletions of the C-terminus of a mature 617 residue polypeptide would have a percent sequence identity of 99% (612/617 identical residues×100, rounded to the nearest whole number) relative to the mature polypeptide. Such a variant would be encompassed by a variant having "at least 99% sequence identity" to a mature polypeptide.

Exemplary Embodiments

The present teachings provide various embodiments of recombinant yeast cells, fermentation compositions, and methods of use thereof. The recombinant yeast cells can include at least one heterologous nucleic acid encoding one or more polypeptide having phosphoketolase activity; phosphotransacetylase activity; and/or acetylating acetaldehyde dehydrogenase activity, wherein the cell does not include a heterologous modified xylose reductase gene, and wherein the cell is capable of increased biochemical end product production in a fermentation process when compared to a parent yeast cell. The following are additional details and alternatives envisioned.

In some embodiments, the present teachings provide a method of making a desired biochemical comprising including the yeast provided by the present teachings in a fermentation process with a feedstock, wherein the desired biochemical is selected from the group consisting of ethanol, butanol, etc. arabinitol, n-butanol, isobutanol, ethanol, glycerol, methanol, ethylene glycol, 1,3-propanediol (propylene glycol), butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, tryptophan, and threonine); a gas (e.g., methane, hydrogen ($H2$), carbon dioxide ($CO_2$), and carbon monoxide (CO)); isoprene, isoprenoid, sesquiterpene; a ketone (e.g., acetone); an aldehyde (e.g., acetaldehyde, butyladehyde); an organic acid (e.g., acetic acid, acetonic acid, adipic acid, ascorbic acid, citric acid, 2,5-diketo-Dgluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); 1-3 propane diol, and polyketide. It will be appreciated that the feedstock is not a limitation of the present teachings, and can include for example, glucose, glucose syrups, sucrose, sucrose syrups, liquefact liquifact from starch, granular starch, and various cellulosic feedstocks appropriately treated to liberate fermentable sugars. In some embodiments, the feedstock is selected from the group consisting of glucose, liquefied starch, granular starch, or cellulose.

The present teachings are useful, for example, in fermentation processes. Fermentation post liquefaction and/or saccharification is envisioned. Exemplary fermentation processes include but are not limited to simultaneous saccharification and fermentation (SSF) and granular starch hydrolyzing enzyme (GSHE) fermentation.

The present teachings herein additionally disclose, inter alia, compositions and methods for the production of acetyl coenzyme A-derived metabolites, isoprenoid precursor molecules, isoprene and/or isoprenoids in recombinant cells that have been engineered to express a phosphoketolase polypeptide. The phosphoketolase enzymes of the present teachings can use various substrates, as described in greater detail infra. In certain embodiments, compositions and methods are provided for the production of acetyl coenzyme A-derived metabolites, isoprenoid precursor molecules, isoprene and/or isoprenoids in recombinant cells that have been engineered to express a phosphoketolase polypeptide capable of catalyzing the conversion of xylulose 5-phosphate to glyceraldehyde 3-phosphate and acetyl phosphate. In other embodiments, provided are compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of fructose 6-phosphate to erythrose 4-phosphate and acetyl phosphate. In still other embodiments, provided are compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of sedoheptulose-7-phosphate to ribose-5-phosphate and acetyl phosphate. In still other embodiments, compositions and methods are provided for the production of acetyl coenzyme A-derived metabolites, isoprenoid precursor molecules, isoprene and/or isoprenoids in recombinant cells that have been engineered to express a phosphoketolase polypeptide capable of catalyzing the conversion of xylulose 5-phosphate to glyceraldehyde 3-phosphate and acetyl phosphate and/or the conversion of fructose 6-phosphate to erythrose 4-phosphate and acetyl phosphate and/or the conversion of sedoheptulose-7-phosphate to ribose-5-phosphate and acetyl phosphate.

Recombinantly expressed phosphoketolase has been used to engineer metabolic pathways in host cells. See U.S. Pat. No. 7,785,858. Sonderegger et al. (Applied and Environmental Microbiology, 2004, 70:5, 2892-97) describe the use of phosphoketolase in *Saccharomyces cerevisiae* for the overproduction of ethanol. Fleige et al. (Appl Microbial Biotechnol., 2011, 91:3, 769-76) describe the expression of a *bifidobacterium* phosphoketolase gene (Meile et al., supra) in a modified *Ralstonia eutropha* strain which restored the capability for the organism to utilize fructose as a sole carbon source for growth.

The present disclosure provides an alternate metabolic process which can potentially produce three molecules of acetyl-CoA from one molecule of glucose using a pathway which does not rely on the Wood-Ljungdahl pathway enzymes. Instead, it makes use of a phosphoketolase enzyme found in certain organisms (see, for example, Biology of the Prokaryotes (ed. Lengeler, Drews and Schlegel); Blackwell Science, New York, 1999, p. 299-301; Meile et al., J. of Bacteriology, 2001, 183:9, 2929-36; Jeong et al., J. Microbiol. Biotechnol., 2007, 17:5, 822-829). Phosphoketolase enzymes allow for formation of acetyl-CoA (via acetyl-phosphate) from xylulose 5-phosphate or fructose 6-phosphate rather than through oxidation of pyruvate as in typical metabolism.

Phosphoketolases have been classified into two types based on their substrate preference: xylulose-5-phosphate (X5P) phosphoketolases, which only act on X5P, and X5P/fructose-6-phosphate (F6P) phosphoketolases, which can act on both X5P and F6P (Suzuki et al., Acta Cryst. F66, 2010, 66:8, 941-43). Phosphoketolases catalyze the cleavage of X5P or F6P utilizing inorganic phosphate (Pi) to produce acetyl phosphate (acetyl-P), $H_2O$ and glyceraldehyde 3-phosphate or erythrose 4-phosphate.

In another aspect, the invention relates to altered metabolic pathways involving the pentose phosphate pathway (PPP), for example, as a result of one or more heterologously expressed nucleic acids affecting the pentose phosphate pathway. *S. cerevisiae* uses the pentose phosphate pathway to provide cells with intermediates for various anabolic pathways. It is also a major producer of NADPH. The pentose phosphate pathway is composed from an oxidative branch (with enzymes like glucose 6-phosphate 1-dehydrogenase, 6-phosphogluconolactonase or 6-phosphogluconate dehydrogenase) and a non-oxidative branch (with enzymes such as transketolase, transaldolase, ribulose-5-phosphate-epimerase and ribose-5-phosphate isomerase.

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase, ribose-5-phosphate isomerase, expression can be modulated (e.g., increase enzyme activity) to allow more carbon to flux towards fructose 6-phosphate and xylulose 5-phosphate, thereby increasing the eventual production of acetyl CoA and ethanol. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into acetyl-CoA dependent ethanol biosynthetic pathway in comparison to cells that do not have increased expression of transketolase, transaldolase, ribulose-5-phosphate-epimerase and (or) ribose-5-phosphate epimerase.

In any aspects of the invention, provided herein are recombinant cells comprising one or more heterologously expressed nucleic acids encoding phosphoketolase polypeptides as disclosed herein and further engineered to increase the activity of transketolase In any aspects of the invention, provided herein are recombinant cells comprising one or more heterologously expressed nucleic acids encoding phosphoketolase polypeptides as disclosed herein and further engineered to decrease the activity of transketolase. In any aspects of the invention, provided herein are recombinant cells comprising one or more heterologously expressed nucleic acids encoding phosphoketolase polypeptides as disclosed herein and further engineered to increase the activity of transaldolase. In any aspects of the invention, provided herein are recombinant cells comprising one or more heterologously expressed nucleic acids encoding phosphoketolase polypeptides as disclosed herein and further engineered to increase the activity of ribose-5-phosphate isomerase. In any aspects of the invention, provided herein are recombinant cells comprising one or more heterologously expressed nucleic acids encoding phosphoketolase polypeptides as disclosed herein and further engineered to increase the activity of ribulose-5-phosphate 3-epimerase. Activity modulation (e.g., decreased or increased) of glucose 6-phosphate 1-dehydrogenase, 6-phosphogluconolactonase, 6-phosphogluconate dehydrogenase, transketolase, transaldolase, ribulose-5-phosphate-epimerase, ribose-5-phosphate epimerase, ribose-5-phosphate isomerase. In any aspects of the invention, provided herein are recombinant cells comprising one or more heterologously expressed nucleic acids encoding phosphoketolase polypeptides as disclosed herein and further engineered to increase the activity of a glucose 6-phosphate 1-dehydrogenase (zwf) isozyme. In any aspects of the invention, provided herein are recombinant cells comprising one or more heterologously expressed nucleic acids encoding phosphoketolase polypeptides as disclosed herein and further engineered to increase the activity of a transketolase isozyme. In any aspects of the invention, provided herein are recombinant cells comprising one or more heterologously expressed nucleic acids encoding phosphoketolase polypeptides as disclosed herein and further engineered to decrease the activity of a transketolase isozyme. In any aspects of the invention, provided herein are recombinant cells comprising one or more heterologously expressed nucleic acids encoding phosphoketolase polypeptides as disclosed herein and further engineered to increase the activity of a transaldolase isozyme. In any aspects of the invention, provided herein are recombinant cells comprising one or more heterologously expressed nucleic acids encoding phosphoketolase polypeptides as disclosed herein and further engineered to increase the activity of a ribose-5-phosphate isomerase isozyme. In any aspects of the invention, provided herein are recombinant cells comprising one or more heterologously expressed nucleic acids encoding phosphoketolase polypeptides as disclosed herein and further engineered to increase the activity of a ribulose-5-phosphate 3-epimerase isozyme.

In order to direct carbon towards the phosphoketolase enzyme, glucose 6-phosphate 1-dehydrogenase can be modulated (e.g., decrease enzyme activity). In some aspects, the activity of glucose 6-phosphate 1-dehydrogenase (e.g., the endogenous glucose 6-phosphate 1-dehydrogenase gene) can be decreased or attenuated. In certain embodiments, attenuation is achieved by deleting glucose 6-phosphate 1-dehydrogenase. In some aspects, the activity of glucose 6-phosphate 1-dehydrogenase is modulated by decreasing the activity of an endogenous glucose 6-phosphate 1-dehydrogenase. This can be accomplished by replacing the endogenous glucose 6-phosphate 1-dehydrogenase gene promoter with a synthetic constitutively low expressing promoter. In any aspects of the invention, provided herein are recombinant cells comprising one or more heterologously expressed nucleic acids encoding phosphoketolase polypeptides as disclosed herein and further engineered to decrease the activity of glucose 6-phosphate 1-dehydrogenase. Activity modulation (e.g., decreased) of glucose 6-phosphate 1-dehydrogenase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a glucose 6-phosphate 1-dehydrogenase isozyme.

In any aspects of the invention, further provided herein are recombinant cells additionally comprising one or more heterologously expressed nucleic acids encoding a variant of the *Trichoderma reseei* glucoamylase gene. In one embodiment the nucleic acid is under control of native *Saccharomyces cerevisiae* FBA1 promoter and transcription terminator. The sequence of this *Trichoderma reseii* glucoamylase gene is shown as SEQ ID NO: 11 herein.

The invention can be further understood by reference to the following examples, which are provided by way of illustration and are not meant to be limiting.

EXAMPLES

Example 1—Construction of Derivatives of Diploid Industrial Yeast Strains with Partially or Completely Deleted Glycerol Biosynthetic Pathway Yeast strain FerMax™ Gold Label Yeast (FG) was purchased from Martrex Inc. This yeast strain is marketed and used for industrial fuel ethanol production. Its growth rate, final ethanol titers and thermotolerance are typical of the yeast strains used by fuel ethanol industry today. To create derivatives of this strain deficient in glycerol production two disruption cassettes specifically targeting GPD1 and GPD2 genes were assembled. These two genes encode two isoenzymes of glycerol-phosphate dehydrogenase, which have similar enzymatic properties but are regulated differently. The deletion cassettes were assembled starting with a minimal-sized derivative of pUC19—plasmid pF1X (described in PCT Publication No. WO 2012/054554; Miasnikov et al.). Each gene disruption cassette contained "5'-flank" and "3'-flank" DNA segments for targeting initial disruption cassette integration into either GPD1 or GPD2 locus of yeast chromosome. Furthermore, downstream of 5'-flank sequence, a "repeat" DNA segment was placed, containing sequence identical to the yeast chromosomal sequence" further downstream from 3'-flank. The detailed description of the disruption vector construction is given by FIGS. 1-5. SEQ ID No 1 provides complete DNA sequence listing of pX(GPD1A1_URA). SEQ ID No. 2 provides complete listing of the DNA sequence of pX(GPD2A1_URA). Tables 1 and 2 specify functional and structural regions within pX(GPD1A1_URA) and pX(GPD2A1_URA).

TABLE 1

Functional and structural elements comprising pX(GPD1A1_URA).

| No | Sequence positions | Functional/Structural element | Origin | Comment |
|---|---|---|---|---|
| 1 | 1-283 | 5'-flanking area yeast GPD1 gene | Synthetic | Synthesized based on yeast strain S288C chromosome IV sequence positions 411198-411480; Sequence ID in GenBank: gi\|329138864\|tpg\|BK006938.2\| |
| 2 | 284-596 | Repeat region downstream of yeast GPD1 gene | Synthetic | Synthesized based on yeast strain S288C chromosome IV sequence positions 412707-413019; Sequence ID in GenBank: gi\|329138864\|tpg\|BK006938.2\| |
| 3 | 597-1758 | Yeast URA3 gene | Yeast FerMax Gold chromosomal DNA | Amplified by PCR, sequence determined experimentally, it is >99% identical to URA3 sequence of S288C chromosome V, 115868-117108; Sequence ID in GenBank: gi\|329138864\|tpg\|BK006938.2\| |
| 4 | 1759-1765 | Creates AscI site | Synthetic | Added for convenience of genetic engineering |
| 5 | 1766-2079 | 3'-flanking area yeast GPD1 gene | Synthetic | Synthesized based on yeast strain S288C chromosome IV sequence positions 412128-412441; Sequence ID in GenBank: gi\|329138864\|tpg\|BK006938.2\| |
| 6 | 2080-2094 | Added to create a SwaI restriction site | Artificial | Artificial sequence introduced to create SwaI site |
| 7 | 2095-3780 | ColE1 origin of replication and ampicillin resistance gene | pUC19 | A fragment of commonly used laboratory vector pUC19 |
| 8 | 3781-3789 | Added to create a SwaI restriction site | Artificial | Artificial sequence introduced to create SwaI site |

TABLE 2

Functional and structural elements comprising pX(GPD2A1_URA)

| No | Sequence positions | Functional/Structural element | Origin | Comment |
|---|---|---|---|---|
| 1 | 1-287 | 5'-flanking area yeast GPD2 gene | Synthetic | Synthesized based on yeast strain S288C chromosome XV sequence positions 216571-216857; Sequence ID in GenBank: gi\|329138864\|tpg\|BK006938.2\| |
| 2 | 288-583 | Repeat region downstream of yeast GPD2 gene | Synthetic | Synthesized based on yeast strain S288C chromosome XV sequence positions 217956-218252; Sequence ID in GenBank: gi\|329138864\|tpg\|BK006938.2\| |
| 3 | 584-1747 | Yeast URA3 gene | Yeast FerMax Gold chromosomal DNA | Amplified by PCR, sequence determined experimentally, it is >99% identical to URA3 sequence of S288C chromosome V, 115868-117108; Sequence ID in GenBank: gi\|329138864\|tpg\|BK006938.2\| |
| 4 | 1748-1754 | Creates AscI site | Synthetic | Added for convenience of genetic engineering |
| 5 | 1755-2047 | 3'-flanking area yeast GPD2gene | Synthetic | Synthesized based on yeast strain S288C chromosome XV sequence positions 217632-217924; Sequence ID in GenBank: gi\|329138864\|tpg\|BK006938.2\| |
| 6 | 2048-2062 | Added to create a SwaI restriction site | Artificial | Artificial sequence introduced to create SwaI site |
| 7 | 2063-3748 | ColE1 origin of replication and ampicillin resistance gene | pUC19 | A fragment of commonly used laboratory vector pUC19 |
| 8 | 3749-3757 | Added to create a SwaI restriction site | Artificial | Artificial sequence introduced to create SwaI site |

An ura3-derivative of FerMax Gold (strain FG-ura) has been described earlier (Miasnikov et al., U.S. Provisional Application Ser. No. 61/896,869, filed Oct. 29, 2013). This strain was transformed to uracil prototrophy using a purified 2079 bp DNA fragment excised from pX(GPD1A1_URA) with endonuclease SwaI. The transformants were screened by PCR using primers oGPD1_MAP_UD2 and oGPD1_MAP_DR2. The clones containing a single GPD1 allele disrupted by the transforming fragment produced two PCR products: a 3.15 kb product generated by the wild-type allele and a 4.0 kb fragment amplified from the disrupted copy of GPD1 (Tables 3 and 4). One strain producing such PCR product mixture was purified by cloning and submitted to a marker excision procedure. Marker excision was done on minimal plates (6.7 g/Yeast nitrogen base w/o amino acids, 20 g/l glucose) supplemented with 100 mg/l of uridine and 1.2 g/l of fluoroorotic acid (FOA). About 24 ura3-clones emerging on FOA plates were purified and again analyzed by PCR using the same primer pair. This time, a clone generating two PCR products: wild-type 3.1 kb fragment and a short, 1.9 kb fragment was selected. The short fragment corresponds to the disrupted GPD1 allele from which the URA3 marker was excised by homologous recombination between the two "repeat" regions. The structure of the GPD1 chromosomal locus during GPD1 gene disruption and marker excision process is illustrated by FIGS. 6A, 6B and 6C. FIG. 6A illustrates GPD1 wt (wild type) before deletion. FIG. 6B illustrates GPD1 disrupted with URA 3. FIG. 6C illustrates the end of the excision process where GPD1 is disrupted and excised. The resulting strain was heterozygous at the GPD1 locus with one wild type allele and one allele with GPD1 gene deletion. Next, the same sequence of manipulations: gene disruption with the SwaI fragment of pX(GPD1A1_URA) and marker excision using FOA (with screening and PCR analysis at each step) was applied to this heterozygous intermediate strain resulting in an isolate with both copies of GPD1 gene disrupted. This strain was named FGG1. The URA3 predecessor of this strain that was not subjected to last marker excision procedure was named FGG1u.

Figure 7A:
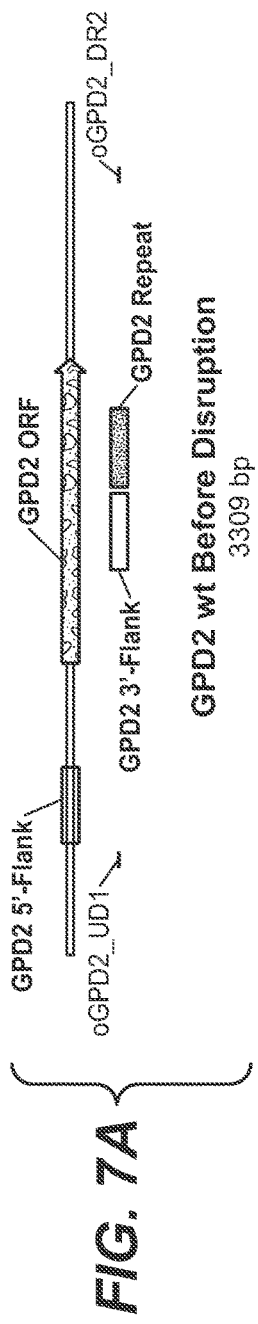
FIGS. 7A, 7B and 7C depict GPD2 chromosomal locus before disruption (FIG. 7A), after disruption with URA3 marker (FIG. 7B), and after excision of URA3 by homologous recombination (FIG. 7C).
Figure 7B:
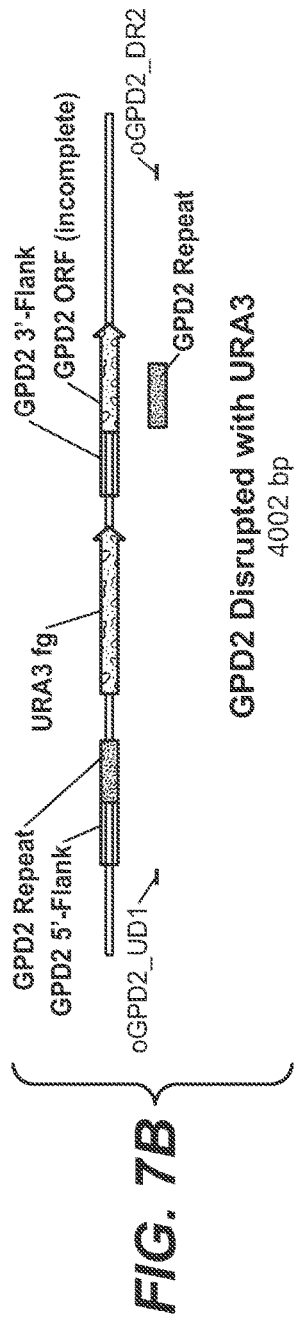
Figure 7C:
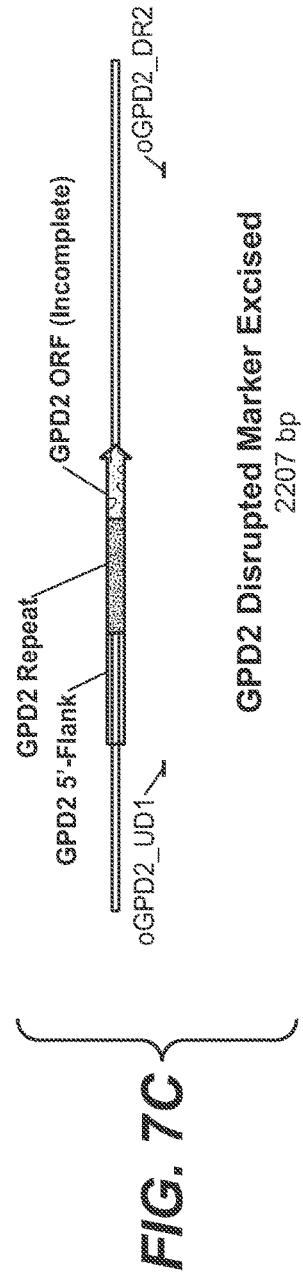

Deletion of GPD2 gene from FGG1 was done using exactly the same two-step strategy as used earlier for deletion GPD1 gene and is illustrated in FIGS. 7A, 7B and 7C. FIG. 7A illustrates GPD2 wt (wild type) before deletion. FIG. 7B illustrates GPD2 disrupted with URA 3. FIG. 7C illustrates the end of the excision process where GPD2 is disrupted and excised. The primers used for screening the transformants and FOA-resistant isolates after marker excision are listed in Table 3. The sizes of characteristic PCR fragments obtained by PCR with primer pair oGPD2_DR2+ oGPD2_UD1 are given in Table 4. The heterozygous strain with a single deleted GPD2 allele and excised URA3 marker (the other GPD2 allele remains wild-type in this strain) was named FGG2. The strain with both GPD2 alleles deleted was named FGGZ. Similarly to the pair of strains FGG1 and FGG1u, the URA3 predecessors of FGG2 and FGGZ were named FGG2u and FGGZu. Table 5 lists genotypes of the strains with completely or partially blocked glycerol biosynthetic pathway used in this study.

TABLE 3

Primers used for mapping deletions of GPD1 and GPD2 genes

| Name | Primer Sequence | SEQ ID NO: |
|---|---|---|
| oGPD1_MAP_DR2 | GAACAATGTCATGACATTGGATGGTGTGCTT GCAGTC | SEQ ID NO: 7 |
| oGDP1_MAP_UD2 | GAGTTATCGTTACTCCGATTATTTTGTACAGC TGATGG | SEQ ID NO: 8 |
| oGPD2_DR2 | CCGTGTATATTAGAACAATGTTCCTTATCGCT GCAC | SEQ ID NO: 9 |
| oGPD2_UD1 | CAGGTAACCGTGCGCGATGAGCTAATCCTGA GCCATC | SEQ ID NO: 10 |

TABLE 4

Characteristic PCR fragment sizes at GPD1 and GPD2 loci during disruption and excision steps (using primer pairs of Table 3, base pairs)

| Modification | GPD1 locus | GPD2 locus |
|---|---|---|
| Wild type | 3152 | 2685 |
| Disrupted with URA3 | 3994 | 3378 |
| After URA3 marker excision | 1929 | 1583 |

TABLE 5

Genotypes of strains with completely or partially blocked glycerol biosynthetic pathway used in this study

| Strain | Genotype |
|---|---|
| FG-ura | Δura3/Δura3 |
| FGG1u | Δgpd1/Δgpd1 Δura3/URA3 |
| FGG1 | Δgpd1/Δgpd1 Δura3/Δura3 |
| FGG2u | Δgpd1/Δgpd1 GPD2/Δgpd2 Δura3/URA3 |
| FGG2 | Δgpd1/Δgpd1 GPD2/Δgpd2 Δura3/Δura3 |
| FGGZ | Δgpd1/Δgpd1 Δgpd2/Δgpd2 Δura3/URA3 |
| FGGZ | Δgpd1/Δgpd1 Δgpd2/Δgpd2 Δura3/Δura3 |

Figure 8:
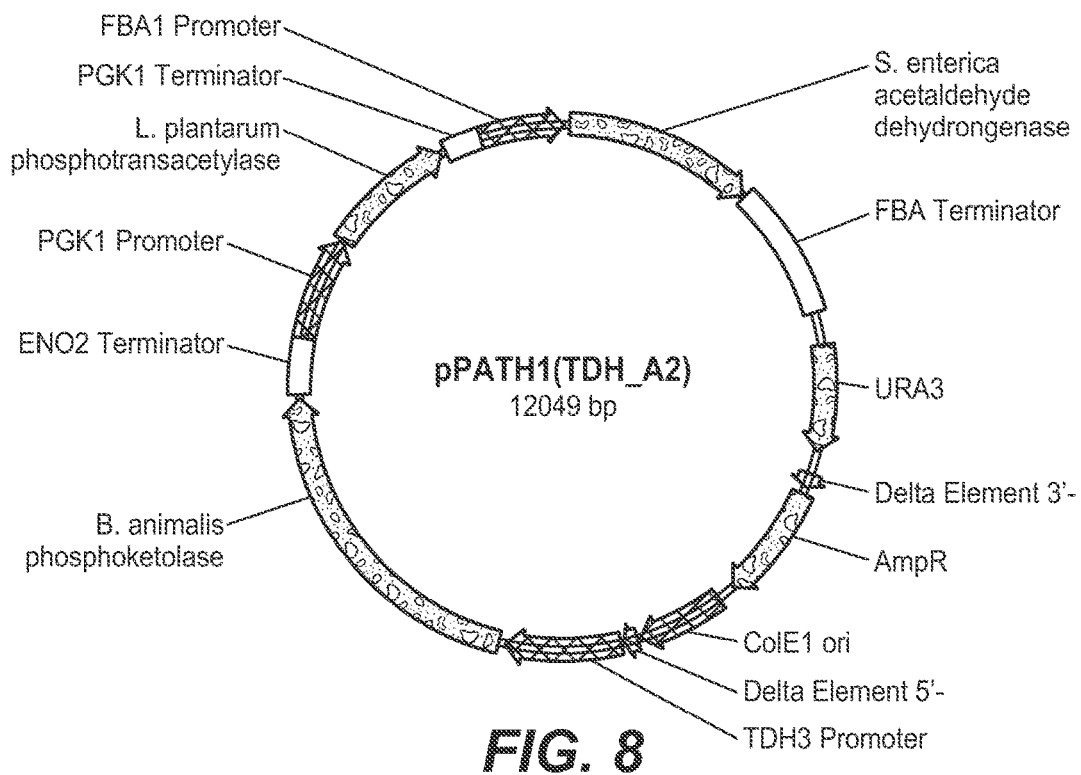
FIG. 8 depicts the structure of recombinant vector pPATH1 (TDH_A2).

Example 2—Construction of a Recombinant Vector pPATH1(TDH_A2) and Transformation of Yeast The genes encoding the three enzymes of the artificial pathway of this invention: phosphoketolase (from *Bifidobacterium animalis*), phosphotransacetylase (*Lactobacillus plantarum*) and acylating acetaldehyde dehydrogenase (*Salmonella enterica*) were synthesized using codons preferred by *Saccharomyces* yeast. The sequences of the three genes are respectively listed below as SEQ ID No 3, SEQ ID No 4 and SEQ ID No 5. These genes were placed under control of the three commonly used strong glycolytic promoters of *S. cerevisiae*: TDH3, PGK1 and FBA1, respectively. DNA fragments comprising promoter and transcription terminator sequences were amplified by PCR from yeast chromosomal DNA templates. The vector was assembled using routine methods of genetic engineering. The structure of pPATH1 (TDH_A2) is illustrated by FIG. 8. Table 6 lists all functional and structural elements comprising pPATH1 (TDH_A2). The DNA sequence listing of this vector is given as SEQ ID No 6.

TABLE 6

Functional and structural elements of vector pPATH1(TDH_A2)

| No | Sequence positions | Functional/Structural element | Origin | Comment |
|---|---|---|---|---|
| 1 | 1-104 | 5'-flank of the yeast □-element | S. cerevisiae chromosomal DNA | Amplified by PCR |
| 2 | 105-123 | SfiI and SalI restriction sites | Artificial | Introduced for convenience of genetic engineering |
| 3 | 124-1002 | TDH3 promoter | S. cerevisiae chromosomal DNA | Amplified by PCR |
| 4 | 1003-1027 | SpeI and EcoRI restriction sites and a sequence for optimal start codon context | Artificial | Introduced for convenience of genetic engineering and improved expression of the downstream coding sequence |
| 5 | 1028-3505 | Encodes B. animalis phosphoketolase | Synthetic | Phosphoketolase protein coding sequence optimized for yeast codon bias |
| 6 | 3506-3527 | BamHI and NotI restriction sites | Artificial | Introduced for convenience of genetic engineering |
| 7 | 3528-3547 | ENO2 transcription terminator | S. cerevisiae chromosomal DNA | Amplified by PCR |
| 8 | 3954-4700 | PGK1 promoter | S. cerevisiae chromosomal DNA | Amplified by PCR |
| 9 | 4701-4710 | SpeI restriction site and a sequence for optimal start codon context | Artificial | Introduced for convenience of genetic engineering and improved expression of the downstream coding sequence |
| 10 | 4711-5688 | Encodes phosphotransacetylase from L. plantarum | Synthetic | Phosphotransacetylase protein coding sequence optimized for yeast codon bias |
| 11 | 5689-5704 | BamHI and NotI restriction sites | Artificial | Introduced for convenience of genetic engineering |
| 12 | 5705-5994 | PGK1 transcription terminator | S. cerevisiae chromosomal DNA | Amplified by PCR |
| 13 | 5995 | A remnant of e restriction site | Artificial | A remnant of a SalI restriction site earlier appended to FBA1 promoter downstream |
| 14 | 5996-6597 | FBA1 promoter | S. cerevisiae chromosomal DNA | Amplified by PCR |
| 15 | 6598-6619 | SpeI and EcoRI restriction sites and a sequence for optimal start codon context | Artificial | Introduced for convenience of genetic engineering and improved expression of the downstream coding sequence |
| 16 | 6220-8023 | Encodes S. enterica acylating acetaldehyde dehydrogenase | Synthetic | AADH coding sequence optimized for yeast codon bias |
| 17 | 8024-8042 | BamHI and NotI restriction sites | Artificial | Introduced for convenience of genetic engineering |
| 18 | 8043-9042 | FBA1 transcription terminator | S. cerevisiae chromosomal DNA | Amplified by PCR |
| 19 | 9043-9059 | SacI and SacII restriction sites | Artificial | Introduced for convenience of genetic engineering |
| 20 | 9060-10224 | S. cerevisiae URA3 gene including native promoter and terminator | S. cerevisiae chromosomal DNA | Amplified by PCR |

TABLE 6-continued

Functional and structural elements of vector pPATH1(TDH_A2)

| No | Sequence positions | Functional/Structural element | Origin | Comment |
|---|---|---|---|---|
| 21 | 10225-10231 | Combined with adjacent sequences creates AscI restriction site | Artificial | Introduced for convenience of genetic engineering |
| 22 | 10232-10340 | 3'-flank of the yeast ☐-element | S. cerevisiae chromosomal DNA | Amplified by PCR |
| 23 | 10341-12049 | ColE1 and AmpR gene | Plasmid vector pUC19 | Amplified by PCR |

For transformation of yeast vector pPATH1(TDH_A2) was digested with restriction endonuclease SwaI and a 10.3 kb DNA fragment containing the three expression cassettes and URA3 selectable marker gene (but not any of the bacterial vector DNA) was purified by agarose gel electrophoresis. S. cerevisiae strains FG-ura, FGG1, FGG2 and FGGZ were transformed with this DNA fragment to uracil prototrophy.

Example 3—Growth and Ethanol Production by Strains Carrying pPATH1(TDH_A2)

Figure 9:
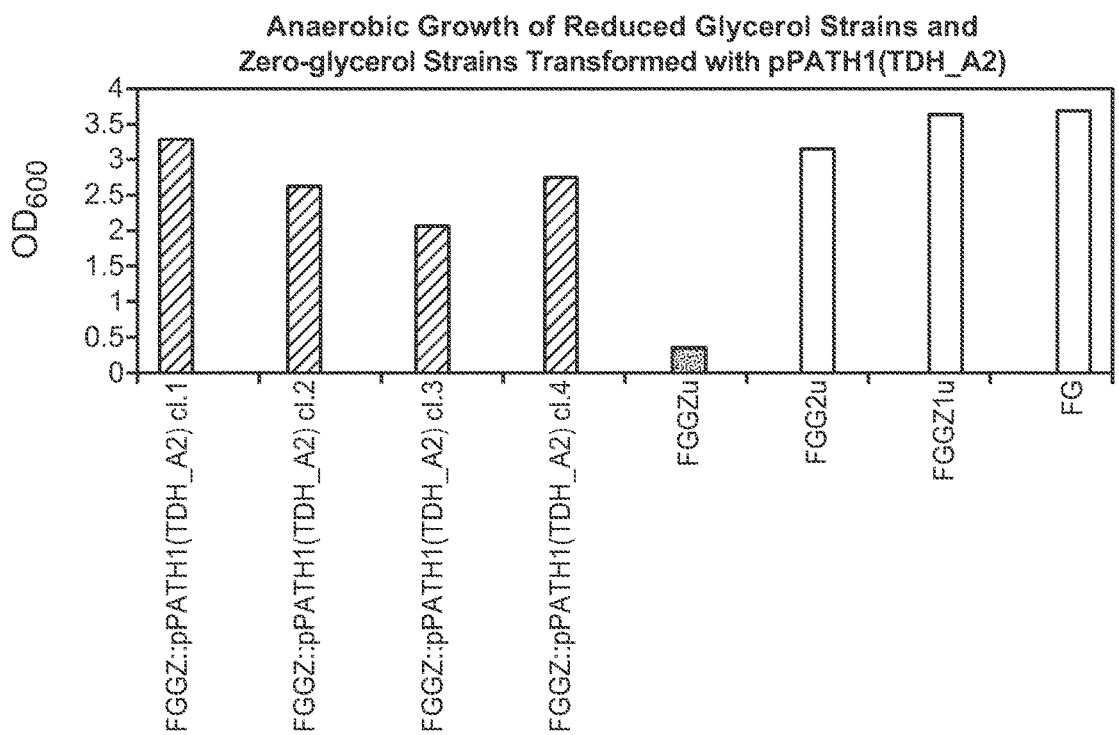
FIG. 9 depicts anaerobic growth values for control and experimental strains including reduced glycerol strains and zero-glycerol strains.
Figure 10A:
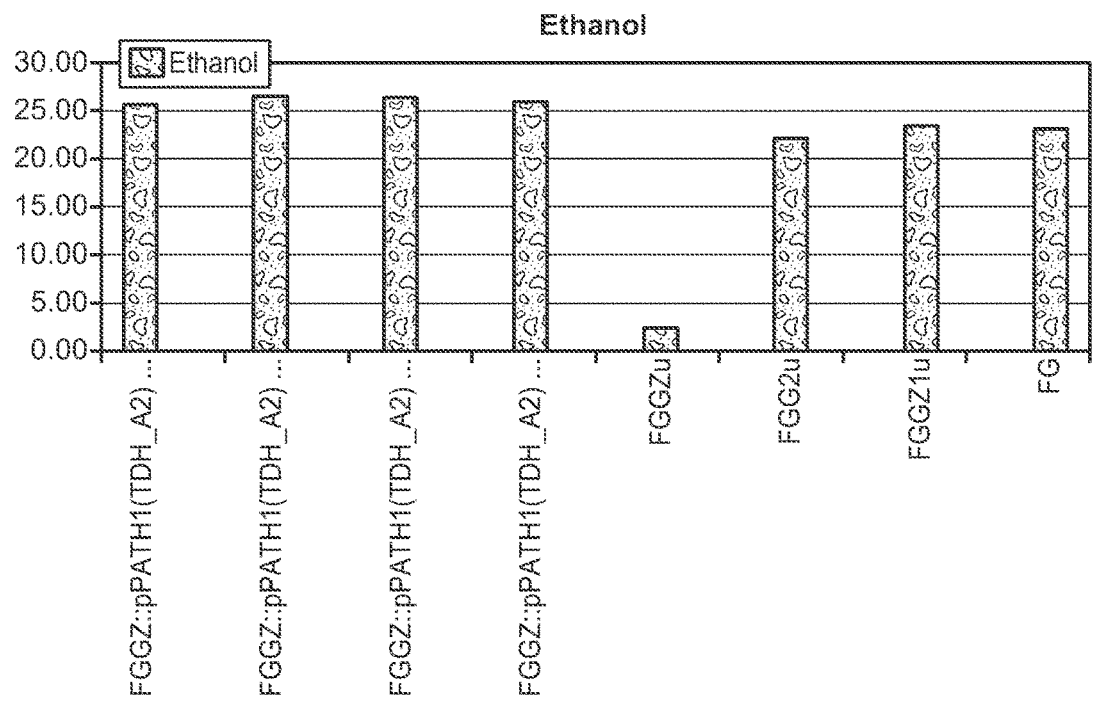
FIGS. 10A and 10B depict ethanol (FIG. 10A) and glycerol (FIG. 10B) production values for anaerobic batch fermentations of control and experimental strains.
Figure 10B:
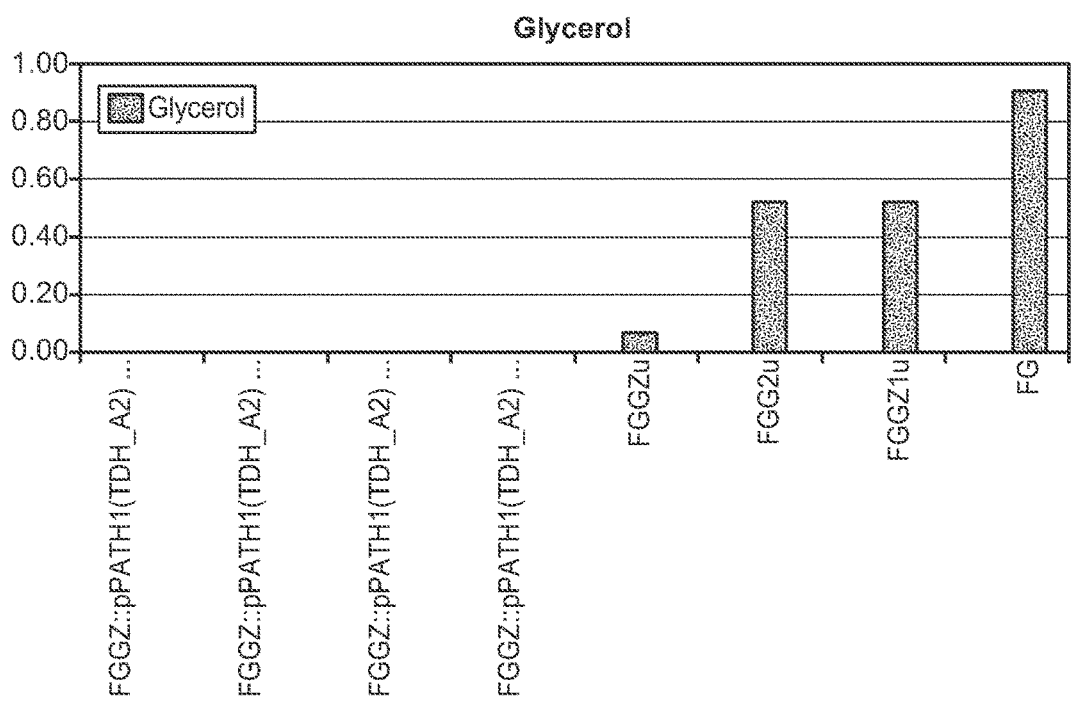

Several transformants of the strain FGGZ with the SwaI fragment of pPATH1(TDH_A2) as well as wild type yeast strain and three control strains with completely or partially blocked glycerol biosynthesis (FGG1u, FGG2u and FGGZu) were grown aerobically overnight in SC6 medium (Yeast Nitrogen Base w/o amino acids ammonium sulfate, 0.2% urea, 6% glucose). These cultures were washed with ice-cold SC6 and used to inoculate 6 ml of the same medium in a 13 mm sterile plastic test tube to initial OD600 of ~0.2. The inoculated cultures were kept on ice until being placed into an anaerobic chamber (<0.1 ppm O2). The cultures were then incubated in vertical position with shaking (500 rpm) at 32° C. for 3 days. At this point the cultures were taken from anaerobic chamber and placed on ice. $OD_{600}$ were measured. An aliquot of supernatant was filtered through a 0.22 μM syringe filter and subjected to HPLC analysis. As shown in FIG. 9 and FIGS. 10A and 10B, the strains with partially deleted glycerol pathway (FGG1u and FGG2u) grow to somewhat lower cell densities and produce equivalent or somewhat lower amount of ethanol than the wild type strain Fermax Gold (FG). Zero-glycerol strain FGGZu does not grow anaerobically (see FIG. 9) and produces only a trace amount of ethanol (See FIG. 10A). However, when a ura3 derivative of this strain (strain FGGZ) is transformed with SwaI fragment of pPATH1(TDH_A2) it recovers the ability to grow anaerobically (see FIG. 9), although biomass yields are reduced relative to the wild type. On the other hand, ethanol yield is consistently higher in the transformants of FGGZ with SwaI fragment of pPATH1(TDH_A2) than in wild type strain (see FIG. 10A). Glycerol production in transformed strains is not detectable (see FIG. 10B). A glycerol signal detected in non-transformed strain FGGZu is likely to be an HPLC artifact, probably caused by the presence of high amount of non-fermented sugar (see FIG. 10B).

Figure 11A:
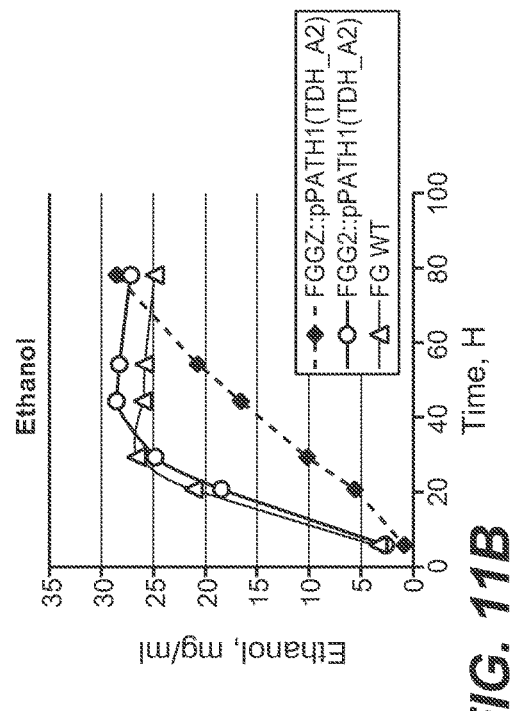
FIGS. 11A, 11B, 11C and 11D depict $OD_{600}$ (FIG. 11A), ethanol (FIG. 11B), glycerol (FIG. 11C) and glucose production (FIG. 11D) values in anaerobic batch fermentations of control and experimental strains.
Figure 11B:
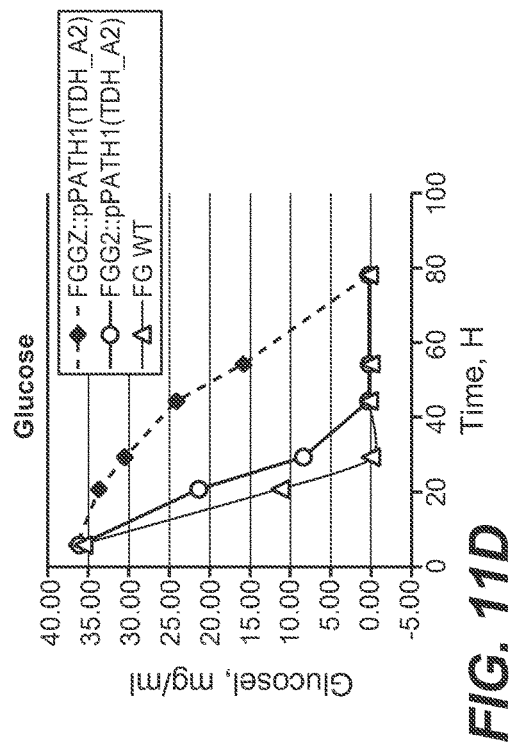
Figure 11C:
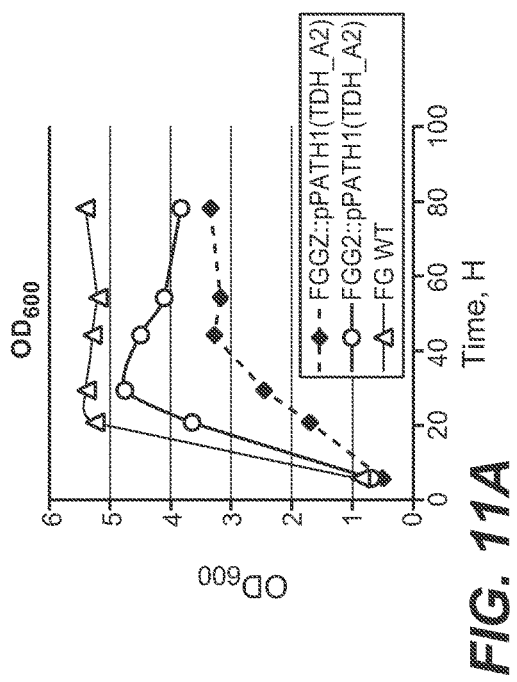
Figure 11D:
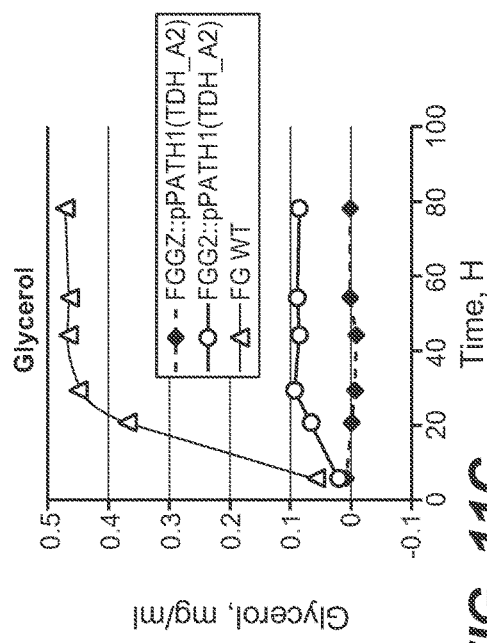
Figure 12:
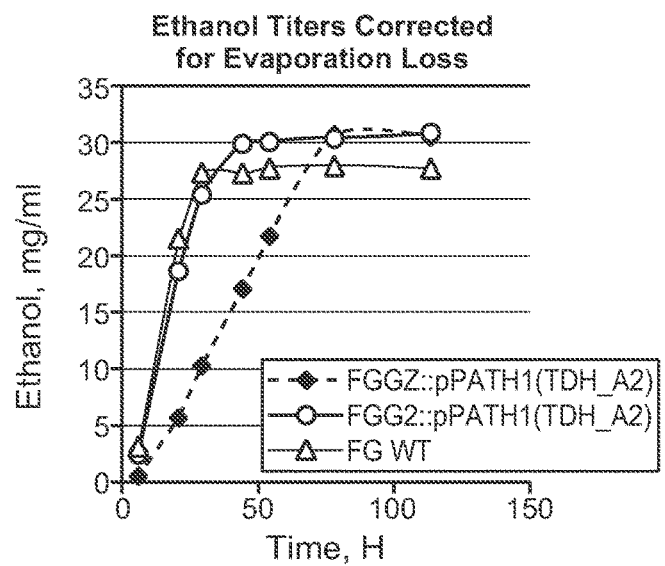
FIG. 12 depicts ethanol production, with correction for calculated evaporation loss, in anaerobic batch fermentations of control and experimental strains, including correction for calculated evaporation loss.

Another experiment was done using a similar setup with the difference that growth and fermentation process was followed kinetically. In this experiment, multiple test tubes were inoculated (to $OD_{600}$=0.5) with each of the strains FGGZ::pPATH1(TDH_A2) cl. 2, FGG2::pPATH1 (TDH_A2) cl. 8 and wild type strain FerMax Gold (FG). The cultures were placed on a shaker in an anaerobic chamber (500 rpm, 32° C.). Individual test tubes were removed from anaerobic chamber at different time points, immediately chilled on ice and analyzed for $OD_{600}$ and extracellular metabolites. The data obtained in this experiment (shown in FIGS. 11A, 11B, 11C and 11D) supports the observations made earlier and allows making several additional conclusions. Firstly, the three strains evaluated in this experiment grow at different rate and reach maximum ethanol titers at different times. In particular, strain FGGZ transformed with the SwaI fragment of pPATH1(TDH_A2) grows much slower than wild type strain FerMax Gold (see FIG. 11A). On the other hand, reduced glycerol strain FGG2 transformed with the same DNA fragment grows at only somewhat slower rate than wild type (see FIG. 11A). As a consequence of differences in growth rate, ethanol concentration in each type of culture reaches its peak at a different time and then slowly decreases due to evaporation (see FIG. 11B). Comparison of the maximum ethanol titers in each culture shows that both strains carrying the triple expression cassette from pPATH1(TDH_A2) produce significantly more ethanol than wild type strain (107% for FGG2::pPATH1(TDH_A2) cl. 8 and 107.5% for FGGZ::pPATH1(TDH_A2) cl. 2). Assuming that ethanol loss due to evaporation is proportional to ethanol concentration and cultivation time and that no ethanol is produced by wild-type strain after 55 h, ethanol loss under conditions of the experiment was estimated to be 0.00185/h. If the ethanol titer data of FIG. 11B is recalculated to correct for evaporation loss, the improvement in ethanol production by strains FGG2::pPATH1(TDH_A2) cl. 8 and FGGZ::pPATH1(TDH_A2) cl. 2 relative to the wild type precursor strain FerMax Gold is even higher than estimated based on maximum titer. Both strains produce ~110-111% of the ethanol produced by the wild-type strain FerMax Gold (FIG. 12).

Figure 13:
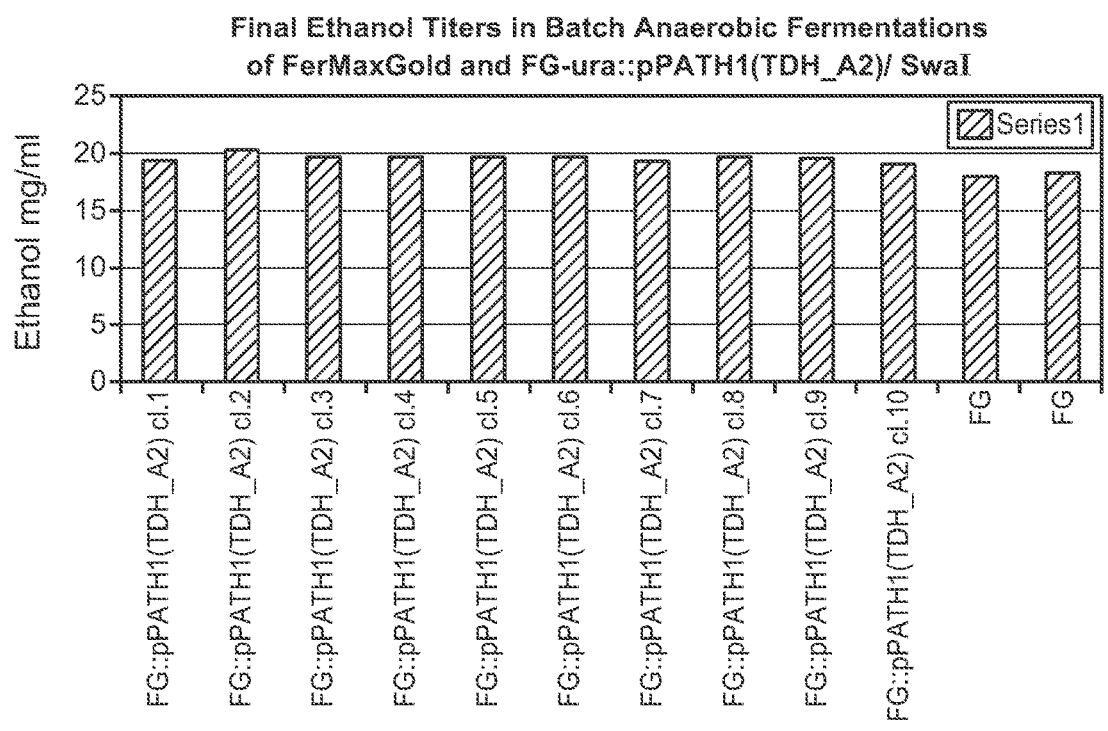
FIG. 13 depicts ethanol production in anaerobic batch fermentations of wild type strain FerMax Gold as well as multiple transformants of FGG1 and FerMax Gold—both transformed with SwaI fragment of pPATH1(TDH_A2).
Figure 14A:
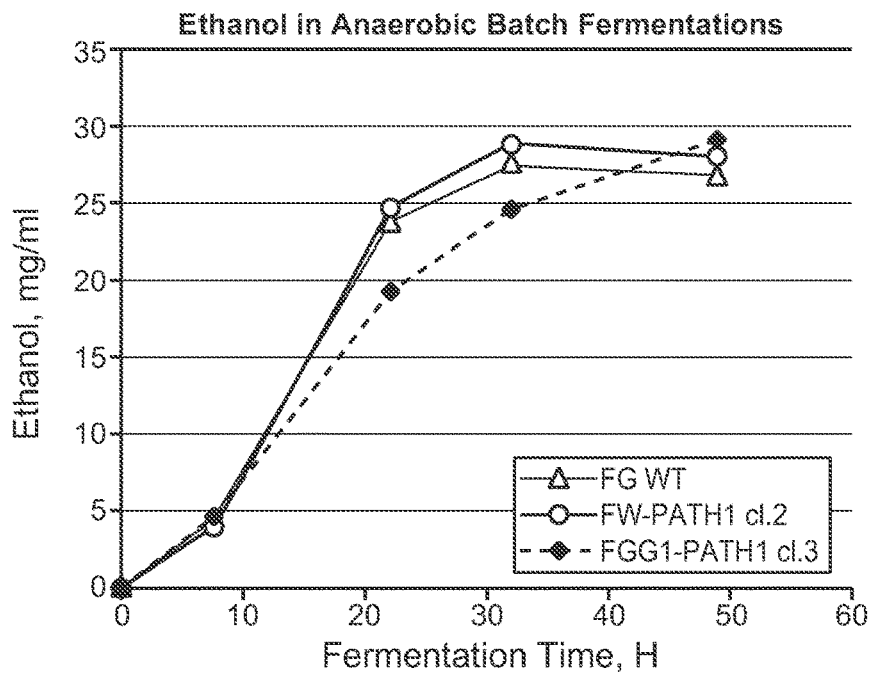
FIGS. 14A and 14B depict time course of ethanol production in anaerobic batch fermentations of wild type strain FerMax Gold and engineered strains: FGG1 transformed with SwaI fragment of pPATH1(TDH_A2) and FerMax Gold transformed with the same DNA.
Figure 14B:
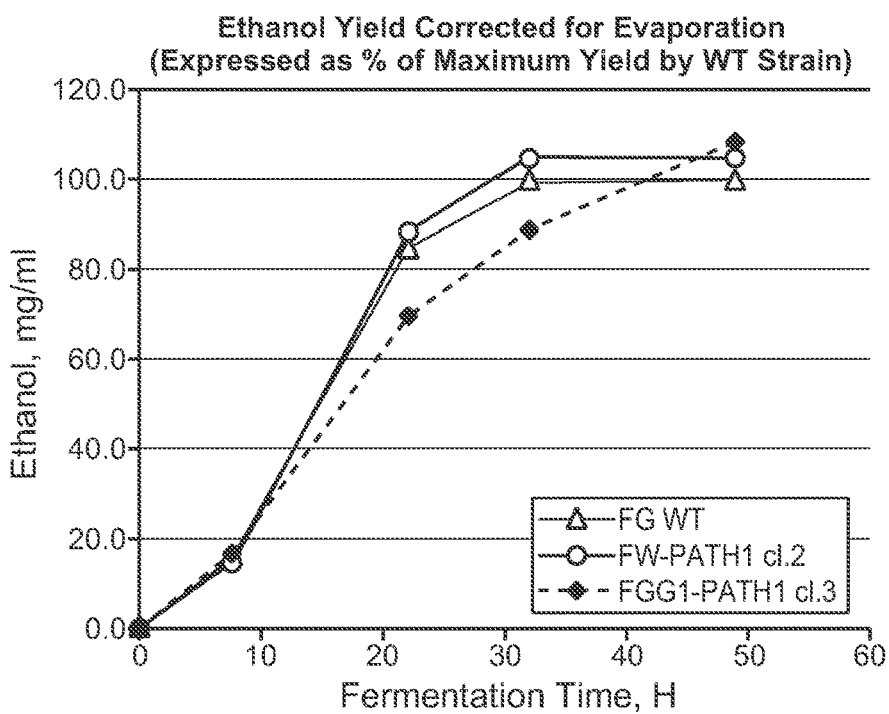

The same large SwaI fragment of pPATH1(TDH_A2) was used to transform strains FGG1 (deleted only for GPD1) and wild-type (with respect to glycerol synthesis) strain FG-ura3. Transformants of both hosts showed significantly improved ethanol yields (FIG. 13) demonstrating that the engineered pathway encoded by pPATH1(TDH_A2) is effective not only in strains with partially or completely reduced glycerol biosynthesis but also strains that are wild type with respect to glycerol biosynthesis. On average FG-ura::pPATH1(TDH_A2)/SwaI transformants produced 8% more ethanol than wild-type strains FerMax Gold. A time course experiment with selected clones of FG-ura:: pPATH1(TDH_A2)/SwaI and FGG1::pPATH1(TDH_A2)/ SwaI (FIGS. 14A and 14B) shows that the strain FG-ura:: pPATH1(TDH_A2)/SwaI, which is wild-type with respect to glycerol biosynthetic pathway, ferments glucose at essentially the same rate as wild-type control strain FerMax Gold. At the same time, maximum ethanol yield by FG-ura::pPATH1(TDH_A2)/SwaI is more than 4% higher than that of wild type control ("FG WT"). The strain lacking GPD1 encoded glycerophosphate dehydrogenase and carrying the recombinant pathway (FGG1::pPATH1(TDH_A2)/SwaI) ferments at a slower rate but has maximum ethanol yield about 8% higher than that of wild type ethanologen yeast strain ("FG WT").

In conclusion, increased ethanol yields have been observed in every yeast strain transformed with the SwaI fragment of pPATH1(TDH_A2). This DNA fragment carries three expression cassettes producing the enzymes of the phosphoketolase pathway: phosphoketolase, phosphotransacetylase and acylating acetaldehyde dehydrogenase. The yields are highest in strains with reduced glycerol biosynthetic capacity. However, anaerobic glucose fermentation by such strains is slower than fermentation with strains that have native glycerol biosynthetic machinery. Without being limited to a particular theory, slow fermentation rate by the strains expressing phosphoketolase pathway may be caused by the imbalance of metabolites of the lower pentose phosphate pathway: erythrose 4-phosphate, sedoheptulose 7-phosphate, ribulose 5-phosphate, ribose 5-phosphate and xylulose 5-phosphate. Such imbalance may be caused by phosphoketolase reaction that can lead to production of excessive amounts of erythrose 4-phosphate or depletion of the pool of xylulose 5-phosphate. To eliminate this imbalance it would be advantageous to over-produce the enzymes of lower pentose phosphate pathway: transaldolase, transketolase, ribulose 5-phosphate epimerase and ribose 5-phosphate isomerase.

Example 4—Acetaldehyde Dehydrogenases Suitable for Enhanced Ethanol Production in Yeast Genes encoding acetaldehyde dehydrogenases (AADH) from a number of different microorganisms were back-translated using *S. cerevisiae* codon preferences and synthesized by GenScript (GenScript USA Inc. Piscataway, N.J.). Table 7 lists the source organisms, enzyme codes used in screening experiments and SEQ ID numbers for protein and nucleotide sequences.

TABLE 7

Acetaldehyde dehydrogenases evaluated for enhanced ethanol production in yeast.

| Acetaldehyde dehydrogenase code | Source organism | DNA sequence SEQ ID | Protein sequence SEQ ID |
|---|---|---|---|
| A_2 | Salmonella enterica | SEQ ID No: 5 | SEQ ID No: 12 |
| A_10 | Escherichia coli | SEQ ID No: 13 | SEQ ID No: 14 |
| A_11 | Citrobacter freundii | SEQ ID No: 15 | SEQ ID No: 16 |
| A_12 | Pseudomonas M1 | SEQ ID No: 17 | SEQ ID No: 18 |
| A_13 | Morganella morganii | SEQ ID No: 19 | SEQ ID No: 20 |
| A_14 | Calditrix abyssii | SEQ ID No: 21 | SEQ ID No: 22 |
| A_15 | Marinobacter aquaeoli | SEQ ID No: 23 | SEQ ID No: 24 |
| A_16 | Shewanella benthica | SEQ ID No: 25 | SEQ ID No: 26 |
| A_17 | Bacillus vireti | SEQ ID No: 27 | SEQ ID No: 28 |
| A_18 | Streptococcus massiliensis | SEQ ID No: 29 | SEQ ID No: 30 |
| A_19 | Desulfospira joergensenii | SEQ ID No: 31 | SEQ ID No: 32 |
| A_20 | Bilophila wadsworthia | SEQ ID No: 33 | SEQ ID No: 34 |
| A_21 | Ilyobacter polytropus | SEQ ID No: 35 | SEQ ID No: 36 |

Each of the synthetic genes was placed between FBA1 promoter and transcription terminator sequences of the vector pPATH1(TDH_A2) replacing the *Salmonella enterica* AADH gene present in the original pPATH1 (TDH_A2). The resulting plasmids were named pPATH1 (TDH_A10), pPATH1(TDH_A11) etc. Large SwaI fragment was excised from each of the eleven new vectors and used to transform the yeast strain FGGZ.

Figure 15A:
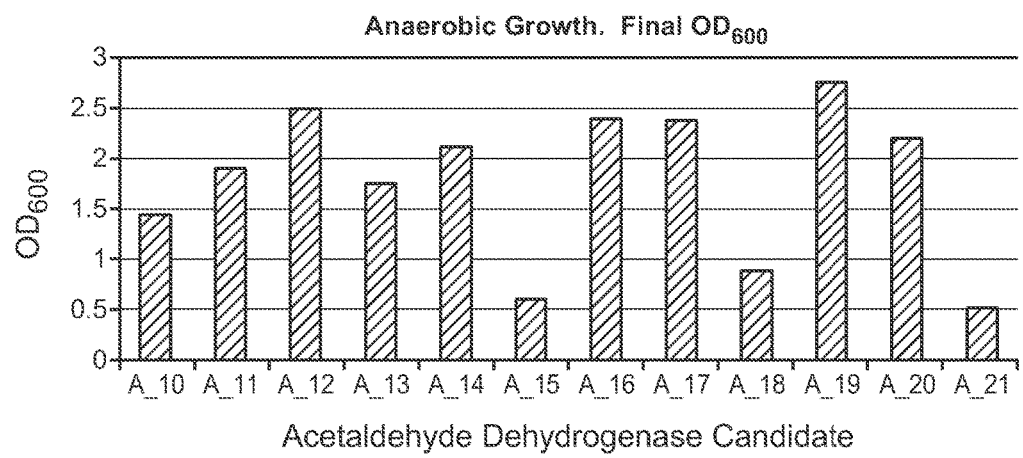
FIG. 15A depicts anaerobic growth by strains obtained by transformation of the strain FGGZ with constructs expressing *B. animalis* phosphoketolase, *L. plantarum* phosphotransacetylase and various acetaldehyde dehydrogenase candidate enzymes.
Figure 15B:
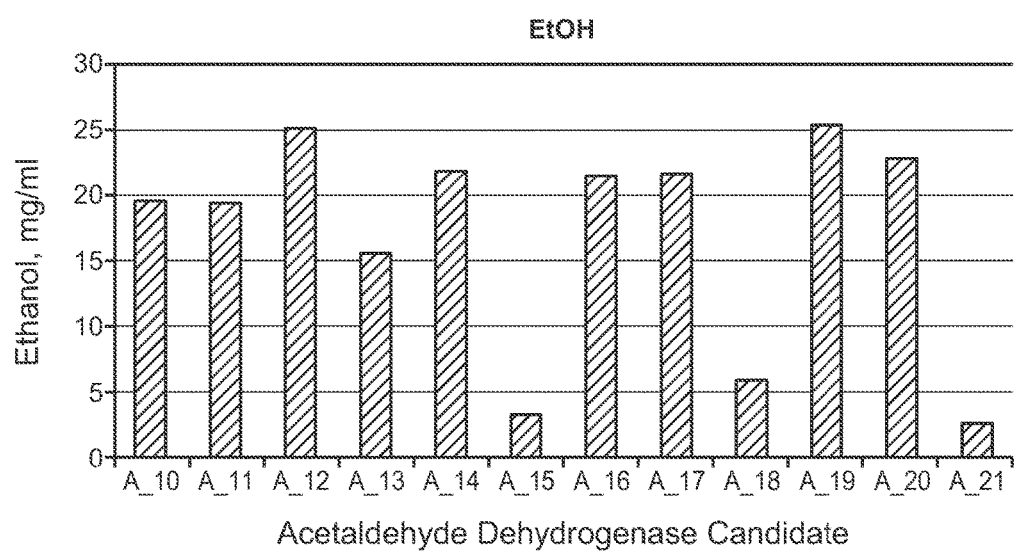
FIG. 15B depicts ethanol production by strains obtained by transformation of the strain FGGZ with constructs expressing *B. animalis* phosphoketolase, *L. plantarum* phosphotransacetylase and various acetaldehyde dehydrogenase candidate enzymes.

The transformants were tested for the restoration of ability to grow anaerobically (FGGZ cannot grow anaerobically because the absence of glycerol production). The total population of transformants was used to inoculate a medium containing 6% glucose, 0.2% urea and 0.67 g/l of Yeast Nitrogen Base without amino acids and ammonium sulfate to initial $OD_{600}$ of 0.3. FIG. 15A shows final $OD_{600}$ values reached by the cultures after 2 days of cultivation under strict anaerobic conditions. The best growth was observed with strains carrying AADH candidates A_12, A_16, A_17 and A_19. The growth of transformants containing AADH candidates A_15 and A_21 was not substantially different from the residual growth of the host strain FGGZ cultivated under the same conditions. Other candidate AADH all rescued anaerobic growth ability of FGGZ to varying degrees. Ethanol production of the various AADH candidates during these fermentations, as shown in FIG. 15B, correlated strongly with the ability to grow anaerobically.

Figure 16:
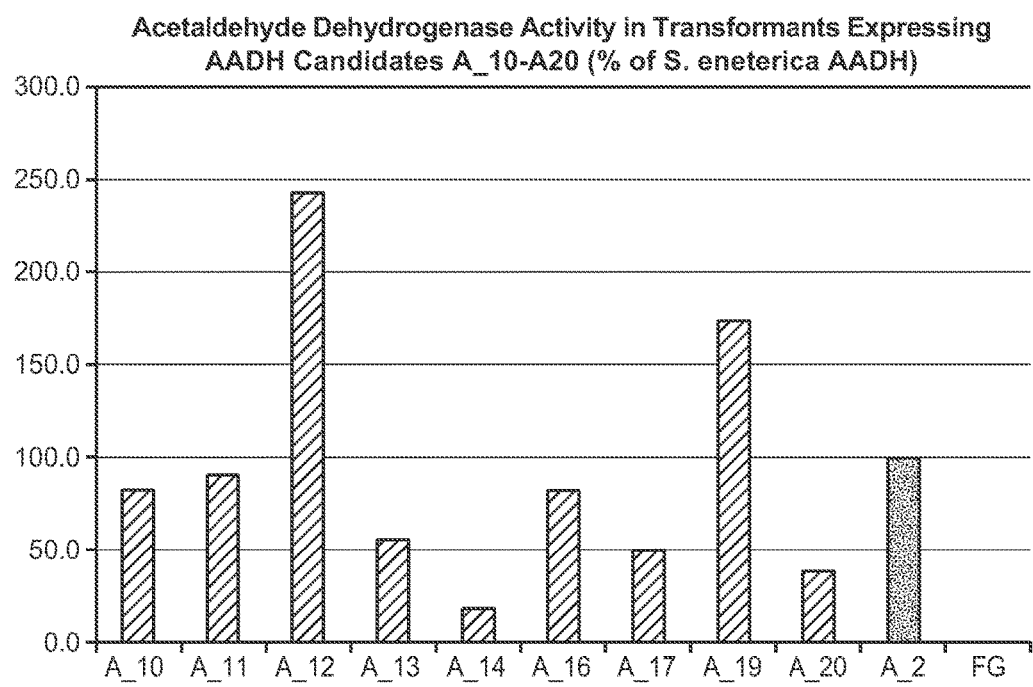
FIG. 16 depicts experimentally determined acetaldehyde dehydrogenase activity in FGGZ transformed with pPATH1 (A_10), pPATH1(A_11), pPATH1(A_12), pPATH1(A_13), pPATH1(A_14), pPATH1(A_16), pPATH1(A_16), pPATH1 (A_17), pPATH1(A_19), pPATH1(A_20), pPATH1(A_2) and the negative control FerMaxGold (FG).

Individual clones of FGGZ yeast transformed with pPATH1(TDH_A10), pPATH1(TDH_A11), pPATH1 (TDH_A12), pPATH1(TDH_A13), pPATH1(TDH_A14), pPATH1(TDH_A16), pPATH1(TDH_A17), pPATH1 (TDH_A19), pPATH1(TDH_A20) were isolated. Two such clones of each type together with two clones of FGGZ transformed with pPATH1(TDH_A2) and wild type Fermax-Gold yeast were grown overnight in 10 ml of YEPPD medium. The cells were collected, washed with water, re-suspended in an Eppendorf tube in 0.5 ml of 100 mM Tris-HCl containing 2 mM phenylmethylsulfonylfluoride (PMSF). Approximately 300 ml of 0.5 mm glass beads were added to each sample. The cells were disrupted by three 40 second pulses of agitation (maximum strength) in a Mini-Beadbeater (model 24; BioSpec Products, Bartlesville, Okla.) with cooling between pulses (approximately 1 min on ice). The cell extracts were cleared by centrifugation (13000 rpm, 10 min) and used to assay AADH activity. The assay was done as follows: 200 ul of 0.2 mM NADH, 0.1 mM AcCoA in 100 mM tris-HCl pH 8.0 was placed in each well of a microtiter plate. $OD_{340}$ followed kinetically using SpectroMax. The value of □ □ $(NADH-NAD^+)_{340}$ used in calculations was 6200 $M^{-1}$. The protein was measured using Pierce BCA assay kit (Life Technologies, Carlsbad, Calif.). The results of this experiment are shown in FIG. 16. The strongest performers in this screening experiment were AADH candidates A_12 and A_19 while candidates A_10, A_11 and A_16 have been expressed at levels similar or slightly below than that of the originally tested AADH from *S. enterica* (A_2). The ranking of AADH candidates based on measurements of enzymatic activity in yeast transformants generally correlated with the earlier data based on physiological evaluation of the transformed strains (rescue of anaerobic growth capacity and anaerobic ethanol production), however, ranking order was not exactly the same in the two types of evaluations. Using the combined data, AADH candidates A_12 (AADH from *Pseudomonas* Ml), A_16 (*Shewanella benthica*) and A_19 (*Desulfospira joergensenii*) were identified as preferred AADH enzymes for practicing the current invention. AADH candidates A_10, A11, A_13, A_17, and A_20 although less efficient according to the screening data are nevertheless also suitable examples for the same purpose.

Example 5—Phosphoketolases Suitable for Enhanced Ethanol Production in Yeast

Genes encoding phosphoketolases (PKL) from a number of different microorganisms were back-translated using *S. cerevisiae* codon preferences and synthesized by GenScript (GenScript USA Inc. Piscataway, N.J.). Table 7 lists the source organisms, enzyme codes used in the screening experiments and SEQ ID numbers for protein and nucleotide sequences Each of the synthetic genes was placed between TDH3 promoter and ENO2 transcription terminator sequences of the vector pPATH1(TDH_A2) replacing the *Bifidobacerium animalis* PKL gene present in the original pPATH1 (TDH_A2). The resulting plasmids were named pPATH1 (TDH_P2_A2), pPATH1(TDH_P3_A2), pPATH1 (TDH_P5_A2) etc. Large SWaI fragment was excised from each of the new vectors and used to transform the yeast strain FGGZ.

Figure 17:
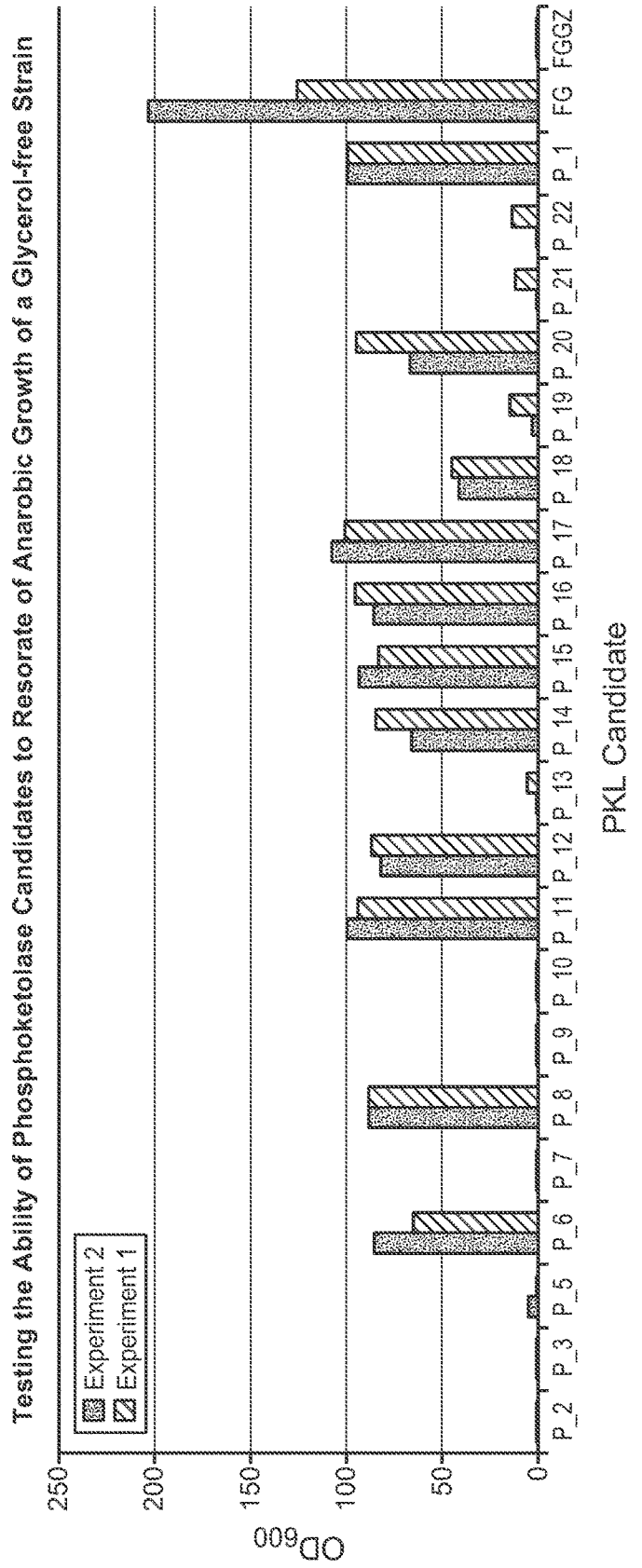
FIG. 17 depicts restoration of the ability of glycerol-free yeast strain FGGZ to grow anaerobically by transformation with recombinant DNA constructs carrying expression cassettes for acetaldehyde dehydrogenase, phosphotransacetylase and various PKL candidates.

The transformants were tested for the restoration of ability to grow anaerobically (FGGZ cannot grow anaerobically because the absence of glycerol production). Four randomly selected transformants of each type were used to inoculate a microtiter plate pre-filled with 250 □l per well of a medium containing 6% glucose, 0.2% urea and 0.67 g/l of Yeast Nitrogen Base without amino acids and ammonium sulfate to initial. The plate was incubated under strict anaerobic conditions with 600 rpm shaking at 32° C. for 48 hours. Final $OD_{600}$ values reached by the cultures were measured and averaged over the four candidate clones of each type. A total of two such experiments were done with well-reproducible results (see FIG. 17).

Figure 18:
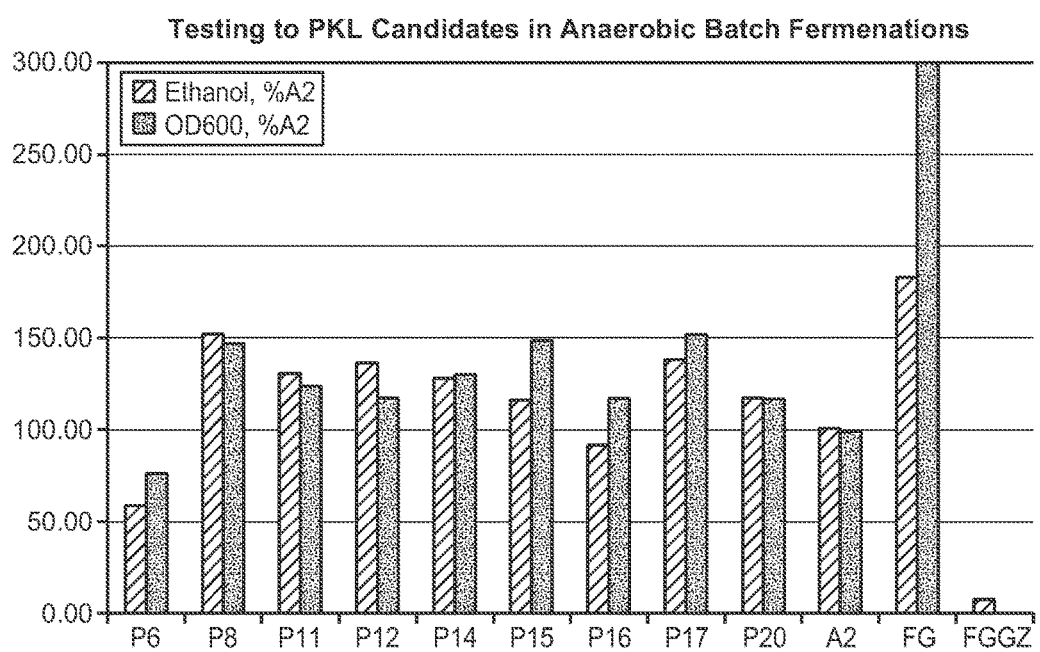
FIG. 18 depicts final OD600 and ethanol titers for transformants of strain FGGZ with recombinant DNA constructs carrying expression cassettes for acetaldehyde dehydrogenase, phosphotransacetylase and various PKL candidates (P_6, P_8, P_11, P_12, P_14, P_15, P_16, P_17, P_20; Table 8) as well as control strains (FGGZ transformed with pPATH1(TDH_A2), FGGZ and wild type FermaxGold, FG).

Clearly, the efficiency of different PKL candidates as components of the three enzyme PKL pathway varied greatly. Half of all the tested candidates failed to restore anaerobic growth ability of FGGZ. Nine preferred candidates from the first round of screening were further tested in batch cultivations. 6 ml aliquots of the same medium were inoculated to initial $OD_{600}$ of 0.2 (using overnight aerobic cultures as the source of inoculum). The tubes were placed (in vertical position) into a shaker located in an anaerobic hood. The cultures were shaken at 600 rpm and 32° C. for two days. Final $OD_{600}$ were measured and ethanol content was analyzed by HPLC. As can be seen from the data shown in FIG. 18, many candidates performed in these tests similarly or better than the original glycerol-free PKL pathway strain (for FGGZ transformed with pPATH1(TDH_A2). Thus, phosphoketolases from *Bifidobacterium asteroides* (P_6), *Clostridium butyricum* (P_8), *Eremococcus coleocola* (P_11), *Gardnerella vaginalis* (P_12), *Kingella kingae* (P_14), *Lactobacillus plantarum* (P_15), *Leuconostoc citreum* (P_16), *Metascardovia criceti* (P_17) and *Scardovia inopinata* (P_20) (see Table 8 for the SEQ ID numbers) were all found suitable for practicing the current invention. The PKL from *C. butyricum* (P_8), *E. coleocola* (P_11) and *G. vaginalis* (P_12) are especially preferable.

TABLE 8

Phosphoketolases evaluated for enhanced ethanol production in yeast.

| Phosphoketolase | Source organism | DNA sequence SEQ ID No: | Protein sequence SEQ ID No |
|---|---|---|---|
| P_1 | *Bifidobacterium animalis* | SEQ ID No: 3 | SEQ ID No: 37 |
| P_2 | *Schizosaccharomyces pombe* | SEQ ID No: 38 | SEQ ID No: 39 |
| P_3 | *Aspergillus niger* | SEQ ID No: 40 | SEQ ID No: 41 |
| P_5 | *Acidithiobacillus ferrooxidans* | SEQ ID No: 42 | SEQ ID No: 43 |
| P_6 | *Bifidobacterium asteroids* | SEQ ID No: 44 | SEQ ID No: 45 |
| P_7 | *Bifidobacterium catenulatum* | SEQ ID No: 46 | SEQ ID No: 47 |
| P_8 | *Clostridium butyricum* | SEQ ID No: 48 | SEQ ID No: 49 |
| P_9 | *Cryptococcus neoformans* | SEQ ID No: 50 | SEQ ID No: 51 |
| P_10 | *Cyanothece* | SEQ ID No: 52 | SEQ ID No: 53 |
| P_11 | *Eremococcus coleocola* | SEQ ID No: 54 | SEQ ID No: 55 |
| P_12 | *Gardnerella vaginalis* | SEQ ID No: 56 | SEQ ID No: 57 |
| P_13 | *Glaciibacter superstes* | SEQ ID No: 58 | SEQ ID No: 59 |
| P_14 | *Kingella kingae* | SEQ ID No: 60 | SEQ ID No: 61 |
| P_15 | *Lactobacillus plantarum* | SEQ ID No: 62 | SEQ ID No: 63 |
| P_16 | *Leuconostoc citreum* | SEQ ID No: 64 | SEQ ID No: 65 |
| P_17 | *Metascardovia criceti* | SEQ ID No: 66 | SEQ ID No: 67 |
| P_18 | *Oenococcus oeni* | SEQ ID No: 68 | SEQ ID No: 69 |
| P_19 | *Rhodosporidium toruloides* | SEQ ID No: 70 | SEQ ID No: 71 |
| P_20 | *Scardovia inopinata* | SEQ ID No: 72 | SEQ ID No: 73 |
| P_21 | *Schizosaccharomyces japonicus* | SEQ ID No: 74 | SEQ ID No: 75 |

TABLE 8-continued

Phosphoketolases evaluated for enhanced ethanol production in yeast.

| Phosphoketolase | Source organism | DNA sequence SEQ ID No: | Protein sequence SEQ ID No |
|---|---|---|---|
| P_22 | Trichodermareesei | SEQ ID No: 76 | SEQ ID No: 77 |

```
                                              SEQ ID NO: 1
AAATAATAAAAAAAGTAACCCCACTTCTACTTCTACATCGGAAAAACATTCCATTC

ACATATCGTCTTTGGCCTATCTTGTTTTGTCCTCGGTAGATCAGGTCAGTACAAACG

CAACACGAAAGAACAAAAAAGAAGAAAACAGAAGGCCAAGACAGGGTCAATGA

GACTGTTGTCCTCCTACTGTCCCTATGTCTCTGGCCGATCACGCGCCATTGTCCCTCA

GAAACAAATCAAACACCCACACCCCGGGCACCCAAAGTCCCCACCCACACCACCAA

TAGAGTCTGCTGGTGTTGCTGATTTGATCACCACCTGCGCTGGTGGTAGAAACGTCA

AGGTTGCTAGGCTAATGGCTACTTCTGGTAAGGACGCCTGGGAATGTGAAAAGGAG

TTGTTGAATGGCCAATCCGCTCAAGGTTTAATTACCTGCAAAGAAGTTCACGAATGG

TTGGAAACATGTGGCTCTGTCGAAGACTTCCCATTATTTGAAGCCGTATACCAAATC

GTTTACAACAACTACCCAATGAAGAACCTGCCGGACATGATTGAAGAATTAGATCT

ACATGAAGATTAGATTTATTGGAGAAAGATAAGCTTTTCAATTCATCATTTTTTTTT

ATTCTTTTTTTTGATTCCGGTTTCCTTGAAATTTTTTGATTCGGTAATCTCCGAACA

GAAGGAAGAACGAAGGAAGGAGCACAGACTTAGATTGGTATATATACGCATATGT

AGTGTTGAAGAAACATGAAATTGCCCAGTATTCTTAACCCAACTGCACAGAACAAA

AACCTGCAGGAAACGAAGATAAATCATGTCGAAAGCTACATATAAGGAACGTGCTG

CTACTCATCCTAGTCCTGTTGCTGCCAAGCTATTTAATATCATGCACGAAAAGCAAA

CAAACTTGTGTGCTTCATTGGATGTTCGTACCACCAAGGAATTACTGGAGTTAGTTG

AAGCATTAGGTCCCAAAATTTGTTTACTAAAAACACATGTGGATATCTTGACTGATT

TTTCCATGGAGGGCACAGTTAAGCCGCTAAAGGCATTATCCGCCAAGTACAATTTTT

TACTCTTCGAAGACAGAAAATTTGCTGACATTGGTAATACAGTCAAATTGCAGTACT

CTGCGGGTGTATACAGAATAGCAGAATGGGCAGACATTACGAATGCACACGGTGTG

GTGGGCCCAGGTATTGTTAGCGGTTTGAAGCAGGCGGCAGAAGAAGTAACAAAGG

AACCTAGAGGCCTTTTGATGTTAGCAGAATTGTCATGCAAGGGCTCCCTAGCTACTG

GAGAATATACTAAGGGTACTGTTGACATTGCGAAGAGCGACAAAGATTTTGTTATC

GGCTTTATTGCTCAAAGAGACATGGGTGGAAGAGATGAAGGTTACGATTGGTTGAT

TATGACACCCGGTGTGGGTTTAGATGACAAGGGAGACGCATTGGGTCAACAGTATA

GAACCGTGGATGATGTGGTCTCTACAGGATCTGACATTATTATTGTTGGAAGAGGA

CTATTTGCAAAGGGAAGGGATGCTAAGGTAGAGGGTGAACGTTACAGAAAAGCAG

GCTGGGAAGCATATTTGAGAAGATGCGGCCAGCAAAACTAAAAAACTGTATTATAA

GTAAATGCATGTATACTAAACTCACAAATTAGAGCTTCAATTTAATTATATCAGTTA

TTACCCGGGAATCTCGGTCGTAATGATTTTTATAATGACGAAAAAAAAAAAATTGG

AAAGAAAAAGGCGCGCCCCCGACAATTTGGTTGCTAATCCAGACTTGATTGATTCA

GTCAAGGATGTCGACATCATCGTTTTCAACATTCCACATCAATTTTTGCCCCGTATCT

GTAGCCAATTGAAAGGTCATGTTGATTCACACGTCAGAGCTATCTCCTGTCTAAAGG
```

-continued

```
GTTTTGAAGTTGGTGCTAAAGGTGTCCAATTGCTATCCTCTTACATCACTGAGGAAC

TAGGTATTCAATGTGGTGCTCTATCTGGTGCTAACATTGCCACCGAAGTCGCTCAAG

AACACTGGTCTGAAACAACAGTTGCTTACCACATTCCAAAGGATTTAAATCCAAAA

ATGGCCATGAGACAATAACCCTGATAAATGCTTCAATAATATTGAAAAAGGAAGAG

TATGAGTATTCAACATTTCCGTGTCGCCCTTATTCCCTTTTTTGCGGCATTTTGCCTT

CCTGTTTTTGCTCACCCAGAAACGCTGGTGAAAGTAAAAGATGCTGAAGATCAGTT

GGGTGCACGAGTGGGTTACATCGAACTGGATCTCAACAGCGGTAAGATCCTTGAGA

GTTTTCGCCCCGAAGAACGTTTTCCAATGATGAGCACTTTTAAAGTTCTGCTATGTG

GCGCGGTATTATCCCGTATTGACGCCGGGCAAGAGCAACTCGGTCGCCGCATACAC

TATTCTCAGAATGACTTGGTTGAGTACTCACCAGTCACAGAAAAGCATCTTACGGAT

GGCATGACAGTAAGAGAATTATGCAGTGCTGCCATAACCATGAGTGATAACACTGC

GGCCAACTTACTTCTGACAACGATCGGAGGACCGAAGGAGCTAACCGCTTTTTTGC

ACAACATGGGGGATCATGTAACTCGCCTTGATCGTTGGGAACCGGAGCTGAATGAA

GCCATACCAAACGACGAGCGTGACACCACGATGCCTGTAGCAATGGCAACAACGTT

GCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTG

GCTGGTTTATTGCTGATAAATCTGGAGCCGGTGAGCGTGGGTCTCGCGGTATCATTG

CAGCACTGGGGCCAGATGGTAAGCCCTCCCGTATCGTAGTTATCTACACGACGGGG

AGTCAGGCAACTATGGATGAACGAAATAGACAGATCGCTGAGATAGGTGCCTCACT

GATTAAGCATTGGTAACTGTCAGACCAAGTTTACTCATATATACTTTAGATTGATTT

AAAACTTCATTTTTAATTTAAAAGGATCTAGGTGAAGATCCTTTTTGATAATCTCAT

GACCAAAATCCCTTAACGTGAGTTTTCGTTCCACTGAGCGTCAGACCCCGTAGAAA

AGATCAAAGGATCTTCTTGAGATCCTTTTTTTCTGCGCGTAATCTGCTGCTTGCAAA

CAAAAAACCACCGCTACCAGCGGTGGTTTGTTTGCCGGATCAAGAGCTACCAACT

CTTTTTCCGAAGGTAACTGGCTTCAGCAGAGCGCAGATACCAAATACTGTCCTTCTA

GTGTAGCCGTAGTTAGGCCACCACTTCAAGAACTCTGTAGCACCGCCTACATACCTC

GCTCTGCTAATCCTGTTACCAGTGGCTGCTGCCAGTGGCGATAAGTCGTGTCTTACC

GGGTTGGACTCAAGACGATAGTTACCGGATAAGGCGCAGCGGTCGGGCTGAACGG

GGGGTTCGTGCACACAGCCCAGCTTGGAGCGAACGACCTACACCGAACTGAGATAC

CTACAGCGTGAGCTATGAGAAAGCGCCACGCTTCCCGAAGGGAGAAAGGCGGACA

GGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCG

TCGATTTTTGTGATGCTCGTCAGGGGGCGGAGCCTATGGAAAAACGCCAGCAACG

CTGCATATTT

SEQ ID NO: 2
AAATAAAAACTGGAGCAAGGAATTACCATCACCGTCACCATCACCATCATATCGCC

TTAGCCTCTAGCCATAGCCATCATGCAAGCGTGTATCTTCTAAGATTCAGTCATCAT

CATTACCGAGTTTGTTTTCCTTCACATGATGAAGAAGGTTTGAGTATGCTCGAAACA

ATAAGACGACGATGGCTCTGCCATTGTTATATTACGCTTTTGCGGCGAGGTGCCGAT

GGGTTGCTGAGGGGAAGAGTGTTTAGCTTACGGAACCTATTGCCATTGTTATTCCGAT

TAACGTCAATGTCATCGATGATGTTGCTGGTATATCCATTGCCGGTGCCTTGAAGAA
```

-continued

```
CGTCGTGGCACTTGCATGTGGTTTCGTAGAAGGTATGGGATGGGGTAACAATGCCT

CCGCAGCCATTCAAAGGCTGGGTTTAGGTGAAATTATCAAGTTCGGTAGAATGTTTT

TCCCAGAATCCAAAGTCGAGACCTACTATCAAGAATCCGCTGGTGTTGCAGATCTG

ATCACCACCTGCTCAGGCGGTAGAAACGTCAAGGTTGCCACATACATGGCCAAGAC

CGGTAAGTCAGCCTTGGAAGCTTTTCAATTCATCATTTTTTTTTATTCTTTTTTTTGA

TTCCGGTTTCCTTGAAATTTTTTTGATTCGGTAATCTCCGAACAGAAGGAAGAACGA

AGGAAGGAGCACAGACTTAGATTGGTATATATACGCATATGTAGTGTTGAAGAAAC

ATGAAATTGCCCAGTATTCTTAACCCAACTGCACAGAACAAAAACCTGCAGGAAAC

GAAGATAAATCATGTCGAAAGCTACATATAAGGAACGTGCTGCTACTCATCCTAGT

CCTGTTGCTGCCAAGCTATTTAATATCATGCACGAAAAGCAAACAAACTTGTGTGCT

TCATTGGATGTTCGTACCACCAAGGAATTACTGGAGTTAGTTGAAGCATTAGGTCCC

AAAATTTGTTTACTAAAAACACATGTGGATATCTTGACTGATTTTTCCATGGAGGGC

ACAGTTAAGCCGCTAAAGGCATTATCCGCCAAGTACAATTTTTTACTCTTCGAAGAC

AGAAAATTTGCTGACATTGGTAATACAGTCAAATTGCAGTACTCTGCGGGTGTATAC

AGAATAGCAGAATGGGCAGACATTACGAATGCACACGGTGTGGTGGGCCCAGGTAT

TGTTAGCGGTTTGAAGCAGGCGGCAGAAGAAGTAACAAAGGAACCTAGAGGCCTTT

TGATGTTAGCAGAATTGTCATGCAAGGGCTCCCTAGCTACTGGAGAATATACTAAG

GGTACTGTTGACATTGCGAAGAGCGACAAAGATTTTGTTATCGGCTTTATTGCTCAA

AGAGACATGGGTGGAAGAGATGAAGGTTACGATTGGTTGATTATGACACCCGGTGT

GGGTTTAGATGACAAGGGAGACGCATTGGGTCAACAGTATAGAACCGTGGATGATG

TGGTCTCTACAGGATCTGACATTATTATTGTTGGAAGAGGACTATTTGCAAAGGGAA

GGGATGCTAAGGTAGAGGGTGAACGTTACAGAAAAGCAGGCTGGGAAGCATATTT

GAGAAGATGCGGCCAGCAAAACTAAAAAACTGTATTATAAGTAAATGCATGTATAC

TAAACTCACAAATTAGAGCTTCAATTTAATTATATCAGTTATTACCCGGGAATCTCG

GTCGTAATGATTTTTATAATGACGAAAAAAAAAAAATTGGAAAGAAAAAGGCGCG

CCCCTTGTTTTCAACATCCCTCATCAATTTTTACCAAACATAGTCAAACAATTGCAA

GGCCACGTGGCCCCTCATGTAAGGGCCATCTCGTGTCTAAAAGGGTTCGAGTTGGG

CTCCAAGGGTGTGCAATTGCTATCCTCCTATGTTACTGATGAGTTAGGAATCCAATG

TGGCGCACTATCTGGTGCAAACTTGGCACCGGAAGTGGCCAAGGAGCATTGGTCCG

AAACCACCGTGGCTTACCAACTACCAAAGGATTATCAAGGTGATGGCAAGGATGTA

GATCATAAGATTTAAATCCAAAAATGGCCATGAGACAATAACCCTGATAAATGCTT

CAATAATATTGAAAAAGGAAGAGTATGAGTATTCAACATTTCCGTGTCGCCCTTATT

CCCTTTTTTGCGGCATTTTGCCTTCCTGTTTTTGCTCACCCAGAAACGCTGGTGAAAG

TAAAAGATGCTGAAGATCAGTTGGGTGCACGAGTGGGTTACATCGAACTGGATCTC

AACAGCGGTAAGATCCTTGAGAGTTTTCGCCCCGAAGAACGTTTTCCAATGATGAG

CACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGT

CACAGAAAAGCATCTTACGGATGGCATGACAGTAAGAGAATTATGCAGTGCTGCCA

TAACCATGAGTGATAACACTGCGGCCAACTTACTTCTGACAACGATCGGAGGACCG

AAGGAGCTAACCGCTTTTTTGCACAACATGGGGGATCATGTAACTCGCCTTGATCGT
```

```
                                  -continued
TGGGAACCGGAGCTGAATGAAGCCATACCAAACGACGAGCGTGACACCACGATGC

CTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACT

TCTGCGCTCGGCCCTTCCGGCTGGCTGGTTTATTGCTGATAAATCTGGAGCCGGTGA

GCGTGGGTCTCGCGGTATCATTGCAGCACTGGGGCCAGATGGTAAGCCCTCCCGTA

TCGTAGTTATCTACACGACGGGGAGTCAGGCAACTATGGATGAACGAAATAGACAG

ATCGCTGAGATAGGTGCCTCACTGATTAAGCATTGGTAACTGTCAGACCAAGTTTAC

TCATATATACTTTAGATTGATTTAAAACTTCATTTTTAATTTAAAAGGATCTAGGTG

AAGATCCTTTTTGATAATCTCATGACCAAAATCCCTTAACGTGAGTTTTCGTTCCACT

GAGCGTCAGACCCCGTAGAAAAGATCAAAGGATCTTCTTGAGATCCTTTTTTTCTGC

GCGTAATCTGCTGCTTGCAAACAAAAAAACCACCGCTACCAGCGGTGGTTTGTTTGC

CGGATCAAGAGCTACCAACTCTTTTTCCGAAGGTAACTGGCTTCAGCAGAGCGCAG

ATACCAAATACTGTCCTTCTAGTGTAGCCGTAGTTAGGCCACCACTTCAAGAACTCT

GTAGCACCGCCTACATACCTCGCTCTGCTAATCCTGTTACCAGTGGCTGCTGCCAGT

GGCGATAAGTCGTGTCTTACCGGGTTGGACTCAAGACGATAGTTACCGGATAAGGC

GCAGCGGTCGGGCTGAACGGGGGGTTCGTGCACACAGCCCAGCTTGGAGCGAACG

ACCTACACCGAACTGAGATACCTACAGCGTGAGCTATGAGAAAGCGCCACGCTTCC

CGAAGGGAGAAAGGCGGACAGGTATCCGGTAAGCGGCAGGGTCGGAACAGGAGAG

CGCACGAGGGAGCTTCCAGGGGGAAACGCCTGGTATCTTTATAGTCCTGTCGGGTTT

CGCCACCTCTGACTTGAGCGTCGATTTTTGTGATGCTCGTCAGGGGGCGGAGCCTA

TGGAAAAACGCCAGCAACGCTGCATATTT
                                                          SEQ ID NO: 3
ATGACCAACCCAGTCATTGGTACTCCATGGCAAAAATTGGATAGACCAGTTTCCGA

AGAAGCCATTGAAGGTATGGATAAGTATTGGAGAGTTGCCAACTACATGTCCATTG

GTCAAATCTACTTGAGATCCAACCCATTGATGAAGGAACCATTCACTAGAGATGAT

GTCAAGCACAGATTGGTTGGTCATTGGGGTACTACTCCAGGTTTGAATTTTTTGTTG

GCCCACATCAACAGATTGATCGCTGATCATCAACAAAACACCGTTTTCATTATGGGT

CCAGGTCATGGTGGTCCAGCTGGTACTGCTCAATCTTATATTGATGGTACTTACACC

GAATATTACCCAAACATCACTAAGGATGAAGCCGGTTTACAAAAGTTCTTCAGACA

ATTTTCTTACCCAGGTGGTATCCCATCTCATTTTGCTCCAGAAACTCCAGGTTCTATT

CATGAAGGTGGTGAATTGGGTTATGCTTTGTCTCATGCTTATGGTGCCATTATGGAT

AACCCATCTTTGTTCGTTCCATGCATTATTGGTGATGGTGAAGCTGAAACTGGTCCA

TTGGCTACTGGTTGGCAATCTAACAAATTGGTTAACCCAAGAACCGATGGTATCGTT

TTGCCAATCTTGCATTTGAACGGTTACAAGATTGCTAACCCAACCATTTTGGCCAGA

ATCTCTGATGAAGAATTGCACGATTTTTTCAGAGGTATGGGTTACCACCCATACGAA

TTTGTTGCTGGTTTTGATAACGAAGATCACTTGTCCATCCATAGAAGATTCGCCGAA

TTATTCGAAACCATCTTCGACGAAATTTGCGATATTAAGGCTGCTGCTCAAACTGAT

GATATGACTAGACCATTTTACCCAATGTTGATCTTCAGAACTCCAAAGGGTTGGACT

TGTCCAAAGTTTATCGATGGTAAAAAGACCGAAGGTTCTTGGAGAGCACATCAAGT

TCCATTGGCTTCAGCTAGAGATACTGAAGCTCATTTCGAAGTTTTGAAGGGTTGGAT

GGAATCTTACAAGCCTGAAGAATTATTCAACGCCGACGGTTCTATCAAGAAGATG
```

```
-continued
TTACTGCTTTTATGCCAAAGGGTGAATTGAGAATTGGTGCTAATCCAAATGCTAACG

GTGGTAGAATTAGAGAAGATTTGAAGTTGCCAGAATTGGACCAATACGAAATTACC

GGTGTCAAAGAATATGGTCATGGTTGGGGTCAAGTTGAAGCTCCAAGATCTTTGGG

TGCTTACTGTAGAGATATCATCAAGAACAACCCAGACTCCTTTAGAGTTTTTGGTCC

AGACGAAACTGCTTCCAATAGATTGAATGCTACTTACGAAGTCACCAAAAAGCAAT

GGGATAACGGTTATTTGTCTGCCTTGGTTGACGAAAACATGGCTGTTACTGGTCAAG

TTGTTGAACAATTGTCTGAACATCAATGCGAAGGTTTTTTGGAAGCCTATTTGTTGA

CTGGTAGACATGGTATTTGGTCCTCTTACGAATCTTTCGTTCACGTTATCGATTCCAT

GTTGAATCAACACGCTAAATGGTTGGAAGCTACCGTTAGAGAAATTCCTTGGAGAA

AGCCAATCTCCTCTGTTAACTTGTTGGTTTCTTCACACGTTTGGAGACAAGATCATA

ACGGTTTCTCTCATCAAGATCCAGGTGTTACTTCTGTCTTGTTGAACAAAACCTTCA

ACAACGATCACGTCACCAATATCTACTTTGCTACTGATGCTAACATGTTGTTGGCTA

TTGCTGAAAAGTGTTTCAAGTCCACCAACAAGATTAACGCTATTTTCGCTGGTAAAC

AACCAGCTGCTACTTGGATTACTTTGGATGAAGTTAGAGCTGAATTGGAAGCTGGT

GCTGCTGAATGGAAATGGGCTTCTAATGCTAAGTCTAACGATGAAGTTCAAGTTGTT

TTGGCTGCTGCTGGTGATGTTCCAACTCAAGAAATTATGGCTGCTTCTGATGCTTTG

AACAAGATGGGTATTAAGTTCAAGGTTGTCAACGTCGTTGATTTGATCAAGTTGCAA

TCCTCCAAAGAAAACGATGAAGCCATGTCTGATGAAGATTTCGCTGATTTGTTTACC

GCTGATAAGCCAGTTTTGTTCGCTTATCATTCTTACGCCCAAGATGTCAGAGGTTTG

ATATACGATAGACCAAACCATGATAACTTCACCGTTGTCGGTTACAAAGAACAAGG

TTCTACTACTACTCCATTCGATATGGTTAGAGTTAACGACATGGATAGATACGCATT

GCAAGCTAAGGCTTTGGAATTGATTGATGCTGATAAGTACGCCGACAAGATCAACG

AATTGAACGAATTTAGAAAGACCGCTTTCCAATTCGCTGTTGATAACGGTTACGATA

TCCCAGAATTTACCGATTGGGTTTACCCAGATGTTAAGGTTGACGAAACTTCTATGT

TGTCTGCTACTGCTGCTACAGCTGGTGATAATGAATAA
                                        SEQ ID NO: 4
ATGGACTTGTTCGAATCTTTGGCCCAAAAGATTACTGGTAAGGATCAAACTATCGTT

TTCCCAGAAGGTACTGAACCTAGAATAGTTGGTGCTGCTGCTAGATTGGCTGCTGAT

GGTTTGGTTAAGCCAATAGTTTTGGGTGCTACTGATAAGGTTCAAGCTGTTGCTAAT

GATTTGAACGCTGATTTGACTGGTGTTCAAGTTTTGGATCCAGCTACTTATCCAGCT

GAAGATAAGCAAGCTATGTTGGATGCTTTGGTCGAAAGAAGAAAGGGTAAGAATA

CTCCAGAACAAGCTGCTAAGATGTTGGAAGATGAAAACTACTTCGGTACTATGTTG

GTCTACATGGGTAAAGCAGATGGTATGGTTTCTGGTGCTATTCATCCAACTGGTGAT

ACTGTTAGACCAGCCTTGCAAATTATCAAAACTAAGCCAGGTTCCCACAGAATTTCA

GGTGCTTTCATTATGCAAAAGGGTGAAGAAAGATACGTTTTCGCTGATTGCGCCATT

AACATTGATCCAGATGCTGATACTTTGGCTGAAATTGCTACTCAATCTGCTGCTACT

GCTAAAGTTTTCGATATTGATCCAAAGGTCGCCATGTTGTCTTTTTCAACAAAAGGT

TCTGCTAAGGGTGAAATGGTTACTAAGGTACAAGAAGCTACAGCTAAAGCTCAAGC

TGCTGAACCAGAATTGGCTATTGATGGTGAATTACAATTCGATGCTGCCTTCGTTGA

AAAGGTCGGTTTACAAAAAGCTCCAGGTTCTAAAGTTGCTGGTCATGCTAATGTTTT

TGTTTTTCCAGAATTGCAATCCGGTAACATCGGTTACAAAATCGCTCAAAGATTTGG
```

-continued

TCATTTCGAAGCTGTTGGTCCAGTTTTACAAGGTTTGAACAAACCAGTTTCCGACTT
GTCTAGAGGTTGTTCTGAAGAAGATGTTTACAAAGTTGCCATTATTACCGCTGCTCA
AGGTTTGGCTTAG

SEQ ID NO: 5

ATGAACCAACAAGACATAGAACAAGTAGTAAAAGCCGTATTATTAAAGATGAAAG
ACTCCTCTCAACCAGCCTCAACCGTACACGAAATGGGTGTTTTTGCCTCTTTGGATG
ACGCTGTCGCTGCAGCCAAAAGAGCCCAACAAGGTTTGAAGTCAGTTGCTATGAGA
CAATTAGCAATCCATGCCATTAGAGAAGCAGGTGAAAAACACGCCAGAGAATTGGC
TGAATTAGCAGTATCCGAAACTGGTATGGGTAGAGTTGATGACAAATTCGCTAAGA
ATGTCGCTCAAGCAAGAGGTACACCAGGTGTCGAATGTTTGAGTCCTCAAGTATTA
ACAGGTGACAATGGTTTGACCTTAATTGAAAACGCCCCATGGGGTGTTGTCGCTTCT
GTTACACCATCAACCAATCCTGCTGCAACTGTTATAAATAACGCAATCTCTTTGATC
GCCGCTGGTAACTCAGTAGTTTTTGCTCCACATCCTGCAGCCAAAAAGGTTTCCCAA
AGAGCAATTACATTGTTAAATCAAGCCGTCGTAGCTGCAGGTGGTCCAGAAAATTT
GTTAGTAACCGTTGCTAACCCTGATATCGAAACTGCACAAAGATTATTCAAGTATCC
AGGTATCGGTTTGTTAGTTGTCACAGGTGGTGAAGCTGTAGTTGATGCCGCTAGAAA
ACACACCAATAAGAGATTGATTGCAGCCGGTGCAGGTAACCCACCTGTCGTAGTTG
ATGAAACTGCTGACTTACCAAGAGCTGCACAATCCATCGTTAAGGGTGCAAGTTTC
GATAACAACATCATCTGCGCTGACGAAAAGGTTTTAATTGTCGTAGATTCTGTCGCT
GACGAATTGATGAGATTAATGGAAGGTCAACATGCAGTTAAATTGACAGCCGCTCA
AGCCGAACAATTGCAACCAGTTTTGTTGAAAAATATAGATGAACGTGGTAAAGGTA
CCGTATCAAGAGATTGGGTTGGTAGAGACGCAGGTAAAATTGCAGCCGCTATAGGT
TTGAACGTTCCTGATCAAACTAGATTGTTGTTCGTTGAAACACCAGCTAACCATCCT
TTCGCAGTAACAGAAATGATGATGCCAGTTTTACCTGTTGTCAGAGTTGCTAATGTC
GAAGAAGCCATAGCTTTGGCAGTTCAATTAGAAGGTGGTTGTCATCACACCGCAGC
CATGCACTCCAGAAATATCGATAATATGAACCAAATGGCCAACGCTATCGACACTT
CTATTTTCGTTAAAAACGGTCCATGCATTGCTGGTTTGGGTTTAGGTGGTGAAGGTT
GGACTACAATGACCATAACCACTCCTACTGGTGAAGGTGTCACTTCTGCAAGAACA
TTTGTAAGATTGAGAAGATGTGTCTTAGTAGATGCTTTCAGAATTGTTTAG

SEQ ID NO: 6

AAATCCACTATCGTCTATCAACTAATAGTTATATTATCAATATATTATCATATACGG
TGTTAAGATGATGACATAAGTTATGAGAAGCTGTCATCGAGGTTAGAGGCCTTAAT
GGCCGTCGACATATTTGACCTCTTAACAGGTTCAGACGCGACTGCCTCATCAGTAAG
ACCCGTTGAAAAGAACTTACCTGAAAAAAACGAATATATACTAGCGTTGAATGTTA
GCGTCAACAACAAGAAGTTTAATGACGCGGAGGCCAAGGCAAAAAGATTCCTTGAT
TACGTAAGGGAGTTAGAATCATTTTGAATAAAAAACACGCTTTTTCAGTTCGAGTTT
ATCATTATCAATACTGCCATTTCAAAGAATACGTAAATAATTAATAGTAGTGATTTT
CCTAACTTTATTTAGTCAAAAAATTAGCCTTTTAATTCTGCTGTAACCCGTACATGCC
CAAAATAGGGGCGGGTTACACAGAATATATAACATCGTAGGTGTCTGGGTGAACA
GTTTATTCCTGGCATCCACTAAATATAATGGAGCCCGCTTTTTAAGCTGGCATCCAG
AAAAAAAAAGAATCCCAGCACCAAAATATTGTTTTCTTCACCAACCATCAGTTCAT
AGGTCCATTCTCTTAGCGCAACTACAGAGAACAGGGGCACAAACAGGCAAAAAAC

-continued

```
GGGCACAACCTCAATGGAGTGATGCAACCTGCCTGGAGTAAATGATGACACAAGGC

AATTGACCCACGCATGTATCTATCTCATTTTCTTACACCTTCTATTACCTTCTGCTCT

CTCTGATTTGGAAAAAGCTGAAAAAAAAGGTTGAAACCAGTTCCCTGAAATTATTC

CCCTACTTGACTAATAAGTATATAAAGACGGTAGGTATTGATTGTAATTCTGTAAAT

CTATTTCTTAAACTTCTTAAATTCTACTTTTATAGTTAGTCTTTTTTTAGTTTTAAAA

CACCAAGAACTTAGTTTCGAATAAACACACATAAACAAACTAGTAAGAATTCAAAC

AACAAAAATGACCAACCCAGTCATTGGTACTCCATGGCAAAAATTGGATAGACCAG

TTTCCGAAGAAGCCATTGAAGGTATGGATAAGTATTGGAGAGTTGCCAACTACATG

TCCATTGGTCAAATCTACTTGAGATCCAACCCATTGATGAAGGAACCATTCACTAGA

GATGATGTCAAGCACAGATTGGTTGGTCATTGGGGTACTACTCCAGGTTTGAATTTT

TTGTTGGCCCACATCAACAGATTGATCGCTGATCATCAACAAAACACCGTTTTCATT

ATGGGTCCAGGTCATGGTGGTCCAGCTGGTACTGCTCAATCTTATATTGATGGTACT

TACACCGAATATTACCCAAACATCACTAAGGATGAAGCCGGTTTACAAAGTTCTT

CAGACAATTTTCTTACCCAGGTGGTATCCCATCTCATTTTGCTCCAGAAACTCCAGG

TTCTATTCATGAAGGTGGTGAATTGGGTTATGCTTTGTCTCATGCTTATGGTGCCATT

ATGGATAACCCATCTTTGTTCGTTCCATGCATTATTGGTGATGGTGAAGCTGAAACT

GGTCCATTGGCTACTGGTTGGCAATCTAACAAATTGGTTAACCCAAGAACCGATGG

TATCGTTTTGCCAATCTTGCATTTGAACGGTTACAAGATTGCTAACCCAACCATTTT

GGCCAGAATCTCTGATGAAGAATTGCACGATTTTTTCAGAGGTATGGGTTACCACCC

ATACGAATTTGTTGCTGGTTTTGATAACGAAGATCACTTGTCCATCCATAGAAGATT

CGCCGAATTATTCGAAACCATCTTCGACGAAATTTGCGATATTAAGGCTGCTGCTCA

AACTGATGATATGACTAGACCATTTTACCCAATGTTGATCTTCAGAACTCCAAAGGG

TTGGACTTGTCCAAAGTTTATCGATGGTAAAAAGACCGAAGGTTCTTGGAGAGCAC

ATCAAGTTCCATTGGCTTCAGCTAGAGATACTGAAGCTCATTTCGAAGTTTTGAAGG

GTTGGATGGAATCTTACAAGCCTGAAGAATTATTCAACGCCGACGGTTCTATCAAA

GAAGATGTTACTGCTTTTATGCCAAAGGGTGAATTGAGAATTGGTGCTAATCCAAAT

GCTAACGGTGGTAGAATTAGAGAAGATTTGAAGTTGCCAGAATTGGACCAATACGA

AATTACCGGTGTCAAAGAATATGGTCATGGTTGGGGTCAAGTTGAAGCTCCAAGAT

CTTTGGGTGCTTACTGTAGAGATATCATCAAGAACAACCCAGACTCCTTTAGAGTTT

TTGGTCCAGACGAAACTGCTTCCAATAGATTGAATGCTACTTACGAAGTCACCAAA

AAGCAATGGGATAACGGTTATTTGTCTGCCTTGGTTGACGAAAACATGGCTGTTACT

GGTCAAGTTGTTGAACAATTGTCTGAACATCAATGCGAAGGTTTTTTGGAAGCCTAT

TTGTTGACTGGTAGACATGGTATTTGGTCCTCTTACGAATCTTTCGTTCACGTTATCG

ATTCCATGTTGAATCAACACGCTAAATGGTTGGAAGCTACCGTTAGAGAAATTCCTT

GGAGAAAGCCAATCTCCTCTGTTAACTTGTTGGTTTCTTCACACGTTTGGAGACAAG

ATCATAACGGTTTCTCTCATCAAGATCCAGGTGTTACTTCTGTCTTGTTGAACAAAA

CCTTCAACAACGATCACGTCACCAATATCTACTTTGCTACTGATGCTAACATGTTGT

TGGCTATTGCTGAAAAGTGTTTCAAGTCCACCAACAAGATTAACGCTATTTTCGCTG

GTAAACAACCAGCTGCTACTTGGATTACTTTGGATGAAGTTAGAGCTGAATTGGAA

GCTGGTGCTGCTGAATGGAAATGGGCTTCTAATGCTAAGTCTAACGATGAAGTTCA
```

-continued

```
AGTTGTTTTGGCTGCTGCTGGTGATGTTCCAACTCAAGAAATTATGGCTGCTTCTGA

TGCTTTGAACAAGATGGGTATTAAGTTCAAGGTTGTCAACGTCGTTGATTTGATCAA

GTTGCAATCCTCCAAAGAAAACGATGAAGCCATGTCTGATGAAGATTTCGCTGATTT

GTTTACCGCTGATAAGCCAGTTTTGTTCGCTTATCATTCTTACGCCCAAGATGTCAG

AGGTTTGATATACGATAGACCAAACCATGATAACTTCACCGTTGTCGGTTACAAAG

AACAAGGTTCTACTACTACTCCATTCGATATGGTTAGAGTTAACGACATGGATAGAT

ACGCATTGCAAGCTAAGGCTTTGGAATTGATTGATGCTGATAAGTACGCCGACAAG

ATCAACGAATTGAACGAATTTAGAAAGACCGCTTTCCAATTCGCTGTTGATAACGGT

TACGATATCCCAGAATTTACCGATTGGGTTTACCCAGATGTTAAGGTTGACGAAACT

TCTATGTTGTCTGCTACTGCTGCTACAGCTGGTGATAATGAATAAGGATCCTGATAA

GCGGCCGCCGGTGAAAACTTCCACCACGGTGACAAGTTGTAAAGTGCTTTTAACTA

AGAATTATTAGTCTTTTCTGCTTATTTTTTCATCATAGTTTAGAACACTTTATATTAA

CGAATAGTTTATGAATCTATTTAGGTTTAAAAATTGATACAGTTTTATAAGTTACTTT

TTCAAAGACTCGTGCTGTCTATTGCATAATGCACTGGAAGGGGAAAAAAAAGGTGC

ACACGCGTGGCTTTTTCTTGAATTTGCAGTTTGAAAAATAACTACATGGATGATAAG

AAAACATGGAGTACAGTCACTTTGAGAACCTTCAATCAGCTGGTAACGTCTTCGTTA

ATTGGATACTCAAAAAAGATGGATAGCATGAATCACAAGATGGAAGGAAATGCGG

GCCACGACCACAGTGATATGCATATGGGAGATGCTCGACTTCAACTCAAGACGCAC

AGATATTATAACATCTGCATAATAGGCATTTGCAAGAATTACTCGTGAGTAAGGAA

AGAGTGAGGAACTATCGCATACCTGCATTTAAAGATGCCGATTTGGGCGCGAATCC

TTTATTTTGGCTTCACCCTCATACTATTATCAGGGCCAGAAAAAGGAAGTGTTTCCC

TCCTTCTTGAATTGATGTTACCCTCATAAAGCACGTGGCCTCTTATCGAGAAAGAAA

TTACCGTCGCTCGTGATTTGTTTGCAAAAAGAACAAAACTGAAAAAACCCAGACAC

GCTCGACTTCCTGTCTTCCTATTGATTGCAGCTTCCAATTTCGTCACACAACAAGGTC

CTAGCGACGGCTCACAGGTTTTGTAACAAGCAATCGAAGGTTCTGGAATGGCGGGA

AAGGGTTTAGTACCACATGCTATGATGCCCACTGTGATCTCCAGAGCAAAGTTCGTT

CGATCGTACTGTTACTCTCTCTTTCAAACAGAATTGTCCGAATCGTGTGACAACA

ACAGCCTGTTCTCACACACTCTTTTCTTCTAACCAAGGGGTGGTTTAGTTTAGTAG

AACCTCGTGAAACTTACATTTACATATATATAAACTTGCATAAATTGGTCAATGCAA

GAAATACATATTTGGTCTTTTCTAATTCGTAGTTTTTCAAGTTCTTAGATGCTTTCTT

TTTCTCTTTTTTACAGATCATCAAGGAAGTAATTATCTACTTTTTACAACTAGTAAAA

ATGGACTTGTTCGAATCTTTGGCCCAAAAGATTACTGGTAAGGATCAAACTATCGTT

TTCCCAGAAGGTACTGAACCTAGAATAGTTGGTGCTGCTGCTAGATTGGCTGCTGAT

GGTTTGGTTAAGCCAATAGTTTTGGGTGCTACTGATAAGGTTCAAGCTGTTGCTAAT

GATTTGAACGCTGATTTGACTGGTGTTCAAGTTTTGGATCCAGCTACTTATCCAGCT

GAAGATAAGCAAGCTATGTTGGATGCTTTGGTCGAAAGAAGAAAGGGTAAGAATA

CTCCAGAACAAGCTGCTAAGATGTTGGAAGATGAAAACTACTTCGGTACTATGTTG

GTCTACATGGGTAAAGCAGATGGTATGGTTTCTGGTGCTATTCATCCAACTGGTGAT

ACTGTTAGACCAGCCTTGCAAATTATCAAAACTAAGCCAGGTTCCCACAGAATTTCA

GGTGCTTTCATTATGCAAAAGGGTGAAGAAAGATACGTTTTCGCTGATTGCGCCATT

AACATTGATCCAGATGCTGATACTTTGGCTGAAATTGCTACTCAATCTGCTGCTACT
```

```
GCTAAAGTTTTCGATATTGATCCAAAGGTCGCCATGTTGTCTTTTTCAACAAAAGGT

TCTGCTAAGGGTGAAATGGTTACTAAGGTACAAGAAGCTACAGCTAAAGCTCAAGC

TGCTGAACCAGAATTGGCTATTGATGGTGAATTACAATTCGATGCTGCCTTCGTTGA

AAAGGTCGGTTTACAAAAAGCTCCAGGTTCTAAAGTTGCTGGTCATGCTAATGTTTT

TGTTTTTCCAGAATTGCAATCCGGTAACATCGGTTACAAAATCGCTCAAAGATTTGG

TCATTTCGAAGCTGTTGGTCCAGTTTTACAAGGTTTGAACAAACCAGTTTCCGACTT

GTCTAGAGGTTGTTCTGAAGAAGATGTTTACAAAGTTGCCATTATTACCGCTGCTCA

AGGTTTGGCTTAGGATCCAAGCGGCCGCCAGGTGTTGCTTTCTTATCCGAAAAGAA

ATAAATTGAATTGAATTGAAATCGATAGATCAATTTTTTTCTTTTCTCTTTCCCCATC

CTTTACGCTAAAATAATAGTTTATTTTATTTTTTGAATATTTTTTATTTATATACGTAT

ATATAGACTATTATTTATCTTTTAATGATTATTAAGATTTTTATTAAAAAAAAATTCG

CTCCTCTTTTAATGCCTTTATGCAGTTTTTTTTTCCCATTCGATATTTCTATGTTCGGG

TTCAGCGTATTTTAAGTTTAATAACTCGACGCCTACTTGGCTTCACATACGTTGCAT

ACGTCGATATAGATAATAATGATAATGACAGCAGGATTATCGTAATACGTAATAGT

TGAAAATCTCAAAAATGTGTGGGTCATTACGTAAATAATGATAGGAATGGGATTCT

TCTATTTTTCCTTTTTCCATTCTAGCAGCCGTCGGGAAAACGTGGCATCCTCTCTTTC

GGGCTCAATTGGAGTCACGCTGCCGTGAGCATCCTCTCTTTCCATATCTAACAACTG

AGCACGTAACCAATGGAAAAGCATGAGCTTAGCGTTGCTCCAAAAAAGTATTGGAT

GGTTAATACCATTTGTCTGTTCTCTTCTGACTTTGACTCCTCAAAAAAAAAAAATCT

ACAATCAACAGATCGCTTCAATTACGCCCTCACAAAAACTTTTTTCCTTCTTCTTCGC

CCACGTTAAATTTTATCCCTCATGTTGTCTAACGGATTTCTGCACTTGATTTATTATA

AAAAGACAAAGACATAATACTTCTCTATCAATTTCAGTTATTGTTCTTCCTTGCGTT

ATTCTTCTGTTCTTCTTTTTCTTTTGTCATATATAACCATAACCAAGTAATACATATT

CAAACTAGTAAGAATTCAAAACAAAAATGAACCAACAAGACATAGAACAAGTAGT

AAAAGCCGTATTATTAAAGATGAAAGACTCCTCTCAACCAGCCTCAACCGTACACG

AAATGGGTGTTTTTGCCTCTTTGGATGACGCTGTCGCTGCAGCCAAAAGAGCCCAAC

AAGGTTTGAAGTCAGTTGCTATGAGACAATTAGCAATCCATGCCATTAGAGAAGCA

GGTGAAAAACACGCCAGAGAATTGGCTGAATTAGCAGTATCCGAAACTGGTATGGG

TAGAGTTGATGACAAATTCGCTAAGAATGTCGCTCAAGCAAGAGGTACACCAGGTG

TCGAATGTTTGAGTCCTCAAGTATTAACAGGTGACAATGGTTTGACCTTAATTGAAA

ACGCCCATGGGGTGTTGTCGCTTCTGTTACACCATCAACCAATCCTGCTGCAACTG

TTATAAATAACGCAATCTCTTTGATCGCCGCTGGTAACTCAGTAGTTTTTGCTCCAC

ATCCTGCAGCCAAAAAGGTTTCCCAAAGAGCAATTACATTGTTAAATCAAGCCGTC

GTAGCTGCAGGTGGTCCAGAAAATTTGTTAGTAACCGTTGCTAACCCTGATATCGAA

ACTGCACAAAGATTATTCAAGTATCCAGGTATCGGTTTGTTAGTTGTCACAGGTGGT

GAAGCTGTAGTTGATGCCGCTAGAAAACACACCAATAAGAGATTGATTGCAGCCGG

TGCAGGTAACCCACCTGTCGTAGTTGATGAAACTGCTGACTTACCAAGAGCTGCAC

AATCCATCGTTAAGGGTGCAAGTTTCGATAACAACATCATCTGCGCTGACGAAAAG

GTTTTAATTGTCGTAGATTCTGTCGCTGACGAATTGATGAGATTAATGGAAGGTCAA

CATGCAGTTAAATTGACAGCCGCTCAAGCCGAACAATTGCAACCAGTTTTGTTGAA
```

-continued
```
AAATATAGATGAACGTGGTAAAGGTACCGTATCAAGAGATTGGGTTGGTAGAGACG

CAGGTAAAATTGCAGCCGCTATAGGTTTGAACGTTCCTGATCAAACTAGATTGTTGT

TCGTTGAAACACCAGCTAACCATCCTTTCGCAGTAACAGAAATGATGATGCCAGTTT

TACCTGTTGTCAGAGTTGCTAATGTCGAAGAAGCCATAGCTTTGGCAGTTCAATTAG

AAGGTGGTTGTCATCACACCGCAGCCATGCACTCCAGAAATATCGATAATATGAAC

CAAATGGCCAACGCTATCGACACTTCTATTTTCGTTAAAAACGGTCCATGCATTGCT

GGTTTGGGTTTAGGTGGTGAAGGTTGGACTACAATGACCATAACCACTCCTACTGGT

GAAGGTGTCACTTCTGCAAGAACATTTGTAAGATTGAGAAGATGTGTCTTAGTAGA

TGCTTTCAGAATTGTTTAGGATCCTGATAAGCGGCCGCGTTAATTCAAATTAATTGA

TATAGTTTTTTAATGAGTATTGAATCTGTTTAGAAATAATGGAATATTATTTTTATTT

ATTTATTTATATTATTGGTCGGCTCTTTTCTTCTGAAGGTCAATGACAAAATGATATG

AAGGAAATAATGATTTCTAAAATTTTACAACGTAAGATATTTTTACAAAAGCCTAGC

TCATCTTTTGTCATGCACTATTTTACTCACGCTTGAAATTAACGGCCAGTCCACTGCG

GAGTCATTTCAAAGTCATCCTAATCGATCTATCGTTTTTGATAGCTCATTTTGGAGTT

CGCGATTGTCTTCTGTTATTCACAACTGTTTTAATTTTTATTTCATTCTGGAACTCTTC

GAGTTCTTTGTAAAGTCTTTCATAGTAGCTTACTTTATCCTCCAACATATTTAACTTC

ATGTCAATTTCGGCTCTTAAATTTTCCACATCATCAAGTTCAACATCATCTTTTAACT

TGAATTTATTCTCTAGCTCTTCCAACCAAGCCTCATTGCTCCTTGATTTACTGGTGAA

AAGTGATACACTTTGCGCGCAATCCAGGTCAAAACTTTCCTGCAAAGAATTCACCA

ATTTCTCGACATCATAGTACAATTTGTTTTGTTCTCCCATCACAATTTAATATACCTG

ATGGATTCTTATGAAGCGCTGGGTAATGGACGTGTCACTCTACTTCGCCTTTTTCCCT

ACTCCTTTTAGTACGGAAGACAATGCTAATAAATAAGAGGGTAATAATAATATTAT

TAATCGGCAAAAAGATTAAACGCCAAGCGTTTAATTATCAGAAAGCAAACGTCGT

ACCAATCCTTGAATGCTTCCCAATTGTATATTAAGAGTCATCACAGCAACATATTCT

TGTTATTAAATTAATTATTATTGATTTTTGATATTGTATAAAAAAACCAAATATGTAT

AAAAAAAGTGAATAAAAAATACCAAGTATGGAGAAATATATTAGAAGTCTATACGT

TAAACCACCGCGGTGGAGCTCAAGCTTTTCAATTCATCTTTTTTTTTTTGTTCTTTTT

TTTGATTCCGGTTTCTTTGAAATTTTTTTGATTCGGTAATCTCCGAGCAGAAGGAAG

AACGAAGGAAGGAGCACAGACTTAGATTGGTATATATACGCATATGTGGTGTTAA

GAAACATGAAATTGCCCAGTATTCTTAACCCAACTGCACAGAACAAAAACCTGCAG

GAAACGAAGATAAATCATGTCGAAAGCTACATATAAGGAACGTGCTGCTACTCATC

CTAGTCCTGTTGCTGCCAAGCTATTTAATATCATGCACGAAAAGCAAACAAACTTGT

GTGCTTCATTGGATGTTCGTACCACCAAGGAATTACTGGAGTTAGTTGAAGCATTAG

GTCCCAAAATTTGTTTACTAAAAACACATGTGGATATCTTGACTGATTTTTCCATGG

AGGGCACAGTTAAGCCGCTAAAGGCATTATCCGCCAAGTACAATTTTTTACTCTTCG

AAGACAGAAAATTTGCTGACATTGGTAATACAGTCAAATTGCAGTACTCTGCGGGT

GTATACAGAATAGCAGAATGGGCAGACATTACGAATGCACACGGTGTGGTGGGCCC

AGGTATTGTTAGCGGTTTGAAGCAGGCGGCGGAAGAAGTAACAAAGGAACCTAGA

GGCCTTTTGATGTTAGCAGAATTGTCATGCAAGGGCTCCCTAGCTACTGGAGAATAT

ACTAAGGGTACTGTTGACATTGCGAAGAGCGACAAAGATTTTGTTATCGGCTTTATT

GCTCAAAGAGACATGGGTGGAAGAGATGAAGGTTACGATTGGTTGATTATGACACC
```

-continued

```
CGGTGTGGGTTTAGATGACAAGGGAGACGCATTGGGTCAACAGTATAGAACCGTGG

ATGATGTGGTCTCTACAGGATCTGACATTATTATTGTTGGAAGAGGACTATTTGCAA

AGGGAAGGGATGCTAAGGTAGAGGGTGAACGTTACAGAAAAGCAGGCTGGGAAGC

ATATTTGAAGATGCGGCCAGCAAAACTAAAAAACTGTATTATAAGTAAATGCAT

GTATACTAAACTCACAAATTAGAGCTTCAATTTAATTATATCAGTTATTACCCGGGA

ATCTCGGTCGTAATGATTTCTATAATGACGAAAAAAAAAAAATTGGAAAGAAAAG

GCGCGCCGAAGCTGAAGTGCAAGGATTGATAATGTAATAGGATCAATGAATATAAA

CATATAAAACGGAATGAGGAATAATCGTAATATTAGTATGTAGAAATATAGATTCC

ATTTAAATCAGAAATGGCCATGAGACAATAACCCTGATAAATGCTTCAATAATATT

GAAAAAGGAAGAGTATGAGTATTCAACATTTCCGTGTCGCCCTTATTCCCTTTTTG

CGGCATTTTGCCTTCCTGTTTTTGCTCACCCAGAAACGCTGGTGAAAGTAAAAGATG

CTGAAGATCAGTTGGGTGCACGAGTGGGTTACATCGAACTGGATCTCAACAGCGGT

AAGATCCTTGAGAGTTTTCGCCCCGAAGAACGTTTTCCAATGATGAGCACTTTTAAA

GTTCTGCTATGTGGCGCGGTATTATCCCGTATTGACGCCGGGCAAGAGCAACTCGGT

CGCCGCATACACTATTCTCAGAATGACTTGGTTGAGTACTCACCAGTCACAGAAAA

GCATCTTACGGATGGCATGACAGTAAGAGAATTATGCAGTGCTGCCATAACCATGA

GTGATAACACTGCGGCCAACTTACTTCTGACAACGATCGGAGGACCGAAGGAGCTA

ACCGCTTTTTTGCACAACATGGGGGATCATGTAACTCGCCTTGATCGTTGGGAACCG

GAGCTGAATGAAGCCATACCAAACGACGAGCGTGACACCACGATGCCTGTAGCAAT

GGCAACAACGTTGCGCAAACTATTAACTGGCGAACTACTTACTCTAGCTTCCCGGCA

ACAATTAATAGACTGGATGGAGGCGGATAAAGTTGCAGGACCACTTCTGCGCTCGG

CCCTTCCGGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTAGTTATCT

ACACGACGGGGAGTCAGGCAACTATGGATGAACGAAATAGACAGATCGCTGAGAT

AGGTGCCTCACTGATTAAGCATTGGTAACTGTCAGACCAAGTTTACTCATATATACT

TTAGATTGATTTAAAACTTCATTTTTAATTTAAAAGGATCTAGGTGAAGATCCTTTTT

GATAATCTCATGACCAAAATCCCTTAACGTGAGTTTTCGTTCCACTGAGCGTCAGAC

CCCGTAGAAAAGATCAAAGGATCTTCTTGAGATCCTTTTTTTCTGCGCGTAATCTGC

TGCTTGCAAACAAAAAAACCACCGCTACCAGCGGTGGTTTGTTTGCCGGATCAAGA

GCTACCAACTCTTTTTCCGAAGGTAACTGGCTTCAGCAGAGCGCAGATACCAAATA

CTGTCCTTCTAGTGTAGCCGTAGTTAGGCCACCACTTCAAGAACTCTGTAGCACCGC

CTACATACCTCGCTCTGCTAATCCTGTTACCAGTGGCTGCTGCCAGTGGCGATAAGT

CGTGTCTTACCGGGTTGGACTCAAGACGATAGTTACCGGATAAGGCGCAGCGGTCG

GGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAA

AGGCGGACAGGTATCCGGTAAGCGGCAGGGTCGGAACAGGAGAGCGCACGAGGGA

GCTTCCAGGGGGAAACGCCTGGTATCTTTATAGTCCTGTCGGGTTTCGCCACCTCTG

ACTTGAGCGTCGATTTTTGTGATGCTCGTCAGGGGGCGGAGCCTATGGAAAAACG

CCAGCAACGCTGCATATTT
```

SEQ ID NO: 11

```
ATGCTACTCCAAGCATTCCTTTTTCTGTTAGCAGGATTTGCTGCCAAAATCTCTGCTA
```

```
GACCTGGATCTTCAGGCTTGTCCGACGTCACAAAAGATCCGTGGATGATTTTATCT
CTACAGAAACACCTATTGCACTTAACAATCTCCTGTGTAATGTTGGACCAGATGGTT
GTAGAGCATTCGGCACAAGTGCAGGCGCTGTTATTGCTTCTCCATCTACAATTGATC
CAGACTATTACTACATGTGGACAAGAGACTCCGCCCTTGTGTTCAAAAACTTGATTG
ATCGTTTTACAGAAACTTACGATGCTGGATTACAAAGACGAATTGAACAATATATC
ACTGCTCAAGTAACTTTACAAGGATTGAGTAATCCAAGTGGAAGTTTGGCAGATGG
CTCAGGACTAGGAGAGCCAAAGTTTGAACTAACCCTTAAGCCATTCACTGGGAACT
GGGGTAGACCACAAAGAGATGGTCCTGCTTTGAGAGCAATAGCCTTAATCGGCTAC
TCAAAATGGTTAATCAACAATAACTACCAATCAACAGTTTCAAATGTTATCTGGCCA
ATTGTTAGGAATGATTTGAACTACGTGGCTCAATACTGGAACCAGACCGGTTTCGAC
CTTTGGGAAGAGGTTAATGGCTCTTCCTTTTTCACAGTGGCAAATCAGCATAGAGCT
TTGGTTGAAGGAGCTACTTTAGCGGCCACTCTCGGTCAGTCAGGTTCAGCTTACTCT
TCTGTAGCTCCTCAAGTACTTTGTTTTCTACAGAGATTCTGGGTATCTTCTGGTGGTT
ACGTTGATTCTAACATTAACACAAATGAAGGGCGTACTGGCAAAGATGTGAATAGC
GTCCTTACCAGCATCCATACATTCGATCCTAATTTGGGTTGTGATGCCGGGACGTTT
CAACCTTGTTCTGACAAGGCTTTGAGCAATCTGAAAGTGGTTGTTGATAGTTTCAGA
AGCATCTACGGTGTAAACAAGGGTATTCCAGCTGGTGCTGCCGTGGCTATCGGCAG
ATATGCAGAAGATGTCTACTATAATGGAAATCCATGGTACTTGGCTACTTTTGCCGC
AGCAGAACAGTTGTACGACGCCATCTACGTTTGGAAAAAGACTGGTAGCATTACTG
TTACAGCTACATCCTTAGCATTTTTCCAAGAGTTAGTCCCAGGGGTCACAGCAGGCA
CGTACTCCTCTTCTAGTTCAACCTTTACCAACATCATAAACGCTGTCTCCACCTATGC
CGACGGTTTTCTATCCGAGGCTGCCAAATACGTTCCTGCAGATGGTTCTCTAGCTGA
ACAATTTGACAGAAATTCAGGTACTCCTCTGTCAGCAGTACACCTCACATGGAGTTA
CGCATCTTTTCTGACAGCAGCCGCGAGAAGAGCCGGCATAGTTCCACCAAGTTGGG
CCAATTCATCAGCCTCTACAATACCATCTACATGCTCAGGCGCTTCTGTTGTAGGGA
GTTACTCTAGGCCAACCGCTACTTCATTCCCACCTTCCCAAACTCCAAAACCAGGCG
TACCTTCCGGAACACCTTATACCCCACTCCCTTGCGCTACACCAACTTCAGTCGCAG
TGACGTTTCACGAATTAGTTTCCACACAATTTGGTCACACAGTGAAAGTTGCAGGAA
ATGCCGCTGCTTTGGGCAATTGGTCAACTTCCGCAGCGGTAGCTTTGGACGCTGTTA
ACTACAGAGATAATCATCCATTGTGGATTGGTACGGTCAACCTAGAAGCTGGTGAC
GTCGTTGAGTATAAGTATATCATAGTTGGTCAAGATGGTTCCGTCACTTGGGAGTCA
GATCCTAATCATACTTACACTGTTCCTGCCGTAGCTTGCGTCACACAAGTTGTGAAG
GAAGATACTTGGCAATCTTAA
                                              SEQ ID No: 12
MNQQDIEQVVKAVLLKMKDSSQPASTVHEMGVFASLDDAVAAAKRAQQGLKSVAMR
QLAIHAIREAGEKHARELAELAVSETGMGRVDDKFAKNVAQARGTPGVECLSPQVLTG
DNGLTLIENAPWGVVASVTPSTNPAATVINNAISLIAAGNSVVFAPHPAAKKVSQRAITL
LNQAVVAAGGPENLLVTVANPDIETAQRLFKYPGIGLLVVTGGEAVVDAARKHTNKRL
IAAGAGNPPVVVDETADLPRAAQSIVKGASFDNNIICADEKVLIVVDSVADELMRLMEG
QHAVKLTAAQAEQLQPVLLKNIDERGKGTVSRDWVGRDAGKIAAAIGLNVPDQTRLLF
VETPANHPFAVTEMMMPVLPVVRVANVEEAIALAVQLEGGCHHTAAMHSRNIDNMN
```

QMANAIDTSIFVKNGPCIAGLGLGGEGWTTMTITTPTGEGVTSARTFVRLRRCVLVDAF

RIV

SEQ ID No: 13

ATGAACCAACAAGACATAGAACAAGTAGTAAAGGCAGTATTATTAAAGATGCAATC

CTCTGACACACCACCAGCCGCAGTACACGAAATGGGTGTATTTGCCTCTTTGGATGA

CGCTGTTGCTGCAGCCAAAATAGCTCAACAAGGTTTGAAGTCAGTTGCAATGAGAC

AATTAGCCATCGCTGCAATTAGAGAAGCTGGTGAAAAACATGCAAGAGATTTGGCC

GAATTAGCTGTCTCCGAAACCGGTATGGGTAGAGTAGAAGACAAATTCGCTAAGAA

TGTTGCTCAAGCAAGAGGTACTCCAGGTGTTGAATGTTTGAGTCCTCAAGTCTTAAC

TGGTGATAACGGTTTGACATTGATCGAAAACGCACCATGGGGTGTTGTCGCCTCTGT

TACTCCATCAACAAATCCTGCCGCTACTGTCATCAATAACGCTATATCTTTGATCGC

AGCCGGTAACTCAGTTATTTTTGCACCACATCCTGCTGCAAAAAAGGTTTCCCAAAG

AGCTATCACATTGTTGAACCAAGCAATCGTTGCCGCTGGTGGTCCAGAAAATTTGTT

AGTCACCGTAGCCAACCCTGATATAGAAACTGCACAAAGATTGTTCAAGTTCCCTG

GTATCGGTTTGTTAGTAGTTACAGGTGGTGAAGCTGTCGTAGAAGCAGCCAGAAAA

CACACCAATAAGAGATTGATTGCTGCAGGTGCTGGTAACCCACCTGTTGTCGTAGAT

GAAACTGCAGACTTAGCCAGAGCCGCTCAATCCATTGTTAAGGGTGCTAGTTTCGAT

AACAACATAATATGCGCAGACGAAAAGGTATTGATAGTTGTCGATTCTGTTGCTGA

CGAATTGATGAGATTAATGGAAGGTCAACATGCAGTTAAATTGACTGCTGAACAAG

CACAACAATTGCAACCAGTTTTGTTGAAGAACATAGATGAAAGAGGCAAGGGTACA

GTCTCAAGAGATTGGGTTGGTAGAGACGCTGGCAAGATTGCAGCCGCTATAGGTTT

AAACGTCCCACAAGAAACTAGATTGTTGTTCGTAGAAACTACAGCCGAACATCCTT

TCGCTGTCACAGAATTGATGATGCCAGTATTACCTGTAGTTAGAGTAGCTAATGTTG

CCGATGCTATCGCATTGGCCGTTAAATTAGAAGGTGGTTGTCATCACACAGCAGCC

ATGCACTCCAGAAACATCGAAAACATGAACCAAATGGCTAACGCAATCGACACCAG

TATTTTTGTTAAGAACGGTCCATGCATAGCTGGTTTGGGTTTAGGTGGTGAAGGTTG

GACCACTATGACAATCACAACCCCTACCGGTGAAGGTGTTACCTCTGCTAGAACTTT

TGTCAGATTGAGAAGATGTGTTTTAGTCGATGCATTCAGAATTGTTTAG

SEQ ID No: 14

MNQQDIEQVVKAVLLKMQSSDTPPAAVHEMGVFASLDDAVAAAKIAQQGLKSVAMR

QLAIAAIREAGEKHARDLAELAVSETGMGRVEDKFAKNVAQARGTPGVECLSPQVLTG

DNGLTLIENAPWGVVASVTPSTNPAATVINNAISLIAAGNSVIFAPHPAAKKVSQRAITL

LNQAIVAAGGPENLLVTVANPDIETAQRLFKFPGIGLLVVTGGEAVVEAARKHTNKRLI

AAGAGNPPVVVDETADLARAAQSIVKGASFDNNIICADEKVLIVVDSVADELMRLMEG

QHAVKLTAEQAQQLQPVLLKNIDERGKGTVSRDWVGRDAGKIAAAIGLNVPQETRLLF

VETTAEHPFAVTELMMPVLPVVRVANVADAIALAVKLEGGCHHTAAMHSRNIENMNQ

MANAIDTSIFVKNGPCIAGLGLGGEGWTTMTITTPTGEGVTSARTFVRLRRCVLVDAFRI

V

SEQ ID No: 15

ATGAACCAACAAGACATAGAACAAGTAGTAAAGGCTGTATTATTAAAAATGAAAG

ACTCCTCACAACCTGTATCTGCCGTCCAAGAAATGGGTGTATTTGCATCCTTGGATG

ACGCCGTTGCTGCAGCCAAATTGGCCCAACAAGGTTTAAAGAGTGTTGCAATGAGA

-continued

```
CAATTGGCCATTACTGCTTTAAGAGAAGCTGGTGAAAAACATGCAAGAGAATTGGC

AGAATTAGCCGTCACTGAAACTGGTATGGGTAGAGTAGAAGATAAATTCGCTAAGA

ATGTTGCACAAGCCAGAGCTACACCAGGTGTTGAATGTTTGTCCCCTCAAGTCTTAA

CAGGTGACAATGGTTTGACCTTAATAGAAACGCACCATGGGGTGTTGTCGCCTCT

GTTACCCCATCAACTAATCCTGCTGCAACCGTTATCAATAACGCTATCTCTTTGATT

GCCGCTGGTAACTCAGTAGTTTTTGCACCACATCCTGCAGCCAAAGGTGTTTCTCAA

AGAGCTATAACATTGTTGAATCAAGCAGTCGTAGCTGCAGGTGGTCCAGCCAATTT

GTTAGTAACTGTTGCTAACCCTGATATCGAAACAGCACAAAGATTATTCAAGTATCC

TGGTATTGGTTTGTTAGTTGTTACTGGTGGTGAAGCTGTAGTTGATGCCGCTAGAAA

ACACACTAATAAGAGATTGATAGCAGCCGGTGCTGGTAACCCACCTGTCGTAGTTG

ATGAAACTGCTGACTTAGCAAGAGCTGCACAATCCATTGTTAAGGGTGCTAGTTTTG

ATAACAACATCATCTGCGCAGACGAAAAGGTATTGATAGTCGTAGATTCCGTTGCT

GACGAATTGATGAGATTGATGGAAAGTCAACATGCAGTTAAATTGACTACAGCACA

AGCCGAACAATTGCAACCAGTATTGTTGAAGAACGTTGATGAAGAGGCAAGGGTA

CAGTCTCTAGAGATTGGGTTGGTAGAGACGCTGGCAAGATAGCCGCTGCAATCGGT

TTAAACGTCCCAGAACAAACAAGATTGTTGTTCGTTGAAACATCAGCCACCCATCCT

TTCGCTGTCACCGAATTGATGATGCCAGTATTACCTGTTGTCAGAGTTGCTAATGTC

GAAGAAGCCATCGAATTGGCTGTTAAATTAGAAGGTGGTTGTCATCACACTGCCGC

TATGCACTCTAGAAACATCGATAACATGAACAGAATGGCTAACGCAATTGACACAT

CAATATTCGTTAAGAACGGTCCATGCATAGCTGGTTTGGGTTTAGGTGGTGAAGGTT

GGACCACTATGACCATCACAACCCCTACTGGTGAAGGTGTTACTTCAGCTAGAACA

TTTGTCAGATTGAGAAGATGTGTCTTAGTAGATGCATTCAGAATTGTTTAG
```

SEQ ID No: 16
```
MNQQDIEQVVKAVLLKMKDSSQPVSAVQEMGVFASLDDAVAAAKLAQQGLKSVAMR

QLAITALREAGEKHARELAELAVTETGMGRVEDKFAKNVAQARATPGVECLSPQVLTG

DNGLTLIENAPWGVVASVTPSTNPAATVINNAISLIAAGNSVVFAPHPAAKGVSQRAITL

LNQAVVAAGGPANLLVTVANPDIETAQRLFKYPGIGLLVVTGGEAVVDAARKHTNKR

LIAAGAGNPPVVVDETADLARAAQSIVKGASFDNNIICADEKVLIVVDSVADELMRLME

SQHAVKLTTAQAEQLQPVLLKNVDERGKGTVSRDWVGRDAGKIAAAIGLNVPEQTRL

LFVETSATHPFAVTELMMPVLPVVRVANVEEAIELAVKLEGGCHHTAAMHSRNIDNMN

RMANAIDTSIFVKNGPCIAGLGLGGEGWTTMTITTPTGEGVTSARTFVRLRRCVLVDAF

RIV
```

SEQ ID No: 17
```
ATGGACATCAACCCTAAAGAAATCGAACAAGTCGTAAAAGCCGTATTGGCAAGTAT

CGGTGCTACATCAACAGCCGCCGTCGCATCACCAGGTGCCACTTGTGCTCCTGGTGT

ATTTGTTGAATTAGATGCTGCAGTTGCCGCTGCAGCCCAAGCACAAAAAGCCTTGA

GATCTGTCGCTATGAGAGACAGAGCAATCGCTGCAATTAGAGCCGCTGGTGAAAGA

CATGCTCAAGAATTAGCTGAATTGGCAGTTGAAGAAACCGGTATGGGTAGAGTCGC

AGATAAAACTGCCAAGAATATTGCCCAAGCTAGACACACTCCAGGTTCTGAATGCT

TACAAGCACAAGTTTTGTCAGGTGACAGAGGTTTAACATTGATCGAAAATGCAGCC

TGGGGTGTAATTGCTTCCGTTACTCCAAGTACAAACCCTGCTGCAACTGTTATAAAC
```

-continued

```
AACGCAATCTCCATGATCGCCGCTGGTAACAGTGTTGTCTTTGCTCCACATCCTGCA

GCCAAAAGAGTCTCTCAAAGAACAGTATCATTGTTGAACGAAGCTATGGTCGAAGC

AGGTGCCCCAGCTAACTTAATAACTACAGTACAAAGACCTGATATCGAAACCGCTC

AAAGATTGTTCAGATATCCAGGTATTGGTTTGTTAGTAGTTACAGGTGGTGAAGCAG

TCGTAGAAGCTGCAAGAAAACACACCGATAAGAGATTAATAGCCGCTGGTGCTGGT

AATCCACCTGTTGTCGTAGATGAAACAGCCGACTTGGCTAGAGCAGCCAGAGATAT

AGTTTTCGGTGCATCTTTCGATAACAACATCATCTGTGCTGACGAAAAGGTATTGAT

CGTTGTCGATTCAGTTGCAGACGCCTTAAAAGCCGAAATGTTGAAGCATCAAGCTG

TTGAATTGTCCGCTGCACAAGGTCAACAATTGTTACCATTGTTATTGCCTAAAGTTG

ATGAACAAGGTAGAGGTTCTGTTTCAAGAGATTGGGTCGGTAGAGACGCCGCTAAG

ATTGCAGCCGCTATAGGTTTGCAAGTTCCAGAACAAACTAGATTGTTGTTGTTGGAA

ACAGCAGCCGATCACCCTTTTGCAATCACAGAAATGATGATGCCAGTTTTGCCTATG

GTCAGAGTAGCTAATGTAGACCAAGCTATTGCATTAGCCGTTAAATTGGAAGGTGG

TTGTCATCACACCGCTGCAATGCATTCCAGAAATTTAGATCACTTGGACAGAATGGC

TAACGCAATGGATACTTCTATCTTCGTTAAGAACGGTCCATGCTTAGCTGGTTTGGG

TTTCGGTGGTGAAGGTTGGACCACTATGACAATCACAACCCCTACCGGTGAAGGTG

TCACCTCAGCTAGAACTTTCGTAAGATTAAGAAGATGCGTTATGGTCGATCATTTGA

GAATTGTTTAG
```

SEQ ID No: 18
```
MDINPKEIEQVVKAVLASIGATSTAAVASPGATCAPGVFVELDAAVAAAAQAQKALRS

VAMRDRAIAAIRAAGERHAQELAELAVEETGMGRVADKTAKNIAQARHTPGSECLQA

QVLSGDRGLTLIENAAWGVIASVTPSTNPAATVINNAISMIAAGNSVVFAPHPAAKRVS

QRTVSLLNEAMVEAGAPANLITTVQRPDIETAQRLFRYPGIGLLVVTGGEAVVEAARKH

TDKRLIAAGAGNPPVVVDETADLARAARDIVFGASFDNNIICADEKVLIVVDSVADALK

AEMLKHQAVELSAAQGQQLLPLLLPKVDEQGRGSVSRDWVGRDAAKIAAAIGLQVPE

QTRLLLLETAADHPFAITEMMMPVLPMRVANVDQAIALAVKLEGGCHHTAAMHSRN

LDHLDRMANAMDTSIFVKNGPCLAGLGFGGEGWTTMTITTPTGEGVTSARTFVRLRRC

VMVDHLRIV
```

SEQ ID No: 19
```
ATGGATCAAAAGGAAATCGAAAATGTAGTCAAAGCCGTATTAGCCTCAATGTCCGC

AGGTACTCAACCAGCCGCCGCCTCCGCCGCACCACAACAAGCTGCAGCCTCCCAAA

ATAACGGTTTTGGTGTATTCGAAAGTTTGGATGACGCTGTTTTAGCTGCAAAAGAAG

CACAAAAATCCTTGAAGACTGTTGAAATGAGAAATTTATGTATTGGTGCTATCAGA

AGAGCCGCTACCGAACATGCAAGAGAATTGGCTGTTTTAGCAGTCGAAGAAACTGG

TATGGGTAGAGTTGAAGATAAATTGGCTAAGAACTTAGCCCAAGCTAACGGTACTC

CAGGTGTAGAATGCTTGAGACCTGAAGTTTTAACAGGTGATCATGGTTTGACCTTAA

TAGAAAATGCAGCCTGGGGTGTCATCGCTTCTGTAACTCCATCAACAAACCCTGCTG

CAACAGCCATCAATAACGCTATCTCTATGATTGCTGGTGGTAATTCAGTCATTTTTG

CACCACACCCTGCCGCTAAAAAGGTTTCTCAAAGAACAATCACCATCTTGAATGAA

GCTATTGTTGCAGCCGGTGGTCCAAATAACTTGTTAGTCACTGTAGCCAAACCTGAT

ATCGAAACAGCTCAAAGATTGTTCAAGTATCCAGGTATAGGTTTGTTAGTTGTCACT

GGTGGTGACGCTGTAGTTGAATCCGCAAGAAAGCATACAAACAAGAGATTGATAGC
```

-continued

```
TGCAGGTGCTGGTAACCCACCTGTCGTAGTTGATGAAACAGCAGACATCGAAAGAG

CCGCTAAAGCCATTGTTCACGGTGCTAGTTTTGATAACAACATCATCTGTGCTGACG

AAAAAGTTTTGATCGCAGTCGATTGCATTGCCGACAAGTTAATCACAGAAATGCAA

AGAAACCATGCAGTTTTGTTGACCAGAGAACAATCTGAAAAATTAATTCCTGTATTG

TTGAAGAACGTTGATGAAACCGGTCACGGTACTGTCTCAAGAGATTGGGTTGGTAG

AGACGCAGCCAAAATAGCTGCAGCCATCGGTATGACTGTTCCAGCAGATACAAGAT

TGTTAATTGCCGAAACCGACTGTAAGCATCCTTTTGCTGTCACTGAATTGATGATGC

CAGTATTGCCTATCATAAGAGTAAAGGATGTTGACCAAGCAATAGATTTGGCCGTT

AAGTTAGAAGGTGGTTGTCATCACACTGCTGCAATGCACTCCAACAACATCAGTAA

CTTGAACAGAATGGCAAACGCCATCGATACATCTATCTTCGTTAAGAACGGTCCAT

GCATAGCTGGTTTGGGTTTAGGTGGTGAAGGTTGGACTACAATGACCATCACCACTC

CTACTGGTGAAGGTGTTACATGTGCAAGAACCTTTGTCAGATTAAGAAGATGCACT

ATGGTTGATTCATTCAGAATTGTCTAG
```

SEQ ID No: 20

```
MDQKEIENVVKAVLASMSAGTQPAAASAAPQQAAASQNNGFGVFESLDDAVLAAKEA

QKSLKTVEMRNLCIGAIRRAATEHARELAVLAVEETGMGRVEDKLAKNLAQANGTPG

VECLRPEVLTGDHGLTLIENAAWGVIASVTPSTNPAATAINNAISMIAGGNSVIFAPHPA

AKKVSQRTITILNEAIVAAGGPNNLLVTVAKPDIETAQRLFKYPGIGLLVVTGGDAVVES

ARKHTNKRLIAAGAGNPPVVVDETADIERAAKAIVHGASFDNNIICADEKVLIAVDCIA

DKLITEMQRNHAVLLTREQSEKLIPVLLKNVDETGHGTVSRDWVGRDAAKIAAAIGMT

VPADTRLLIAETDCKHPFAVTELMMPVLPIIRVKDVDQAIDLAVKLEGGCHHTAAMHS

NNISNLNRMANAIDTSIFVKNGPCIAGLGLGGEGWTTMTITTPTGEGVTCARTFVRLRR

CTMVDSFRIV
```

SEQ ID No: 21

```
ATGCATTTAGACGACAAACAAATCGCACAAATAGTAGAAACCGTATTATCAAGATT

AGAAAGAAACGAAAGTAGAACAGGTAGAAGTAGACACCCACAAGGTGTCTTTGAA

ACCTTGGATGAAGCTGTAGAAGCTGCAAGACAAGCACAAAAGAAAATTAGAAAAT

TGGAATTGAGAGCTAAGATCATCCAAGCAATCAGACAAGCCGGTGTTAAACATGCA

AGAGAATTGGCAGAAATGGCCGTTCAAGAAACTGGTATGGGTAGAGTCGAAGATA

AGATAGCAAAGAACATCTCTCAAGCCGAAAAGACCCCAGGTATTGAAGATTTACAA

CCTTTTGGCTTTATCAGGTGACCACGGTTTGACTTTAATCGAAAATGCCGCTTGGGGT

GTTATTGCCTCTGTCACACCATCAACCAACCCTGGTGCTACTGTTATCAATAACTCT

ATCTCAATGATTGCAGCCGGTAATGCTGTTGTCTATGCACCACATCCTGCTGCAAAA

AAGGTCTCCCAAAGAGCCATTGAAATATTGAACAAAGCTATTGAAGCCGCTGGTGG

TCCAGCAACATTGTTAACTACAGTCGCCGAACCTAGTATCGAAACCGCTCAAAAGT

TATTCGTATATCCAGGTATTGATTTGTTAGTAGTTACTGGTGGTGAAGCTGTCGTAA

AAGCAGCCAGAAAGGTTACAGACAAAAGATTAATGGCTGCAGGTGCAGGTAATCC

ACCTGTTGTCGTAGATGAAACAGCTGACATTGCAAAGCCGCTAGAGATATAGTCT

GGGGTGCTTCTTTCGATAATAACATCGTATGTGCAGACGAAAAGAAATCATTGCC

GTTGATGCCATTGCTGACAGATTGAAGGAAGAAATGAAAAAGCACCAAGCAGTTGA

ATTAACTCCACAACAAGGTGAAGAATTGGCTCAAATCATCTTAGAAGATTATCCAG
```

```
GTCCTAATGCAAGAATAAACAGAAAGTGGGTTGGTAAAGACGCCTACAAGTTCGCT

AGAGAAATAGGTTTGAACGTATCAAAGGAAACAAGATTGTTGTTCGTTGAAGCTGA

TAAGGACCATCCTTTCGCACAATTGGAATTAATGATGCCAGTTATCCCTTTGATCAG

AGCAGCCGATGCCGACAAAGCTATCGATTTGGCTATTGAATTAGAACACGGTTATA

GACATACAGCTGCAATGCATTCCAGACACATTGATCATATGGACAGAATGGCTAAC

GAAATCAACACCAGTATCTTCGTTAAAAACGGTCCATGTTTGGCAGGTTTAGGTTTC

GGTGGTGAAGGTTGGACTTCCATGACAATTACCACTCCTACCGGTGAAGGTGTAAC

TTCCGCTAGAAGTTTTGTTAGATTGAGAAGATGCGTTGTCGTAGATCATTTCAGAAT

TGTTTAG
```

SEQ ID No: 22
```
MHLDDKQIAQIVETVLSRLERNESRTGRSRHPQGVFETLDEAVEAARQAQKKIRKLELR

AKIIQAIRQAGVKHARELAEMAVQETGMGRVEDKIAKNISQAEKTPGIEDLQPLALSGD

HGLTLIENAAWGVIASVTPSTNPGATVINNSISMIAAGNAVVYAPHPAAKKVSQRAIEIL

NKAIEAAGGPATLLTTVAEPSIETAQKLFVYPGIDLLVVTGGEAVVKAARKVTDKRLM

AAGAGNPPVVVDETADIAKAARDIVWGASFDNNIVCADEKEIIAVDAIADRLKEEMKK

HQAVELTPQQGEELAQIILEDYPGPNARINRKWVGKDAYKFAREIGLNVSKETRLLFVE

ADKDHPFAQLELMMPVIPLIRAADADKAIDLAIELEHGYRHTAAMHSRHIDHMDRMAN

EINTSIFVKNGPCLAGLGFGGEGWTSMTITTPTGEGVTSARSFVRLRRCVVVDHFRIV
```

SEQ ID No: 23
```
ATGCAAACAGACGCCCAACAAATAGAAAGTATCGTTAGAAGAGTCATAGAACAATT

ACACAGTCCACAAAGAGATGGTGAAAGTTATGGTGTCTTTAGAACCTTGGATGACG

CAGTAGCCGGTGCTCAAGGTGCTTATAAAAAGATAAGAACCATGGCTCAAAGAGAA

GCAATTATAGCTGCAATCAGAAGAACTGGTAGTGAAAATGTTCAAGCATTGTCTGA

ATTAGCCGTCCAAGAAACAGGTTTCGGTAGAGTAGAAGATAAGATCAGAAAGCATA

GATTGGTTTTAGACAAAACTCCTGGTATCGAAGCTATTGTTCCAATGGCAGTCACAG

GTGATCACGGTTTGTCTTTAATTGAAAATGCTCCATGGGGTGTAATAGCATCCGTTA

CCCCTAGTACTAACCCATCTGCTACTATCTTGAACAACGCAATCTCAATGATCGCCG

CTGGTAATTCAGTTGTCTTTTCCCCACATCCTGCAGCCAGAGCTGTCTCCCAAAGAA

CAATCCAATTGATCAACAGAGCCTCTGTTTCAGCTGGTGGTCCTGCAAACTTAGTCA

CCTGTGTAGAAGAACCAACAATTGAAGCTGCAACCAGATTGTTTTCATTCCCTGGTA

TACAATTGTTAACCATCACTGGTGGTGAAGGTGTAGTTAATGCCGCTAGAAAAGTT

ACTGATAAGAGATTAATCGCAGCCGGTCCAGGTAACCCACCTGTCGTAGTTGATGA

AACAGCTGACATTGAAAGAGCTGCAATTTCAATAGTTCAAGGTGCATCCTTCGATA

ACAACATCATATGTGTTGACGAAAAGGAAATAATCGCCGTCGAATCCATTGCTACT

GAATTGAAGACAGCTATGTGCAGACATGGTGCCGCTGAAATAAATGCAGATCAAGC

AGACGCCGTCGCTAGATTGGTATTAGCTGGTTACCCAGGTCCTAACCCACACCCTAA

ACCAGAATGGGTTGGTAGAGATGCTGAAAAGATTGCAGCCGCTGCAGGTTTTAGTG

TACCTGCAGGTACTAGATTGTTAGTTACAGAAACCGAAAGAGATCATGCATTCGCC

ACTACAGAAATGATGTTGCCAGTTATCTCTTTAATAAGAGCTAGAGATGCAGACCA

AGCCATTGATTGGGCAGTTGAATTGGAAGCCGGTAATAGACATACAGCCGCTATGC

ACTCAAGAAATATCGACAACTTGTCCAGAATGGGTTTAGAAATAAACTGTTCTTTGT

TCGTTAAAAACGGTCCTTGCTTGGCCGGTTTAGGTGCTGGTGGTGAAGGTTGGACAA
```

-continued

```
GTATGACCATATCTACTCCAACAGGTGAAGGTGTAACCAACGCTAGTACTTTCGTTA
GAAAGAGAAGATGCACAATGGTTGATTCTTTCAGAATTGTCTAG
```

SEQ ID No: 24
```
MQTDAQQIESIVRRVIEQLHSPQRDGESYGVFRTLDDAVAGAQGAYKKIRTMAQREAII
AAIRRTGSENVQALSELAVQETGFGRVEDKIRKHRLVLDKTPGIEAIVPMAVTGDHGLS
LIENAPWGVIASVTPSTNPSATILNNAISMIAAGNSVVFSPHPAARAVSQRTIQLINRASV
SAGGPANLVTCVEEPTIEAATRLFSFPGIQLLTITGGEGVVNAARKVTDKRLIAAGPGNP
PVVVDETADIERAAISIVQGASFDNNIICVDEKEIIAVESIATELKTAMCRHGAAEINADQ
ADAVARLVLAGYPGPNPHPKPEWVGRDAEKIAAAAGFSVPAGTRLLVTETERDHAFAT
TEMMLPVISLIRARDADQAIDWAVELEAGNRHTAAMHSRNIDNLSRMGLEINCSLFVK
NGPCLAGLGAGGEGWTSMTISTPTGEGVTNASTFVRKRRCTMVDSFRIV
```

SEQ ID No: 25
```
ATGGATCAAAAACAAATCGAAGAAATCGTAAAATCAATCGTATTACAATTAAATGA
CAACCCAGGTATAGCCTCCTCAGCCAACACCTTGAATCAAAACACATTAACCGAAC
AGGGTGATTATGGTGTCTTTGAAACTTTGGACGGTGCTGTAGCTGCAGCCACTGCTG
CACAAAAGCAAATTAGAACAGTTGCAATGAGAGATGAAATCATCACAGCCATCAG
AAGAATGACCAAAAAGCATGCCAGAGAATTATCAGAAATGGCTGTTGAAGAAACA
GGTTTCGGTAGAGTCGAAGATAAGATAAAAAAGCACATCTTGGTCGCTCAAAGAAC
TCCTGGTACAGAAATTTTATCCCCACAAGCAGTATCCGGTGATAGTGGTTTCTCTTT
GATGGAAAATGCTCCATGGGGTGTCATCGCATCAGTAACCCCTTCCACTAACCCAA
CTTGTACAGTTATAAACAACGCTATATCAATGATAGCCGCTGGTAATGCAGTTGTCT
TTGCCCCACATCCTGCAGCCAAAAAGGTTTCCCAATACACTATCCAATTAGTAAACA
AGGCTTCTGAATCAGTTGGTGGTCCTGCATACATATGCACTACAGTAGCCAAACCAT
CTTTGGAAAATGCTCAAGCATTATTCGTTTACCCTGGTATTAGATTGTTAGTAGTTA
CTGGTGGTGATGCTGTCGTAGAAGCTGCAAGAGCAGTTACAGACAAAAGATTGATC
GCCGCTGGTCCAGGTAACCCACCTGTTGTCGTAGATGAAACCGCTGACATAGAAAG
AGCAGCCATAAGTATCGTAGAAGGTGCTTCTTTCGATAATAACATAGTTTGTGCAAC
AGAAAAGGAAATCATTGCTGTCGATTCAATCGCAGACGAATTAAAAGCTGCAATGT
GCAGAAATGGTGCCCATTTGTTAACTGCTGATCAAGCCGAAGCTGTTGCAAGAGTT
GTCTTGAAAGGTTATCCTGGTGACAAGCCATCACCTAACCCAAAATGGGTTGGTAG
AGATGCTTCCAAGTTAGCCGCTGCAGCCGGTATAGACGTCCCAGCAGAAACAAGAT
TGTTAATCTTTGAAGCCGATAAATCTCACGTTTTCGCTGTAGTTGAACAAATGATGC
CTATTTTGCCATTAATCAGAGCTGCAAATGCCGATCAAGCTATTGACTGGGCTGTTG
AATTGGAAAATAAGAACAGACATACAGCCGCTATCCACAGTAAGAACATCGATGTT
TTGACCAGAATGGCTTACGAAATGGACTGTTCTTTGTTAGCAAAGAACGGTCCTGCC
ATCGCAGCCATTGGTGCAGGTGGTGAAGGTTGGACCACTATGACCATTAGTACCCC
AACTGGTGAAGGTGTTACTAACGCTTTGACATTCACCAGAAAGAGAAGATGCACTG
CAGTTGATTCTTTCAGAATTGTCTAG
```

SEQ ID No: 26
```
MDQKQIEEIVKSIVLQLNDNPGIASSANTLNQNTLTEQGDYGVFETLDGAVAAATAAQ
KQIRTVAMRDEIITAIRRMTKKHARELSEMAVEETGFGRVEDKIKKHILVAQRTPGTEIL
SPQAVSGDSGFSLMENAPWGVIASVTPSTNPTCTVINNAISMIAAGNAVVFAPHPAAKK
```

-continued

VSQYTIQLVNKASESVGGPAYICTTVAKPSLENAQALFVYPGIRLLVVTGGDAVVEAAR

AVTDKRLIAAGPGNPPVVVDETADIERAAISIVEGASFDNNIVCATEKEIIAVDSIADELK

AAMCRNGAHLLTADQAEAVARVVLKGYPGDKPSPNPKWVGRDASKLAAAAGIDVPA

ETRLLIFEADKSHVFAVVEQMMPILPLIRAANADQAIDWAVELENKNRHTAAIHSKNID

VLTRMAYEMDCSLLAKNGPAIAAIGAGGEGWTTMTISTPTGEGVTNALTFTRKRRCTA

VDSFRIV

SEQ ID No: 27
ATGCAAATCAACGAAACCGACATAAAGAAAATGGTAGAACAAGTATTAAAACAAT

TAGGTCAAACAGAAGCTGCTGGTGCCCCAATCGCTCCACAAAATGATGTTTCTTTAG

GTGACGGTGTATTTGCAACTGTTGATGAAGCTGCAGCCGCTGCAAGAGTTGCTTGG

GAAAAATTGAGAAAGTTGCCTTTAGCATCAAGAAGACAAATGATTGACAATATGAG

AGAAGTTTCCTGTGCCCAAGCTAACGAATTGGCACAATTAGCCGTTGATGAAACAG

GTTTAGGTAGAGTCGAAGACAAAGTAGCTAAGATTTTGTTAGCCGCTAATAAAACA

CCAGGTGTTGAAGATTTGGTCTCTACCTCATATTCCGGTGATGACGGTTTGACTTTA

GTCGAATACGCTCCTATCGGTGTATTCGGTTCAATTACTCCATCCACAAACCCTGCA

GCCACTGTTATAAATAACAGTATTTCTTTAATCGCTGCAGGTAATACAGTTGTCTAT

AACCCACATCCTAGTGCTAAGAGAGTTTCTTTGAAGACTTTGAAGTTGTTAAATCAA

GCCATTGTCGCCGCTGGTGGTCCAGAAAATGCTTTGACAAGTGTTGCAGCCCCTAAC

TTAGAAACCTCTGCACAAGTTATGAATCACCCAAAAGTCAACGCCTTAGTAGTTAC

AGGTGGTGGTCCTGTCGTAAAGGCTGCAATGGCTGTAGGTAAAAAGGTTATCGCCG

CTGGTCCAGGTAATCCACCTGTTGTCGTAGATGAAACAGCAATTATATCACAAGCA

GCCGCTCATATTGTTCAAGGTGCTTCCTTTGATAATAACGTTTTGTGTACCGCAGAA

AAAGAAGTCTTCGTTGTTGATAAGGCAGCCAATGCTTTAAAAGCAGAAATGGTTAA

GAACGGTGCTATAGAATTGAAAGGTTTTCAATTCGAAAAATTGTTAGAAAAGGTAT

TAGTTAAAAAGAATGATAAATTTTACCCAAACAGAGATTTCATTGGCAAGGACGCT

AGTGTTATATTGCAAGCTGCAGGTATCCAAGTCTCTCCAAACGTAAAATTGATCATA

GCAGAAACTACAAAGGATCACCCTTTGGTTATGACTGAAATGTTGATGCCAATCTTA

CCTATTGTCAGAGTACCAGATGTAGACAAAGCTATTGAATTAGCCGTTATAGCTGA

AAAGGGTAATAGACATACCGCAATAATGCACTCACAAAACATCACCAACTTGACTA

AGATGGCACAAGAAATACAAGCCACTATCTTTGTAAAGAACGGTCCATCAGTTGCT

GGTTTGGGTTTTGAATCCGAAGGTTTCACCACTTTAACAATTGCCGGTCCTACCGGT

GAAGGTTTGACTTCTGCAAAAACATTTACCAGACAAAGAAGATGCGTTTTGGTCGA

TGGTTTCAGAATAATCTAG

SEQ ID No: 28
MQINETDIKKMVEQVLKQLGQTEAAGAPIAPQNDVSLGDGVFATVDEAAAAARVAWE

KLRKLPLASRRQMIDNMREVSCAQANELAQLAVDETGLGRVEDKVAKILLAANKTPG

VEDLVSTSYSGDDGLTLVEYAPIGVFGSITPSTNPAATVINNSISLIAAGNTVVYNPHPSA

KRVSLKTLKLLNQAIVAAGGPENALTSVAAPNLETSAQVMNHPKVNALVVTGGGPVV

KAAMAVGKKVIAAGPGNPPVVVDETAIISQAAAHIVQGASFDNNVLCTAEKEVFVVDK

AANALKAEMVKNGAIELKGFQFEKLLEKVLVKKNDKFYPNRDFIGKDASVILQAAGIQ

VSPNVKLIIAETTKDHPLVMTEMLMPILPIVRVPDVDKAIELAVIAEKGNRHTAIMHSQN

-continued
ITNLTKMAQEIQATIFVKNGPSVAGLGFESEGFTTLTIAGPTGEGLTSAKTFTRQRRCVL

VDGFRII

SEQ ID No: 29
ATGGGTTTATCAGAAATCGAACAATTAGTCAAGCAAATCTTATCAGAAGACATATT

AGAAAGTCAAGAATCCGCACAATACAGTCAATCCTTGGTTGGTACAAAGGAAATCC

AAGGTGATATCTTAGAAGGCAAGGAAACAGAATCTGGTGTCTTTTCAACCGTAGAT

CAAGCAGTTCAAGCTGCAAAGATAGCCCAAAAGAAATACTTCGACACTTCTATCGA

AAGAAGAAAAAAGATTATCGCCGCTATAAGATCAAGATTGTTACCAGAAGTTGAAG

AAATAGCTAAAAGAGCATTGGAAGAAACCGGTATGGGTAACTTCCAAGATAAGAT

AGCTAAGAACAGATTGGCCTTAGAAGCTACTCCAGGTGTCGAAGATTTGATGTATG

CAACCAGAGCCTTAACTGGTGACAATGGTTTGACTTTATATGAAATGTGTCCTTACG

GTGTTATCGGTGCAATTGCCCCATCAACAAACCCTACTGAAACAATCATCAATAACT

CCATCAGTATGTTGGCAGCCGGTAACACAATTTACTTCGCTCCACATCCTGGTGCAA

GAGAAACTACAATCTGGTTGATCAGAAAGATAAACAAGATAGCTAAAGATGCATCC

GGTATAGACAACTTGATCGTCACCATAGAAAACCCAAGTATACAAGCTGCACAAGA

AATGATGGTACACCCAGATATTGCTATATTAGTTGTCACTGGTGGTCCTGGTGTAGT

TGCTCAAGCAATGAAATCTGGTAAAAAGGTTATTGGTGCCGGTGCTGGTAATCCAC

CTGCAATCGTCGATGAAACTGCCAACATTGAAAAGGCTGGTCAAGATATAGTTGAC

GGTGCCTCATTTGACAATAACATTCCTTGTACTGCTGAAAAGAATATAATCGTCGTA

TCTTCAGTTGCTGAATACTTGATCTTCAACATGCAAAAGGCAGGTGCCTTCTACGTC

AAAGATATCGAAGACATCAAAAAGTTAGAAAACTTGTGCTTGACAGAAAAGGGTA

CCACTAACAAAAAGTATGTTGGTAAGTCTGCTGAAAAAATCTTGACCGATGCAGGT

GTTACCTATACTGGTCATCCAAGATTAGTAATTGTTGAAGGTTACCCAGATATGCCT

TTTGCTGTTGAAGAAATGTTGATGCCAGTTGTCCCTTTAATTAGAGTCCCTGATTTCG

ACACTGCCTTGGAAGTAGCTTTGGAATTAGAACATGGTTACAAACACACAGCTACC

ATTCACTCCCAAAATGTAAGTAGATTAAACAAGGCCGCTAGAGCTATGGAAACATC

TATCTTCGTTAAGAACGGTCCATCATTCGCAGGTTTGGGTTTAAGAGGTGAAGGTCC

AACAACCTTTACTATTGCTACTCCTACAGGTGAAGGTACTACAACCGCAAGATCCTT

TGCCAGAATAAGAAGATGCGTTTTAAGTGATGCATTCATGATCAGATAG

SEQ ID No: 30
MGLSEIEQLVKQILSEDILESQESAQYSQSLVGTKEIQGDILEGKETESGVFSTVDQAVQA

AKIAQKKYFDTSIERRKKIIAAIRSRLLPEVEEIAKRALEETGMGNFQDKIAKNRLALEAT

PGVEDLMYATRALTGDNGLTLYEMCPYGVIGAIAPSTNPTETIINNSISMLAAGNTIYFA

PHPGARETTIWLIRKINKIAKDASGIDNLIVTIENPSIQAAQEMNIVHPDIAILVVTGGPGV

VAQAMKSGKKVIGAGAGNPPAIVDETANIEKAGQDIVDGASFDNNIPCTAEKNIIVVSS

VAEYLIFNMQKAGAFYVKDIEDIKKLENLCLTEKGTTNKKYVGKSAEKILTDAGVTYT

GHPRLVIVEGYPDMPFAVEEMLMPVVPLIRVPDFDTALEVALELEHGYKHTATIHSQNV

SRLNKAARAMETSIFVKNGPSFAGLGLRGEGPTTFTIATPTGEGTTTARSFARIRRCVLS

DAFMIR

SEQ ID No: 31
ATGGCTGACGTATTGGAAAAAGACATAGAAGCTATCGTAACAGAAGTATTAAAGAA

GATGACATTGCCAACCTCCTCTCCTAACGGTTCTTCACCTCAAGAAACTTTGTTAGA

-continued

```
TTCTGACGGTGATTGGGGTGTCTTTCCAGGTTTAGATCAAGCTGTAGCTGCAGCCTC

AGCTGCACAAAAAAGAATACCAACAATAGCTGTTAGAGAACAAGTTGTCAGAATG

GTCAGAAGAGCCGCTAGAGCAAATGCCAGAAGATTAGCCGAAATGGCTGTTGATGA

AACCGGTATGGGTAGAGTCGAAGCAAGGTAAAAAAGAATTTGTTAGTTGCCAACA

GAACACCAGGTCCTGAAATTTTGTCTCCTGCAGCCGCTACTGGTGATGCTGGTTTAA

CATTGTTTGAAAATGCCCCATGGGGTGTTATTGCTTCTGTCACTCCTTCAACAAACC

CAGCAGCCACAATCTTCAATAACACCATTTCCATGGTCTCTGGTGGTAATACTGTAG

TTTATGCAGTTCATCCAGGTGCCAAGAGAACTACATTAGAAACAGTTAAGGTCGTA

AACAAGGCAGTCTACGAAGAATTGGGTATAAACAACATAATCACTTGTGTTAAGGA

ACCTTCTATCGAAACCGCTCAAAAGTTATTCACTTATCCAGGTATCAACTTGTTAGT

TGTTACTGGTGGTGAAGCAGTAGTTGATGCTGCAAAAAAGATAACTGACAAGAGAT

TGATCGCCGCTGGTGCTGGTAACCCACCTGTCGTTGTTGATGACACTGCAGATTTGG

CCAGAGCAGCCCAATCTATCTACGATGGTGCTTCATTCGACAACAACATCGTTTGTT

GCGATGAAAAGGAAATCATAGCTTTAGACACAGTTGCAGATAAATTGAAGGACGA

ATTGAAGAATTGCGGTGCTGTTGAAATTTCCTTGGACCAAGCTGATGCAATAGCCA

GAAAGGTTTTGTTGGATTACCCTGGTTCAAATCCAAGACCTAACCCAAAGTGGGTTG

GTAGAGATGCTGCAGTTTTGGCTTCTGCCGCTGGTATATCAGTACCAGAAACATGTA

GATTGTTAATCGTTGATGCAGGTACCGACACTGGTTACACCTTTGCCAAAATGGAAC

AAATGATGCCTTTAATACCAATCTTGAGAGCAAGAGATTTCAATCAAGCATTGGAA

TGGGCATTGTTATTGGAAAACGATTGCAGACATTCCGCTGGTTTGCACAGTAAGAAT

ATTGACAACATGGATACAATGGCTAAAGCAGTCAATACCTCATTATTCGTAAAGAA

CGGTCCTCACATTGCCGGTTTGGGTGCTGGTGGTGAAGGTTGGACCTCCATGACTAT

AAGTACACCAACCGGTGAAGGTGTATCCAATGCAAGAACTTTCGTTAGATTGAGAA

GATGTACATTGGTTGGTAGTTTCAGAATTGCTTAG
```

SEQ ID No: 32
```
MADVLEKDIEAIVTEVLKKMTLPTSSPNGSSPQETLLDSDGDWGVFPGLDQAVAAASA

AQKRIPTIAVREQVVRMVRRAARANARRLAEMAVDETGMGRVEDKVKKNLLVANRT

PGPEILSPAAATGDAGLTLFENAPWGVIASVTPSTNPAATIFNNTISMVSGGNTVVYAVH

PGAKRTTLETVKVVNKAVYEELGINNIITCVKEPSIETAQKLFTYPGINLLVVTGGEAVV

DAAKKITDKRLIAAGAGNPPVVVDDTADLARAAQSIYDGASFDNNIVCCDEKEIIALDT

VADKLKDELKNCGAVEISLDQADAIARKVLLDYPGSNPRPNPKWVGRDAAVLASAAGI

SVPETCRLLIVDAGTDTGYTFAKMEQMNIPLIPILRARDFNQALEWALLLENDCRHSAGL

HSKNIDNMDTMAKAVNTSLFVKNGPHIAGLGAGGEGWTSMTISTPTGEGVSNARTFVR

LRRCTLVGSFRIA
```

SEQ ID No: 33
```
ATGGACGTTAGACAACAAGATGTAGAAAGAATCGTAGTCGAAGTATTAAAGAAAA

TGATGAGTGACCAACCAACAGCCGCAGCAACCACAGTTGTCGCTGCATCCGGTTGT

GATTGCGGTGACTTTGGTTTGTTCGATAGATTAGAAGACGCTGTCCAAGCCGCTGAA

GCAGCCCAAAAGAAAATTAGTACAGTAGCAATGAGAGATAAGATAATCGCTGCAA

TAAGAAAGGCTGGTTTGGAAAATGCCAAAGCATTTGCAGAAATTGCACATAACGAA

ACCGGTATGGGTAGAGTCTCTGATAAGATCGCTAAGAACATCTTGGTATGCGAAAG

AACTCCTGGTACAGAATGCTTATCCCCAATGGCAATTAGTGGTGACATGGGTTTGAC
```

```
TTTAATAGAAAATGCACCATGGGGTGTAATCGCCTCTGTTACCCCTTCAACTAACCC
AACCGCTACTGTTATAAATAACGCCATCTCCATGATTGCTGGTGGTAATAGTGTTAT
CTTTGCTCCACATCCTAACGCTAAGAGAGCATCTCAAACTGCAATTCAAGTATTGAA
CAAGGCTATCATCGAAGCAACAGGTGTTGCCAACTTGTTAGTCGCTGTAAAAGAAC
CTACCATTGAAGTTGCACAAGAATTATTCTCACACCCAAGAATAAAGTTGTTAGTAG
TTACTGGTGGTGAAGCCGTCGTAGCCCAAGCTAGAAAAGTTGCTACAATGAGATTG
ATTGCCGCTGGTGCAGGTAATCCACCTGTTGTCGTAGATGAAACAGCCAACATTGCT
AGAGCAGCCAGATCTATATATGATGGTGCCTCATTCGACAATAACATCATCTGTGCT
GACGAAAAGGAAATCATCGCAGTTGATTCTATAGCCGACCAATTAAAAGCTGAAAT
GAAGGCAATTGGTGCCGTTGAAATATCATTGGAACAAGCAGATGCCGTCGCTAGAG
TTGTCTTAAGAAATTACCCTCAAGTTGAAGGTGGCAAGGCTCCAAATCCTAACCCA
AAATGGGTCGGTAGAGATGCTGCATTGATAGCAAAGGCCGCTGGTATCGATGTTCC
AGACTCCTGCAGATTGTTGATCGTTGATGTCAAGAGAGACATAAACCATGTCTTTGC
TAGAGTAGAACAATTGATGCCTGTAATTCCATTGTTAAGAGCAGCCAACGTTGATG
AAGCTATCGAATGGGCATTGATTTTAGAAAGAGGTTTGTCTCATACCGCTGGTATGC
ACTCAAGAAATATTGATAACATGGACAAGATGGCAAGAGCCATGAACACTTCATTA
TTCGTTAAGAACGGTCCTCACTTGGCTGCATTAGGTGCTGGTGGTGAAGGTTGGACT
ACAATGACAATTTCCACACCAACCGGTGAAGGTGTTACCTGTGCTAGAAGTTTTGTC
AGATTGAGAAGATGTTGCGTAGTTGATAATTTCAGAATAGTTTAG
```

SEQ ID No: 34
```
MDVRQQDVERIVVEVLKKMMSDQPTAAATTVVAASGCDCGDFGLFDRLEDAVQAAE
AAQKKISTVAMRDKIIAAIRKAGLENAKAFAEIAHNETGMGRVSDKIAKNILVCERTPG
TECLSPMAISGDMGLTLIENAPWGVIASVTPSTNPTATVINNAISMIAGGNSVIFAPHPNA
KRASQTAIQVLNKAIIEATGVANLLVAVKEPTIEVAQELFSHPRIKLLVVTGGEAVVAQA
RKVATMRLIAAGAGNPPVVVDETANIARAARSIYDGASFDNNIICADEKEIIAVDSIADQ
LKAEMKAIGAVEISLEQADAVARVVLRNYPQVEGGKAPNPNPKWVGRDAALIAKAAG
IDVPDSCRLLIVDVKRDINHVFARVEQLMPVIPLLRAANVDEAIEWALILERGLSHTAGM
HSRNIDNMDKMARAMNTSLFVKNGPHLAALGAGGEGWTTMTISTPTGEGVTCARSFV
RLRRCCVVDNFRIV
```

SEQ ID No: 35
```
ATGAACTTGGATGCTAACAACTTGAACAACATAGTCTCCTTAATAATGAAAGAATT
GGACAAAAATAACAACATAGATGACACTGGTCAAGGTTGTGGTGGTGAAGAAGGC
AAGAACGGTATTTTCTCTTCTATGGACACTGCTGTTTCTAAAGCCAAGGAAGCTCAA
GTAACATTGTTCGCCTCTAAATTGGAATTAAGAGAAAGAATCATCAAGGCTATCAG
AGAAGATGTTAGAGAAGCTGCAGCCGAATTGGCAGAAATCGCCGTTGAAGAAACC
GGTATGGGTAGAGTCGATGACAAGACTTTGAAGCATTACGTCACTGTAGATAAAAC
ACCAGGTGTTGAAGACTTGAGAGCATTTGCCTATAGTGGTGATAACGGTTTAACTGT
AATGGAATTGTCTCCTTACGGTGTTATTGGTTCTATAACACCATCAACCAATCCTTC
CGAAACAATTGTTTGCAACGCTATCGGTATGATTGCTGCAGGTAATTCAGTTGTCTT
TGCCCCACACCCTGGTGCTAAAAAGACATCCTTAAGAGCAGTTGAAATTTTGAACA
AAGCTGTCGCAAGAGCCGGTGGTCCAAACAACTTGGTAGTTACAATCTTCGAACCT
```

-continued

```
TCAATCGAAAACACCAACAAGATGGTCAAGAACCCAGATATAAAGATGGTCGTAGC
TACCGGTGGTCCTGGTGTTGTCAAGTCCGTTATGTCCAGTGGTAAAAAGGCTATAGG
TGCTGGTGCAGGTAATCCACCTGTTTTGGTCGATGAAACTGCAGACATCGAAAAAG
CCGCTAAGGATATAGTTAACGGTTGTAGTTTCGACAACAACTTACCATGCATTACCG
AAAAAGAAGTAGTTGCCGTAGATTCTATCACTGACTACTTGATCTTCGAAATGCAA
AAGAATGGTGCATACTTGGTTCAAGATTCAAAGACAATAAAAAAGTTGTGTGAAAT
GGTCATCAATGACGGTTCACCAAACAGAGCTTATGTAGGTAAAAACGCATCCTACA
TCTTGAAGGATTTAGGTATTGATGTTGGTGACGAAATAAAGGTCATCATTGTAGAA
ACTGATGCAGGTCATCCTTTGGCCGTATTAGAAATGTTGATGCCAGTTTTGCCTATA
GTAAGAGTTAAGGATGCTTTGGAAGGTATAAAGGTTTGCAAAAAGTTAGAAGACGG
TTTGAGACATACAGCAATGATACACTCTAAGAACATCGATATCTTAACCAAGTACG
CCAGAGACATGGAAACTACAATCTTGGTTAAAAACGGTCCATCTTATTCAGGTATTG
GTGTCGGTGGTGAAGGTTACACCACTTTTACCATTGCTGGTCCTACTGGTGAAGGTT
TAACATCCGCTAAAAGTTTCGCAAGAAATAGAAGATGTGCATTAGTTGGTGGTTTGT
CTATTAAGTAG
```

SEQ ID No: 36
```
MNLDANNLNNIVSLIMKELDKNNNIDDTGQGCGGEEGKNGIFSSMDTAVSKAKEAQVT
LFASKLELRERIIKAIREDVREAAAELAEIAVEETGMGRVDDKTLKHYVTVDKTPGVED
LRAFAYSGDNGLTVMELSPYGVIGSITPSTNPSETIVCNAIGMIAAGNSVVFAPHPGAKK
TSLRAVEILNKAVARAGGPNNLVVTIFEPSIENTNKMVKNPDIKMVVATGGPGVVKSV
MSSGKKAIGAGAGNPPVLVDETADIEKAAKDIVNGCSFDNNLPCITEKEVVAVDSITDY
LIFEMQKNGAYLVQDSKTIKKLCEMVINDGSPNRAYVGKNASYILKDLGIDVGDEIKVII
VETDAGHPLAVLEMLMPVLPIVRVKDALEGIKVCKKLEDGLRHTAMIHSKNIDILTKYA
RDMETTILVKNGPSYSGIGVGGEGYTTFTIAGPTGEGLTSAKSFARNRRCALVGGLSIK
```

SEQ ID No: 37
```
MTNPVIGTPWQKLDRPVSEEAIEGMDKYWRVANYMSIGQIYLRSNPLMKEPFTRDDVK
HRLVGHWGTTPGLNFLLAHINRLIADHQQNTVFIMGPGHGGPAGTAQSYIDGTYTEYY
PNITKDEAGLQKFFRQFSYPGGIPSHFAPETPGSIHEGGELGYALSHAYGAIMDNPSLFVP
CIIGDGEAETGPLATGWQSNKLVNPRTDGIVLPILHLNGYKIANPTILARISDEELHDFFR
GMGYHPYEFVAGFDNEDHLSIHRRFAELFETIFDEICDIKAAAQTDDMTRPFYPMLIFRT
PKGWTCPKFIDGKKTEGSWRAHQVPLASARDTEAHFEVLKGWMESYKPEELFNADGSI
KEDVTAFMPKGELRIGANPNANGGRIREDLKLPELDQYEITGVKEYGHGWGQVEAPRS
LGAYCRDIIKNNPDSFRVFGPDETASNRLNATYEVTKKQWDNGYLSALVDENMAVTG
QVVEQLSEHQCEGFLEAYLLTGRHGIWSSYESFVHVIDSMLNQHAKWLEATVREIPWR
KPISSVNLLVSSHVWRQDHNGFSHQDPGVTSVLLNKTFNNDHVTNIYFATDANMLLAI
AEKCFKSTNKINAIFAGKQPAATWITLDEVRAELEAGAAEWKWASNAKSNDEVQVVL
AAAGDVPTQEIMAASDALNKMGIKFKVVNVVDLIKLQSSKENDEAMSDEDFADLFTAD
KPVLFAYHSYAQDVRGLIYDRPNHDNFTVVGYKEQGSTTTPFDMVRVNDMDRYALQA
KALELIDADKYADKINELNEFRKTAFQFAVDNGYDIPEFTDWVYPDVKVDETSMLSAT
AATAGDNE
```

SEQ ID No: 38
```
ATGGCTACTCAAAACGATATCCCTAACTCGACTCCCGAGGATTTAGCGAAACAAGT
```

-continued

```
TGAAATTGCCGAAAAACACCCCGATCCTCCTGCTATGCCCTCGCGTCTTCCTGACTC

TTTAAAAACCCTCGAAGCTAAAATCGACACTTCAAAGATTACCGACGAAGAGGTTG

CCAATGTCCATCGTTTTCAACGTGCATGTGATTACCTCGCAGCTTCCCTGATTTTCCT

TTCCAACGGTCTCTACACCGGCGGTGACCTAGAGGAAAAAGATATCAAAACTAGAC

TGCTAGGCCATTGGGGTACTTGTCCCGGCTTGAGCATCGTTTACTCTCACTGTAATC

GTATCATTAATAAATATGATCTCAACATGCTCTTTGTCGTAGGCCCTGGCCATGGTG

CTCCTGCCATTTTATCGGCTCTTTTCCTTGAAGATTCTTTGGGCCCCTTTTACCCTCG

ATACCAATTTACCAAGGAAGGCTTGAACAACCTTATTAACACCTTCTCCCTTCCCGG

TGGTTTTCCTTCTCATGTCAACGCCGAGGTCCCTGGTGCCATTCACGAGGGCGGTGA

ATTGGGTTATGCGTTGTCCGTCAGTTACGGTGCAGTTCTTGATCGTCCCGACCTGAT

TGTAACTTGCGTTGTCGGTGATGGTGAGGCAGAGACCGGCCCCACTGCCACTTCTTG

GCATGCTCATAAATTCTTGGATCCTGCTGAATCGGGTGCTGTGATTCCTGTTTTGGA

ACTTAATGGTTACAAGATTTCCGAGCGTACCATTTACGGTTGCATGGATGATAGTGA

GCTTCTCTCTTTGTTTAGCGGTTTTGGCTATGAAGTTGCCATTGTAAACGATACCCCC

GACCAAAACAGGGTTATGGCTGCAACTATGGATTGGGCCGTTGAACGCATTCATGA

CATCCAACATCGCGCTCGTGTTAACAGAGAAGAAATCAAACCCAGATGGCCCATGA

TTATCCTTCGTACCCCTAAGGGTAAAGGATGTCCCAAGTATTTGAATGGCAAATTTT

TAGAAGGTACCTTCCGTGCTCACCAAGTTCCTTTGAAATTGGCTCGCACCGATACCA

ACCAGCGCAATCTTCTAAAGGATTGGCTGAACAGCTACAACTGCCAAGACTTCTTA

GACGAACATGGACTTCCTACTAAGGGCATCACCGAGCATCTTCCGCCTCGTGAGAA

GCGCATGGGTCAGCGTCATGAGACATACAATTCTTATCTACCTTTGAAGGTACCTGA

TTGGAAAAAATACGGTGTCAAGAAGGGAGAAACCACTAGTGCCACTTCGGTCGTTG

GTCAATATCTTGATGAACTCCTCGTAACCAACGATTCAACCCTTAGAATTTTCTCAC

CCGATGAGTTGGAAAGTAATAAATTAGATGGCGCTTTGAAGCACTCATATCGTACC

ATGCAAACTGATCCAGAGCTCATGGCAAAGCGTGGTCGCGTTACCGAAGTCCTTTC

AGAGCACCTTTGCCAAGGTTTCATGCAGGGTTATACTTTAACTGGACGTACCGCGAT

TTTCCCCTCATATGAAGCCTTTATGACTATTGTTGTTAGTATGCTTGTTCAGTACTCC

AAATTTTTGAAGATGGGCTTGGAGACCGGATGGCATGGAAAATTTGGTAGCTTGAA

CTATGTTACTTCCAGTACTTGGGCAAGACAAGAGCATAACGGTTTCTCCCATCAATC

ACCCAGGTTTATCACCACTATGCTCTCTCTGAAACCTGGTGTTAGCCGCGTATACTT

CCCACCGGATGCCAATTGCTTCTTAGCAACCGTCGCCCGATGCATGAAGTCTGAGA

ATACTATCAACCTTATGGTTTCTAGTAAAAATCCACAACCAGCCTACCTATCTGTTG

AAGAGGCCAACATCATTGCAAGGCCGGTGCTAGTGTTTGGAAGTTTGCTAGTACA

GATAATGGCGAAAATCCTGATGTTGTTATTGCCGGCGTCGGAAATGAGATTATGTTT

GAAGTAGTTAAAGCCGCAGAGATGCTTCAAAATGACATTCCTGAGCTCCGAGTGCG

TGTCATTAACGTCACTGACTTGATGGTACTTTCGAGCTTACATCCCCATGGTATGAA

TCCTGCGGAATTTGATTCTTTGTTTACCAAAGATCGCCATGTTCATTTCAACTATCAC

GGTTATGTGATGGACTTGAAGGCTCTCTTGTTTGATCGCATACAAGGTACACGGGTC

ACTATGGAGGGCTATCGAGAGGAAGGTACTACTACCACTCCTTTTAATATGATGAT

GTGTAACAATACCTCTCGTTATCATGTTGCAAGAATGGCTTTGCAACATGCTTTACA

CAATCCTACCGTGGCCGTTAATTGTAACATGTTGTGTGCCAAATATGCTTGGAAGCT
```

CGAAGAGATTGAAAATTATATTATGGAAAACAAGGATGATCCTCCTGAAATTTATG

CTGCTCCTGTCTTTAAAAATAAGACTTCCACATTATAG

SEQ ID No: 39

MATQNDIPNSTPEDLAKQVEIAEKHPDPPAMPSRLPDSLKTLEAKIDTSKITDEEVANVH

RFQRACDYLAASLIFLSNGLYTGGDLEEKDIKTRLLGHWGTCPGLSIVYSHCNRIINKYD

LNMLFVVGPGHGAPAILSALFLEDSLGPFYPRYQFTKEGLNNLINTFSLPGGFPSHVNAE

VPGAIHEGGELGYALSVSYGAVLDRPDLIVTCVVGDGEAETGPTATSWHAHKFLDPAE

SGAVIPVLELNGYKISERTIYGCMDDSELLSLFSGFGYEVAIVNDTPDQNRVMAATMDW

AVERIHDIQHRARVNREEIKPRWPMIILRTPKGKGCPKYLNGKFLEGTFRAHQVPLKLA

RTDTNQRNLLKDWLNSYNCQDFLDEHGLPTKGITEHLPPREKRMGQRHETYNSYLPLK

VPDWKKYGVKKGETTSATSVVGQYLDELLVTNDSTLRIFSPDELESNKLDGALKHSYR

TMQTDPELMAKRGRVTEVLSEHLCQGFMQGYTLTGRTAIFPSYEAFMTIVVSMLVQYS

KFLKMGLETGWHGKFGSLNYVTSSTWARQEHNGFSHQSPRFITTMLSLKPGVSRVYFP

PDANCFLATVARCMKSENTINLMVSSKNPQPAYLSVEEAEHHCKAGASVWKFASTDN

GENPDVVIAGVGNEIMFEVVKAAEMLQNDIPELRVRVINVTDLMVLSSLHPHGMNPAE

FDSLFTKDRHVHFNYHGYVMDLKALLFDRIQGTRVTMEGYREEGTTTTPFNMMMCNN

TSRYHVARMALQHALHNPTVAVNCNMLCAKYAWKLEEIENYIMENKDDPPEIYAAPV

FKNKTSTL

SEQ ID No: 40

ATGCCTGGTGAAGTCATAGAAAGACCTAACCCTGCTCCTAAGCCATCCCACGTTCCT

GATTTGGTAGAAAAGTTGATTATCCCTGCCCAAAAGACTAAGTTGGAAAAGTCAGA

TTGTGACGCTTTACATAAATATAGAAGAGCTGCAGCCTACATTGCTGCAGGTCACTG

GGGTACTTGCCCAGGTTTGATCTTAGTTTACTCTCATTTGAACTACTTAATTAAAAA

GCAAAACTTGGATATGTTATATGTTGTCGGTCCAGGTCACGGTGCCCCTGGTTTGTT

AGCTTCATTGTGGTTAGAAGGTTCCTTGGGTAAATTCTACCCACAATACACAAAGGA

TAAGGAAGGTTTGCATAATTTGATATCAACCTTCTCTACTTCAGCAGGTTTACCATC

CCATATAAACGCAGAAACTCCTGGTGCCATCCACGAAGGTGGTGAATTGGGTTATG

CCTTATCCGTTAGTTTTGGTGCTGTCATGGACAATCCAGATTTGATTGTTACATGTGT

AGTTGGTGACGGTGAAGCTGAAACCGGTCCTACCGCTACTTCATGGCACGCTATTA

AATATATCGATCCAGCCGAATCCGGTGCTGTTTTGCCTATATTGCATGTCAACGGTT

TTAAAATCTCAGAAAGAACCATATTCGGTTGTATGGACAACAGAGAAATAGTTTGC

TTGTTTACTGGTTATGGTTACCAAGTTAGAATTGTCGAAGATTTGGAAGATATCGAC

AACGATTTGCATTCTGCAATGTCATGGGCCGTCGAAGAAATTAGAAACATACAAAA

AGCCGCTAGAAGTGGTAAACCAATTATGAAACCACAATGGCCTATGATAGTTTTGA

GAACACCAAAGGGTTGGTCTGGTCCTAAAGAATTACATGGTCAATTCATTGAAGGT

TCCTTCCATAGTCACCAAGTTCCATTGCCTAATGCTAAAAAGGATGACGAAGAATTG

CAAGCATTACAAAAGTGGTTGTCTTCATACAAGCCAGATGAATTGTTTACTGAATCT

GGTGACGTTATCGATGAAATATTGTCCATAATCCCAAGTGATGACAAAAAGTTGGG

TATGAGACCTGAAGCATACAAAACTCATTTGCCACCTGACTTACCAGATTGGAGAC

AATTTTGTGTTAAAAAGGGTGACCAATTCAGTGCTATGAAGGCAATTGGTTCTTTTA

TAGATCAAGTATTCGTTAAAAATCCACACACAGTTAGATTGTTTTCACCTGATGAAT

-continued

```
TAGAATCTAACAAGTTGTCAGCAGCCTTATCCCATACCGGTAGAAACTTCCAATGG

GATGAATTTTCTAACGCTAAAGGTGGTAGAGTAATCGAAGTTTTGTCTGAACACTTA

TGCCAAGGTTTTATGCAAGGTTATACATTGACCGGTAGAACAGGTATTTTTCCATCT

TACGAATCATTCTTAGGTATCATTCATACCATGATGGTACAATATGCCAAATTCGCT

AAGATGGCAAAAGAAACTGCCTGGCATCACGATGTTTCCAGTATAAATTACATCGA

AACTTCTACATGGGCTAGACAAGAACATAATGGTTTTAGTCACCAAAACCCATCTTT

CATTGGTGCAGTCTTGAAATTAAAGCCTTATGCTGCAAGAGTATACTTGCCACCTGA

TGCTAACACATTTTTGACTACATTGCATCACTGTTTGAAGAGTAAGAATTACATAAA

CTTAATGGTTGGTTCTAAGCAACCAACACCTGTTTACTTAAGTCCAGAAGAAGCTGA

ATCTCATTGTAGAGCAGGTGCCTCAATTTTTAAGTTCTGCTCCACCGACGGTGGTTT

GAGACCTGATGTCGTATTAGTTGGTATCGGTGTCGAAGTAATGTTTGAAGTCATAAA

AGCCGCTGCAATCTTGAGAGAAAGATGCCCAGAATTAAGAGTAAGAGTTGTCAACG

TTACTGATTTGTTCATATTAGAAAACGAAGGTGCTCATCCTCACGCATTGAAGCATG

AAGCATTCGACAATTTGTTTACTGAAGATAGATCTATCCATTTCAACTACCACGGTT

ACGTTAACGAATTGCAAGGTTTGTTATTCGGTAGACCAAGATTAGACAGAGCTACA

ATTAAGGGTTATAAAGAAGAAGGTTCAACCACTACACCTTTCGATATGATGTTGGTC

AACGAAGTATCCAGATACCATGTCGCAAAGGCCGCTGTAACTGGTGGTGCCAGATT

CAATGAAAAGGTTAAGTTGAGACATCAAGAATTGTGTTCAGAATTTGATCACAACA

TCGCTGAAACTAGAAAGTACATAATGAACAACCATCAAGACCCAGAAGATACATAC

AATATGCCTTCCTTCAACTAG
```

SEQ ID No: 41

```
MPSDSNDQSISAYGAARSTVKGQNLDPEEVRKMDAYFRASMYLCLGMLYLRENVLLK

QPLKVEHLKARLLGHWGSDAGQSFTWIHMNRLIKKYDLDVLFISGPGHGAPGILSQSYL

EGVYSEVYPDKSEDERGMQRFFKQFSFPGGIGSHATPETPGSLHEGGELGYSISHAFGTV

FDHPNLITLTMVGDGEAETGPLATSWHSTKYLNPCTDGAVLPVLHLNGYKINNPTLLAR

ISHDELSALMKGYGWTPYFVEGSDRETMHQAMAATLEHCVLEIRKFQKKARESKEPFR

PHWPMIILRSPKGWSAPREVDGKLLEGFWRAHQIPITDVLTNPSHLQLLESWMKSYKPE

ELFTHDGRLISELKALAPTGNSRMSANPVGNGGLLRRPLDLPDFRKYALTSIDPGATIRG

SMVNMSHYLRDVVAFNQTNFRVFGPDETESNKLSEIYKAGKKVWLAEYFPEDNNGGN

LSMAGRVMEMLSEHTCEGWLEGYVLSGRHGLLNSYEPPFIHIIDSMVNQHCKWIEKCLE

VEWRAKVASLNILLTATVWRQDHNGFTHQDPGFLDVVANKSPEVVRIYLPPDGNSLLS

VMDHCFRSANYVNVIVADKQDHIQFMDMDAAIAHCTKGVGIWDWASNDQGAEPDVV

MAACGDVPTHEALAATALLREHLPQLKVRFVNVVDLFKLMSKIHHPHGMSDREWKAI

FTADRPIVFNFHSYPWLIHRLTYKRPGQENIHVRGYKEKGNIDTPFELAVRNQTDRYSLA

VDAIDHARGLGNTASGVREKFLNMQLLAKQKAYDDGIDPDYIRNWTWQYPRKKGEG

V
```

SEQ ID No: 42

```
ATGACCACAGAACACGATGCTGCCTGCGAAGGTGAAAGTATATCCGCTTACGGTAC

AGCCAGAGCCACAGTCGAAGATCAACCATTAAATACTGATGACTTGAGAAAAATCG

ATGCCTATTGGAGAGCTTCTTTGTACTTATGTTTGGGCATGTTGTATTTGAGAGATA

ACCCATTGTTAAGAGACCCATTAAAGCCTGAACATATAAAGCCTAGATTGTTAGGT

CACTGGGGTTCTGATGCTGGTCAATGCTTCACATACATCCATTTCAACAGATTAATT
```

```
AACAAATATGACTTGAATGCCATATACATCTCCGGTCCAGGTCACGGTGCTCCTGCA

ATATTATCTCAAGCATATTTGGAAGGTACATATTCCGAAACCTACCCAGATAAAAGT

CAAGACATCGCTGGTATGAGAAGATTTTTCAAGCAATTTTCTTTCCCTGGTGGTATT

GGTTCACATGCTACCCCAGAAACTCCTGGTTCTATACACGAAGGTGGTGAATTGGGT

TATTCCGTAAGTCATGCCTTTGGTACTGTTTACGATAATCCAGACTTAATTGCTTTGG

TCATGGTTGGTGACGGTGAAGCTGAAACTGGTCCTTTAGCAACATCTTGGCATTCAA

ATAAGTTCTTGAACCCAATCACAGATGGTGCTGTATTGCCTGTTTTGCATTTGAACG

GTTACAAGATTAATAACCCAACCATTTTGGCTAGAATAACTCACGAAGAATTAGAA

GCATTGTTTATAGGTTACGGTTACACTCCATACTTCGTCGAAGGTTCCGATCCTGCC

AGTATGCATCAAGCTATGGCTGCAACAATGGAAAGATGTGTATTGAAAATTAGAGA

ATTTCAAGATAAGGCCAGACACACTGGTACAGCTTTCAGACCAAGATGGCCTATGA

TTATATTGAGATCCCCAAAAGGTTGGACTGCTCCTAGAAAGGTTGATGGTCATTATT

TGGAAGGTTTTTGGAGAGCACATCAAATTCCAATACCTGACGTTGTCTCAAATCCAG

CACATTTGCAATTGTTAGAATCTTGGATGAGATCATACAGACCTGAAGAATTATTTG

ATGCACAAGGTAGATTGATTCCAGAATTACATGAATTGGCCCCTAAAGGTAAAAGA

AGAATGTCCGCAAATCCAGTTGCCAACGGTGGTTTGTTAAGAAGACCATTAGATAT

GCCTGACTTTAGAGTTTTCAGTATTGCTGTCCAAGATGCAGGTGGTACAAGAGCAG

ACAATGTTCCAACCTTAGGTCATTTCTTGAGAGAAATCACTAGAAGAAACATGCAA

AACTTTAGAATTTTCGGTCCTGATGAAACCCAATCTAACAAATTAGATGCTATCTAT

GACGTCACTCAAAAAGTATGGTTGGGTGCATACTTTCCAGAAGATGCCGACGGTGG

TGCCTTAGCTTTGTCCGGTAGAGTTATGGAAATGTTGAGTGAACATACATTAGAAGG

TTGGTTGGAAGGTTATTTGTTATCTGGTAGACATGGTTTGATTAATTCATACGAAGC

CTTTATCCATATCATAGATTCTATGTTCAACCAACACGCTAAATGGTTAGAAAAGTG

TAACGAATTGCCATGGAGAGCAAAAGTAGCCTCATTAAATTTGTTGATCACAGGTTT

GGTTTGGAGACAAGATCATAACGGTTTTACCCACCAAGATCCAGGTTTCTTAGACGT

AGTTGCTAATAAGTCACCTAACGTCGTAAGAATATATTTGCCACCTGATGCAAATTG

TTTGTTATCCGTCACCGACCATTGCTTGAGAAGTGTAAACTACATCAACGTTATCGT

CGCTGATAAGCAAACTCATTTGCAATACTTGGATATGGACGCCGCTATGGCTCACTG

TGCAAAGGGTGCCGGTATTTGGGAATGGGCATCTAATGATATGGGTGAAGAACCAG

ACGTTGTCATGGCCTCTTGCGGTGACGTTCCTACTATGGAATCATTAGCAGCCACAG

CATTGTTGAGACAACATTTGCCAGATATCAAGATCAGATTCGTTAACGTAGTTGACT

TATTCAAGTTGGTCCCACACACCGAACATCCTCACGGTATGACTGATAGAGAATTTG

AAGCATTGTTTACTTCTTCTAAGCCAGTTATTTTTAATTTCCATTCATATCCTTGGTT

AATCCACAGATTGACCTACAGAAGACCAGCACAACATCACATACATGTTAGAGGTT

ACAAGGAAAAGGGTAACATCGATACTCCTTTAGAATTGGCTATAAGAAACCAAACA

GACAGATTTTCTTTGGCTATTGATGCAATAGACAGAATCCCAAGATTCTGTGATACA

GGTTCAGGTGTTAGAGAAATTTTGTTGAATTTGCAATTCGCATGCAAGAACCATGCC

TATGAATACGGTGTCGATCCACAAGAAATAACAGACTGGCAATGGCCATTCAGAGA

TACCCCTTAA
```

SEQ ID No: 43

MTTEHDAACEGESISAYGTARATVEDQPLNTDDLRKIDAYWRASLYLCLGMLYLRDNP

-continued

LLRDPLKPEHIKPRLLGHWGSDAGQCFTYIHFNRLINKYDLNAIYISGPGHGAPAILSQA

YLEGTYSETYPDKSQDIAGMRRFFKQFSFPGGIGSHATPETPGSIHEGGELGYSVSHAFG

TVYDNPDLIALVMVGDGEAETGPLATSWHSNKFLNPITDGAVLPVLHLNGYKINNPTIL

ARITHEELEALFIGYGYTPYFVEGSDPASMHQAMAATMERCVLKIREFQDKARHTGTAF

RPRWPMIILRSPKGWTAPRKVDGHYLEGFWRAHQIPIPDVVSNPAHLQLLESWMRSYR

PEELFDAQGRLIPELHELAPKGKRRMSANPVANGGLLRRPLDMPDFRVFSIAVQDAGGT

RADNVPTLGHFLREITRRNMQNFRIFGPDETQSNKLDAIYDVTQKVWLGAYFPEDADG

GALALSGRVMEMLSEHTLEGWLEGYLLSGRHGLINSYEAFIHIIDSMFNQHAKWLEKC

NELPWRAKVASLNLLITGLVWRQDHNGFTHQDPGFLDVVANKSPNVVRIYLPPDANCL

LSVTDHCLRSVNYINVIVADKQTHLQYLDMDAAMAHCAKGAGIWEWASNDMGEEPD

VVMASCGDVPTMESLAATALLRQHLPDIKIRFVNVVDLFKLVPHTEHPHGMTDREFEA

LFTSSKPVIFNFHSYPWLIHRLTYRRPAQHHIHVRGYKEKGNIDTPLELAIRNQTDRFSLA

IDAIDRIPRFCDTGSGVREILLNLQFACKNHAYEYGVDPQEITDWQWPFRDTP

SEQ ID No: 44
ATGACAAATCCTGTAATAGGTACTCCTTGGGCAAAGTTAGAAACACCAATAGCCGA

AGAAACCATAGAAGCCGTAGATAAATACTGGAGAGCTGCAAACTATTTGTCCATAG

GTCAAATCTACTTGAGAAGTAATCCATTAATGAAGGAACCTTTTACAAGAGAAGAT

GTCAAGCATAGATTAGTAGGTCACTGGGGTACTACACCAGGTTTGAACTTCTTGTTG

GGTCATATCAACAGATTGATCGCTGATCACCAACAAAACACTGTTATTATCATGGGT

CCAGGTCATGGTGGTCCTGCAGGTACCTCCCAAAGTTATTTGGATGGTACTTACTCA

GAATACTACCCAAAGATCACAAACGACGAAGCTGGTTTGCAAAAGTTTTTCAGACA

ATTTTCCTATCCAGGTGGTATACCTAGTCATTTCGCTCCAGAAACTCCTGGTTCCATC

CACGAAGGTGGTGAATTGGGTTATGCATTATCCCATGCTTACGGTGCAATCATGAAT

AACCCAAGTTTGTTTGTTCCTTGTATTGTCGGTGACGGTGAAGCAGAAACCGGTCCA

TTAGCCACTGGTTGGCAATCTAACAAATTGGTTAATCCAAGAACCGATGGTATTGTC

TTGCCTATCTTGCATTTGAATGGTTACAAGATTGCTAATCCAACTATCTTGTCTAGA

ATCTCAGATGAAGAATTACACGAATACTTCAAGGGTATGGGTTACGAACCTTTTGA

ATTTGTTGCTGGTTTCGATGACGAAGATCATTTGTCAATACACAGAAGATTTGCAGA

TTTGTTAGAAACAGTCTTCGACAAGATCTGCAACATCAAGGCTAGAGCAGAAACTG

ATGACATGACAAGACCATGTTACCCTATGATCATTTTTAGAACACCAAAAGGTTGG

ACCTGCCCTAAGTTCATAGATGGTAAAAAGACTGAAGGTTCTTGGAGAGCACATCA

AGTTCCATTGACTTCAGCAAGAGACACAGAAGCCCACTTCCAAATCTTGAAAAATT

GGTTAGCTTCTTACAAGCCTGAAGAATTGTTCGATGAAAAGGGTGCATTAAGACCA

GAAGTTACATCATTCATGCCTAAGGGTGACTTAAGAATTGGTGAAAATCCAAACGC

TAATGGTGGTAGATTGTTGAAGCCATTGGAATTACCTGATATCCATGACTACGAAAT

AGATGTTAAAAAGCATGGTCACGGTTGGGGTGCCACCGAAGCTACTAGAGTATTGG

GTTATTACAAGAGATGTTTTAGCTAAGAATCCAACCGATTTTAGAATTTTCGGTC

CTGACGAAACTGCATCTAACAGATTAGCCGCTGCATATGAAGTAACAAATAAGCAA

TGGGATGCAGACTACTTGTCCGAATTAACAGATGAACATATGGCCCACACCGGTCA

AGTTATCGAACAATTAAGTGAACATCAAATGGAAGGTTTCTTGGAAGGTTATTTGTT

AACTGGTAGACACGGTATTTGGTCTTCATACGAATCTTTCGTTCATGTCATAGATTC

-continued

```
AATGATCAATCAACACGCTAAATGGTTGGAAGCAACTGTTAGAGAAATACCATGGA
GAAAGCCTATCGCTGGTTTGAACTTGTTAGTAACATCTCATGTTTGGAGACAAGATC
ATAATGGTTTTTCACACCAAGACCCAGGTTTCGTTGATATATTGTTGAACAAAAACT
TCAACAACGATCATGTTGTCAACATCTATTTCCCTGCCGACGCTAACATGTTGTTGA
ACGTTGGTGAAAGATGTTACAAATCCACAAACTGCATCAATGCAATTTTTGCCGGTA
AACAACCAGCCGCTACCTATCAAAGTGTCGATGAAGCAGCCGCTGAATTGGAAAAA
GGTGCAGCCAGATGGGATTGGGCTTCTAATGCAAAGGACGCCGAAGATGCTGACGT
TGTTATTGCTACTGCTGGTGACATACCAACTCAAGAAGCATTGGCTGCTGATGACAT
GTTGCAAAAATTGGGTGTAAAGGTTCAATTCGTTAACGTCGTAGATTTGTTGAAGAT
CCAAGACGCTGAAGAAAACGATCAAGCATTGTCTGACGAAGAGTTTACTGAATTAT
TCTCAAAGGATAAGCCAGTCTTGTTTGCATTCCATGCCTATCCTGGTTCAATCTATA
GATTGATACATGGTAGACCAAACCACGATAATTTTTCCGTACATGGTTATGAAGAA
CAAGGTAGTACCACTACACCTTTCGATATGGTCAGAGTAAATAACATGGACAGATG
GTGTTTAGCCGCTTCTGCCTTGCAATTAGTTGATGCTAATAAGTACACTGATCAAAT
AGACAAGTGGACAAAGTTTAGAGATGAAGCCTTTCAATTCGCTGTTGATAAAGGTT
ATGATCATCCAGACTACACCGATTGGGTATGGCCTGATGCTAACAGAGCAGGTCAA
GAAACTATTTCTGCCACAGCAGCCACCGCTGGTGACAATGAATAA
                                                SEQ ID No: 45
MTNPVIGTPWAKLETPIAEETIEAVDKYWRAANYLSIGQIYLRSNPLMKEPFTREDVKH
RLVGHWGTTPGLNFLLGHINRLIADHQQNTVIIMGPGHGGPAGTSQSYLDGTYSEYYPK
ITNDEAGLQKFFRQFSYPGGIPSHFAPETPGSIHEGGELGYALSHAYGAIMNNPSLFVPCI
VGDGEAETGPLATGWQSNKLVNPRTDGIVLPILHLNGYKIANPTILSRISDEELHEYFKG
MGYEPFEFVAGFDDEDHLSIHRRFADLLETVFDKICNIKARAETDDMTRPCYPMIIFRTP
KGWTCPKFIDGKKTEGSWRAHQVPLTSARDTEAHFQILKNWLASYKPEELFDEKGALR
PEVTSFMPKGDLRIGENPNANGGRLLKPLELPDIHDYEIDVKKHGHGWGATEATRVLG
YYTRDVLAKNPTDFRIFGPDETASNRLAAAYEVTNKQWDADYLSELTDEHMAHTGQVI
EQLSEHQMEGFLEGYLLTGRHGIWSSYESFVHVIDSMINQHAKWLEATVREIPWRKPIA
GLNLLVTSHVWRQDHNGFSHQDPGFVDILLNKNFNNDHVVNIYFPADANMLLNVGER
CYKSTNCINAIFAGKQPAATYQSVDEAAAELEKGAARWDWASNAKDAEDADVVIATA
GDIPTQEALAADDMLQKLGVKVQFVNVVDLLKIQDAEENDQALSDEEFTELFSKDKPV
LFAFHAYPGSIYRLIHGRPNHDNFSVHGYEEQGSTTTPFDMVRVNNMDRWCLAASALQ
LVDANKYTDQIDKWTKFRDEAFQFAVDKGYDHPDYTDWVWPDANRAGQETISATAA
TAGDNE
                                                SEQ ID No: 46
ATGACCTCCCCTGTAATTGGTACCCCATGGAAGAAGTTAAACGCTCCTGTAAGTGA
AGAAGCTATTGAAGGTGTCGATAAGTATTGGGGTGCTGCAAACTACTTGTCCATCG
GTCAAATATATTTGAGAAGTAACCCATTGATGAAAGAACCTTTCACTAGAGAAGAT
GTAAAGCATAGATTGGTTGGTCACTGGGGTACTACACCAGGTTTGAACTTTTTAATC
GGTCATATCAACAGATTGATCGCTGATCACAAGCAAAACACCGTTATTATCATGGG
TCCAGGTCATGGTGGTCCTGCAGGTACTGCCCAATCTTATTTGGATGGTACCTACAC
TGAAACATTCCCTAAAATAACTAAGGACGAAGCAGGTTTGCAAAAGTTTTTCAGAC
```

```
AATTTTCCTACCCAGGTGGTATTCCTAGTCATTATGCTCCAGAAACACCTGGTTCAA

TACACGAAGGTGGTGAATTGGGTTACGCATTATCCCATGCTTATGGTGCAGTTATGA

ATAACCCAAGTTTGTTTGTTCCTGCAATTGTCGGTGACGGTGAAGCCGAAACTGGTC

CATTAGCAACAGCCTGGGATTACGACAACATCATTAATCCAAGAACTGATGGTATC

GTTTTGCCTATATTGCACTTAAACGGTTACAAGATCGCTAACCCAACAATCTTGTCT

AGAATCTCAGATGAAGAATTGCATGAATTTTTCCACGGTATGGGTTATGAACCTTAC

GAATTTGTTGCTAGATTCGATAATGAAGACCATTTGTCTATTCACAGAAGATTTGCA

GAATTGTTCGAAACTGTCTTCGACGAAATCTGTGATATCAAAGCCGCTGCACATACC

GATGACATGACTAGACCATTCTACCCTATGATAATCTTTAGAACCCCAAAAGGTTGG

ACTTGCCCTAAGTTCATTGATGGTAAAAAGACAGAAGGTTCCTGGAGAAGTCATCA

AGTACCATTGGCTTCCGCAAGAGATACCGAAGCTCACTTTGAAGTTTTGACTAACTG

GTTGGAATCTTACAACCCTGAAGAATTGTTCGATGAAAACGGTGCTGTAAAACCAG

AAGTTACAGCTTTTATGCCTACCGGTGAATTAAGAATCGGTGCTAATCCAAACGCA

AATGGTGGTGTTATTAGAGAAGAATTGAATTTGCCTGCCTTAGAAGATTACGAAGT

AAAAGAAGTTGCTGAATATGGTCATGGTTGGGGTCAATTGGAAGCTACTAGAAGAT

TAGGTGTTTACACAAGAGACATTTTTAAGAACAACCCAGATTCTTTTAGAATATTCG

GTCCTGATGAAACTGCATCAAACAGATTGCAAGCCGCTTACGACGTCACAAATAAG

AAATGGGATGCAGGTTATTTGTCTTCACAAGTAGATGACCATATGGCCGTCACAGG

TCAAGTAACCGAACAATTGTCTGAACACCAAATGGAAGGTTTCTTGGAAGCTTACTT

GTTAACTGGTAGACATGGTATCTGGTCCAGTTATGAATCTATTGTCCATGTAAACGA

TTCAATGTTGAATCAACACGCAAAATGGTTCGCAGCCACAGTTAGAGAAATTCCAT

GGAGAAAGCCTATCTCTTCAATGAATTTGTTAGTTTCCAGTCATGTCTGGAGACAAG

ACCAAACAGGTTTTTCTCACCAAGATCCAGGTGTCACCTCCGTATTGTTGAGTAGAT

GTTTCAACAACGATAACGTTATAGGTATATACTTTGCTGTCGATTCCGACATGTTGT

TAGCCGGTGCTGATAAATGCTATCAAAGTAGAAAGGTCATGAATGCCGGTATAGTA

GGTAGAGCTCCAGCTGCAACCTGGTTGATCTTAGGTGAAGCAAGAGCCGAATTGGA

AAAAGGTGCCGCTGAATGGGAATGGGCCTCTACTGCTAAGTCAAATGACGAAGCTC

AAATTGTATTAGCTTCAGCAGGTGACGTTCCTGCACAAGAAATCATGGCAGCCGCT

GACAAGTTGAACGAATTGGGTATTAAGTTTAAAGTTGTCAACGTAGTTGATTTGGTT

AAGTTGCAATCTACAAAGGAAAATGACCAAGCTATATCAGATGCAGACTTCGCCGA

CTTGTTTACCGAAGATAAGCCAGTCTTATTCGCTTATCATTCTTACGCATCAGACGTT

AGAGGTTTGATCTACGATAGACCAAATCATGATGACTTTAACGTTCACGGTAATCA

AGAACAAGGTTCTACCACTACACCTTACGACATGGTTAGAGTCAACAACATCGATT

CATACGAATTGGTTGCCGAAGCTTTAAGAATGATAGATGCCGACAAGTACGCTGAT

GAAATCAACGAATTGGAAGCTTTTAGACAAGAAGCATTTCAATTCGCCGTTGATAA

TGGTTATGATCATCCAGACTACACTGATTGGGTCTATTCTGGTGTCAACACAACCAA

GCAAGGTGCAGTCTCAGCCACAGCAGCAACCGCAGGTGACAACGAATAA

SEQ ID No: 47
MTSPVIGTPWKKLNAPVSEEAIEGVDKYWGAANYLSIGQIYLRSNPLMKEPFTREDVKH

RLVGHWGTTPGLNFLIGHINRLIADHKQNTVIIMGPGHGGPAGTAQSYLDGTYTETFPKI

TKDEAGLQKFFRQFSYPGGIPSHYAPETPGSIHEGGELGYALSHAYGAVMNNPSLFVPAI
```

-continued

```
VGDGEAETGPLATAWDYDNIINPRTDGIVLPILHLNGYKIANPTILSRISDEELHEFFHGM

GYEPYEFVARFDNEDHLSIHRRFAELFETVFDEICDIKAAAHTDDMTRPFYPMIIFRTPKG

WTCPKFIDGKKTEGSWRSHQVPLASARDTEAHFEVLTNWLESYNPEELFDENGAVKPE

VTAFMPTGELRIGANPNANGGVIREELNLPALEDYEVKEVAEYGHGWGQLEATRRLGV

YTRDIFKNNPDSFRIFGPDETASNRLQAAYDVTNKKWDAGYLSSQVDDHMAVTGQVT

EQLSEHQMEGFLEAYLLTGRHGIWSSYESIVHVNDSMLNQHAKWFAATVREIPWRKPIS

SMNLLVSSHVWRQDQTGFSHQDPGVTSVLLSRCFNNDNVIGIYFAVDSDMLLAGADKC

YQSRKVMNAGIVGRAPAATWLILGEARAELEKGAAEWEWASTAKSNDEAQIVLASAG

DVPAQEIMAAADKLNELGIKFKVVNVVDLVKLQSTKENDQAISDADFADLFTEDKPVL

FAYHSYASDVRGLIYDRPNHDDFNVHGNQEQGSTTTPYDMVRVNNIDSYELVAEALR

MIDADKYADEINELEAFRQEAFQFAVDNGYDHPDYTDWVYSGVNTTKQGAVSATAAT

AGDNE
```

SEQ ID No: 48
```
ATGACAAACATCAACTATTCCTCAGAATCATACTTAAAGAAGGTAGACGCTTATTG

GAGAGCCACAAACTACATTTCAGTCGGTCAATTGTATTTGAAGGGTAACCCATTGTT

AAGAGAACCATTAAAGCCTGAACATGTTAAAAATGCTGTTTTTGGTCACTGGGGTA

CTATAGCTGGTCAAAACTTCATCTACGCACATTTGAATAGAGTTATCAACAAATACG

ATTTGTCCATGTTGTACATTAGTGGTCCAGGTCACGGTGGTCAAGTCATGGTATCTA

ACTCATATTTGGATGGTTCCTATAGTGAAGTTTACCCTGAAATTACTCAAGACTTGG

AAGGTTTATCCAAGTTGTACAAGCAATTTTCTTTCTCAGGTGGTATCGGTTCTCATG

CTACACCACAAGCACCTGGTTCAATTCACGAAGGTGGTGAATTAGGTTATTCTTTGG

TTCATGGTTTTGGTGCCATCTTAGATAATCCAGACTTGATTGCTACCGTTGTCGTAG

GTGACGGTGAAGCCGAAACTGGTCCTTTAGCTACATCTTGGCAATTGAATAAGTTTA

TAAACCCAGTTACAGATGGTGTTGTCTTACCTATCTTGTATTTGAATGGTTTCAAAA

TCTCAAACCCAACAATTATGGCTAAGATGACCGATGAAGAATTACAAAAGTACTTC

GAAGGTTTGGGTTGGGACCCAATTTTCGTCGAGGGTAATGAACCTGAAGTAATGCA

TCAATTGATGGCAGAAAAGATGGATGAAGCCATAGAAAAGATTTTGACAATCAAAA

AGCACGCATTGGAAGAAATGATATGTCTAGACCAAAGTGGCCTGTTATTTTAAAC

AGAACCCCAAAAGGTTGGACTGGTCCTAAGGAATTGGATGGTAAACCAATTGAAGG

TTCCTTTAGAGCCCATCAAGTTCCAATACCTTTCGATAGTAAGCACATGGAATGTGC

TGATGACTTTGTCAAATGGATGAATACCTATGGTCCTGAAGAATTATTCACTGAAGA

TGGTAAATTGGTTGAAGAAATCGCAGAAATCATCCCAAAGGGTGACAGAAGAATGT

CATGCAATCCTGCCACTAACGGTGGTAAAATAATGAAGGGTTTGAGATTGCCAGAT

TATAGAGAATACGCAATCGACAATAAGGAAAAGGGTAAAAACGTTGCCCAAGATA

TGTTGATATTGGGTAAATACGTCAGAGATGTAATGAAGTTAAACGACAAGGAAAGA

AACTTTAGAGTCTTCTCTCCAGATGAAGCTGCATCAAACAGATTGTACGCTATGTTC

GAAGAAACAAAGAGACAATGGGTTGGTGAAATTGATGAACCATACGACGAATTTTT

AGCACCTGATGGTAGAATTTTAGACTCCATGTTGAGTGAACATATAGCTGAAGGTG

CATTGGAAGCCTATTTGTTAACAGGTAGACATGGTTTTATCCACTCTTACGAATCAT

TCTTAAGAGTAGTTGATTCAATGATCACCCAACATTTCAAGTGGTTGAACCAATGTG

AAGATATTCCATGGAGAGCTGACATCCCTTCCTTGAATTTGATTAATACTTCTCATA
```

-continued

```
TCTGGCAACAAGATCATAACGGTTATACACACCAAGACCCAGGCATGTTAGGTCAT

TTGGCTGATAAAAATTCTGGTTTAATTCACGAATACTTGCCTGTTGATGCAAACACA

TTGTTAGTCACCTTCGACAAGTGCATTAGATCTATAAATCAAGTTAACGTCATGACA

GCCTCAAAACATCCAAGACAACAATGGTTCACCATCGAAGAAGCTGAATATTTGGT

AAATAAGGGTTTGGGTATCGTTGATTGGGCATCTACTGACAAAAACGGTGAAACAG

ATATTGTATTTGCAATGGCCGGTGACACCCCAACTTTAGAAGGTTTGGCCGCTGTTC

AATTGTTACATGATTATTTGCCTGACTTGAAGATTAGATTCGTTAACATCGTCGATTT

GTTGAAATTGCAATCCCCAGAAGTTTACGAACATGGTATCAGTGATGAAGAGTTTA

ATATGATCTTCACCAAGGACAAACCTATCATTTTTGGTTTCCACGGTTACGAAAACT

TAGTCGATACTTTGTTTTTCAAGAGAGACAACCATAACGTATCTGTTCACGGTTACA

GAGATAAAGGTGAAATAACTACAGGTTTTGACATGAGAGTCATGAACGAATTAGAT

AGATTCAACTTGGTAAAGGACGCTATCTATAATTTGCCACAATTGGGTAACAAAGG

TGCACATATCATCCAAGAAATGAACGAAAAGTTGGAAATCCATACTAAGTTCGTTC

ACGAAAACGGTATCGATTTGCCTGAAATTGCTAACTGGCAATGGAAGGGTTTGAAA

TAA
```

SEQ ID No: 49
```
MTNINYSSESYLKKVDAYWRATNYISVGQLYLKGNPLLREPLKPEHVKNAVFGHWGTI

AGQNFIYAHLNRVINKYDLSMLYISGPGHGGQVMVSNSYLDGSYSEVYPEITQDLEGLS

KLYKQFSFSGGIGSHATPQAPGSIHEGGELGYSLVHGFGAILDNPDLIATVVVGDEAET

GPLATSWQLNKFINPVTDGVVLPILYLNGFKISNPTIMAKMTDEELQKYFEGLGWDPIFV

EGNEPEVMHQLMAEKMDEAIEKILTIKKHALEENDMSRPKWPVILNRTPKGWTGPKEL

DGKPIEGSFRAHQVPIPFDSKHMECADDFVKWMNTYGPEELFTEDGKLVEEIAEIIPKGD

RRMSCNPATNGGKIMKGLRLPDYREYAIDNKEKGKNVAQDMLILGKYVRDVMKLND

KERNFRVFSPDEAASNRLYAMFEETKRQWVGEIDEPYDEFLAPDGRILDSMLSEHIAEG

ALEAYLLTGRHGFIHSYESFLRVVDSMITQHFKWLNQCEDIPWRADIPSLNLINTSHIWQ

QDHNGYTHQDPGMLGHLADKNSGLIHEYLPVDANTLLVTFDKCIRSINQVNVMTASKH

PRQQWFTIEEAEYLVNKGLGIVDWASTDKNGETDIVFAMAGDTPTLEGLAAVQLLHDY

LPDLKIRFVNIVDLLKLQSPEVYEHGISDEEFNMIFTKDKPIIFGFHGYENLVDTLFFKRD

NHNVSVHGYRDKGEITTGFDMRVMNELDRFNLVKDAIYNLPQLGNKGAHIIQEMNEKL

EIHTKFVHENGIDLPEIANWQWKGLK
```

SEQ ID No: 50
```
ATGGCAGAAGAAACCTCATCATTAACATCATTCGGTCAAGCAAGATCCACTGTCAA

AGACCAACCATTAACTGTAGAAGAATTAAAAAAAATTGATGCCTATATGAGAGCTT

CTTTGTACTTATGTTTGGGCATGTTGTATTTGAGACAAAACCCATTGTTGAAGGAAC

CTTTGAAGAAGAACATTTGAAGGCCAGATTGTTAGGTCACTGGGGTTCCGATGCT

GGTCAAATCTTTACTTACATCCATATGAACAGATTGATTAAGAAATACGATTTGGAC

GCTTTGTTCGTTAGTGGTCCAGGTCACGGTGCACCTGCCGTCTTATCCCAAAGTTAT

TTGGAAGGTGTATATACCGAAGTTTACCCAAATATTACTGAAGATGTCGAGGGTAT

GAGAAGATTTTTCAAGCAATTTTCCTTCCCTGGTGGTGTTGGTAGTCATGCAACACC

AGAAACCCCTGGTTCTTTACACGAAGGTGGTGAATTGGGTTACTCTATTTCACATGC

TTTTGGTACAGTCTTCGATAACCCAAACTTAATCACTTTGACAATGGTTGGTGACGG

TGAATCAGAAACCGGTCCTTTAGCTGCATCCTGGCATAGTACAAAGTTCTTGAACCC
```

-continued

```
AATCACCGATGGTGCTGTATTGCCTGTTTTGCATTTGAATGGTTACAAGATCAATAA

CCCAACAGTTTTAGCTAGAATATCCCACGAAGAAATCGAAGCATTGTTTATTGGTTA

TGGTTGGAAACCTTACTTCGTTGAAGGTTCTGATTTGACCTCAATGCATCAAGCAAT

GGCCGCTACTTTAGAAAAGGCCGTTTTGGAAATTAAAGCATACCAAAAGCAAGCCA

GAGATTCTGGTAAAGCCTTTAGACCAAGATGGCCTATGATTATATTAAGATCTCCAA

AGGGTTGGACTGCACCTAGAAACGTTTCAGGTCATCACTTGGAAGGTTATTGGAGA

GCCCATCAAATTCCATTAGCCGATGTTGCTTCCAATAGTGAACACTTGAAATTGTTA

GAAGACTGGATGAGATCTTACAAGCCAGAAGAATTATTCACAGAAGATGGTAAATT

GATACCTGAATTAAAGGCATTGCCACCTGCAGGTCAAGCCAGAATGTCTGCCAATC

CAGTCTCAAACGGTGGTTTAGTAAGAAAAGCATTAAACTTGCCTGATTTCAAGGAC

TACGCTATTAAGGATATAGCACCAGGTGTTACTTTAGCCCCTTCTATGTCAAATATG

GCTTTGTTCGTCAGAGATGTAATTAAAAAGAATCAAACAAACTTCAGATTATTCGGT

CCAGACGAAACCGAATCAAACAAATTGGCAGCCGTTTATGAAGCTGGTAAAAAGGT

CTGGATGGGTGAATACTTACCAGAAGATACCGACGGTGGTAATTTGGCTCATGCAG

GTAGAGTTATGGAAATTTTGTCCGAACACACTGTCGAAGGTTGGTTAGAAGGTTAT

GTATTGTCTGGTAGACATGGTTTGTTAAACTCATACGAACCTTTTATTCATATCATCG

ATAGTATGGTTAACCAACACTGTAAGTGGATAGAAAAGTGCTTAGAAGTCGAATGG

AGAGTTAAAGTCTCTTCATTGAACATCTTGTTGACCGCAACTGTTTGGAGACAAGAT

CATAATGGTTTTACTCACCAAGATCCAGGTTTCTTAGACGTTGTCGCTAATAAGTCT

CCTGAAGTAGTTAGAATATATTTGCCACCTGATGGTAATTGTTTGTTATCCGTAATG

AACCATTGCTTCGACAGTAAAAATTACGTTAACGTCGTAGTTGCTGATAAGCAAGA

CCATTTGCAATACTTGGATATGGAAGCTGCAGTAGCTCACTGTACAAAAGGTTTAG

GTATTTGGGAATGGGCATGCGTTGGTGACCCAAATGAAAACCCTGACTTAGTAATG

GCATGTTGCGGTGACGTTCCAACTATGGAATCTTTGGCCGCTACAGCTTTGTTGAAG

GAATATTTGCCTGAATTGAAGATCAGATTCGTTAACGTCGTTGATTTGTTTAAATTG

ATATCACATGTCGATCATCCACACGGTTTGACCGACAGACAATGGGTATCCTACTTC

ACTGAAGACACACCAATCATCTTTAATTTCCATAGTTACCCTTGGTTAATACACAGA

TTGACATACAAGAGACCAGGTTCACAAAACATCCATGTTAGAGGTTACAAGGAAAA

GGGTAACATAGATACTCCTTTAGAATTGGCAATCAGAAATGAAACAGACAGATACT

CTTTAGCTATGGATGCAATAGACAGATTGCCACATTTGAAAAATAAGGGTTCAATG

GCTAGAGAAAAATTGTACGATGCACAAATTAAGGCCAGAGACTGGGCTTTTGAACA

CGGTATAGATCCAGAAGACGTTAGAAAATGGAAGTGGCCATACGGTCCTAAAACTG

AAGGTATTGCCTCTAAGTTGGGTTTCGGTGGTGAAAATAAGCAACAAGTTGCTTCCG

TCGGTACAAGTGAATAA
```

SEQ ID No: 51

```
MAEETSSLTSFGQARSTVKDQPLTVEELKKIDAYMRASLYLCLGMLYLRQNPLLKEPLK

KEHLKARLLGHWGSDAGQIFTYIHMNRLIKKYDLDALFVSGPGHGAPAVLSQSYLEGV

YTEVYPNITEDVEGMRRFFKQFSFPGGVGSHATPETPGSLHEGGELGYSISHAFGTVFDN

PNLITLTMVGDGESETGPLAASWHSTKFLNPITDGAVLPVLHLNGYKINNPTVLARISHE

EIEALFIGYGWKPYFVEGSDLTSMHQAMAATLEKAVLEIKAYQKQARDSGKAFRPRWP

MIILRSPKGWTAPRNVSGHHLEGYWRAHQIPLADVASNSEHLKLLEDWMRSYKPEELF
```

TEDGKLIPELKALPPAGQARMSANPVSNGGLVRKALNLPDFKDYAIKDIAPGVTLAPSM
SNMALFVRDVIKKNQTNFRLFGPDETESNKLAAVYEAGKKVWMGEYLPEDTDGGNLA
HAGRVMEILSEHTVEGWLEGYVLSGRHGLLNSYEPFIHIIDSMVNQHCKWIEKCLEVEW
RVKVSSLNILLTATVWRQDHNGFTHQDPGFLDVVANKSPEVVRIYLPPDGNCLLSVMN
HCFDSKNYVNVVVADKQDHLQYLDMEAAVAHCTKGLGIWEWACVGDPNENPDLVM
ACCGDVPTMESLAATALLKEYLPELKIRFVNVVDLFKLISHVDHPHGLTDRQWVSYFTE
DTPIIFNFHSYPWLIHRLTYKRPGSQNIHVRGYKEKGNIDTPLELAIRNETDRYSLAMDAI
DRLPHLKNKGSMAREKLYDAQIKARDWAFEHGIDPEDVRKWKWPYGPKTEGIASKLG
FGGENKQQVASVGTSE

SEQ ID No: 52
ATGGTTGCCACACCTGAAAGACCTACATTAGAACAAACCCCATTATCCGCAGAAGA
ATTAAGACAAATACAAGCATACTGGAGAGCATGTAACTATTTGGCTGTTGGTATGA
TATATTTGAGAGATAACCCATTGTTGAAAGACCCTTTGACTGAAGATCATGTTAAGA
ATAGATTGTTGGGTCACTGGGGTTCTTCACCAGGTTTGTCTTTTATATATATCCATTT
GAACAGATTAATTAAAAAGTATGGTTTAGATGTTATATACATGGCCGGTCCAGGTC
ACGGTGCTCCTGGTATTTTGGGTCCAGTCTACTTAGAAGGTACTTATTCCGAAACAT
ACCCTGACAAAAGTGAAGATGAAGAGGGTATGAAAAAGTTTTTCAAGCAATTTTCT
TTCCCAGGTGGTATTGGTTCACATTGTACCCCAGAAACTCCTGGTTCTATACACGAA
GGTGGTGAATTGGGTTATTCCTTAAGTCATGCTTACGGTGCTGCATTGGACAATCCT
GATTTGATTGTTGCCGCTGTTGTCGGTGACGGTGAAGCAGAAACAGGTCCATTGGCC
ACCGCTTGGCATTCTAATAAGTTTATTAACCCTATTAGAGATGGTGCTGTTTTGCCA
ATCTTGCATTTGAATGGTTATAAGATTGCAAACCCAACTATCTTAGCCAGAATTTCC
CACGAAGAATTGGAATATTTGTTTAAAGGTTACGGTTACAAGCCTTACTTTGTTGAA
GGTAGTGATCCAGAAGTCATGCATCAAAGATGGCAGCCACATTAGAAACCGCAAT
AGCCGAAATCAAGCACATTCAACAAGAAGCTAGAACATCAGGTGTCGCAAAAAGA
CCAATATGGCCTATGATCGTATTGAGATCTCCTAAGGGTTGGACTGGTCCAGCTTCA
GTTGACGGTAAAAAGACAGAAGATTTCTGGAGATCTCATCAAGTCCCTTTATCAGG
CATGCATGGTAATCCAGCACACATTAAAGTATTGGAAGACTGGTTAAAGTCCTATA
CCCCTGAAGAATTGTTCGATGAAAACGGTACTTTAATTCCTGAATTGAAGGAATTAG
CTCCAACTGGTCATCACAGAATGTCAGCAAATCCACATGCCAACGGTGGTTTGTTAA
GAAAAGACTTGAAGATGCCTGATTTCAGAAATTACGGTGTAGAAGTTGCTAAACCA
GGTACTGTCGAAGTTGGTAACACAGCATTGTTGGGTAACTTTTTAAGAGATGTTATG
GCCAACAACATGACAAACTTCAGAGTCTTCGGTCCTGATGAAACCGCCTCTAATAG
ATTGAACGCTATCTATGAAATCTCTAAGAAAGTTTGGATGGGTGAAATATTACCAG
AAGATGCAGACGGTACTGAAATCACTACAGATGGTAGAGTTATGGAAATGTTATCA
GAACATACATTGCAAGGTTGGTTAGAAGGTTATTTGTTAACAGGTAGACATGGTTTC
TTTCACACCTACGAAGCATTTGCACATGTAGTTGACTCTATGTTTAATCAACACGCT
AAATGGTTGGATATTTGTAAGAACGAAGTCCCATGGAGAGCATCAGTATCCAGTTT
AAACATCTTGTTATCTTCAACAGTTTGGAGACAAGATCATAACGGTTTCTCCCACCA
AGACCCAGGTTATGTTGATTTGGTCACCAATAAGAGTGCTGACGTCGTAAGAGTCT
ACTTTCCACCTGATGCAAATTGTTTGTTATCCGTAGCCAACCATTGCTTGAAAAGTA

-continued

```
CAGACTACGTTAACGTCATCGTATCTGATAAGCAAATCCATTTGCAATACTTAAACA
TGGACCAAGCCATTAAACACTGCACCAAGGGTATTGGTATATGGGATTGGGCTTCT
AATGATGACTGTGGTACTGAACCAGACCATCCTGATGTAATAATGGCATCATGCGG
TGACGTTGCTACCAAAGAAGCATTGGCTGCAACTGCCATATTAAGAGAAGAATTTC
CTGACTTGAAAGTTAGATTCATCAACGTTGTCGATTTGTTTAAGTTACAATCCGAAA
TAGAACATCCACACGGTTTGAGTGATAGAGACTTCGATAATTTGTTTACTAAGGATA
AGCCTATCATTTTCAATTTCCATGGTTACCCATGGTTGATTCACAAATTAACCTACA
GAAGAACTAACCATCACAACTTACATGTTAGAGGTTACAAGGAAAAGGGTAACATC
AACACACCTTTGGAATTAGCTATTAATAACCAAATCGACAGATTCAATTTGGTTATT
GATGTTATAAACAGAGTACCAAAATTAGGTTCTGCCGCTGCATACGTTTACGAAAG
AATGAAGAACGCAATCATAGAACATAGAGCCTATGCTTACGAACACGGTATCGATA
AGCCTGAAATTAATAACTGGAAGTGGCCACATTAA
```

SEQ ID No: 53
```
MVATPERPTLEQTPLSAEELRQIQAYWRACNYLAVGMIYLRDNPLLKDPLTEDHVKNR
LLGHWGSSPGLSFIYIHLNRLIKKYGLDVIYMAGPGHGAPGILGPVYLEGTYSETYPDKS
EDEEGMKKFFKQFSFPGGIGSHCTPETPGSIHEGGELGYSLSHAYGAALDNPDLIVAAVV
GDGEAETGPLATAWHSNKFINPIRDGAVLPILHLNGYKIANPTILARISHEELEYLFKGY
GYKPYFVEGSDPEVMHQKMAATLETAIAEIKHIQQEARTSGVAKRPIWPMIVLRSPKG
WTGPASVDGKKTEDFWRSHQVPLSGMHGNPAHIKVLEDWLKSYTPEELFDENGTLIPE
LKELAPTGHHRMSANPHANGGLLRKDLKMPDFRNYGVEVAKPGTVEVGNTALLGNFL
RDVMANNMTNFRVFGPDETASNRLNAIYEISKKVWMGEILPEDADGTEITTDGRVMEM
LSEHTLQGWLEGYLLTGRHGFFHTYEAFAHVVDSMFNQHAKWLDICKNEVPWRASVS
SLNILLSSTVWRQDHNGFSHQDPGYVDLVTNKSADVVRVYFPPDANCLLSVANHCLKS
TDYVNVIVSDKQIHLQYLNMDQAIKHCTKGIGIWDWASNDDCGTEPDHPDVIMASCGD
VATKEALAATAILREEFPDLKVRFINVVDLFKLQSEIEHPHGLSDRDFDNLFTKDKPIIFN
FHGYPWLIHKLTYRRTNHHNLHVRGYKEKGNINTPLELAINNQIDRFNLVIDVINRVPKL
GSAAAYVYERMKNAIIEHRAYAYEHGIDKPEINNWKWPH
```

SEQ ID No: 54
```
ATGACTGTAGACTATAACTCAAAAGAATACTTAACATTGGTCGATAAATGGTGGAG
AGCAGCAAACTACTTGTCCGTTGGTCAAATGTTCTTGAGAGATAACCCATTGTTGCA
AGAAGAAGTTACTGCAGACCATGTCAAATTGAATCCTATCGGTCACTGGGGTACAA
TTGGTGGTCAAAACTTCTTGTATGCTCATTTGAATAGAATTATAAACAAGTACAATG
TTAACATGTTTTACATTGAAGGTCCAGGTCACGGTGGTCAAGTCATGGTAACTAATT
CCTACTTGGATGGTAGTTATACTGAAAGATACCCAGAGTTTACTCAAGACATCGCTG
GTATGAAGAAATTGTTTAAAACCTTTTCTTTCCCTGGTGGTATTGGTTCACATGCTGC
ACCAGAAACTCCTGGTTCCATGCACGAAGGTGGTGAATTGGGTTATGCTTTAAGTCA
TGCAACAGGTGCCATATTGGATAACCCAGACGTTATCGCCGCTACAGTTGTCGGTG
ACGGTGAAGCAGAAACCGGTCCTTTGGCAGCCGGTTGGTTTTCCAATGTATTCATAA
ACCCAGTTAGTGATGGTGCTGTCTTACCTATCTTGTACTTAAATGGTGGTAAAATTG
CTAACCCAACCATCTTGGCAAGAAAGTCAAACGAAGATTTGACTAAGTACTTTGAG
GGTATGGGTTGGAAACCTTACATCGTCGAAGGTACTGATCCAGAACAAGTACATCC
```

-continued

```
TATTATGGCTAAGGTATTGGATGAAGTTATCGAAGAAATTCAAGCAATACAAGCCG

AAGCTAGAAAGGGTAAAGCTGAAGATGCAAAAATGCCACATTGGCCTATGATTTTA

TATAGAACCCCAAAAGGTTGGACTGGTCCTGAAGAAGTTGAAGGTAAAACTATTCA

AGGTTCTTTTAGAGCACATCAAGTCCCAATACCTGTATCAGGTAGAAACATGGAAG

ATATCGACTTGTTAATCAACTGGTTGAAGTCTTACGGTCCAGAAGAATTATTCACAG

AAAACGGTGAATTGGTTGATGAATTAAAGGAATTTGCCCCAAAGGGTGACCATAGA

ATGGCTATGAATCCTTTGACTAATGGTGGTAACCCAAAACCTTTAAATATGCCAAAC

TGGAAGGATTATGCTTTGGAAATAGGTACACCTGGTTCTAAAGATGCACAAGACAT

GATCGAATTTGGTGGTTTCGCCAGAGATATAGTTAAGGAAAACCCAGAAAACTTTA

GAATTTTCGGTCCTGATGAAACAAAGTCTAACAGATTGAACAAGGTTTTCGAAGTC

ACCAATAGACAATGGTTAGAACCAATTTCAGAAAAGTTCGATGAAAACATGTCTGC

TTCAGGTAGAGTTATAGACTCTCAATTGTCAGAACATCAAAACCAAGGTTTCTTGGA

AGCATATGTCTTAACAGGTAGACACGGTTTCTTTGCTTCTTACGAATCTTTCTTTAGA

ACAGTTGATTCCATGATAACCCAACATTTCAAGTGGATAAGAAAATCTGCCAAGCA

CTCATGGAGAAAGCCATATCAAAGTTTGAATTTGATCTCCGCTAGTACAGTTTTTCA

ACAAGATCATAACGGTTACACCCACCAAGACCCAGGTTTGTTAACTCATATTGGTG

AAAAACACGGTGAATATATGAGAGCTTACTTACCTGCAGATACCAATTCTTTGTTAG

CCGTTATGGACAAGGCTTTTAGATCCGAAAACGTCATTAACTACGTAGTTACTTCTA

AGCATCCAAGACCTCAATTTTTCACAGCCGATGAAGCTGAAGAATTGGTAAACGAA

GGTTTGAAAGTTATAGATTGGGCTTCTACAGTTAAGGATAACGAAGAACCAGACGT

CGTAATCGCTGCAGCCGGTACCGAACCTAATTTCGAAGCTATCGCTGCAATTTCATA

TTTGGTAAAAGCATTTCCAGAATTAAAGATCAGATTCGTTAACGTTGTCGATTTGTT

TAGATTGAGATCTCCAGAAATCGACCCTAGAGGTTTGTCAGATGACGAATTTGATG

CAATCTTCACCAAAGACAAGCCAGTTTTCTTTGCCTTTCATTCCTACGAAGGCATGT

TGAAGGATATTTTCTTTACTAGACATAACCACAACTTATACGCACACGGTTACAGAG

AAAATGGTGAAATAACTACACCTTTCGATATGAGAGTCTTGAACGAATTAGACAGA

TTTCATTTGTCAGCACACGTAGCCGATGTAGTTTATGGTGACAAGGCAAGAGACTAC

GTCGCCGAAATGAAGGGTAAAGTACAAGAACATAGAGATTACGTTGAAGAATACG

GTGCTGACATGCCAGAAGTTGAAGATTGGAAATGGGAAGACATTAAGTAA
```

SEQ ID No: 55

```
MTVDYNSKEYLTLVDKWWRAANYLSVGQMFLRDNPLLQEEVTADHVKLNPIGHWGT

IGGQNFLYAHLNRIINKYNVNMFYIEGPGHGGQVMVTNSYLDGSYTERYPEFTQDIAG

MKKLFKTFSFPGGIGSHAAPETPGSMHEGGELGYALSHATGAILDNPDVIAATVVGDGE

AETGPLAAGWFSNVFINPVSDGAVLPILYLNGGKIANPTILARKSNEDLTKYFEGMGWK

PYIVEGTDPEQVHPIMAKVLDEVIEEIQAIQAEARKGKAEDAKMPHWPMILYRTPKGWT

GPEEVEGKTIQGSFRAHQVPIPVSGRNMEDIDLLINWLKSYGPEELFTENGELVDELKEF

APKGDHRMAMNPLTNGGNPKPLNMPNWKDYALEIGTPGSKDAQDMIEFGGFARDIVK

ENPENFRIFGPDETKSNRLNKVFEVTNRQWLEPISEKFDENMSASGRVIDSQLSEHQNQG

FLEAYVLTGRHGFFASYESFFRTVDSMITQHFKWIRKSAKHSWRKPYQSLNLISASTVFQ

QDHNGYTHQDPGLLTHIGEKHGEYMRAYLPADTNSLLAVMDKAFRSENVINYVVTSK

HPRPQFFTADEAEELVNEGLKVIDWASTVKDNEEPDVVIAAAGTEPNFEAIAAISYLVK
```

AFPELKIRFVNVVDLFRLRSPEIDPRGLSDDEFDAIFTKDKPVFFAFHSYEGMLKDIFFTR

HNHNLYAHGYRENGEITTPFDMRVLNELDRFHLSAHVADVVYGDKARDYVAEMKGK

VQEHRDYVEEYGADMPEVEDWKWEDIK

SEQ ID No: 56

ATGACCTCCCCTGTAATCGGTACCCCATGGAAAAAGTTAAATGCCCCAGTATCAGA

AGCAGCCATAGAAGGTGTAGACAAGTATTGGAGAGTTGCTAACTATTTGTCCATTG

GTCAAATATACTTGAGAAGTAATCCATTAATGAAGGAACCTTTTACAAGAGAAGAT

GTCAAGCATAGATTAGTAGGTCACTGGGGTACTACACCAGGTTTGAACTTCTTAATC

GGTCATATCAACAGATTCATTGCAGAACACCAACAAAACACCGTTATTATCATGGG

TCCAGGTCATGGTGGTCCTGCCGGTACTGCTCAATCCTATTTGGATGGTACCTACAC

TGAATATTACCCAAAAATTACCAAGGACGAAGCTGGTTTGCAAAAGTTTTTCAGAC

AATTCTCTTATCCAGGTGGTATACCTTCACATTTTGCTCCAGAAACTCCTGGTTCAAT

CCACGAAGGTGGTGAATTGGGTTATGCATTATCTCATGCATACGGTGCCGTTATGAA

TAACCCATCATTGTTTGTTCCTGCAATTGTCGGTGACGGTGAAGCCGAAACCGGTCC

ATTGGCTACTGGTTGGCAATCAAACAAGTTAGTCAATCCAAGAACTGATGGTATCG

TATTGCCTATATTGCATTTGAATGGTTACAAGATTGCTAATCCAACAATATTGTCCA

GAATCAGTGATGAAGAATTACATGAATTTTTCCACGGTATGGGTTATGAACCTTACG

AATTTGTTGCAGGTTTCGATGACGAAGACCATATGTCTATACACAGAAGATTTGCCG

ATATGTTCGAAACTATCTTCGACGAAATCTGTGATATCAAAGCCGAAGCTCAAACC

AATGATGTTACTAGACCATTCTACCCTATGATCATTTTTAGAACACCAAAGGGTTGG

ACCTGCCCTAAGTTCATTGATGGTAAAAAGACAGAAGGTTCCTGGAGAGCCCATCA

AGTTCCATTGGCAAGTGCCAGAGATACCGAAGCTCACTTTGAAGTCTTGAAGAACT

GGTTGAAGTCTTACAAGCCTGAAGAATTATTCAATGAAGACGGTTCCATTAAAGAA

GATGTTTTGAGTTTTATGCCACAGGGTGAATTAAGAATTGGTCAAATCCTAACGCT

AATGGTGGTAGAATAAGAGAAGATTTGAAATTGCCAAATTTGGATGACTACGAAGT

AAAGGAAGTTAAGGAATTTGGTCATGGTTGGGGTCAATTGGAAGCCACTAGAAGAT

TAGGTGTTTACACAAGAGACGTCATCAAGAATAACCCAGATTCCTTTAGAATTTTCG

GTCCTGATGAAACTGCTAGTAACAGATTGCAAGCTGCATACGAAGTAACAAATAAG

CAATGGGACGCTGGTTACTTGTCCGAATTAGTTGATGAACATATGGCAGTAACAGG

TCAAGTTACCGAACAATTGAGTGAACACCAAATGGAAGGTTTCTTAGAAGCATATT

TGTTAACAGGTAGACATGGTATCTGGTCTTCATACGAATCTTTTGTCCATGTAATCG

ATTCAATGTTGAATCAACACGCAAAGTGGTTAGAAGCCACTGTTAGAGAAATTCCA

TGGAGAAAACCTATATCCAGTATGAACTTGTTAGTCTCTTCACATGTATGGAGACAA

GACCATAATGGTTTCTCTCACCAAGATCCAGGTGTCACCTCAGTATTGTTGAACAAA

ACTTTCAATAACGACCATGTAATCGGTATCTATTTCCCTGTTGATTCTAACATGTTGT

TAGCTGTTGGTGAAAAGGTCTACAAGTCAACAAACATGATCAACGCTATCTTCGCA

GGTAAACAACCAGCCGCTACTTGGTTGACATTAGATGAAGCAAGAGAAGAATTGGA

AAAAGGTGCAGCCGAATGGAAGTGGGCCTCTAATGCTAAAAATAACGACGAAGTA

CAAGTTGTCTTGGCTGGTATTGGTGACGTTCCTCAACAAGAATTAATGGCTGCAGCC

GACAAATTGAACAAGTTAGGTGTTAAGTTTAAAGTAGTTAACATCGTCGATTTGTTG

AAATTGCAATCTGCAAAGGAAAATAACGAAGCCTTGACTGACGAAGAGTTTACTGA

-continued
```
ATTGTTTACTGCTGATAAGCCAGTCTTGTTAGCTTATCATTCTTACGCACACGATGTA

AGAGGTTTAATTTTCGACAGACCAAACCATGATAACTTCAACGTTCACGGTTACAA

GGAACAAGGTTCAACCACTACACCTTACGATATGGTTAGAGTCAATGATATGGACA

GATATGAATTGACAGCTGAAGCATTAAGAATGGTCGATGCTGACAAGTACGAGAC

GAAATTAAAAAGTTGGAAGATTTCAGATTAGAAGCCTTTCAATTCGCTGTTGATAA

AGGTTATGATCATCCAGACTACACAGACTGGGTATGGCCAGGTGTTAAAACCGATA

AGCCTGGTGCAGTTACAGCCACCGCTGCAACTGCTGGTGACAATGAATAAT
```

SEQ ID No: 57
```
MTSPVIGTPWKKLNAPVSEAAIEGVDKYWRVANYLSIGQIYLRSNPLMKEPFTREDVKH

RLVGHWGTTPGLNFLIGHINRFIAEHQQNTVIIMGPGHGGPAGTAQSYLDGTYTEYYPKI

TKDEAGLQKFFRQFSYPGGIPSHFAPETPGSIHEGGELGYALSHAYGAVMNNPSLFVPAI

VGDGEAETGPLATGWQSNKLVNPRTDGIVLPILHLNGYKIANPTILSRISDEELHEFFHG

MGYEPYEFVAGFDDEDHMSIHRRFADMFETIFDEICDIKAEAQTNDVTRPFYPMIIFRTP

KGWTCPKFIDGKKTEGSWRAHQVPLASARDTEAHFEVLKNWLKSYKPEELFNEDGSIK

EDVLSFMPQGELRIGQNPNANGGRIREDLKLPNLDDYEVKEVKEFGHGWGQLEATRRL

GVYTRDVIKNNPDSFRIFGPDETASNRLQAAYEVTNKQWDAGYLSELVDEHMAVTGQ

VTEQLSEHQMEGFLEAYLLTGRHGIWSSYESFVHVIDSMLNQHAKWLEATVREIPWRK

PISSMNLLVSSHVWRQDHNGFSHQDPGVTSVLLNKTFNNDHVIGIYFPVDSNMLLAVGE

KVYKSTNMINAIFAGKQPAATWLTLDEAREELEKGAAEWKWASNAKNNDEVQVVLA

GIGDVPQQELMAAADKLNKLGVKFKVVNIVDLLKLQSAKENNEALTDEEFTELFTADK

PVLLAYHSYAHDVRGLIFDRPNHDNFNVHGYKEQGSTTTPYDMVRVNDMDRYELTAE

ALRMVDADKYADEIKKLEDFRLEAFQFAVDKGYDHPDYTDWVWPGVKTDKPGAVTA

TAATAGDNE
```

SEQ ID No: 58
```
ATGACAGACTCCGCTACAGCCCCAGTTCCTGACAGAAGAGCCACCGCTTTCGCACA

TAGAGACCCAGCAGAATTAGACGATGGTACATTGGCTGCATTAGATGCCTGGTGGA

GAACTGCTAACTATTTGTCTGTTGGTCAAATATACTTGTTGGATAACCCATTGTTAA

GACAACCTTTGGAAAGAGAACAATTAAAGCCAAGATTGTTAGGTCATTGGGGTACT

ACACCTGGTTTGAATTTCTTGTACGCTCACTTGAACAGAGTTATCAGAGAAAGAGAT

TTGTCTACTATCTTCATTACCGGTCCAGGTCATGGTGGTCCTGGTATGGTCGCAAAT

GCCTATTTGGATGGTACTTATTCCGAATTATACCCACACGTAGCAAGAAGTGAAGA

CGGTATTAGAGAATTGTTTAGACAATTTTCATTCCCAGGTGGTATTCCTTCTCATGCT

TCACCAGAAACACCTGGTTCCATACACGAAGGTGGTGAATTGGGTTATGCCTTAAG

TCATGCTTACGGTGCCGCTTTTGATAATCCAGGTTTGTTAGTTGCAGCCGTTGTCGGT

GACGGTGAAGCCGAAACTGGTCCTTTAGCTACATCCTGGCATAGTAACAAGTTCTTA

GATCCATTAGCTGACGGTGTAGTTTTGCCTATCTTGCACTTAAATGGTTACAAAATC

GCAAACCCAACAGTTTTGGCTAGAATACCAGAACATGAATTGTTATCCTTGATGAG

AGGTTATGGTCACACCCCATACTTAGTTAGTGGTGGTTTTGATGGTGAAGACCCTGC

TGCAGTACATAGAAGATTCGCTAAGACCTTGGATACTGTTTTGAACCAAATCGCAG

AAATCAAAGCCTCAGCCGCTGCAGGTACATTGGAAGGTAGACCAGCATGGCCTATG

ATTATATTAAGAACCCCAAAAGGTTGGACTTGTCCTGAAGAAATTGATGGTTTGCCA

GCTGAAAACTCTTGGAGATCACATCAAGTACCATTAGCTTCTGCAAGAGATACTCCT
```

-continued

```
GAACACTTGGGTGTTTTAGACGGTTGGTTGAGATCATACAGACCAGAAGAATTATTT
GATGCCGCTGGTGCACCAATGCCTGTTGCCACAGCTTTGGCACCAGATGGTGAATTA
AGAATGTCTGCTAATCCTGTCGCAAACGGTGGTATTTTGAAGAGAGATTTGGTATTA
CCAGATTTCAGAGACTATGCTGTTGACGTCCCAGTACCTGGTGCAACAGTCAATGA
AGCCACCAGAGTATTGGGTCAATGGTTAGCTGATGTTATTAGAGCAAACCCAGACA
CTTTTAGAATATTCGGTCCTGATGAAACCGCTTCCAATAGATTGGGTGCAGTTTTAG
AAGTCACTGATAAACAATGGAACGCTGAATACTTGCCAACAGACGAACATTTGGCT
AGAAGAGGTAGAGTTATTGAAATGTTGAGTGAACACCAATGCCAAGGTTGGTTAGA
AGGTTATTTGTTAACCGGTAGACATGGTTTGTTTAATACTTACGAAGCATTCGTACA
TATCGTTGGTTCTATGTTCAACCAACACGCTAAATGGTTGAAGGTTTCAAAAGAAAT
CCCATGGAGAAGACCTATTGCATCCTTAAACTACTTGTTGACTTCTCATGTTTGGAG
ACAAGATCATAACGGTTTATCTCACCAAGATCCAGGTTTTATTGACCACGTCGTAAA
TAAGAAAGCTGATGTTGTCAGAGTTTATTTGCCTTTCGACGCCAACACCTTGTTGTC
TGCTTACGATCATTGTTTGAGATCAGTTGATTACGTAAACGTAGTTGTCGCAGGTAA
ACAACCAACTTTTAACTGGTTGTCCATGGATAGAGCCATCGCTCATATGACCAGAG
GTTTAGGTATTTTCGAATGGGCTGGAACTGAAGTTGAAGGTGAAGAACCAGATGTT
GTTTTGGCTTGTGCTGGTGACGTACCTACATTGGAAGTTTTAGCAGCCGCTTCTATTT
TGAGACAAGCTATACCAGATTTGAAGGTTAGAGTCGTAAACGTTGTTGATTTGATG
AGATTAGTCTCTGAAGGTGAACATCCTCACGGCATGTCAGATAGAGAATATGACGC
CGTTTTTACTAAAGATAGACCAGTCATATTCGCTTATCATGGTTACCCTTGGTTGATC
CACAGATTAACATATAGAAGAAACGGTCATGCTAACTTGCACGTTAGAGGTTACAA
AGAAGAAGGTACCACTACAACCCCATTCGATATGGTCATGTTGAACGATATCGACA
GATACCATTTGGTAGTTGATGTCGTAGACAGAGTTCCTGGTTTAGGTGAAAGATATG
CTGGTTTGAGACAAAGAATGTTAGATGCCAGAGTAAGAGCTAGAGCATATACAAGA
GAACATGGTGAAGATATACCAGAAGTTGCAGACTGGACTTGGACAGCCGGTCCTGA
AAGACAAGCTAGAGAAGTCAATACCGGTGTTGGTCAAGTCAATACTGGTGCTGCTG
CTACTGGTGGTGACAATGAATCATAA
                                                      SEQ ID No: 59
MTDSATAPVPDRRATAFAHRDPAELDDGTLAALDAWWRTANYLSVGQIYLLDNPLLR
QPLEREQLKPRLLGHWGTTPGLNFLYAHLNRVIRERDLSTIFITGPGHGGPGMVANAYL
DGTYSELYPHVARSEDGIRELFRQFSFPGGIPSHASPETPGSIHEGGELGYALSHAYGAAF
DNPGLLVAAVVGDGEAETGPLATSWHSNKFLDPLADGVVLPILHLNGYKIANPTVLARI
PEHELLSLMRGYGHTPYLVSGGFDGEDPAAVHRRFAKTLDTVLNQIAEIKASAAAGTLE
GRPAWPMIILRTPKGWTCPEEIDGLPAENSWRSHQVPLASARDTPEHLGVLDGWLRSY
RPEELFDAAGAPMPVATALAPDGELRMSANPVANGGILKRDLVLPDFRDYAVDVPVPG
ATVNEATRVLGQWLADVIRANPDTFRIFGPDETASNRLGAVLEVTDKQWNAEYLPTDE
HLARRGRVIEMLSEHQCQGWLEGYLLTGRHGLFNTYEAFVHIVGSMFNQHAKWLKVS
KEIPWRRPIASLNYLLTSHVWRQDHNGLSHQDPGFIDHVVNKKADVVRVYLPFDANTL
LSAYDHCLRSVDYVNVVVAGKQPTFNWLSMDRAIAHMTRGLGIFEWAGTEVEGEEPD
VVLACAGDVPTLEVLAAASILRQAIPDLKVRVVNVVDLMRLVSEGEHPHGMSDREYD
AVFTKDRPVIFAYHGYPWLIHRLTYRRNGHANLHVRGYKEEGTTTTPFDMVMLNDIDR
```

-continued

YHLVVDVVDRVPGLGERYAGLRQRMLDARVRARAYTREHGEDIPEVADWTWTAGPE
RQAREVNTGVGQVNTGAAATGGDNES

SEQ ID No: 60
ATGACTAATAAGACACAATTTGACACCCCTGAATACTTGGGTAAAGTCGATGCTTG
GTGGAGAGCCGCTAACTACATTTCCGTCGCTCAAATGTATTTGAAGGATAACCCATT
GTTGAAGACACCTTTAGTAGCAAACGACGTTAAAGCCCATCCAATTGGTCATTGGG
GTACTGTTCCTGGTCAAAACTTCATCTATGCTCATTTGAATAGAGCAATCAACAAGT
ATGATGTTGACATGTTCTACATAGAAGGTCCAGGTCACGGTGGTCAAGTCATGGTAT
CTAATTCATACTTAGATGGTTCTTACACTGAAATCTACCCAGATATTACACAAGACA
CCGCAGGTTTGAAAAAGTTATGCAAGATATTTTCTTTCCCTGGTGGTATCGCCTCAC
ATGCTGCACCAGAAACACCTGGTTCTATTCACGAAGGTGGTGAATTGGGTTATGCTT
TATCACATGCCTTTGGTGCTGTTTTGGATAATCCAAACGTTATAGCCGCTGCAGTCA
TCGGTGACGGTGAAGCAGAAACAGGTCCTTTGTGCGCCGGTTGGTTTGGTAATACCT
TCATAAATCCAGTAAACGATGGTGCTGTTTTACCTATCTTGTACTTAAATGGTGGTA
AAATACATAACCCAACAATATTGGCAAGAAAAACCGATGAAGAATTAAAGCAATA
CTTCAACGGTATGGGTTGGGAACCTATCTTCGTTGATGTCAATAACGTTGACAACTA
CCATGAAATTATGTCCCAAAAAGTCGATGAAGCTGTAGAACACATCTTGAGTATTT
GGCAAACTGCAAGAACACAAAAGGCAGAAGATGCCACTATGCCACATTGGCCTGTT
TTGGTTGCTAGAATACCAAAAGGTTGGACCGGTCCTAAGACTTGGCACGGTGAACC
AATTGAAGGTGGTTTTAGAGCACATCAAGTTCCAATACCTGCATCTTCACACGATAT
GGAAACAGCTGGTGAATTGGAAAAGTGGTTAAGATCTTATAGACCTGAAGAATTGT
TCGATGACAATGGTTGTTTCTTAGACAAGTGGAGAGACATTTCCCCAAAAGGTGCA
AAGAGAATGAGTGTTCATCCTATCACTAATGGTGGTATTAACCCAAAAGCATTGGT
CATGCCTGATTGGACACAACACGCCTTAGAAATTGGTGTCCCAGGTTCTCAAGATGC
TCAAGACATGGTAGAATGCGGTAGATTAATGGCCGATGTTGTCACTGCTAACCCAA
ACAACTTTAGAATTTTCGGTCCTGACGAAACCAAGTCAAACAGATTGAACCAAGTC
TTCCAAGTAACTAAGAGACAATGGTTAGGTAGAAGAGATGAAGCATATGACGAATG
GATTGCACCAGTTGGTAGAGTCATAGATTCCCAATTGAGTGAACATCAAGCTGAAG
GTTTCTTGGAAGGTTATGTTTTAACAGGTAGACACGGTTTCTTTGCTTCTTACGAATC
ATTTTTCAGAGTAGTTGATTCCATGATCACTCAACATTTCAAGTGGTTGAGAAAGTG
TAAGACACACGCCGCTTGGAGAAATGATTATCCATCCTTGAACTTAGTCGCTACCAG
TACTGTATTCCAACAAGATCATAACGGTTACACTCACCAAGACCCTGGTTTGTTAAC
ACATTTGGCCGAAAAGAAACCAGAATTTGTAAGAGAATATTTGCCTGCTGATTCAA
ACACCTTAATGGCAGTTATGTCCGAAGCCTTAACTTCTAGAGATAGAATTAATTTGA
TCGTTTCCAGTAAGCATTTGAGACCACAATTTTTCAACGCTGAAGAAGCAAAAGAA
TTGGTTAGAGAAGGTTACAAGGTCATAGATTGGGCTTCCACCTGTCATGATGGTGA
ACCAGACGTCGTAATCGCAGCCGCTGGTACTGAACCTAATATGGAAGCATTGGCAG
CCATTAGTATCTTGCATAAGCAATTCCCAGAATTAAAGATTAGATTCATAAACGTTG
TCGATATATTGAAATTGAGACACCCATCTATAGACCCTAGAGGTTTGTCAGATGAAC
AATTTGACGCTTTATTCACTCAAGAAAAGCCAGTAGTTTTCTGTTTCCATGGTTATG
AAGGTATGATTAGAGATTTGTTTTTCCCTAGAGCAAATCATAACGTTAGAATCCACG

-continued

```
GTTACAGAGAAAATGGTGACATTACTACACCATTTGACATGAGAGTTTTATCAGAA

ATGGATAGATTCCATGTAGCCAAAGACGCTGCACAAGCTGTTTATGGTGACAAGGC

CTCTGAATTTGCTAAAAAGATGGGTGAAACAGTCGCTTTCCATAGATCATACATCAG

AGAACACGGTACCGATATTCCAGAAGTTGCCGAATGGAAATGGCAACCTTTGGCTA

AGTAA
```

SEQ ID No: 61
```
MTNKTQFDTPEYLGKVDAWWRAANYISVAQMYLKDNPLLKTPLVANDVKAHPIGHW

GTVPGQNFIYAHLNRAINKYDVDMFYIEGPGHGGQVMVSNSYLDGSYTEIYPDITQDTA

GLKKLCKIFSFPGGIASHAAPETPGSIHEGGELGYALSHAFGAVLDNPNVIAAAVIGDGE

AETGPLCAGWFGNTFINPVNDGAVLPILYLNGGKIHNPTILARKTDEELKQYFNGMGW

EPIFVDVNNVDNYHEIMSQKVDEAVEHILSIWQTARTQKAEDATMPHWPVLVARIPKG

WTGPKTWHGEPIEGGFRAHQVPIPASSHDMETAGELEKWLRSYRPEELFDDNGCFLDK

WRDISPKGAKRMSVHPITNGGINPKALVMPDWTQHALEIGVPGSQDAQDMVECGRLM

ADVVTANPNNFRIFGPDETKSNRLNQVFQVTKRQWLGRRDEAYDEWIAPVGRVIDSQL

SEHQAEGFLEGYVLTGRHGFFASYESFFRVVDSMITQHFKWLRKCKTHAAWRNDYPSL

NLVATSTVFQQDHNGYTHQDPGLLTHLAEKKPEFVREYLPADSNTLMAVMSEALTSRD

RINLIVSSKHLRPQFFNAEEAKELVREGYKVIDWASTCHDGEPDVVIAAAGTEPNMEAL

AAISILHKQFPELKIRFINVVDILKLRHPSIDPRGLSDEQFDALFTQEKPVVFCFHGYEGMI

RDLFFPRANHNVRIHGYRENGDITTPPFDMRVLSEMDRFHVAKDAAQAVYGDKASEFA

KKMGETVAFHRSYIREHGTDIPEVAEWKWQPLAK
```

SEQ ID No: 62
```
ATGACAACAGATTACTCATCCCCTGCATACTTACAAAAGGTAGACAAATACTGGAG

AGCCGCTAACTACTTATCCGTCGGTCAATTATATTTGAAGGACAACCCATTGTTGCA

AAGACCTTTAAAAGCATCTGATGTAAAGGTTCATCCAATAGGTCACTGGGGTACTA

TCGCTGGTCAAAACTTCATCTATGCACATTTGAATAGAGTCATTAACAAATACGGTT

TGAAGATGTTCTACGTAGAAGGTCCTGGTCACGGTGGTCAAGTCATGGTATCTAATT

CATACTTGGACGGTACATATACCGATATCTATCCAGAAATAACCCAAGATGTTGAG

GGTATGCAAAAATTGTTTAAACAATTTTCTTTCCCTGGTGGTGTCGCTTCACATGCT

GCACCAGAAACACCTGGTTCCATTCACGAAGGTGGTGAATTGGGTTATTCCATAAG

TCATGGTGTTGGTGCAATCTTAGATAATCCAGACGAAATTGCCGCTGTTGTCGTAGG

TGACGGTGAATCAGAAACTGGTCCTTTGGCTACATCTTGGCAATCAACCAAGTTTAT

CAATCCAATTAACGATGGTGCAGTTTTACCTATATTGAATTTGAATGGTTTTAAAAT

CTCTAATCCAACTATTTTCGGTAGAACATCAGATGCTAAGATTAAAGAATACTTCGA

ATCAATGAACTGGGAACCTATCTTCGTAGAAGGTGACGACCCAGAAAAGGTTCATC

CTGCCTTGGCTAAAGCAATGGATGAAGCAGTTGAAAAGATTAAAGCCATCCAAAAA

CACGCTAGAGAAAATAACGATGCTACTTTACCAGTCTGGCCTATGATAGTTTTTAGA

GCACCAAAAGGTTGGACAGGTCCTAAGTCCTGGGATGGTGACAAAATCGAAGGTTC

TTTTAGAGCACATCAAATTCCAATACCTGTTGATCAAAATGACATGGAACACGCCG

ATGCTTTGGTTGATTGGTTAGAATCCTATCAACCAAAGGAATTGTTTAACGAAGATG

GTAGTTTAAAGGATGACATAAAGGAAATAATACCAACAGGTGACTCTAGAATGGCA

GCCAATCCTATAACCAACGGTGGTGTCGATCCAAAAGCATTGAATTTGCCTAACTTC
```

-continued

```
AGAGATTATGCAGTAGACACTTCTAAGGAAGGTGCCAATGTTAAACAAGATATGAT

CGTCTGGTCAGATTACTTGAGAGACGTTATTAAAAAGAATCCAGACAACTTCAGAT

TGTTCGGTCCTGATGAAACAATGTCTAACAGATTGTACGGTGTTTTTGAAACTACAA

ACAGACAATGGATGGAAGACATTCATCCAGATTCCGACCAATACGAAGCACCTGCC

GGTAGAGTATTGGATGCCCAATTAAGTGAACATCAAGCTGAAGGTTGGTTGGAAGG

TTATGTTTTAACAGGTAGACACGGTTTGTTTGCATCTTACGAAGCCTTCTTGAGAGT

TGTCGATTCAATGTTGACCCAACATTTCAAGTGGTTGAGAAAGGCTAACGAATTAG

ATTGGAGAAAGAAATACCCATCCTTAAACATCATAGCTGCAAGTACTGTTTTCCAAC

AAGACCATAATGGTTACACCCACCAAGATCCTGGTGCATTGACTCATTTGGCCGAA

AAGAAACCAGAATACATTAGAGAATACTTGCCTGCTGACGCAAATACCTTGTTAGC

TGTAGGTGACGTTATTTTTAGATCACAAGAAAAGATCAACTACGTAGTTACTTCTAA

ACACCCAAGACAACAATGGTTCTCAATTGAAGAAGCCAAACAATTGGTCGATAATG

GTTTAGGTATAATCGACTGGGCTTCCACTGATCAAGGTAGTGAACCAGATATCGTTT

TTGCCGCTGCAGGTACTGAACCTACATTGGAAACCTTAGCCGCTATTCAATTGTTAC

ATGATTCTTTCCCAGAAATGAAGATCAGATTCGTTAACGTCGTAGACATCTTGAAGT

TAAGATCCCCAGAAAAGATCCTAGAGGTTTGAGTGATGCAGAATTTGACCATTAC

TTCACAAAGGATAAGCCAGTTGTCTTTGCCTTCCACGGTTACGAAGATTTGGTTAGA

GATATTTTCTTTGATAGACATAACCACAACTTATACGTTCATGGTTACAGAGAAAAC

GGTGACATAACCACTCCATTTGATGTTAGAGTCATGAACCAAATGGATAGATTCGA

CTTGGCCAAGTCTGCTATTGCAGCCCAACCTGCTATGGAAAATACTGGTGCTGCATT

TGTTCAATCAATGGATAACATGTTAGCTAAACATAACGCATACATTAGAGACGCAG

GTACAGATTTGCCAGAAGTTAACGATTGGCAATGGAAAGGTTTAAAGTAA
```

SEQ ID No: 63
```
MTTDYSSPAYLQKVDKYWRAANYLSVGQLYLKDNPLLQRPLKASDVKVHPIGHWGTI

AGQNFIYAHLNRVINKYGLKMFYVEGPGHGGQVMVSNSYLDGTYTDIYPEITQDVEGM

QKLFKQFSFPGGVASHAAPETPGSIHEGGELGYSISHGVGAILDNPDEIAAVVVGDGESE

TGPLATSWQSTKFINPINDGAVLPILNLNGFKISNPTIFGRTSDAKIKEYFESMNWEPIFVE

GDDPEKVHPALAKAMDEAVEKIKAIQKHARENNDATLPVWPMIVFRAPKGWTGPKSW

DGDKIEGSFRAHQIPIPVDQNDMEHADALVDWLESYQPKELFNEDGSLKDDIKEIIPTGD

SRMAANPITNGGVDPKALNLPNFRDYAVDTSKEGANVKQDMIVWSDYLRDVIKKNPD

NFRLFGPDETMSNRLYGVFETTNRQWMEDIHPDSDQYEAPAGRVLDAQLSEHQAEGW

LEGYVLTGRHGLFASYEAFLRVVDSMLTQHFKWLRKANELDWRKKYPSLNIIAASTVF

QQDHNGYTHQDPGALTHLAEKKPEYIREYLPADANTLLAVGDVIFRSQEKINYVVTSK

HPRQQWFSIEEAKQLVDNGLGIIDWASTDQGSEPDIVFAAAGTEPTLETLAAIQLLHDSF

PEMKIRFVNVVDILKLRSPEKDPRGLSDAEFDHYFTKDKPVVFAFHGYEDLVRDIFFDR

HNHNLYVHGYRENGDITTPFDVRVMNQMDRFDLAKSAIAAQPAMENTGAAFVQSMD

NMLAKHNAYIRDAGTDLPEVNDWQWKGLK
```

SEQ ID No: 64
```
ATGGCAGACTTCGACTCAAAGGAATACTTAGAATTGGTAGACAAATGGTGGAGAGC

AACAAACTACTTATCCGCTGGTATGATTTTCTTGAAAAGTAATCCATTATTTTCTGTT

ACAAACACCCCTATTCAAGCTGAAGATGTTAAAGTCAAGCCAATTGGTCATTGGGG

TACTATATCTGGTCAAACATTCTTGTATGCCCACGCTAACAGATTGATTAACAAATA
```

-continued

```
CGATTTGAATATGTTTTACATAGGTGGTCCAGGTCATGGTGGTCAAGTAATGGTTAC
TAACGCATACTTAGATGGTGAATATACCGAAGACTACCCTGAAATTACTCAAGATTT
GGAAGGCATGTCTAGATTGTTTAAAAGATTTTCTTTCCCAGGTGGTATCGGTTCACA
TATGACAGCTCAAACCCCTGGTTCTTTGCACGAAGGTGGTGAATTGGGTTATTCCTT
AAGTCATGCCTTCGGTGCTGTTTTAGATAATCCAGACCAAATTGCATTTGCCGTTGT
CGGTGACGGTGAAGCAGAAACCGGTCCTTCCATGACTTCTTGGCACTCTACAAAATT
CTTGAATGCAAAGAACGATGGTGCCGTCTTACCAATCTTGGACTTAAATGGTTTCAA
AATCTCTAACCCTACAATTTTCTCTAGAATGTCCGATGAAGAAATCACTAAGTTTTT
CGAAGGTTTGGGTTACTCACCAAGATTCATTGAAAACGATGACATCCATGATTATGC
TGCATACCACGAATTGGCCGCTAAAGTTTTAGATCAAGCTATCGAAGACATTCAAG
CTATACAAAAGATGCAAGAGAAAACGGTAAATACGAAGACGGTACAATTCCAGC
ATGGCCTGTCATTATAGCCAGATTGCCAAAGGGTTGGGGTGGTCCTACTCATGATGA
AGACGGTAACCCAATCGAAAATTCTTTTAGAGCACATCAAGTACCATTGCCTTTAGC
ACAAAATAAGTTGGAAACTTTGTCTCAATTCGAAGATTGGATGAACTCTTACAAGC
CTGAAGAATTGTTTAATGCAGATGGTTCCTTGAAAGACGAATTAAAGGCTATAGCA
CCAAAAGGTGACAAGAGAATGAGTGCAAATCCTATCGCCAACGGTGGTAGAAGAA
GAGGTGAAGAAGCTACTGATTTGACATTACCAGACTGGAGACAATTCACAAACGAT
ATAACCAACGAAAACAGAGGTCATGAATTGCCTAAGGTTACTCAAAACATGGATAT
GACTACATTGTCTAACTATTTGGAAGAAGTCGCTAAGTTAAACCCAACATCATTCAG
AGTATTTGGTCCTGATGAAACTATGTCAAACAGATTGTGGTCCTTGTTTAATACCAC
TAACAGACAATGGATGGAAGAAGTAAAAGAACCAAATGATCAATACGTTGGTCCTG
AAGGTAGAATCATTGACAGTCAATTATCTGAACATCAAGCCGAAGGTTGGTTGGAA
GGTTACACTTTGACAGGTAGAGTAGGTATATTCGCTTCATACGAATCCTTTTTGAGA
GTAGTTGACACTATGGTTACTCAACATTTCAAGTGGTTGAGACACGCTTCTGAACAA
GCATGGAGAAACGATTACCCATCCTTGAACTTAATTGCCACCAGTACTGCTTTCCAA
CAAGATCATAATGGTTACACACACCAAGACCCAGGCATGTTGACCCATTTGGCTGA
AAAGAAATCTAACTTCATTAGAGAATATTTGCCTGCAGATGGTAACTCCTTGTTAGC
CGTTCAAGACAGAGCTTTTAGTGAAAGACACAAGGTCAATTTGATAATCGCATCTA
AGCAACCAAGACAACAATGGTTCACAGCAGATGAAGCCGACGAATTGGCTAACGA
AGGTTTGAAGATCATCGATTGGGCTTCAACAGCACCATCCGGTGACGTTGACATTAC
CTTTGCATCTTCAGGTACAGAACCTACCATAGAAACTTTGGCAGCCTTGTGGTTAAT
CAATCAAGCATTTCCAGAGGTTAAGTTTAGATACGTCAACGTCGTAGAATTGTTGAG
ATTGCAAAAGAAATCTGAATCTCATATGAACGATGAAAGAGAATTATCCGACGCCG
AGTTTAATAAGTTTTTCCAAGCTGATAAGCCTGTTATCTTCGGTTTTCATGCTTACGA
AGACTTAATCGAATCATTTTTCTTTGAAAGAAAATTCAAGGGTGACGTCTATGTACA
CGGTTACAGAGAAGATGGTGACATTACAACCACTTACGATATGAGAGTTTACTCTA
AATTGGACAGATTTCATCAAGCAAAGGAAGCTGCAGAAATCTTAAGTGCCAATTCT
ACTATTGATCAAGCCGCTGCAGACACATTCATCGAAAAGATGGATGCCACCTTGGC
TAAGCATTTTGAAGTTACTAGAAATGAAGGTAGAGATATTGAAGAGTTTACTGACT
GGAACTGGTCAGCTTTAAAATAA
```

-continued

SEQ ID No: 65
MADFDSKEYLELVDKWWRATNYLSAGMIFLKSNPLFSVTNTPIQAEDVKVKPIGHWGT

ISGQTFLYAHANRLINKYDLNMFYIGGPGHGGQVMVTNAYLDGEYTEDYPEITQDLEG

MSRLFKRFSFPGGIGSHMTAQTPGSLHEGGELGYSLSHAFGAVLDNPDQIAFAVVGDGE

AETGPSMTSWHSTKFLNAKNDGAVLPILDLNGFKISNPTIFSRMSDEEITKFFEGLGYSPR

FIENDDIHDYAAYHELAAKVLDQAIEDIQAIQKDARENGKYEDGTIPAWPVIIARLPKG

WGGPTHDEDGNPIENSFRAHQVPLPLAQNKLETLSQFEDWMNSYKPEELFNADGSLKD

ELKAIAPKGDKRMSANPIANGGRRRGEEATDLTLPDWRQFTNDITNENRGHELPKVTQ

NMDMTTLSNYLEEVAKLNPTSFRVFGPDETMSNRLWSLFNTTNRQWMEEVKEPNDQY

VGPEGRIIDSQLSEHQAEGWLEGYTLTGRVGIFASYESFLRVVDTMVTQHFKWLRHASE

QAWRNDYPSLNLIATSTAFQQDHNGYTHQDPGMLTHLAEKKSNFIREYLPADGNSLLA

VQDRAFSERHKVNLIIASKQPRQQWFTADEADELANEGLKIIDWASTAPSGDVDITFASS

GTEPTIETLAALWLINQAFPEVKFRYVNVVELLRLQKKSESHMNDERELSDAEFNKFFQ

ADKPVIFGFHAYEDLIESFFFERKFKGDVYVHGYREDGDITTTYDMRVYSKLDRFHQAK

EAAEILSANSTIDQAAADTFIEKMDATLAKHFEVTRNEGRDIEEFTDWNWSALK

SEQ ID No: 66
ATGACATCCCCAGTTATTGGTACCCCATGGAGAAAGTTGGACGCCCCTGTATCCGA

AGAAGCATTAGAAGGTGTAGACAAGTATTGGAGAGCTTCCAACTATTTGAGTATAG

GTCAAATCTACTTGAGATCAAACCCATTGATGAAGGAACCTTTCACAAGAGAAGAT

GTCAAGCATAGATTAGTAGGTCACTGGGGTACTACACCAGGTTTGAACTTTTTAATA

GGTCATATCAACAGATTGATCGCAGATCACGGTCAAAACACTGTTATTATCATGGGT

CCAGGTCATGGTGGTCCTGCTGGTACATCCCAAAGTTATTTGGACGGTACCTACTCT

GAATACTTCCCAGAAATCACAAAGGATGAAGCAGGTTTGCAAAAGTTTTTCAGACA

ATTCTCTTACCCAGGTGGTATCCCTTCACATTTTGCACCAGAAACCCCTGGTTCAATT

CACGAAGGTGGTGAATTGGGTTATGCTTTATCTCATGCCTACGGTGCTGTTATGAAT

AACCCATCATTATTTGTACCTGCTATTGTTGGTGACGGTGAAGCTGAAACAGGTCCA

TTAGCAACCGGTTGGCAATCTAACAAATTGGTTAATCCAAGAACCGATGGTATAGT

CTTGCCTATCTTGCATTTGAACGGTTATAAGATTGCCAATCCAACTATATTGGCTAG

AATCTCTGATGAAGAATTGCATGAATTTTTCCACGGTATGGGTTATGAACCTTACGA

ATTTGTTGCTGGTTTCGATGACGAAGACGCAATGTCAATTCACAGAAGATTTGCTGA

TTTGTTCGAAACAGTTTTCGACGAAATCTGTGATATCAAGGCTACCGCACAAACTAA

CGATGTTGACAGACCATTCTACCCTATGATCATTTTTAGAACTCCAAAGGGTTGGAC

ATGCCCTAAGTTCATTGATGGTAAAAAGACAGAAGGTTCTTGGAGATCACATCAAG

TACCATTGGCCTCCGCTAGAGATACCGAAGAACACTTTGAAGTTTTGAAAAATTGGT

TGGAAAGTTACAAGCCTGAAGAATTATTCACTGAAGATGGTGCCGTCAGACCAGAA

GTAACAGCTTTTATGCCTGAGGGTGAATTGAGAATAGGTGAAAATCCAAACGCCAA

TGGTGGTAGAATCAGAGAAGAATTGGACTTACCTGCTTTGGAAGATTACGAAGTAA

CTGAAGTTAAAGAATTTGGTCATGGTTGGGGTCAATTGGAAGCAACCAGAAAGTTG

GGTGAATACACTAGAGACATAATCAAGAGAAACCCAGATTCCTTTAGAATTTTCGG

TCCTGATGAAACCGCTAGTAATAGATTGCAAGCTGCATATGAAGTCACTAACAAAC

AATGGGACAATGGTTACTTGTCTGAATTAGTTGATGAACATATGGCAGTTACTGGTC

AAGTCACAGAACAATTATCAGAACACCAAATGGAAGGTTTCTTGGAAGCTTATTTG

```
TTAACAGGTAGACATGGTATTTGGTCTTCATACGAATCCTTCGTCCATGTAATCGAT

AGTATGTTGAACCAACACGCTAAATGGTTAGAAGCAACTGTTAGAGAAATCCCATG

GAGAAAGCCTATTTCCAGTATGAACTTGTTAGTATCTTCACATGTTTGGAGACAAGA

TCATAATGGTTTTTCCCACCAAGACCCAGGTGTTATCGATATATTGTTGAACAAAA

CTTCAACAACGACCACGTTGTCGGTATCTATTTCCCTGTAGATTCTAACATGTTGTTA

GCCGTTTCCGAAAAGGCTTACAAGAGTACAAACATGATCAACGCAATAATCGCCGG

TAAACAACCAGCCGCTACATGGTTGACCTTAGATGAAGCAAGAGAAGAATTAGCCA

AAGGTGCAGCCGAATGGAAGTGGGCTTCTAACGCAGAAGGTGACGACGTTGATATT

GTATTGGCTTCAGTTGGTGACGTCCCTACTCAAGAATTGATGGCTGCAGCCGACAAA

TTAAAGGGTTACGGTATAAAATACAAGTTCGTTAACGTAGTTGATTTGTTATCTATC

CAAAACGCATCAGAAAATGACCAAGCCTTGTCTGATGAAGAGTTTACTGAATTGTT

TACTGCAGATAAACCAGTCTTGATGGCCTATCATGCATACGCCAGAGAAGTAAGAT

CCTTAATTTGGGACAGACCAAATCATGATAACTTCAATGTTCACGGTTATGAAGAAC

AAGGTAGTACCACTACACCTTTTGACATGGTTAGAGTCAACAACATAGATAGATAC

GAATTGACTGCTGAAGCATTAAGAGCCGTTGATGCTGACAAATTCGCTGACGAAAT

AGAAAAGTTGGAAGCTTTTAGAACTGAAGCATTTCAATTCGCCGTTGATAATGGTTA

TGATCATCCAGACTACACAGATTGGGTCTGGTCTGGTGTCCAAACTGAAAAGCCAG

GTGCTGTATCTGCCACTGCTGCCACTGCCGGTGACAACGAATAA
```
SEQ ID No: 67
```
MTSPVIGTPWRKLDAPVSEEALEGVDKYWRASNYLSIGQIYLRSNPLMKEPFTREDVKH

RLVGHWGTTPGLNFLIGHINRLIADHGQNTVIIMGPGHGGPAGTSQSYLDGTYSEYFPEI

TKDEAGLQKFFRQFSYPGGIPSHFAPETPGSIHEGGELGYALSHAYGAVMNNPSLFVPAI

VGDGEAETGPLATGWQSNKLVNPRTDGIVLPILHLNGYKIANPTILARISDEELHEFFHG

MGYEPYEFVAGFDDEDAMSIHRRFADLFETVFDEICDIKATAQTNDVDRPFYPMIIFRTP

KGWTCPKFIDGKKTEGSWRSHQVPLASARDTEEHFEVLKNWLESYKPEELFTEDGAVR

PEVTAFMPEGELRIGENPNANGGRIREELDLPALEDYEVTEVKEFGHGWGQLEATRKLG

EYTRDIIKRNPDSFRIFGPDETASNRLQAAYEVTNKQWDNGYLSELVDEHMAVTGQVT

EQLSEHQMEGFLEAYLLTGRHGIWSSYESFVHVIDSMLNQHAKWLEATVREIPWRKPIS

SMNLLVSSHVWRQDHNGFSHQDPGVIDILLNKNFNNDHVVGIYFPVDSNMLLAVSEKA

YKSTNMINAIIAGKQPAATWLTLDEAREELAKGAAEWKWASNAEGDDVDIVLASVGD

VPTQELMAAADKLKGYGIKYKFVNVVDLLSIQNASENDQALSDEEFTELFTADKPVLM

AYHAYAREVRSLIWDRPNHDNFNVHGYEEQGSTTTPFDMVRVNNIDRYELTAEALRA

VDADKFADEIEKLEAFRTEAFQFAVDNGYDHPDYTDWVWSGVQTEKPGAVSATAATA

GDNE
```
SEQ ID No: 68
```
ATGACTATCAACTACGATTCAAAAGACTACTTAAAATACGTCGATGCTTACTGGAG

AGCCGCTAACTACTTATCCGTCGGTCAATTGTTCTTGAGAAACAACCCATTGTTGAA

GGATGAATTACAATCTAAGGACGTCAAAATCAAGCCAATTGGTCATTGGGGTACTG

TAGCTCCTCAAAACTTTATCTATGCACACTTGAATAGAGCCATTTTGAAATATGATT

TGAATATGTTCTACATTGAAGGTAGTGGTCATGGTGGTCAAGTTATGGTCTCTAACT

CATACTTGGATGGTTCTTATACCGAAACTTACCCAAAAGTTACACAAGATATTCAGG
```

-continued
```
GTATGCAAAGATTGTTTAAACAATTTTCATTCCCTGGTGGTATAGCTTCCCATGCTG

CACCAGAAACCCCTGGTTCTATCCACGAAGGTGGTGAATTGGGTTATTCCATTAGTC

ATGGTGTTGGTGCAATATTAGATAATCCAGACGTCATTGCCGCTGTAGAAATAGGT

GACGGTGAATCTGAAACAGGTCCTTTGGCAGCCTCTTGGTTCTCAGATAAATTCATA

AACCCAATCCATGACGGTGCTGTTTTACCTATCGTCCAAATTAATGGTTTTAAGATC

TCAAACCCAACAATATTGTCCAGAATGAGTGATAGAGACTTAACCAACTACTACCA

TGGTATGGGTTGGGAACCTTTGTTTGTTGAAACTGATGGTTCCGACAACTTCAAAGT

TCACGCAGAAATGGCAGATGCCGTTGATAAAGCCATCGAAAAGATTAAAGCTATCC

AAAAGAATGCAAGAAACAACAACGATGACAGTTTGCCAATATGGCCTATGATCGTT

TTAAGAGCACCAAAAGGTTGGACAGGTCCTAAAAAGGATTTGGACGGTAACCCAAT

CGAAAATTCTTTTAGAGCACATCAAGTACCAATTCCTGTTGATGCAAACCATTTGGA

ACACAAGGATATGTTGATCGACTGGATGAAGAGTTACAAGCCTGAAGAATTGTTCA

ACGAAGATGGTTCTTTAAAGGAAATCGTAAAGGTTAACCAACCAAAAGGTCAAGA

AGAATGGCTATGAACCCTATAACAAATGGTGGTATCAAGCCAAGAACCTTGAACAT

GCCTGATATGGAAAGATTTGCATTCCCTAAAAATTCTTTGAAGAACAATAAGAAAC

CTGGTATGGATTTGCAAGTTGTCTCCACTTTTATAGCTGAAATTATTAAGAAAAATC

CAATCAATTTCAGACAATTCGGTCCTGATGAAACTATGTCAAACAGATTGTGGGAT

GAGTTTAAAGTAACAAACAGACAATGGATGCAAGCCGTTCATGAACCAAATGATCA

ATACATGGCTCACAGTGGTAGAATTTTGGATGCCCAATTATCTGAACATCAAGCTGA

AGGTTGGATGGAAGGTTATGTTTTGACAGGTAGACACGCCTTTTTCGCTTCATACGA

AGCCTTTACTAGAATCATCGATTCCATGTTGACACAATACTACAAGTGGTTGAGAAA

GGCCGTTGAACAAGATTGGAGACATGACTATCCAAGTTTAAACGTCATTAATGCAT

CTCACGCCTTCCAACAAGATCATAATGGTTACACCCACCAAGACCCAGGCATGTTA

ACTCATATGGCTGAAAAGGGTCACGAATTTGTTAACGAATTTTTGCCTGCTGATGCA

AACTCATTGTTAGCAGTCATGAATAAGTCTTTGCAAGTAAGAAACAAGATTAATAT

CATCGTCGCATCAAAGCATCCAAGAACTCAATGGTTTACAATAGATGAAGCCAAGG

AATTGGTAGACAACGGTTTAGGTATTATACCATGGGCTTCCAATGATGACGGTGTTG

AACCTGATGTAGTTTTTGCTGCAGGTGGTACAGAAGCTACCATGGAATCTTTGGCCG

CTATTTCATTGTTACATGAATCCTTCCCAGAATTAAAGTTTAGATTCATTAACGTTAT

TGATTTGTTAAAGTTGAGAAAGAAAGGTGACAATGATGACTATAGAGGTTTGTCAG

ATTTGGAATTTGACCATTACTTCACTAGAGAAAAACCAGTCGTTTTCTCTTTCCACG

GTTTCGAATCTTTGGCTAGAGATTTGTTTTATGACAGACATAACCACAATGTCATTT

TTCATGGTTACAGAGAAAACGGTGACATAACTACACCTTTTGACATGAGAGTATTG

AATCATTTGGATAGATTCCACTTAGCTAAAGACGCAATTAACGCCACCAAGTATGCT

GATGTTGCAGGTCAATTTGACCAAAGAATGGATGACATGTTAGCCAAACATACTGC

TTACATTTGTGATCAAGGTACCGACTTGCCAGAAGTTACTTCTTGGCAATGGCAAGA

TATTAAGTAA
```
SEQ ID No: 69
```
MTINYDSKDYLKYVDAYWRAANYLSVGQLFLRNNPLLKDELQSKDVKIKPIGHWGTV

APQNFIYAHLNRAILKYDLNMFYIEGSGHGGQVMVSNSYLDGSYTETYPKVTQDIQGM

QRLFKQFSFPGGIASHAAPETPGSIHEGGELGYSISHGVGAILDNPDVIAAVEIGDGESET
```

-continued

```
GPLAASWFSDKFINPIHDGAVLPIVQINGFKISNPTILSRMSDRDLTNYYHGMGWEPLFV
ETDGSDNFKVHAEMADAVDKAIEKIKAIQKNARNNNDDSLPIWPMIVLRAPKGWTGPK
KDLDGNPIENSFRAHQVPIPVDANHLEHKDMLIDWMKSYKPEELFNEDGSLKEIVKVN
QPKGQRRMAMNPITNGGIKPRTLNMPDMERFAFPKNSLKNNKKPGMDLQVVSTFIAEII
KKNPINFRQFGPDETMSNRLWDEFKVTNRQWMQAVHEPNDQYMAHSGRILDAQLSEH
QAEGWMEGYVLTGRHAFFASYEAFTRIIDSMLTQYYKWLRKAVEQDWRHDYPSLNVI
NASHAFQQDHNGYTHQDPGMLTHMAEKGHEFVNEFLPADANSLLAVMNKSLQVRNKI
NIIVASKHPRTQWFTIDEAKELVDNGLGIIPWASNDDGVEPDVVFAAGGTEATMESLAA
ISLLHESFPELKFRFINVIDLLKLRKKGDNDDYRGLSDLEFDHYFTREKPVVFSFHGFESL
ARDLFYDRHNHNVIFHGYRENGDITTPFDMRVLNHLDRFHLAKDAINATKYADVAGQF
DQRMDDMLAKHTAYICDQGTDLPEVTSWQWQDIK
```

SEQ ID No: 70
```
ATGGCTGACAACGCCGACGCTCCACCACCTCCAATAGTCCCTTCACAATACGCTCAA
CATCCAGACGCTCCATTATCCTCATTACCAGTTCAATTGGACCCTTCTCAATATACA
GCTAAATACCCAGCAAAGCATTTGGATGCCATTGTCGCTAATTGGAGATTGTCCTGT
TATTTGGGTGCTAGTCAAATTTTCTTGCAATCTAACGCAATCTTGTCAAGAAAATTG
ACTAAGGATGACGTAAAACCAAGAAGAGCACATACAAATTTGGCTGGTGACATCCA
AGGTGGTTTGTCTTTAGCCTACGTTCACACCCAAGCATTGATCAGAAGAAAAGGTG
ACGAAGAAGGTGCTGAACCAAAGATGATTTTCGTCACTGGTCCAGGTCATGGTGCC
CCTGCTATATTGTCTCCATTGTACATCGAAGGTGCTATCTCAAAGTTCTACCCACAA
TACCCTTTGAACGAACAAGGTTTAGAAAAGTTCGTTAAGTACTTCTCCTGGCCAGGT
GGTTTCCCTAGTCATGTCAACGCTGAAACACCAGGTTGCATACACGAAGGTGGTGA
ATTGGGTTATGCCTTAGGTGTAGCTTACGGTTCCGTTATGGACAGACCTGAACAAAT
CAGTGTTGTCGTAGTTGGTGACGGTGAATCTGAAACTGGTCCAACTGCAACAGCCT
GGCATTCACACAAATGGTTAGATCCTGCAGAATCCGGTGCCGTTTTGCCAATCTTGC
ATGTCAACGGTTTTAAGATCTCTGAAAGAACTATCCCAGGTACAATGGATAACGTT
GAATTGTCTTTGTTGTACTCAGGTTACGGTTACCAAGTCAGATTCGTAGAATACAAA
GCTCAAGGTGAAGCACATATGGGTGGTAATGATCCTGCTGACAGAGTTTTGCACGA
AGACATGGCTGCAAGTTTAGATTGGGCATATGGTGAAATAAGAAAAATCCAAAAGG
CCGCTAGATCTGGTGGTAAACCAATTGATAAGCCAAGATGGCCTATGATAATCTTG
AGATCACCTAAGGGTTGGACAGGTCCATCTTCAGAACATGGTAAACAATTGTTGAA
CAACTTTGCCTCTCACCAAGTTCCATTGCCTGATGCTAAAACTGATGACGAAGCTAA
CGCATATTTGGAAAGATGGTTGAAGAGTTACGAAGCTGATAAGTTGTTCGACTTCTC
TGAAGATAACTTAAAGAGAGGTACAATCTTCGACCAATTGTTGTACGAAGCATTGC
CTAAGGATATGGAAAGAAGATTAGGTTTCGTTAAGGAAACTTACAACGGTTACAAG
CCATTGGAATTAGATGACTGGAAAAAGTACGGTTTTAAAAAGGGTGAAGACGTATC
ATGTATGAAAGCCATCGCTGGTTACTTAACAGATGTTATTAAAAGAAACCCTAAGG
AGTTTAGAATTTTCAGTCCAGACGAATTGGCTTTAAATAAGTTGGATGGTGTTTTCT
CTGTCACTGAAAGAAACATGCAATGGGACCCAGAAACTGCTCATAAGGGTGGTAGA
GTTACAGAAATGTTGTCTGAACACTCATTGCAAGCATGGTTACAAGGTTATACCTTA
ACTGGTAGACATGGTGTTTTTCCATCTTACGAAGCATTCTTGGGTATTGTCGCCACA
```

-continued

```
ATGACCGTACAATATACCAAGTTTATGAAGATGGCATTGGAAACTAATTGGAGAGG

TCCTACCGCCTCTTTAACTTACATCGAAACTTCAACATGGACCAGACAAGAACATAA

TGGTTACTCCCACCAAAACCCAGGTTTCGTAAGTACTGTTTTGTCCTTACCTAGTCA

ATTAGCTAGAGTTTACTTTCCATCAGATGCAAATACATCCGTAAGTGTTATCGCCCA

TTGTTTGAGATCCAAAAATTACATAAACTTAATAGTTGGTACAAAGGCTCCAACCCC

TGTCTACTTGTCTGTAGAAGAAGCAGAAAGACATTGCATTGCAGGTGCCTCTGTTTG

GGAAAATTATTCAGTTGATAAGGGTGTCGATCCAGACGTCGTATTGGTAGGCATCG

GTTACGAATTAACAGAAGAAGTTATCCATGCAGCCGCTTTGTTGAGAAAGGATTTT

GGTACTGAATTGAGAGTCAGAGTTGTCAACGTAGTTGATTTGTTAGTATTAGCTCCT

AAGGGTGACCATCCACACGCCTTGGATGAAGCTGGTTTTAATTCATTATTCCCACCT

GGTGTTCCTATCATTTTTAACTACCATGGTTACGCAGGTCAATTAGCCTCCTTGTTAT

TCGATAGAAAACACTCCGTTGGTAGAAGTAGAATGAGAATCTTCGCTTACTCAGAA

CAAGGTACTACAACCACTCCATTTGCAATGATGTGTTGCAATAACACTGATAGATTC

AATTTGGCTGCTGAAGCATTGGAAATGGTCACATTGAATTTGACAACCCAACATAA

CATTACCGGTGAAGAAAAGAGACACAGAGTAGGTTCAGTCGTAGCTAGAGCACATG

AAAGAATGTCCTTCTACAAGCACAAAAAGGTTGTCATGATGAGATACGCTGCAGAA

ACCCAAAAGGATCATCCAGAAATTGGTGAAGTTGCAACTTTGGCCGAACAATAA
```

SEQ ID No: 71

```
MADNADAPPPPIVPSQYAQHPDAPLSSLPVQLDPSQYTAKYPAKHLDAIVANWRLSCY

LGASQIFLQSNAILSRKLTKDDVKPRRAHTNLAGDIQGGLSLAYVHTQALIRRKGDEEG

AEPKMIFVTGPGHGAPAILSPLYIEGAISKFYPQYPLNEQGLEKFVKYFSWPGGFPSHVN

AETPGCIHEGGELGYALGVAYGSVMDRPEQISVVVVGDGESETGPTATAWHSHKWLD

PAESGAVLPILHVNGFKISERTIPGTMDNVELSLLYSGYGYQVRFVEYKAQGEAHMGG

NDPADRVLHEDMAASLDWAYGEIRKIQKAARSGGKPIDKPRWPMIILRSPKGWTGPSSE

HGKQLLNNFASHQVPLPDAKTDDEANAYLERWLKSYEADKLFDFSEDNLKRGTIFDQL

LYEALPKDMERRLGFVKETYNGYKPLELDDWKKYGFKKGEDVSCMKAIAGYLTDVIK

RNPKEFRIFSPDELALNKLDGVFSVTERNMQWDPETAHKGGRVTEMLSEHSLQAWLQG

YTLTGRHGVFPSYEAFLGIVATMTVQYTKFMKMALETNWRGPTASLTYIETSTWTRQE

HNGYSHQNPGFVSTVLSLPSQLARVYFPSDANTSVSVIAHCLRSKNYINLIVGTKAPTPV

YLSVEEAERHCIAGASVWENYSVDKGVDPDVVLVGIGYELTEEVIHAAALLRKDFGTE

LRVRVVNVVDLLVLAPKGDHPHALDEAGFNSLFPPGVPIIFNYHGYAGQLASLLFDRKH

SVGRSRMRIFAYSEQGTTTTPFAMMCCNNTDRFNLAAEALEMVTLNLTTQHNITGEEK

RHRVGSVVARAHERMSFYKHKKVVMMRYAAETQKDHPEIGEVATLAEQ
```

SEQ ID No: 72

```
ATGACATCTCCTGTAATTGGTACCCCATGGAAGAAGTTGGATAGACCTGTAACCGA

CGAAGCATTGGAAGGTGTTGATAAGTATTGGAGAGCTGCAAACTATATGTCCATCG

GTCAAATATATTTGAGAAGTAATCCATTAATGAAGGAACCTTTTACAAGAGAAGAT

GTAAAGCATAGATTGGTTGGTCACTGGGGTACTACACCAGGTTTGAACTTTTTATTC

GGTCATATCAACAGATTGATCGCAGATCACCAACAAAACACTGTTTTCATTATGGGT

CCAGGTCATGGTGGTCCTGCTGGTACTTCTCAATCTTATTTGGATGGTACCTACACT

GAATACTACCCAAAGATAACAAACGACGAAGCTGGTTTGCAAAAGTTTTTCAGACA

ATTTTCCTACCCAGGTGGTATCCCTAGTCATTACGCACCAGAAACTCCTGGTTCAAT
```

-continued

```
TCACGAAGGTGGTGAATTGGGTTATGCTTTATCTCATGCCTACGGTGCTATCATGAA
TAACCCATCATTGTTTGTAGCCGCTATTGTTGGTGACGGTGAAGCTGAAACTGGTCC
TTTAGCAACAGGTTGGCAATCTAACAAGTTGGTCAATCCAAGAACAGATGGTATCG
TATTGCCTATATTGCATTTGAATGGTTACAAGATTGCCAATCCAACCATATTGGCTA
GAATCTCTGACGAAGAATTACACGATTTCTTTAGAGGTATGGGTTATAATCCTTACG
AATTTGTTGCAGGTTTCGATGACGAAGACCATATGTCTATTCACAGAAGATTCGCTG
ATTTGTTAGAAACTGTATTCGACGAAATCTGTGATATCAAAGCTACTGCACAAACA
AATGATGTTGACAGACCATTCTACCCTATGATCATATTCAGAACCCCAAAAGGTTGG
ACTTGCCCTAAGTTTATTGATGGTAAAAAGACCGAAGGTTCCTGGAGAGCACATCA
AGTCCCATTGGCCAGTGCTAGAGATACTGAAGAACACTTCCAAGTATTGAAGAATT
GGTTAGAATCTTACAAGCCTGAAGAATTGTTCGATGAAAAGGGTACATTGAGACCA
GAAGTTACCGAGTTTATGCCTAAGGGTGACTTGAGAATTGGTGCTAATCCAAACGC
AAATGGTGGTAGAATCAGAGAAGATTTGAAATTGCCTGTTTTGGATGACTACAAAG
TCAAGGAAGTAGAAGAATTTGGTCATGGTTGGGGTCAATTGGAAGCAACTAGAAGA
TTAGGTGTTTACACAAGAGACATCATTAAGTTAAACCCAGATTCCTTTAGAATATTC
GGTCCTGATGAAACTGCTAGTAATAGATTGCAAGCAGCCTATGAAGTTACAAACAA
ACAATGGGACAATGGTTACTTGTCTTCATTAGTCGATGAACATATGGCTGTCACCGG
TCAAGTAACTGAACAATTATCAGAACACCAAATGGAAGGTTTTATTGAAGGTTACG
TTTTGACAGGTAGACATGGTATATGGTCCAGTTACGAATCTTTCGTTCATGTCATCG
ATTCAATGTTGAATCAACACGCTAAGTGGTTAGAAGCAACTGTTAGAGAAATTCCA
TGGAGAAAGCCTATATCTTCAGTTAACTTGTTAGTCTCCAGTCATGTATGGAGACAA
GACCATAATGGTTTTTCTCACCAAGATCCAGGTGTTGTCTCAGTTTTGTTGAACAAA
ACTTTTAATAACGACCATGTCATTGGTATCTATTTCGCAACCGATGCCAATATGTTG
TTAGCCATTGGTGAAAAAGCATATAAATCTACTAACAAGATAAATGCTATAATCGC
AGGTAAACAACCAGCTGCAACCTGGTTGTCATTAGATGAAGCAAGAGCCGAATTAA
CTAAAGGTGCCGCTGAATGGAAGTGGGCCTCCACCGCTAAAAATAACGACGAAACT
GAAATAGTTTTAGCAAGTGTTGGTGACGTCCCAACTCAAGAAATAATGGCAGCCGC
TGACAAATTGAAGGGTTACGGTATTAAGTTTAAAGTAGTTAACGTCGTAGATTTGTT
ATCTTTACAAAACCCAAAGGAAAACAACGAAGCATTGTCAGACGAAGAGTTTACTG
AATTATTCACCGCCGATAAGCCTGTATTGATGGCATATCATTCCTACGCCAGAGAAG
TTAAGGGTTTGTTGTTCGATAGACCAAACAACGCTAACTTCAATATTCACGGTTATC
AAGAACAAGGTTCAACCACTACACCTTTCGATATGGTTAGAGTTAACGATATCGAC
AGATACGAATTGACAGCTGAAGCATTGAGAATGTTAGATGCCGACAAGTACGCTGA
TGACATTAAAAAGTTAGAAGATTTCAGACAAGAAGCATTCCAATATGCCGTTGATA
ACGGTCATGATCACCCAGACTACACAGATTGGGTTTGGTCTGGTGTCAAAACCGAT
AAGCCTGGTGCAGTTACAGCCACCGCAGCCACTGCTGGTGACAATGAATAA
```

SEQ ID No: 73
MTSPVIGTPWKKLDRPVTDEALEGVDKYWRAANYMSIGQIYLRSNPLMKEPFTREDVK

HRLVGHWGTTPGLNFLFGHINRLIADHQQNTVFIMGPGHGGPAGTSQSYLDGTYTEYY

PKITNDEAGLQKFFRQFSYPGGIPSHYAPETPGSIHEGGELGYALSHAYGAIMNNPSLFV

AAIVGDGEAETGPLATGWQSNKLVNPRTDGIVLPILHLNGYKIANPTILARISDEELHDF

-continued

FRGMGYNPYEFVAGFDDEDHMSIHRRFADLLETVFDEICDIKATAQTNDVDRPFYPMIIF
RTPKGWTCPKFIDGKKTEGSWRAHQVPLASARDTEEHFQVLKNWLESYKPEELFDEKG
TLRPEVTEFMPKGDLRIGANPNANGGRIREDLKLPVLDDYKVKEVEEFGHGWGQLEAT
RRLGVYTRDIIKLNPDSFRIFGPDETASNRLQAAYEVTNKQWDNGYLSSLVDEHMAVT
GQVTEQLSEHQMEGFIEGYVLTGRHGIWSSYESFVHVIDSMLNQHAKWLEATVREIPW
RKPISSVNLLVSSHVWRQDHNGFSHQDPGVVSVLLNKTFNNDHVIGIYFATDANMLLAI
GEKAYKSTNKINAIIAGKQPAATWLSLDEARAELTKGAAEWKWASTAKNNDETEIVLA
SVGDVPTQEIMAAADKLKGYGIKFKVVNVVDLLSLQNPKENNEALSDEEFTELFTADK
PVLMAYHSYAREVKGLLFDRPNNANFNIHGYQEQGSTTTPFDMVRVNDIDRYELTAEA
LRMLDADKYADDIKKLEDFRQEAFQYAVDNGHDHPDYTDWVWSGVKTDKPGAVTAT
AATAGDNE

SEQ ID No: 74
ATGAAGTTCGAAGCCACCAAAGAATTTATGAACGAATCCAGAACAGAAGCCGCAA
AAGCCGACCCATCACCATTACAATCCCACTTACCAGCTACTTTGGATACATTGCAAG
TTCATTTGTTGAAAGACTATGTACCTGAAGATGACTTGGTTACATTAAAGAATTTCC
AAAGAGTATGTAACTACATCGCTGCAGCCATGATTTTCTTGTGCGATAACGTTTTGT
TAGAAAACAAATTAACATCTGACCATATTAAGCCAAGATTGTTAGGTCATTGGGGT
ACTTGTCCTGCCTTGGCTTTAGCATACTCCCATTGCAACAGAATCATCAGTAAGTAC
AATTTGGATATGTTATTTGTTACTGGTCCAGGTCACGGTGCCCCTGCTATTTTGGCTG
CATTATACATCGAAGGTTCTTTACAAGCATATTACCCACAATACGGTCATAACATGC
AAGGTTTGCACAGATTGATCACCAAATTTTCTGTCACTGGTGGTTTCCCATCACATG
TCAATGCCGAAGTACCTGGTGCTATACACGAAGGTGGTGAATTGGGTTATGCATTAT
CTGTATCATACGGTGCCGTTTTGGATAGACCAAATTTGATTGTTGCCTGTGTTGTCG
GTGACGGTGAAGCTGAAACCGGTCCTACTGCCGCTTCTTGGCATTGCCACAAATTCA
TAGATCCAGCAGAATCAGGTGCCGTCATACCTATCTTGAATTTGAATGGTTTTAAGA
TCTCAGAAAGAACAGTATATGGTTGTATGGATAGAAGAGAATTGTCTGCTTTGTTTT
CTGGTTTCGGTTACCAAGTAGTTTTCGTAGATTACAGAACTGCTGATGACGTTAATA
GAGATATGGCAGCCGCTATGGACTGGTGTGTTGAAATCATACATGAAATACAAGAT
GCAGCCAGAGCAGGTACACCAATAATCAAACCAAGATGGCCTATGATTATATTGCA
CACCCCAAAGGGTTGGGGTTGCCCTAAAACTTTGCATGGTAAACCATTAGAAGGTA
CTTTTAGAGCACATCAAGTTCCTTTGAAAAATGCTAAGACTGATGCAGAAGAATTG
GGTCAATTAGAAAACTGGTTGAAGTCTTACCATATAGAAGATTTCATCGACAAGTC
AAACGGTTTGCCATTAAAGGGTTTGATTGAACACTTACCACCTAGAGTAAAAAGAA
TGGGTCAAAAGACTGATGCTAATAACGACTTCCAACCATTATGTGTTCCTGATTGGA
ACGACTTTTCTATCGATAGAGGTATTTTGGAATCTGCTACCTCAATTGTTGGTAAAT
ACTTGGATAGAGTCTTACAAGCAAACCCAAAGACTTTGAGATTATTTTCCCCTGATG
AATTAGCCAGTAACAAATTGGACGGTGTTTTAGAACATTCAAACAGAACATTGCAA
ACCGATGCCATATCCGCTTGGAGTAGAGGTAGAGTAACAGAAGTTTTGTCTGAACA
TATGTGCCAAGGTTTCATGCAAGGTTATACCTTAACTGGTAGAACCGCTATTTTTCC
ATCCTACGAAGCATTCTTGCCTATCATAACTTCTATGACAGTTCAATACACCAAGTT
CTTGAAGATGGCATTAGAAACTAAGTGGCATGGTAGAGTCGGTTCCTTAAACTACG

-continued

```
TAACTACAAGTACATGGGCTAGACAAGAACATAATGGTTTTTCTCACCAATCACCA

AGATTCATAACCACTATGTTGTCCTTTAAGCCTACATTAACCAGAGTTTATTTCCCA

CCTGATACAAACTGTTTCTTGTCTACTATCGCACATTGCTTATCTTCAGACAATGGTG

TTAACTTGATGGTCTCCAGTAAAAATCCAGGTCCTTCCTGGTTAAGTAGAGAAGAA

GCTGAAGAACATTGTGTCGCAGGTGCCTCTGTATGGAAGTTCGCATCAACTGATGGT

GGTTTAGATCCAGACGTCGTATTAGTTGGTATCGGTAACGAAATCATGTTCGAAGTC

ATAGCTGCAGCCTCTATCTTGGCTCATGATTTGCCAAAATTGAGAATTAGAGTTGTC

AACATCACAGATTTGATGATCTTAGCCGACAATCATCCACACTCCATGAGTGAAATC

GAGTTTAATGCTTTATTCACTCCTAACAGACATGTCCACTTCAATTATCATGGTTAC

GTAATGGATTTGCAATCTTTGTTATTTTCAAGAATCGACGCATCTAGAGTTTCAATG

GAAGGTTATTGTGAAGAAGGTACAACCACTACACCATTCAATATGATGATTGCAAA

CAGAACTTCTAGATACCATGTTGCCATGGCTGCAGTCGCTGGTGCAACATGTAACCC

TGAAGTTGCTATGAATTGCCACAAATTGATATCAAACTACAAGCATAGATTGACTC

AAATTAAACACTATATATACGAAAACGGTGTTGATCCAGAAGGTACTTTTGATATCC

CTGACAATTTGACAAAGGGTCAAGTCATTTAA
```

SEQ ID No: 75
```
MKFEATKEFMNESRTEAAKADPSPLQSHLPATLDTLQVHLLKDYVPEDDLVTLKNFQR

VCNYIAAAMIFLCDNVLLENKLTSDHIKPRLLGHWGTCPALALAYSHCNRIISKYNLDM

LFVTGPGHGAPAILAALYIEGSLQAYYPQYGHNMQGLHRLITKFSVTGGFPSHVNAEVP

GAIHEGGELGYALSVSYGAVLDRPNLIVACVVGDGEAETGPTAASWHCHKFIDPAESG

AVIPILNLNGFKISERTVYGCMDRRELSALFSGFGYQVVFVDYRTADDVNRDMAAAMD

WCVEIIHEIQDAARAGTPIIKPRWPMIILHTPKGWGCPKTLHGKPLEGTFRAHQVPLKNA

KTDAEELGQLENWLKSYHIEDFIDKSNGLPLKGLIEHLPPRVKRMGQKTDANNDFQPLC

VPDWNDFSIDRGILESATSIVGKYLDRVLQANPKTLRLFSPDELASNKLDGVLEHSNRTL

QTDAISAWSRGRVTEVLSEHMCQGFMQGYTLTGRTAIFPSYEAFLPIITSMTVQYTKFLK

MALETKWHGRVGSLNYVTTSTWARQEHNGFSHQSPRFITTMLSFKPTLTRVYFPPDTN

CFLSTIAHCLSSDNGVNLMVSSKNPGPSWLSREEAEEHCVAGASVWKFASTDGGLDPD

VVLVGIGNEIMFEVIAAASILAHDLPKLRIRVVNITDLMILADNHPHSMSEIEFNALFTPN

RHVHFNYHGYVMDLQSLLFSRIDASRVSMEGYCEEGTTTTPFNMMIANRTSRYHVAM

AAVAGATCNPEVANINCHKLISNYKHRLTQIKHYIYENGVDPEGTFDIPDNLTKGQVI
```

SEQ ID No: 76
```
ATGCCAGGTGAAGTCATAGACCAACCAAACCCTCCTCCATTAACATCCCACTTGCCA

GATACCATAGAAGAATTAGCAGTAAAGCCTAGTAAAGCTCCATTGTCTAATTTGGA

TTTGGTTTCTTTGAGAGAATTTCAAAGAGCTGCATGTTATATAGCTTCCGCAATGAT

CTTCTTAAAGGATAACGTATTGTTGGACAGAGAATTGAGATTTGAAGATGTTAAGC

CTAGATTGTTAGGTCATTGGGGTACTTGCCCAGGTTTGATATTGATCTGGTCACACT

TAAATTTGTTAATTAGAGATTCTTCACAAGACATGTTGTTCGTTATAGGTCCTGGTC

ATGGTGCACCAGCCGCTTTAGCCTGTTTGTGGTTAGAAGGTTCTTTGGAAAGATTTT

ACCCTGATAAGTACAGAACAGACAAGGAAGGTTTGCATAATTTGATAACAAAATTT

TCTGTTCCAACCGGTTTCCCTTCTCATATAAACCCAGAAACTCCTGGTTGTATCCAC

GAAGGTGGTGAATTGGGTTATGCCTTAGCTGTCTCATTTGGTGCTGTAATGGATAAG
```

-continued

```
CCTGACTTGATAGTTCCATGCGTTGTCGGTGACGGTGAAGCAGAAACAGGTCCAAC
CGCAGCCGCTTGGCATTCAATCAAATACTTAGATCCTGCTGAATCCGGTGCAGTTAT
CCCAATTTTGCACGTCAACGGTTTTAAGATATCTGAAAGAACTATCTTCGGTTGTAT
GGATAACACAGAATTGGTTTTGTTATTCTCTGGTTATGGTTACGAAGTTTGCATCGT
CGAAAATTTGGATGCTATTGACACTGAATTGCATACAGCCTTATTTTGGGCTTTGAG
TGAAATTAAAAGAATACAAGGTGCAGCCAGATCTGGTAACCCTATTACCAAGCCAA
GATGGCCTATGATTATATTGAGAACTCCTAAAGGTTGGACCGGTCCAAGAACTGTT
GATGACAAGATCATTGAAGGTTCTTTCCATGCACACCAAGTACCAGTTACAAAAGC
CAATAAGGATGAAGGTCATTTGAGAATTTTACAAGATTGGTTGAAGAGTTACGACG
TTAGAGGTTTGTTACCAGATGGTAAACCTTCTGGTGACTTTTTGGACATTTTACCAC
CTGATCCTCATAAAAGATTAGGTCAATCTAAGTTGGCTTACGACTGTCATCAACCAT
TGGATTTGCCTGACTGGAGACCACACTCAGTTGATAAATTTGAAGAAGCCTCCAGT
ATGCAACAATCCGGTAAATTCTTGGATGTAGTTGCTAGACAAAACATGAAGACTTTT
AGAATTTTCTCTCCAGATGAATTAGAATCAAATAAGTTATCCGCAGTATTGGATCAT
TCTTCAAGAAACTTCCAATGGGACCAATATTCTAGAGCACAAGGTGGTAGAGTTAT
AGAAATCTTGTCCGAACACTGTTGCCAAGGTTTCTTGCAAGGTTATACTTTGACAGG
TAGAACTGCTATTTTTCCTTCTTACGAATCATTCTTAGGTATCATCCATACAATGATG
ATACAATACTCCAAATTCAGTAAGATATCTAGAAAATTGCCATGGAGAGGTGACTT
GTCTTCTATTAATTACATCGAAACCTCTACTTGGGCAAGACAAGAACATAATGGTTT
TTCACACCAAAACCCATCCTTCATAGGTGCTGTCTTGAATTTGAAAGCAGAAATCGC
CAGAGTATACTTGCCACCTGATGCAAACTGTTTCTTGTCTACTTTGCATCACTGCTTG
CAATCCAAAAATTACGTCAACTTGATGATAGGTAGTAAGCAACCAACCCCTGTATA
CTTGTCTGCTGAAGATGCACAAAGACATTGTGAAGACGGTGCCAGTATATGGAGAT
GGGCTTCTACCCATGATGGTGAACACCCTGACGTCGTATTAGTTGGTATCGGTGTCG
AAGTAACTTTTGAAGTCATTAAAGCTGCACAATTGTTATCTAGATTAGCTCCAAATT
TGAGAGTTAGAGTTGTCAACGTCACAGATTGTTAGTATTACCTCATGAAAGTCATC
ACCCACACGCTTTGGACTCTAAAGCATTTGAAGATATGTTCACATTGGACAAGCCA
GTCTGCTTCAATTATCATTCATACGCTACCGAATTACAAGGTTTGTTATTTGGTAGA
CCTGCATTGCACAGAATGTCAGTTGAAGGTTATAAAGAAGAAGGTTCCACTACAAC
CCCCATTCGATATGATGTTGGTAAACACTGTTTCAAGATTCCATGTTGCCTCCAGAGC
TTTGAAGGCCGCTGCAGCCCAAAACGATGAAGTCAAGGAAAACTTAAGTGCATTGT
TAGCCAAGGTAGATGACGAAATGAAGTCTGTTAAGGATTACATCGAACAATGGGGT
AAAGTTGACCCAGATGACATCTATGAATTGGATTTCTTGAAGAAAGACTAA
```

SEQ ID No: 77

```
MPGEVIDQPNPPPLTSHLPDTIEELAVKPSKAPLSNLDLVSLREFQRAACYIASAMIFLKD
NVLLDRELRFEDVKPRLLGHWGTCPGLILIWSHLNLLIRDSSQDMLFVIGPGHGAPAAL
ACLWLEGSLERFYPDKYRTDKEGLHNLITKFSVPTGFPSHINPETPGCIHEGGELGYALA
VSFGAVMDKPDLIVPCVVGDGEAETGPTAAAWHSIKYLDPAESGAVIPILHVNGFKISE
RTIFGCMDNTELVLLFSGYGYEVCIVENLDAIDTELHTALFWALSEIKRIQGAARSGNPIT
KPRWPMIILRTPKGWTGPRTVDDKIIEGSFHAHQVPVTKANKDEGHLRILQDWLKSYD
VRGLLPDGKPSGDFLDILPPDPHKRLGQSKLAYDCHQPLDLPDWRPHSVDKFEEASSMQ
```

-continued

QSGKFLDVVARQNMKTFRIFSPDELESNKLSAVLDHSSRNFQWDQYSRAQGGRVIEILS

EHCCQGFLQGYTLTGRTAIFPSYESFLGIIHTMMIQYSKFSKISRKLPWRGDLSSINYIETS

TWARQEHNGFSHQNPSFIGAVLNLKAEIARVYLPPDANCFLSTLHHCLQSKNYVNLMIG

SKQPTPVYLSAEDAQRHCEDGASIWRWASTHDGEHPDVVLVGIGVEVTFEVIKAAQLL

SRLAPNLRVRVVNVTDLLVLPHESHHPHALDSKAFEDMFTLDKPVCFNYHSYATELQG

LLFGRPALHRMSVEGYKEEGSTTTPFDMMLVNTVSRFHVASRALKAAAAQNDEVKEN

LSALLAKVDDEMKSVKDYIEQWGKVDPDDIYELDFLKKD

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

What is claimed is:

1. A recombinant yeast cell comprising at least one heterologous nucleic acid encoding one or more polypeptide having:
   i) phosphoketolase activity;
   ii) phosphotransacetylase activity; and
   iii) acetylating acetaldehyde dehydrogenase activity,
   wherein said cell does not comprise a heterologous modified xylose reductase gene,
   wherein said cell is capable of increased ethanol production from glucose in a fermentation process when compared to the yeast cell without the at least one heterologous nucleic acid, and wherein the polypeptide having phosphoketolase activity has the amino acid of SEQ ID NO: 57, the polypeptide having acetylating acetaldehyde dehydrogenase activity has the amino acid of SEQ ID NO: 32, and the polypeptide having phophotransacetylase activity is the phophotransacetylase from *Lactobacillus plantarum*.

2. The recombinant yeast cell of claim 1, wherein said cell has a reduced NAD-dependant glycerol phosphate dehydrogenase (GPD) activity when compared to a parent yeast cell.

3. The recombinant yeast cell of claim 1, wherein said cell comprises an altered pentose phosphate pathway resulting from one or more heterologously expressed nucleic acid affecting the pentose phosphate pathway.

4. The recombinant yeast cell of claim 1 wherein the species of the yeast cell is *Saccharomyces cerevisiae*.

5. The recombinant yeast cell of claim 1, wherein said fermentation process is selected from the group consisting of post-liquefaction and saccharification fermentation, simultaneous saccharification and fermentation (SSF) and granular starch hydrolyzing enzyme (GSHE) fermentation.

6. The recombinant yeast cell of claim 1, wherein the biochemical end product is selected from the group consisting of an organic acid, an amino acid and an alcohol.

7. The recombinant yeast cell of claim 6, wherein the biochemical end product is ethanol.

8. A fermentation composition comprising the recombinant yeast cell of claim 1 further comprising glucose and xylose.

9. The fermentation composition of claim 8, wherein the glucose to xylose concentration is greater than 1:1.

10. The fermentation composition of claim 9, wherein the glucose to xylose concentration is greater than 5:1.

11. The fermentation composition of claim 10 further comprising glucoamylase.

12. The fermentation composition of claim 11, wherein the glucoamylase is expressed by the recombinant yeast cell.

13. The fermentation composition according to claim 8 further comprising at least one additional recombinant gene, wherein the at least one additional recombinant gene encodes one or more of an enzyme selected from the group consisting of a dehydrogenase, a transketolase, a phosphoketolase, a transladolase, an epimerase, a phytase, a xylanase, a β-glucanase, a phosphatase, a protease, an alpha-amylase, a beta-amylase, a different glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase.

14. The fermentation composition according to claim 13, wherein the at least one additional recombinant gene encodes an alpha-amylase, a glucoamylase, a cutinase, a trehalase or combinations thereof.

15. The fermentation composition according to claim 14, wherein the at least one additional recombinant gene encodes an alpha-amylase.

16. The fermentation composition according to claim 8 further comprising an additional yeast species.

* * * * *

SEQUENCE LISTING

<160> NUMBER OF SEQ ID NOS: 77

<210> SEQ ID NO 1
<211> LENGTH: 3789
<212> TYPE: DNA
<213> ORGANISM: artificial sequence
<220> FEATURE:
<223> OTHER INFORMATION: Constructed Vector

<400> SEQUENCE: 1

```
aaataataaa aaaagtaacc ccacttctac ttctacatcg gaaaaacatt ccattcacat      60
atcgtctttg gcctatcttg ttttgtcctc ggtagatcag gtcagtacaa acgcaacacg     120
aaagaacaaa aaaagaagaa aacagaaggc caagacaggg tcaatgagac tgttgtcctc     180
ctactgtccc tatgtctctg gccgatcacg cgccattgtc cctcagaaac aaatcaaaca     240
cccacacccc gggcacccaa agtccccacc cacaccacca atagagtctg ctggtgttgc     300
tgatttgatc accacctgcg ctggtggtag aaacgtcaag gttgctaggc taatggctac     360
ttctggtaag gacgcctggg aatgtgaaaa ggagttgttg aatggccaat ccgctcaagg     420
tttaattacc tgcaaagaag ttcacgaatg gttggaaaca tgtggctctg tcgaagactt     480
cccattattt gaagccgtat accaaatcgt ttacaacaac tacccaatga agaacctgcc     540
ggacatgatt gaagaattag atctacatga agattagatt tattggagaa agataagctt     600
ttcaattcat cattttttt ttattctttt ttttgattcc ggtttccttg aaatttttt      660 gattcggtaa tctccgaaca gaaggaagaa cgaaggaagg agcacagact tagattggta     720
tatatacgca tatgtagtgt tgaagaaaca tgaaattgcc cagtattctt aacccaactg     780
cacagaacaa aaacctgcag gaaacgaaga taaatcatgt cgaaagctac atataaggaa     840
cgtgctgcta ctcatcctag tcctgttgct gccaagctat ttaatatcat gcacgaaaag     900
caaacaaact tgtgtgcttc attggatgtt cgtaccacca aggaattact ggagttagtt     960
gaagcattag gtcccaaaat ttgtttacta aaaacacatg tggatatctt gactgatttt    1020
tccatggagg gcacagttaa gccgctaaag gcattatccg ccaagtacaa tttttttactc   1080 ttcgaagaca gaaaatttgc tgacattggt aatacagtca aattgcagta ctctgcgggt    1140
gtatacgaaa tagcagaatg ggcagacatt acgaatgcac acggtgtggt gggcccaggt    1200
attgttagcg gtttgaagca ggcggcagaa gaagtaacaa aggaacctag aggccttttg    1260
```

```
atgttagcag aattgtcatg caagggctcc ctagctactg gagaatatac taagggtact   1320
gttgacattg cgaagagcga caaagatttt gttatcggct ttattgctca aagagacatg   1380
ggtggaagag atgaaggtta cgattggttg attatgacac ccggtgtggg tttagatgac   1440
aagggagacg cattgggtca acagtataga accgtggatg atgtggtctc tacaggatct   1500
gacattatta ttgttggaag aggactattt gcaaagggaa gggatgctaa ggtagagggt   1560
gaacgttaca gaaaagcagg ctgggaagca tatttgagaa gatgcggcca gcaaaactaa   1620
aaaactgtat tataagtaaa tgcatgtata ctaaactcac aaattagagc ttcaatttaa   1680
ttatatcagt tattacccgg gaatctcggt cgtaatgatt tttataatga cgaaaaaaaa   1740
aaaattggaa agaaaaaggc gcgcccccga caatttggtt gctaatccag acttgattga   1800
ttcagtcaag gatgtcgaca tcatcgtttt caacattcca catcaatttt tgccccgtat   1860
ctgtagccaa ttgaaaggtc atgttgattc acacgtcaga gctatctcct gtctaaaggg   1920
ttttgaagtt ggtgctaaag gtgtccaatt gctatcctct tacatcactg aggaactagg   1980
tattcaatgt ggtgctctat ctggtgctaa cattgccacc gaagtcgctc aagaacactg   2040
gtctgaaaca acagttgctt accacattcc aaaggattta aatccaaaaa tggccatgag   2100
acaataaccc tgataaatgc ttcaataata ttgaaaaagg aagagtatga gtattcaaca   2160
tttccgtgtc gcccttattc ccttttttgc ggcattttgc cttcctgttt ttgctcaccc   2220
agaaacgctg gtgaaagtaa aagatgctga agatcagttg ggtgcacgag tgggttacat   2280
cgaactggat ctcaacagcg gtaagatcct tgagagtttt cgccccgaag aacgttttcc   2340
aatgatgagc acttttaaag ttctgctatg tggcgcggta ttatcccgta ttgacgccgg   2400
gcaagagcaa ctcggtcgcc gcatacacta ttctcagaat gacttggttg agtactcacc   2460
agtcacagaa aagcatctta cggatggcat gacagtaaga gaattatgca gtgctgccat   2520
aaccatgagt gataacactg cggccaactt acttctgaca acgatcggag gaccgaagga   2580
gctaaccgct tttttgcaca acatggggga tcatgtaact cgccttgatc gttgggaacc   2640
ggagctgaat gaagccatac caaacgacga gcgtgacacc acgatgcctg tagcaatggc   2700
aacaacgttg cgcaaactat taactggcga actacttact ctagcttccc ggcaacaatt   2760
aatagactgg atggaggcgg ataaagttgc aggaccactt ctgcgctcgg cccttccggc   2820
tggctggttt attgctgata atctggagcc ggtgagcgt gggtctcgcg gtatcattgc    2880
agcactgggg ccagatggta agccctcccg tatcgtagtt atctacacga cggggagtca   2940
ggcaactatg gatgaacgaa atagacagat cgctgagata ggtgcctcac tgattaagca   3000
ttggtaactg tcagaccaag tttactcata tatactttag attgatttaa aacttcattt   3060
ttaatttaaa aggatctagg tgaagatcct ttttgataat ctcatgacca aaatccctta   3120
acgtgagttt tcgttccact gagcgtcaga ccccgtagaa aagatcaaag gatcttcttg   3180
agatcctttt tttctgcgcg taatctgctg cttgcaaaca aaaaaaccac cgctaccagc   3240
ggtggtttgt ttgccggatc aagagctacc aactcttttt ccgaaggtaa ctggcttcag   3300
cagagcgcag ataccaaata ctgtccttct agtgtagccg tagttaggcc accacttcaa   3360
gaactctgta gcaccgccta catacctcgc tctgctaatc ctgttaccag tggctgctgc   3420
cagtggcgat aagtcgtgtc ttaccgggtt ggactcaaga cgatagttac cggataaggc   3480
gcagcggtcg gctgaacgg gggttcgtg cacacagccc agcttggagc gaacgaccta    3540
caccgaactg agatacctac agcgtgagct atgagaaagc gccacgcttc ccgaagggag   3600
```

```
aaaggcggac aggtatccgg taagcggcag ggtcggaaca ggagagcgca cgagggagct   3660
tccaggggga aacgcctggt atctttatag tcctgtcggg tttcgccacc tctgacttga   3720
gcgtcgattt ttgtgatgct cgtcaggggg gcggagccta tggaaaaacg ccagcaacgc   3780
tgcatattt                                                           3789

<210> SEQ ID NO 2
<211> LENGTH: 3757
<212> TYPE: DNA
<213> ORGANISM: artificial sequence
<220> FEATURE:
<223> OTHER INFORMATION: Constructed Vector

<400> SEQUENCE: 2
aaataaaaac tggagcaagg aattaccatc accgtcacca tcaccatcat atcgccttag     60
cctctagcca tagccatcat gcaagcgtgt atcttctaag attcagtcat catcattacc    120
gagtttgttt tccttcacat gatgaagaag gtttgagtat gctcgaaaca ataagacgac    180
gatggctctg ccattgttat attacgcttt tgcggcgagg tgccgatggg ttgctgaggg    240
gaagagtgtt tagcttacgg acctattgcc attgttattc cgattaacgt caatgtcatc    300
gatgatgttg ctggtatatc cattgccggt gccttgaaga acgtcgtggc acttgcatgt    360
ggtttcgtag aaggtatggg atggggtaac aatgcctccg cagccattca aaggctgggt    420
ttaggtgaaa ttatcaagtt cggtagaatg ttttcccag aatccaaagt cgagacctac     480
tatcaagaat ccgctggtgt tgcagatctg atcaccacct gctcaggcgg tagaaacgtc    540
aaggttgcca catacatggc caagaccggt aagtcagcct ggaagctttt caattcatc     600 attttttttt tattcttttt tttgattccg gtttccttga aattttttg attcggtaat     660 ctccgaacag aaggaagaac gaaggaagga gcacagactt agattggtat atatacgcat    720
atgtagtgtt gaagaaacat gaaattgccc agtattctta acccaactgc acagaacaaa    780
aacctgcagg aaacgaagat aaatcatgtc gaaagctaca taaggaac gtgctgctac      840 tcatcctagt cctgttgctg ccaagctatt taatatcatg cacgaaaagc aaacaaactt    900
gtgtgcttca ttgatgtttc gtaccaccaa ggaattactg gagttagttg aagcattagg    960
tcccaaaatt tgtttactaa aaacacatgt ggatatcttg actgattttt ccatggaggg   1020
cacagttaag ccgctaaagg cattatccgc caagtacaat ttttactct tcgaagacag    1080 aaaatttgct gacattggta atacagtcaa attgcagtac tctgcgggtg tatacagaat   1140
agcagaatgg gcagacatta cgaatgcaca cggtgtggtg ggcccaggta ttgttagcgg   1200
tttgaagcag gcggcagaag aagtaacaaa ggaacctaga ggccttttga tgttagcaga   1260
attgtcatgc aagggctccc tagctactgg agaatatact aagggtactg ttgacattgc   1320
gaagagcgac aaagattttg ttatcggctt tattgctcaa agagacatgg gtggaagaga   1380
tgaaggttac gattggttga ttatgacacc cggtgtgggt ttagatgaca agggagacgc   1440
attgggtcaa cagtatagaa ccgtggatga tgtggtctct acaggatctg acattattat   1500
tgttggaaga ggactatttg caagggaag ggatgctaag gtagagggtg aacgttacag    1560
aaaagcaggc tggaagcat atttgagaag atgcggccag caaaactaaa aaactgtatt    1620
ataagtaaat gcatgtatac taaactcaca aattagagct tcaatttaat tatatcagtt   1680
attacccggg aatctcggtc gtaatgattt ttataatgac gaaaaaaaaa aaattggaaa   1740
gaaaaaggcg cgcccttgt tttcaacatc cctcatcaat ttttaccaaa catagtcaaa    1800
caattgcaag gccacgtggc ccctcatgta agggccatct cgtgtctaaa agggttcgag   1860
```

```
ttgggctcca agggtgtgca attgctatcc tcctatgtta ctgatgagtt aggaatccaa    1920
tgtggcgcac tatctggtgc aaacttggca ccggaagtgg ccaaggagca ttggtccgaa    1980
accaccgtgg cttaccaact accaaaggat tatcaaggtg atggcaagga tgtagatcat    2040
aagatttaaa tccaaaaatg gccatgagac aataaccctg ataaatgctt caataatatt    2100
gaaaaaggaa gagtatgagt attcaacatt tccgtgtcgc ccttattccc ttttttgcgg    2160
cattttgcct tcctgttttt gctcacccag aaacgctggt gaaagtaaaa gatgctgaag    2220
atcagttggg tgcacgagtg ggttacatcg aactggatct caacagcggt aagatccttg    2280
agagttttcg ccccgaagaa cgttttccaa tgatgagcac ttttaaagtt ctgctatgtg    2340
gcgcggtatt atcccgtatt gacgccgggc aagagcaact cggtcgccgc atacactatt    2400
ctcagaatga cttggttgag tactcaccag tcacagaaaa gcatcttacg gatggcatga    2460
cagtaagaga attatgcagt gctgccataa ccatgagtga taacactgcg gccaacttac    2520
ttctgacaac gatcggagga ccgaaggagc taaccgcttt tttgcacaac atgggggatc    2580
atgtaactcg ccttgatcgt tgggaaccgg agctgaatga agccatacca aacgacgagc    2640
gtgacaccac gatgcctgta gcaatggcaa caacgttgcg caaactatta actggcgaac    2700
tacttactct agcttcccgg caacaattaa tagactggat ggaggcggat aaagttgcag    2760
gaccacttct gcgctcggcc cttccggctg gctggtttat tgctgataaa tctgagccg     2820 gtgagcgtgg gtctcgcggt atcattgcag cactggggcc agatggtaag ccctcccgta    2880
tcgtagttat ctacacgacg gggagtcagg caactatgga tgaacgaaat agacagatcg    2940
ctgagatagg tgcctcactg attaagcatt ggtaactgtc agaccaagtt tactcatata    3000
tactttagat tgatttaaaa cttcattttt aatttaaaag gatctaggtg aagatccttt    3060
ttgataatct catgaccaaa atcccttaac gtgagttttc gttccactga gcgtcagacc    3120
ccgtagaaaa gatcaaagga tcttcttgag atcctttttt tctgcgcgta atctgctgct    3180
tgcaaacaaa aaaaccaccg ctaccagcgg tggtttgttt gccggatcaa gagctaccaa    3240
ctctttttcc gaaggtaact ggcttcagca gagcgcagat accaaatact gtccttctag    3300
tgtagccgta gttaggccac cacttcaaga actctgtagc accgcctaca tacctcgctc    3360
tgctaatcct gttaccagtg gctgctgcca gtggcgataa gtcgtgtctt accgggttgg    3420
actcaagacg atagttaccg gataaggcgc agcggtcggg ctgaacgggg gttcgtgca    3480 cacagcccag cttggagcga acgacctaca ccgaactgag atacctacag cgtgagctat    3540
gagaaagcgc cacgcttccc gaagggagaa aggcggacag gtatccggta agcggcaggg    3600
tcggaacagg agagcgcacg agggagcttc caggggggaaa cgcctggtat ctttatagtc    3660
ctgtcgggtt tcgccacctc tgacttgagc gtcgatttt tgtgatgctcg tcaggggggc    3720 ggagcctatg gaaaaacgcc agcaacgctg catattt                             3757
```

<210> SEQ ID NO 3
<211> LENGTH: 2478
<212> TYPE: DNA
<213> ORGANISM: Bifidobacterium animalis

<400> SEQUENCE: 3

```
atgaccaacc cagtcattgg tactccatgg caaaaattgg atagaccagt ttccgaagaa     60
gccattgaag gtatggataa gtattggaga gttgccaact acatgtccat tggtcaaatc    120
tacttgagat ccaacccatt gatgaaggaa ccattcacta gagatgatgt caagcacaga    180
```

```
ttggttggtc attggggtac tactccaggt ttgaattttt tgttggccca catcaacaga      240
ttgatcgctg atcatcaaca aaacaccgtt ttcattatgg gtccaggtca tggtggtcca      300
gctggtactg ctcaatctta tattgatggt acttacaccg aatattaccc aaacatcact      360
aaggatgaag ccggtttaca aaagttcttc agacaatttt cttacccagg tggtatccca      420
tctcattttg ctccagaaac tccaggttct attcatgaag tggtgaatt gggttatgct       480 ttgtctcatg cttatggtgc cattatggat aacccatctt tgttcgttcc atgcattatt      540
ggtgatggtg aagctgaaac tggtccattg gctactggtt ggcaatctaa caaattggtt     600
aacccaagaa ccgatggtat cgttttgcca atcttgcatt tgaacggtta caagattgct      660
aacccaacca ttttggccag aatctctgat gaagaattgc acgattttt cagaggtatg       720 ggttaccacc catacgaatt tgttgctggt tttgataacg aagatcactt gtccatccat     780
agaagattcg ccgaattatt cgaaaccatc ttcgacgaaa tttgcgatat taaggctgct    840
gctcaaactg atgatatgac tagaccattt tacccaatgt tgatcttcag aactccaaag      900
ggttggactt gtccaaagtt tatcgatggt aaaaagaccg aaggttcttg gagagcacat      960
caagttccat tggcttcagc tagagatact gaagctcatt tcgaagtttt gaagggttgg     1020
atggaatctt acaagcctga agaattattc aacgccgacg ttctatcaa agaagatgtt      1080 actgcttta tgccaagggg tgaattgaga attggtgcta atccaaatgc taacggtggt      1140
agaattagag aagatttgaa gttgccagaa ttggaccaat acgaaattac cggtgtcaaa     1200
gaatatggtc atggttgggg tcaagttgaa gctccaagat ctttgggtgc ttactgtaga     1260
gatatcatca gaacaacccc agactccttt agagttttg gtccagacga aactgcttcc     1320
aatagattga atgctactta cgaagtcacc aaaaagcaat gggataacgg ttatttgtct     1380
gccttggttg acgaaaacat ggctgttact ggtcaagttg ttgaacaatt gtctgaacat     1440
caatgcgaag gttttttgga agcctatttg ttgactggta gacatggtat ttggtcctct     1500
tacgaatctt tcgttcacgt tatcgattcc atgttgaatc aacacgctaa atggttggaa     1560
gctaccgtta gagaaattcc ttggagaaag ccaatctcct ctgttaactt gttggtttct    1620
tcacacgttt ggagacaaga tcataacggt ttctctcatc aagatccagg tgttacttct    1680
gtcttgttga caaaaccttt caacaacgat cacgtcacca atatctactt tgctactgat     1740
gctaacatgt tgttggctat tgctgaaaag tgtttcaagt ccaccaacaa gattaacgct    1800
attttcgctg gtaaacaacc agctgctact tggattactt tggatgaagt tagagctgaa    1860
ttggaagctg gtgctgctga atggaaatgg gcttctaatg ctaagtctaa cgatgaagtt    1920
caagttgttt tggctgctgc tggtgatgtt ccaactcaag aaattatggc tgcttctgat    1980
gctttgaaca agatgggtat taagttcaag gttgtcaacg tcgttgattt gatcaagttg    2040
caatcctcca agaaaacga tgaagccatg tctgatgaag atttcgctga tttgtttacc     2100
gctgataagc cagttttgtt cgcttatcat tcttacgccc aagatgtcag aggtttgata    2160
tacgatagac caaccatga taacttcacc gttgtcggtt acaaagaaca aggttctact     2220
actactccat tcgatatggt tagagttaac gacatggata gatacgcatt gcaagctaag    2280
gctttggaat tgattgatgc tgataagtac gccgacaaga tcaacgaatt gaacgaattt    2340
agaaagaccg cttttccaatt cgctgttgat aacggttacg atatcccaga atttaccgat    2400
tgggtttacc cagatgttaa ggttgacgaa acttctatgt tgtctgctac tgctgctaca     2460
gctggtgata atgaataa                                                    2478
```

<210> SEQ ID NO 4
<211> LENGTH: 978
<212> TYPE: DNA
<213> ORGANISM: Lactobacillus plantarum

<400> SEQUENCE: 4

| | | |
|---|---|---|
| atggacttgt tcgaatcttt ggcccaaaag attactggta aggatcaaac tatcgttttc | 60 |
| ccagaaggta ctgaacctag aatagttggt gctgctgcta gattggctgc tgatggtttg | 120 |
| gttaagccaa tagttttggg tgctactgat aaggttcaag ctgttgctaa tgatttgaac | 180 |
| gctgatttga ctggtgttca agttttggat ccagctactt atccagctga agataagcaa | 240 |
| gctatgttgg atgctttggt cgaaagaaga aagggtaaga atactccaga caagctgct | 300 |
| aagatgttgg aagatgaaaa ctacttcggt actatgttgg tctacatggg taaagcagat | 360 |
| ggtatggttt ctggtgctat tcatccaact ggtgatactg ttagaccagc cttgcaaatt | 420 |
| atcaaaacta agccaggttc ccacagaatt tcaggtgctt tcattatgca aagggtgaa | 480 |
| gaaagatacg ttttcgctga ttgcgccatt aacattgatc cagatgctga tactttggct | 540 |
| gaaattgcta ctcaatctgc tgctactgct aaagttttcg atattgatcc aaaggtcgcc | 600 |
| atgttgtctt tttcaacaaa aggttctgct aagggtgaaa tggttactaa ggtacaagaa | 660 |
| gctacagcta agctcaagc tgctgaacca gaattggcta ttgatggtga attacaattc | 720 |
| gatgctgcct tcgttgaaaa ggtcggttta caaaaagctc caggtctaa agttgctggt | 780 |
| catgctaatg ttttttgttt tccagaattg caatccggta acatcggtta caaaatcgct | 840 |
| caaagatttg gtcatttcga agctgttggt ccagttttac aaggtttgaa caaaccagtt | 900 |
| tccgacttgt ctagaggttg ttctgaagaa gatgtttaca agttgccat tattaccgct | 960 |
| gctcaaggtt tggcttag | 978 |

<210> SEQ ID NO 5
<211> LENGTH: 1404
<212> TYPE: DNA
<213> ORGANISM: Salmonella enterica

<400> SEQUENCE: 5

| | | |
|---|---|---|
| atgaaccaac aagacataga acaagtagta aaagccgtat tattaaagat gaaagactcc | 60 |
| tctcaaccag cctcaaccgt acacgaaatg ggtgttttg cctctttgga tgacgctgtc | 120 |
| gctgcagcca aaagagccca acaaggtttg aagtcagttg ctatgagaca attagcaatc | 180 |
| catgccatta gaagcagg tgaaaaacac gccagagaat ggctgaatt agcagtatcc | 240 |
| gaaactggta tgggtagagt tgatgacaaa ttcgctaaga atgtcgctca agcaagaggt | 300 |
| acaccaggtg tcgaatgttt gagtcctcaa gtattaacag gtgacaatgg tttgacctta | 360 |
| attgaaaacg ccccatgggg tgttgtcgct tctgttacac catcaaccaa tcctgctgca | 420 |
| actgttataa ataacgcaat ctctttgatc gccgctggta actcagtagt ttttgctcca | 480 |
| catcctgcag ccaaaaaggt tcccaaaga gcaattacat tgttaaatca gccgtcgta | 540 |
| gctgcaggtg gtccagaaaa tttgttagta accgttgcta accctgatat cgaaactgca | 600 |
| caaagattat tcaagtatcc aggtatcggt ttgttagttg tcacaggtgg tgaagctgta | 660 |
| gttgatgccg ctgaaaaca caccaataag agattgattg cagccggtgc aggtaaccca | 720 |
| cctgtcgtag ttgatgaaac tgctgactta ccaagagctg cacaatccat cgttaagggt | 780 |
| gcaagtttcg ataacaacat catctgcgct gacgaaaagg ttttaattgt cgtagattct | 840 |
| gtcgctgacg aattgatgag attaatggaa ggtcaacatg cagttaaatt gacagccgct | 900 |

| | |
|---|---|
| caagccgaac aattgcaacc agttttgttg aaaaatatag atgaacgtgg taaaggtacc | 960 |
| gtatcaagag attgggttgg tagagacgca ggtaaaattg cagccgctat aggtttgaac | 1020 |
| gttcctgatc aaactagatt gttgttcgtt gaaacaccag ctaaccatcc tttcgcagta | 1080 |
| acagaaatga tgatgccagt tttacctgtt gtcagagttg ctaatgtcga agaagccata | 1140 |
| gctttggcag ttcaattaga aggtggttgt catcacaccg cagccatgca ctccagaaat | 1200 |
| atcgataata tgaaccaaat ggccaacgct atcgacactt ctattttcgt taaaaacggt | 1260 |
| ccatgcattg ctggtttggg tttaggtggt gaaggttgga ctacaatgac cataaccact | 1320 |
| cctactggtg aaggtgtcac ttctgcaaga acatttgtaa gattgagaag atgtgtctta | 1380 |
| gtagatgctt tcagaattgt ttag | 1404 |

<210> SEQ ID NO 6
<211> LENGTH: 12049
<212> TYPE: DNA
<213> ORGANISM: artificial sequence
<220> FEATURE:
<223> OTHER INFORMATION: Constructed Vector

<400> SEQUENCE: 6

| | |
|---|---|
| aaatccacta tcgtctatca actaatagtt atattatcaa tatattatca tatacggtgt | 60 |
| taagatgatg acataagtta tgagaagctg tcatcgaggt tagaggcctt aatggccgtc | 120 |
| gacatatttg acctcttaac aggttcagac gcgactgcct catcagtaag acccgttgaa | 180 |
| aagaacttac ctgaaaaaaa cgaatatata ctagcgttga atgttagcgt caacaacaag | 240 |
| aagtttaatg acgcggaggc caaggcaaaa agattccttg attacgtaag ggagttagaa | 300 |
| tcattttgaa taaaaaacac gcttttcag ttcgagttta tcattatcaa tactgccatt | 360 |
| tcaaagaata cgtaaataat taatagtagt gattttccta actttattta gtcaaaaat | 420 |
| tagccttta attctgctgt aacccgtaca tgcccaaaat aggggcggg ttacacagaa | 480 |
| tatataacat cgtaggtgtc tgggtgaaca gtttattcct ggcatccact aaatataatg | 540 |
| gagcccgctt tttaagctgg catccagaaa aaaaagaat cccagcacca aatattgtt | 600 |
| ttcttcacca accatcagtt cataggtcca ttctcttagc gcaactacag agaacagggg | 660 |
| cacaaacagg caaaaaacgg gcacaacctc aatggagtga tgcaacctgc ctggagtaaa | 720 |
| tgatgacaca aggcaattga cccacgcatg tatctatctc attttcttac accttctatt | 780 |
| accttctgct ctctctgatt tggaaaaagc tgaaaaaaa ggttgaaacc agttccctga | 840 |
| aattattccc ctacttgact aataagtata taagacggt aggtattgat tgtaattctg | 900 |
| taaatctatt tcttaaactt cttaaattct acttttatag ttagtctttt ttttagtttt | 960 |
| aaaacaccaa gaacttagtt tcgaataaac acacataaac aaactagtaa gaattcaaac | 1020 |
| aacaaaatg accaacccag tcattggtac tccatggcaa aaattggata gaccagtttc | 1080 |
| cgaagaagcc attgaaggta tggataagta ttggagagtt gccaactaca tgtccattgg | 1140 |
| tcaaatctac ttgagatcca acccattgat gaaggaacca ttcactagag atgatgtcaa | 1200 |
| gcacagattg gttggtcatt ggggtactac tccaggtttg aattttttgt tggcccacat | 1260 |
| caacagattg atcgctgatc atcaacaaaa caccgttttc attatgggtc aggtcatgg | 1320 |
| tggtccagct ggtactgctc aatcttatat tgatggtact tacaccgaat attcccaaaa | 1380 |
| catcactaag gatgaagccg gtttacaaaa gttcttcaga caattttctt acccaggtgg | 1440 |
| tatcccatct cattttgctc agaaactcc aggttctatt catgaaggtg gtgaattggg | 1500 |
| ttatgctttg tctcatgctt atggtgccat tatggataac ccatctttgt tcgttccatg | 1560 |

```
cattattggt gatggtgaag ctgaaactgg tccattggct actggttggc aatctaacaa    1620
attggttaac ccaagaaccg atggtatcgt tttgccaatc ttgcatttga acggttacaa    1680
gattgctaac ccaaccattt tggccagaat ctctgatgaa gaattgcacg attttttcag    1740
aggtatgggt taccacccat acgaatttgt tgctggtttt gataacgaag atcacttgtc    1800
catccataga agattcgccg aattattcga aaccatcttc gacgaaattt gcgatattaa    1860
ggctgctgct caaactgatg atatgactag accattttac ccaatgttga tcttcagaac    1920
tccaaagggt tggacttgtc caaagtttat cgatggtaaa aagaccgaag gttcttggag    1980
agcacatcaa gttccattgg cttcagctag agatactgaa gctcatttcg aagttttgaa    2040
gggttggatg gaatcttaca agcctgaaga attattcaac gccgacggtt ctatcaaaga    2100
agatgttact gcttttatgc caagggtga attgagaatt ggtgctaatc caaatgctaa    2160
cggtggtaga attagagaag atttgaagtt gccagaattg gaccaatacg aaattaccgg    2220
tgtcaaagaa tatggtcatg gttggggtca agttgaagct ccaagatctt tgggtgctta    2280
ctgtagagat atcatcaaga acaacccaga ctcctttaga gttttggtc cagacgaaac    2340 tgcttccaat agattgaatg ctacttacga agtcaccaaa aagcaatggg ataacggtta    2400
tttgtctgcc ttggttgacg aaaacatggc tgttactggt caagttgttg aacaattgtc    2460
tgaacatcaa tgcgaaggtt ttttggaagc ctatttgttg actggtagac atggtatttg    2520
gtcctcttac gaatctttcg ttcacgttat cgattccatg ttgaatcaac acgctaaatg    2580
gttggaagct accgttagag aaattccttg gagaaagcca atctcctctg ttaacttgtt    2640
ggtttcttca cacgtttgga gacaagatca taacggtttc tctcatcaag atccaggtgt    2700
tacttctgtc ttgttgaaca aaaccttcaa caacgatcac gtcaccaata tctactttgc    2760
tactgatgct aacatgttgt tggctattgc tgaaaagtgt ttcaagtcca ccaacaagat    2820
taacgctatt ttcgctggta acaaccagc tgctacttgg attactttgg atgaagttag    2880
agctgaattg gaagctggtg ctgctgaatg gaaatgggct tctaatgcta agtctaacga    2940
tgaagttcaa gttgttttgg ctgctgctgg tgatgttcca actcaagaaa ttatggctgc    3000
ttctgatgct ttgaacaaga tgggtattaa gttcaaggtt gtcaacgtcg ttgatttgat    3060
caagttgcaa tcctccaaag aaaacgatga agccatgtct gatgaagatt tcgctgattt    3120
gtttaccgct gataagccag ttttgttcgc ttatcattct tacgcccaag atgtcagagg    3180
tttgatatac gatagaccaa accatgataa cttcaccgtt gtcggttaca agaacaagg    3240 ttctactact actccattcg atatggttag agttaacgac atggatagat acgcattgca    3300
agctaaggct ttggaattga ttgatgctga taagtacgcc gacaagatca acgaattgaa    3360
cgaatttaga aagaccgctt tccaattcgc tgttgataac ggttacgata tcccagaatt    3420
taccgattgg gtttacccag atgttaaggt tgacgaaact tctatgttgt ctgctactgc    3480
tgctacagct ggtgataatg aataaggatc ctgataagcg gccgccgtg aaaacttcca    3540 ccacggtgac aagttgtaaa gtgctttaa ctaagaatta ttagtctttt ctgcttattt    3600
tttcatcata gtttagaaca ctttatatta acgaatagtt tatgaatcta tttaggttta    3660
aaaattgata cagtttata agttactttt tcaaagactc gtgctgtcta ttgcataatg    3720
cactggaagg ggaaaaaaaa ggtgcacacg cgtggctttt tcttgaattt gcagtttgaa    3780
aaataactac atggatgata agaaaacatg gagtacagtc actttgagaa ccttcaatca    3840
gctggtaacg tcttcgttaa ttggatactc aaaaaagatg gatagcatga atcacaagat    3900
```

```
ggaaggaaat gcgggccacg accacagtga tatgcatatg ggagatgctc gacttcaact    3960
caagacgcac agatattata acatctgcat aataggcatt tgcaagaatt actcgtgagt    4020
aaggaaagag tgaggaacta tcgcatacct gcatttaaag atgccgattt gggcgcgaat    4080
cctttatttt ggcttcaccc tcatactatt atcagggcca gaaaaaggaa gtgtttccct    4140
ccttcttgaa ttgatgttac cctcataaag cacgtggcct cttatcgaga aagaaattac    4200
cgtcgctcgt gatttgtttg caaaaagaac aaaactgaaa aaacccagac acgtcgact     4260
tcctgtcttc ctattgattg cagcttccaa tttcgtcaca caacaaggtc ctagcgacgg    4320
ctcacaggtt ttgtaacaag caatcgaagg ttctggaatg gcgggaaagg gtttagtacc    4380
acatgctatg atgcccactg tgatctccag agcaaagttc gttcgatcgt actgttactc    4440
tctctctttc aaacagaatt gtccgaatcg tgtgacaaca acagcctgtt ctcacacact    4500
cttttcttct aaccaagggg gtggtttagt ttagtagaac ctcgtgaaac ttacatttac    4560
atatatataa acttgcataa attggtcaat gcaagaaata catatttggt cttttctaat    4620
tcgtagtttt tcaagttctt agatgctttc ttttctctt ttttacagat catcaaggaa     4680
gtaattatct acttttaca actagtaaaa atggacttgt tcgaatcttt ggcccaaaag     4740
attactggta aggatcaaac tatcgttttc ccagaaggta ctgaacctag aatagttggt    4800
gctgctgcta gattggctgc tgatggtttg gttaagccaa tagttttggg tgctactgat    4860
aaggttcaag ctgttgctaa tgatttgaac gctgatttga ctggtgttca agttttggat    4920
ccagctactt atccagctga agataagcaa gctatgttgg atgctttggt cgaaagaaga    4980
aagggtaaga atactccaga acaagctgct aagatgttgg aagatgaaaa ctacttcggt    5040
actatgttgg tctacatggg taaagcagat ggtatggttt ctggtgctat tcatccaact    5100
ggtgatactg ttagaccagc cttgcaaatt atcaaaacta agccaggttc ccacagaatt    5160
tcaggtgctt tcattatgca aaagggtgaa gaaagatacg ttttcgctga ttgcgccatt    5220
aacattgatc cagatgctga tactttggct gaaattgcta ctcaatctgc tgctactgct    5280
aaagttttcg atattgatcc aaaggtcgcc atgttgtctt tttcaacaaa aggttctgct    5340
aagggtgaaa tggttactaa ggtacaagaa gctacagcta aagctcaagc tgctgaacca    5400
gaattggcta ttgatggtga attacaattc gatgctgcct tcgttgaaaa ggtcggttta    5460
caaaaagctc caggttctaa agttgctggt catgctaatg ttttttgtttt tccagaattg    5520
caatccggta acatcggtta caaaatcgct caaagatttg gtcatttcga agctgttggt    5580
ccagttttac aaggtttgaa caaccagtt tccgacttgt ctagaggttg ttctgaagaa      5640
gatgtttaca agttgccat tattaccgct gctcaaggtt tggcttagga tccaagcggc      5700
cgccaggtgt tgctttctta tccgaaaaga aataaattga attgaattga aatcgataga    5760
tcaattttt tcttttctct ttccccatcc tttacgctaa aataatagtt tattttattt      5820
tttgaatatt ttttatttat atacgtatat atagactatt atttatcttt taatgattat    5880
taagattttt attaaaaaaa aattcgctcc tcttttaatg cctttatgca gtttttttt      5940
cccattcgat atttctatgt tcgggttcag cgtatttaa gtttaataac tcgacgccta     6000
cttggcttca catacgttgc atacgtcgat atagataata atgataatga cagcaggatt    6060
atcgtaatac gtaatagttg aaaatctcaa aaatgtgtgg gtcattacgt aaataatgat    6120
aggaatggga ttcttctatt tttccttttt ccattctagc agccgtcggg aaaacgtggc    6180
atcctctctt tcgggctcaa ttggagtcac gctgccgtga gcatcctctc tttccatatc    6240
taacaactga gcacgtaacc aatggaaaag catgagctta gcgttgctcc aaaaaagtat    6300
```

```
tggatggtta ataccatttg tctgttctct tctgactttg actcctcaaa aaaaaaaaat    6360
ctacaatcaa cagatcgctt caattacgcc ctcacaaaaa ctttttttcct tcttcttcgc    6420 ccacgttaaa ttttatccct catgttgtct aacggatttc tgcacttgat ttattataaa    6480
aagacaaaga cataatactt ctctatcaat ttcagttatt gttcttcctt gcgttattct    6540
tctgttcttc ttttcttttt gtcatatata accataacca agtaatacat attcaaacta    6600
gtaagaattc aaaacaaaaa tgaaccaaca agacatagaa caagtagtaa aagccgtatt    6660
attaaagatg aaagactcct ctcaaccagc ctcaaccgta cacgaaatgg gtgttttttgc   6720 ctctttggat gacgctgtcg ctgcagccaa aagagcccaa caaggtttga agtcagttgc    6780
tatgagacaa ttagcaatcc atgccattag agaagcaggt gaaaaacacg ccagagaatt    6840
ggctgaatta gcagtatccg aaactggtat gggtagagtt gatgacaaat cgctaagaa     6900 tgtcgctcaa gcaagaggta caccaggtgt cgaatgtttg agtcctcaag tattaacagg    6960
tgacaatggt tgaccttaa ttgaaaacgc cccatggggt gttgtcgctt ctgttacacc      7020
atcaaccaat cctgctgcaa ctgttataaa taacgcaatc tctttgatcg ccgctggtaa    7080
ctcagtagtt tttgctccac atcctgcagc caaaaaggtt tcccaaagag caattacatt    7140
gttaaatcaa gccgtcgtag ctgcaggtgg tccagaaaat ttgttagtaa ccgttgctaa    7200
ccctgatatc gaaactgcac aaagattatt caagtatcca ggtatcggtt tgttagttgt    7260
cacaggtggt gaagctgtag ttgatgccgc tagaaaacac accaataaga gattgattgc    7320
agccggtgca ggtaacccac ctgtcgtagt tgatgaaact gctgacttac caagagctgc    7380
acaatccatc gttaagggtg caagtttcga taacaacatc atctgcgctg acgaaaaggt    7440
tttaattgtc gtagattctg tcgctgacga attgatgaga ttaatggaag gtcaacatgc    7500
agttaaattg acagccgctc aagccgaaca attgcaacca gttttgttga aaaatataga    7560
tgaacgtggt aaaggtaccg tatcaagaga ttgggttggt agagacgcag gtaaaattgc    7620
agccgctata ggtttgaacg ttcctgatca aactagattg ttgttcgttg aaacaccagc    7680
taaccatcct ttcgcagtaa cagaaatgat gatgccagtt ttacctgttg tcagagttgc    7740
taatgtcgaa gaagccatag cttttggcagt tcaattagaa ggtggttgtc atcacaccgc    7800
agccatgcac tccagaaata tcgataatat gaaccaaatg gccaacgcta tcgacacttc    7860
tattttcgtt aaaaacggtc catgcattgc tggtttgggt ttaggtggtg aaggttggac    7920
tacaatgacc ataaccactc ctactggtga aggtgtcact tctgcaagaa catttgtaag    7980
attgagaaga tgtgtcttag tagatgcttt cagaattgtt taggatcctg ataagcggcc    8040
gcgttaattc aaattaattg atatagtttt ttaatgagta ttgaatctgt ttagaaataa    8100
tggaatatta ttttattta tttatttata ttattggtcg gctctttct tctgaaggtc        8160 aatgacaaaa tgatatgaag gaaataatga tttctaaaat tttacaacgt aagatatttt    8220
tacaaaagcc tagctcatct tttgtcatgc actattttac tcacgcttga aattaacggc    8280
cagtccactg cggagtcatt tcaaagtcat cctaatcgat ctatcgtttt tgatagctca    8340
ttttggagtt cgcgattgtc ttctgttatt cacaactgtt ttaatttta tttcattctg     8400 gaactcttcg agttctttgt aaagtctttc atagtagctt actttatcct ccaacatatt    8460
taacttcatg tcaatttcgg ctcttaaatt ttccacatca tcaagttcaa catcatcttt    8520
taacttgaat ttattctcta gctcttccaa ccaagcctca ttgctccttg atttactggt    8580
gaaaagtgat acactttgcg cgcaatccag gtcaaaactt tcctgcaaag aattcaccaa    8640
```

```
tttctcgaca tcatagtaca atttgttttg ttctcccatc acaatttaat atacctgatg   8700
gattcttatg aagcgctggg taatggacgt gtcactctac ttcgcctttt tccctactcc   8760
ttttagtacg gaagacaatg ctaataaata agagggtaat aataatatta ttaatcggca   8820
aaaaagatta aacgccaagc gtttaattat cagaaagcaa acgtcgtacc aatccttgaa   8880
tgcttcccaa ttgtatatta agagtcatca cagcaacata ttcttgttat taaattaatt   8940
attattgatt tttgatattg tataaaaaaa ccaaatatgt ataaaaaaag tgaataaaaa   9000
ataccaagta tggagaaata tattagaagt ctatacgtta aaccaccgcg gtggagctca   9060
agcttttcaa ttcatctttt ttttttttgt tcttttttt gattccggtt tctttgaaat    9120 tttttttgatt cggtaatctc cgagcagaag gaagaacgag ggaaggagca cagacttaga  9180
ttggtatata tacgcatatg tggtgttgaa gaaacatgaa attgcccagt attcttaacc   9240
caactgcaca gaacaaaaac ctgcaggaaa cgaagataaa tcatgtcgaa agctacatat   9300
aaggaacgtg ctgctactca tcctagtcct gttgctgcca agctatttaa tatcatgcac   9360
gaaaagcaaa caaacttgtg tgcttcattg gatgttcgta ccaccaagga attactggag   9420
ttagttgaag cattaggtcc caaaatttgt ttactaaaaa cacatgtgga tatcttgact   9480
gatttttcca tggagggcac agttaagccg ctaaaggcat tatccgccaa gtacaatttt   9540
ttactcttcg aagacagaaa atttgctgac attggtaata cagtcaaatt gcagtactct   9600
gcgggtgtat acagaatagc agaatgggca gacattacga atgcacacgg tgtggtgggc   9660
ccaggtattg ttagcggttt gaagcaggcg gcggaagaag taacaaagga acctagaggc   9720
cttttgatgt tagcagaatt gtcatgcaag ggctccctag ctactggaga atatactaag   9780
ggtactgttg acattgcgaa gagcgacaaa gattttgtta tcggctttat tgctcaaaga   9840
gacatgggtg gaagagatga aggttacgat tggttgatta tgacacccgg tgtgggttta   9900
gatgacaagg gagacgcatt gggtcaacag tatagaaccg tggatgatgt ggtctctaca   9960
ggatctgaca ttattattgt tggaagagga ctatttgcaa agggaaggga tgctaaggta  10020
gagggtgaac gttacagaaa agcaggctgg gaagcatatt tgagaagatg cggccagcaa  10080
aactaaaaaa ctgtattata agtaaatgca tgtatactaa actcacaaat tagagcttca  10140
atttaattat atcagttatt acccgggaat ctcggtcgta atgatttcta taatgacgaa  10200
aaaaaaaaaa ttggaaagaa aaaggcgcgc cgaagctgaa gtgcaaggat tgataatgta  10260
ataggatcaa tgaatataaa catataaaac ggaatgagga ataatcgtaa tattagtatg  10320
tagaaatata gattccattt aaatcagaaa tggccatgag acaataaccc tgataaatgc  10380
ttcaataata ttgaaaaagg aagagtatga gtattcaaca tttccgtgtc gcccttattc  10440 cctttttgc ggcattttgc cttcctgttt ttgctcaccc agaaacgctg gtgaaagtaa   10500
aagatgctga agatcagttg ggtgcacgag tgggttacat cgaactggat ctcaacagcg  10560
gtaagatcct tgagagtttt cgccccgaag aacgttttcc aatgatgagc acttttaaag  10620
ttctgctatg tggcgcggta ttatcccgta ttgacgccgg gcaagagcaa ctcggtcgcc  10680
gcatacacta ttctcagaat gacttggttg agtactcacc agtcacagaa aagcatctta  10740
cggatggcat gacagtaaga gaattatgca gtgctgccat aaccatgagt gataacactg  10800
cggccaactt acttctgaca acgatcggag gaccgaagga gctaaccgct tttttgcaca  10860
acatggggga tcatgtaact cgccttgatc gttgggaacc ggagctgaat gaagccatac  10920
caaacgacga gcgtgacacc acgatgcctg tagcaatggc aacaacgttg cgcaaactat  10980
taactggcga actacttact ctagcttccc ggcaacaatt aatagactgg atggaggcgg  11040
```

```
ataaagttgc aggaccactt ctgcgctcgg cccttccggc tggctggttt attgctgata    11100
aatctggagc cggtgagcgt gggtctcgcg gtatcattgc agcactgggg ccagatggta    11160
agccctcccg tatcgtagtt atctacacga cggggagtca ggcaactatg gatgaacgaa    11220
atagacagat cgctgagata ggtgcctcac tgattaagca ttggtaactg tcagaccaag    11280
tttactcata tatactttag attgatttaa aacttcattt ttaatttaaa aggatctagg    11340
tgaagatcct ttttgataat ctcatgacca aaatcccttta acgtgagttt tcgttccact    11400
gagcgtcaga ccccgtagaa aagatcaaag gatcttcttg agatcctttt tttctgcgcg    11460
taatctgctg cttgcaaaca aaaaaaccac cgctaccagc ggtggtttgt ttgccggatc    11520
aagagctacc aactctttt ccgaaggtaa ctggcttcag cagagcgcag ataccaaata    11580
ctgtccttct agtgtagccg tagttaggcc accacttcaa gaactctgta gcaccgccta    11640
catacctcgc tctgctaatc ctgttaccag tggctgctgc cagtggcgat aagtcgtgtc    11700
ttaccgggtt ggactcaaga cgatagttac cggataaggc gcagcggtcg ggctgaacgg    11760
ggggttcgtg cacacagccc agcttggagc gaacgaccta caccgaactg agatacctac    11820
agcgtgagct atgagaaagc gccacgcttc ccgaagggag aaaggcggac aggtatccgg    11880
taagcggcag ggtcggaaca ggagagcgca cgagggagct tccagggga aacgcctggt    11940 atctttatag tcctgtcggg tttcgccacc tctgacttga gcgtcgattt ttgtgatgct    12000
cgtcaggggg gcggagccta tggaaaaacg ccagcaacgc tgcatatt             12049

<210> SEQ ID NO 7
<211> LENGTH: 37
<212> TYPE: DNA
<213> ORGANISM: artificial sequence
<220> FEATURE:
<223> OTHER INFORMATION: Primer

<400> SEQUENCE: 7
gaacaatgtc atgacattgg atggtgtgct tgcagtc                              37

<210> SEQ ID NO 8
<211> LENGTH: 38
<212> TYPE: DNA
<213> ORGANISM: artificial sequence
<220> FEATURE:
<223> OTHER INFORMATION: Primer

<400> SEQUENCE: 8
gagttatcgt tactccgatt attttgtaca gctgatgg                             38

<210> SEQ ID NO 9
<211> LENGTH: 36
<212> TYPE: DNA
<213> ORGANISM: artificial sequence
<220> FEATURE:
<223> OTHER INFORMATION: Primer

<400> SEQUENCE: 9
ccgtgtatat tagaacaatg ttccttatcg ctgcac                               36

<210> SEQ ID NO 10
<211> LENGTH: 37
<212> TYPE: DNA
<213> ORGANISM: artificial sequence
<220> FEATURE:
<223> OTHER INFORMATION: Primer
```

<400> SEQUENCE: 10
caggtaaccg tgcgcgatga gctaatcctg agccatc                                    37

<210> SEQ ID NO 11
<211> LENGTH: 1896
<212> TYPE: DNA
<213> ORGANISM: Trichoderma reseii

<400> SEQUENCE: 11
atgctactcc aagcattcct ttttctgtta gcaggatttg ctgccaaaat ctctgctaga      60
cctggatctt caggcttgtc cgacgtcaca aaaagatccg tggatgattt tatctctaca     120
gaaacaccta ttgcacttaa caatctcctg tgtaatgttg accagatgg ttgtagagca      180
ttcggcacaa gtgcaggcgc tgttattgct tctccatcta caattgatcc agactattac     240
tacatgtgga caagagactc cgcccttgtg ttcaaaaact tgattgatcg ttttacagaa     300
acttacgatg ctggattaca aagacgaatt gaacaatata tcactgctca agtaacttta     360
caaggattga gtaatccaag tggaagtttg gcagatggct caggactagg agagccaaag     420
tttgaactaa cccttaagcc attcactggg aactggggta gaccacaaag agatggtcct     480
gctttgagag caatagcctt aatcggctac tcaaaatggt taatcaacaa taactaccaa     540
tcaacagttt caaatgttat ctggccaatt gttaggaatg atttgaacta cgtggctcaa     600
tactggaacc agaccggttt cgaccttggg aagaggtta atggctcttc cttttcaca      660
gtggcaaatc agcatagagc tttggttgaa ggagctactt tagcggccac tctcggtcag     720
tcaggttcag cttactcttc tgtagctcct caagtacttt gttttctaca gagattctgg     780
gtatcttctg gtggttacgt tgattctaac attaacacaa atgaagggcg tactggcaaa     840
gatgtgaata gcgtccttac cagcatccat acattcgatc ctaatttggg ttgtgatgcc     900
gggacgtttc aaccttgttc tgacaaggct ttgagcaatc tgaaagtggt tgttgatagt     960
ttcagaagca tctacggtgt aaacaagggt attccagctg gtgctgccgt ggctatcggc    1020
agatatgcag aagatgtcta ctataatgga aatccatggt acttggctac ttttgccgca    1080
gcagaacagt tgtacgacgc catctacgtt tggaaaaaga ctggtagcat tactgttaca    1140
gctacatcct tagcatttt ccaagagtta gtcccagggg tcacagcagg cacgtactcc    1200
tcttctagtt caacctttac caacatcata aacgctgtct ccaccatgc cgacggtttt    1260
ctatccgagg ctgccaaata cgttcctgca gatggttctc tagctgaaca atttgacaga    1320
aattcaggta ctcctctgtc agcagtacac ctcacatgga gttacgcatc tttttctgaca   1380
gcagccgcga gaagagccgg catagttcca ccaagttggg ccaattcatc agcctctaca    1440
ataccatcta catgctcagg cgcttctgtt gtagggagtt actctaggcc aaccgctact    1500
tcattcccac cttcccaaac tccaaaacca ggcgtacctt ccggaacacc ttataccccca   1560
ctcccttgcg ctacaccaac ttcagtcgca gtgacgtttc acgaattagt ttccacacaa    1620
tttggtcaca cagtgaaagt tgcaggaaat gccgctgctt tgggcaattg gtcaacttcc    1680
gcagcggtag cttttggacgc tgttaactac agagataatc atccattgtg gattggtacg    1740
gtcaacctag aagctggtga cgtcgttgag tataagtata tcatagttgg tcaagatggt    1800
tccgtcactt gggagtcaga tcctaatcat acttacactg ttcctgccgt agcttgcgtc    1860
acacaagttg tgaaggaaga tacttggcaa tcttaa                              1896

<210> SEQ ID NO 12
<211> LENGTH: 467

<212> TYPE: PRT
<213> ORGANISM: Salmonella enterica

<400> SEQUENCE: 12

| | | | | | | | | | | | | | | |
|---|---|---|---|---|---|---|---|---|---|---|---|---|---|---|
| Met<br>1 | Asn | Gln | Gln | Asp<br>5 | Ile | Glu | Gln | Val | Val<br>10 | Lys | Ala | Val | Leu | Leu<br>15 | Lys |
| Met | Lys | Asp | Ser<br>20 | Ser | Gln | Pro | Ala | Ser<br>25 | Thr | Val | His | Glu | Met<br>30 | Gly | Val |
| Phe | Ala | Ser<br>35 | Leu | Asp | Asp | Ala | Val<br>40 | Ala | Ala | Lys | Arg | Ala<br>45 | Gln | Gln |
| Gly | Leu<br>50 | Lys | Ser | Val | Ala | Met<br>55 | Arg | Gln | Leu | Ala | Ile<br>60 | His | Ala | Ile | Arg |
| Glu<br>65 | Ala | Gly | Glu | Lys | His<br>70 | Ala | Arg | Glu | Leu | Ala<br>75 | Glu | Leu | Ala | Val | Ser<br>80 |
| Glu | Thr | Gly | Met | Gly<br>85 | Arg | Val | Asp | Asp | Lys<br>90 | Phe | Ala | Lys | Asn | Val<br>95 | Ala |
| Gln | Ala | Arg | Gly<br>100 | Thr | Pro | Gly | Val | Glu<br>105 | Cys | Leu | Ser | Pro | Gln<br>110 | Val | Leu |
| Thr | Gly | Asp<br>115 | Asn | Gly | Leu | Thr | Leu<br>120 | Ile | Glu | Asn | Ala | Pro<br>125 | Trp | Gly | Val |
| Val | Ala<br>130 | Ser | Val | Thr | Pro | Ser<br>135 | Thr | Asn | Pro | Ala | Ala<br>140 | Thr | Val | Ile | Asn |
| Asn<br>145 | Ala | Ile | Ser | Leu | Ile<br>150 | Ala | Ala | Gly | Asn | Ser<br>155 | Val | Val | Phe | Ala | Pro<br>160 |
| His | Pro | Ala | Ala | Lys<br>165 | Lys | Val | Ser | Gln | Arg<br>170 | Ala | Ile | Thr | Leu | Leu<br>175 | Asn |
| Gln | Ala | Val | Val<br>180 | Ala | Ala | Gly | Gly | Pro<br>185 | Glu | Asn | Leu | Leu | Val<br>190 | Thr | Val |
| Ala | Asn | Pro<br>195 | Asp | Ile | Glu | Thr | Ala<br>200 | Gln | Arg | Leu | Phe | Lys<br>205 | Tyr | Pro | Gly |
| Ile | Gly<br>210 | Leu | Leu | Val | Val | Thr<br>215 | Gly | Gly | Glu | Ala | Val<br>220 | Val | Asp | Ala | Ala |
| Arg<br>225 | Lys | His | Thr | Asn | Lys<br>230 | Arg | Leu | Ile | Ala | Ala<br>235 | Gly | Ala | Gly | Asn | Pro<br>240 |
| Pro | Val | Val | Val | Asp<br>245 | Glu | Thr | Ala | Asp | Leu<br>250 | Pro | Arg | Ala | Ala | Gln<br>255 | Ser |
| Ile | Val | Lys | Gly<br>260 | Ala | Ser | Phe | Asp | Asn<br>265 | Asn | Ile | Ile | Cys | Ala<br>270 | Asp | Glu |
| Lys | Val | Leu<br>275 | Ile | Val | Val | Asp | Ser<br>280 | Val | Ala | Asp | Glu | Leu<br>285 | Met | Arg | Leu |
| Met | Glu<br>290 | Gly | Gln | His | Ala | Val<br>295 | Lys | Leu | Thr | Ala | Ala<br>300 | Gln | Ala | Glu | Gln |
| Leu<br>305 | Gln | Pro | Val | Leu | Leu<br>310 | Lys | Asn | Ile | Asp | Glu<br>315 | Arg | Gly | Lys | Gly | Thr<br>320 |
| Val | Ser | Arg | Asp | Trp<br>325 | Val | Gly | Arg | Asp | Ala<br>330 | Gly | Lys | Ile | Ala | Ala<br>335 | Ala |
| Ile | Gly | Leu | Asn<br>340 | Val | Pro | Asp | Gln | Thr<br>345 | Arg | Leu | Leu | Phe | Val<br>350 | Glu | Thr |
| Pro | Ala | Asn<br>355 | His | Pro | Phe | Ala | Val<br>360 | Thr | Glu | Met | Met | Met<br>365 | Pro | Val | Leu |
| Pro | Val<br>370 | Val | Arg | Val | Ala | Asn<br>375 | Val | Glu | Glu | Ala | Ile<br>380 | Ala | Leu | Ala | Val |
| Gln<br>385 | Leu | Glu | Gly | Gly | Cys<br>390 | His | His | Thr | Ala | Ala<br>395 | Met | His | Ser | Arg | Asn<br>400 |

Ile Asp Asn Met Asn Gln Met Ala Asn Ala Ile Asp Thr Ser Ile Phe
            405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
            435                 440                 445

Ala Arg Thr Phe Val Arg Leu Arg Arg Cys Val Leu Val Asp Ala Phe
            450                 455                 460

Arg Ile Val
465

<210> SEQ ID NO 13
<211> LENGTH: 1404
<212> TYPE: DNA
<213> ORGANISM: Escherichia coli

<400> SEQUENCE: 13

```
atgaaccaac aagacataga acaagtagta aaggcagtat tattaaagat gcaatcctct      60
gacacaccac cagccgcagt acacgaaatg ggtgtatttg cctctttgga tgacgctgtt     120
gctgcagcca aatagctca acaaggtttg aagtcagttg caatgagaca attagccatc     180
gctgcaatta gagaagctgg tgaaaaacat gcaagagatt tggccgaatt agctgtctcc     240
gaaaccggta tgggtagagt agaagacaaa ttcgctaaga atgttgctca agcaagaggt     300
actccaggtg ttgaatgttt gagtcctcaa gtcttaactg gtgataacgg tttgacattg     360
atcgaaaacg caccatgggg tgttgtcgcc tctgttactc catcaacaaa tcctgccgct     420
actgtcatca ataacgctat atctttgatc gcagccggta actcagttat ttttgcacca     480
catcctgctg caaaaaaggt ttcccaaaga gctatacat tgttgaacca agcaatcgtt     540
gccgctggtg gtccagaaaa tttgttagtc accgtagcca accctgatat agaaactgca     600
caaagattgt tcaagttccc tggtatcggt tgttagtag ttacaggtgg tgaagctgtc     660
gtagaagcag ccagaaaaca caccaataag agattgattg ctgcaggtgc tggtaaccca     720
cctgttgtcg tagatgaaac tgcagactta gccagagccg ctcaatccat tgttaagggt     780
gctagtttcg ataacaacat aatatgcgca gacgaaaagg tattgatagt tgtcgattct     840
gttgctgacg aattgatgag attaatgaa ggtcaacatg cagttaaatt gactgctgaa     900
caagcacaac aattgcaacc agttttgttg aagaacatag atgaaagagg caagggtaca     960
gtctcaagag attgggttgg tagagacgct ggcaagattg cagccgctat aggtttaaac    1020
gtcccacaag aaactagatt gttgttcgta gaaactacag ccgaacatcc tttcgctgtc    1080
acagaattga tgatgccagt attacctgta gttagagtag ctaatgttgc cgatgctatc    1140
gcattggccg ttaaattaga aggtggttgt catcacacag cagccatgca ctccagaaac    1200
atcgaaaaca tgaaccaaat ggctaacgca atcgacacca gtatttttgt taagaacggt    1260
ccatgcatag ctggtttggg tttaggtggt gaaggttgga ccactatgac aatcacaacc    1320
cctaccggtg aaggtgttac ctctgctaga acttttgtca gattgagaag atgtgttta    1380 gtcgatgcat tcagaattgt ttag                                           1404
```

<210> SEQ ID NO 14
<211> LENGTH: 467
<212> TYPE: PRT
<213> ORGANISM: Escherichia coli

<400> SEQUENCE: 14

```
Met Asn Gln Gln Asp Ile Glu Gln Val Val Lys Ala Val Leu Leu Lys
1               5                   10                  15

Met Gln Ser Ser Asp Thr Pro Pro Ala Ala Val His Glu Met Gly Val
            20                  25                  30

Phe Ala Ser Leu Asp Asp Ala Val Ala Ala Lys Ile Ala Gln Gln
            35                  40                  45

Gly Leu Lys Ser Val Ala Met Arg Gln Leu Ala Ile Ala Ala Ile Arg
    50                  55                  60

Glu Ala Gly Glu Lys His Ala Arg Asp Leu Ala Glu Leu Ala Val Ser
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190

Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Val Glu Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
        275                 280                 285

Met Glu Gly Gln His Ala Val Lys Leu Thr Ala Glu Gln Ala Gln Gln
    290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Asn Val Pro Gln Glu Thr Arg Leu Leu Phe Val Glu Thr
            340                 345                 350

Thr Ala Glu His Pro Phe Ala Val Thr Glu Leu Met Met Pro Val Leu
        355                 360                 365

Pro Val Val Arg Val Ala Asn Val Ala Asp Ala Ile Ala Leu Ala Val
370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
                405                 410                 415
```

```
Val Lys Asn Gly Pro Cys Ile Ala Gly Leu Gly Leu Gly Gly Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
    450                 455                 460

Arg Ile Val
465

<210> SEQ ID NO 15
<211> LENGTH: 1404
<212> TYPE: DNA
<213> ORGANISM: Citrobacter freundii

<400> SEQUENCE: 15
atgaaccaac aagacataga acaagtagta aaggctgtat tattaaaaat gaaagactcc      60
tcacaacctg tatctgccgt ccaagaaatg ggtgtatttg catccttgga tgacgccgtt    120
gctgcagcca aattggccca acaaggttta aagagtgttg caatgagaca attggccatt    180
actgctttaa gagaagctgg tgaaaaacat gcaagagaat ggcagaatt agccgtcact     240 gaaactggta tgggtagagt agaagataaa ttcgctaaga atgttgcaca agccagagct    300
acaccaggtg ttgaatgttt gtcccctcaa gtcttaacag gtgacaatgg tttgaccta    360 atagaaaacg caccatgggg tgttgtcgcc tctgttaccc catcaactaa tcctgctgca    420
accgttatca taacgctat ctctttgatt gccgctggta actcagtagt ttttgcacca     480
catcctgcag ccaaaggtgt ttctcaaaga gctataacat tgttgaatca agcagtcgta    540
gctgcaggtg gtccagccaa tttgttagta actgttgcta accctgatat cgaaacagca    600
caaagattat tcaagtatcc tggtattggt ttgttagttg ttactggtgg tgaagctgta    660
gttgatgccg ctagaaaaca cactaataag agattgatag cagccggtgc tggtaaccca    720
cctgtcgtag ttgatgaaac tgctgactta gcaagagctg cacaatccat tgttaagggt    780
gctagttttg ataacaacat catctgcgca gacgaaaagg tattgatagt cgtagattcc    840
gttgctgacg aattgatgag attgatggaa agtcaacatg cagttaaatt gactacagca    900
caagccgaac aattgcaacc agtattgttg aagaacgttg atgaaagagg caagggtaca    960
gtctctagag attgggttgg tagagacgct ggcaagatag ccgctgcaat cggtttaaac   1020
gtcccagaac aaacaagatt gttgttcgtt gaaacatcag ccacccatcc tttcgctgtc   1080
accgaattga tgatgccagt attacctgtt gtcagagttg ctaatgtcga agaagccatc   1140
gaattggctg ttaaattaga aggtggttgt catcacactg ccgctatgca ctctagaaac   1200
atcgataaca tgaacagaat ggctaacgca attgacacat caatattcgt taagaacggt   1260
ccatgcatag ctggtttggg tttaggtggt gaaggttgga ccactatgac catcacaacc   1320
cctactggtg aaggtgttac ttcagctaga acatttgtca gattgagaag atgtgtctta   1380
gtagatgcat tcagaattgt ttag                                          1404

<210> SEQ ID NO 16
<211> LENGTH: 467
<212> TYPE: PRT
<213> ORGANISM: Citrobacter freundii

<400> SEQUENCE: 16

Met Asn Gln Gln Asp Ile Glu Gln Val Val Lys Ala Val Leu Leu Lys
1               5                   10                  15
```

```
Met Lys Asp Ser Ser Gln Pro Val Ser Ala Val Gln Glu Met Gly Val
             20                  25                  30

Phe Ala Ser Leu Asp Asp Ala Val Ala Ala Ala Lys Leu Ala Gln Gln
         35                  40                  45

Gly Leu Lys Ser Val Ala Met Arg Gln Leu Ala Ile Thr Ala Leu Arg
 50                  55                  60

Glu Ala Gly Glu Lys His Ala Arg Glu Leu Ala Glu Leu Ala Val Thr
 65                  70                  75                  80

Glu Thr Gly Met Gly Arg Val Glu Asp Lys Phe Ala Lys Asn Val Ala
                 85                  90                  95

Gln Ala Arg Ala Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
            115                 120                 125

Val Ala Ser Val Thr Pro Ser Thr Asn Pro Ala Ala Thr Val Ile Asn
        130                 135                 140

Asn Ala Ile Ser Leu Ile Ala Ala Gly Asn Ser Val Val Phe Ala Pro
145                 150                 155                 160

His Pro Ala Ala Lys Gly Val Ser Gln Arg Ala Ile Thr Leu Leu Asn
                165                 170                 175

Gln Ala Val Val Ala Ala Gly Gly Pro Ala Asn Leu Leu Val Thr Val
            180                 185                 190

Ala Asn Pro Asp Ile Glu Thr Ala Gln Arg Leu Phe Lys Tyr Pro Gly
        195                 200                 205

Ile Gly Leu Leu Val Val Thr Gly Gly Glu Ala Val Val Asp Ala Ala
210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
        275                 280                 285

Met Glu Ser Gln His Ala Val Lys Leu Thr Thr Ala Gln Ala Glu Gln
290                 295                 300

Leu Gln Pro Val Leu Leu Lys Asn Val Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Asn Val Pro Glu Gln Thr Arg Leu Leu Phe Val Glu Thr
            340                 345                 350

Ser Ala Thr His Pro Phe Ala Val Thr Glu Leu Met Met Pro Val Leu
        355                 360                 365

Pro Val Val Arg Val Ala Asn Val Glu Glu Ala Ile Glu Leu Ala Val
370                 375                 380

Lys Leu Glu Gly Gly Cys His His Thr Ala Ala Met His Ser Arg Asn
385                 390                 395                 400

Ile Asp Asn Met Asn Arg Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
```

```
                435                 440                 445
Ala Arg Thr Phe Val Arg Leu Arg Arg Cys Val Leu Val Asp Ala Phe
    450                 455                 460

Arg Ile Val
465

<210> SEQ ID NO 17
<211> LENGTH: 1422
<212> TYPE: DNA
<213> ORGANISM: Pseudomonas M1

<400> SEQUENCE: 17
atggacatca accctaaaga atcgaacaa gtcgtaaaag ccgtattggc aagtatcggt      60
gctacatcaa cagccgccgt cgcatcacca ggtgccactt gtgctcctgg tgtatttgtt     120
gaattagatg ctgcagttgc cgctgcagcc caagcacaaa aagccttgag atctgtcgct     180
atgagagaca gagcaatcgc tgcaattaga gccgctggtg aaagacatgc tcaagaatta     240
gctgaattgg cagttgaaga aaccggtatg gtagagtcg cagataaaac tgccaagaat      300
attgcccaag ctagacacac tccaggttct gaatgcttac aagcacaagt tttgtcaggt     360
gacagaggtt taacattgat cgaaaatgca gcctggggtg taattgcttc cgttactcca     420
agtacaaacc ctgctgcaac tgttataaac aacgcaatct ccatgatcgc cgctggtaac     480
agtgttgtct ttgctccaca tcctgcagcc aaaagagtc ctcaaagaac agtatcattg      540
ttgaacgaag ctatggtcga agcaggtgcc ccagctaact aataactac agtacaaaga     600 cctgatatcg aaaccgctca agattgttc agatatccag gtattggttt gttagtagtt     660
acaggtggtg aagcagtcgt agaagctgca agaaaacaca ccgataagag attaatagcc     720
gctggtgctg gtaatccacc tgttgtcgta gatgaaacag ccgacttggc tagagcagcc     780
agagatatag ttttcggtgc atctttcgat aacaacatca tctgtgctga cgaaaaggta     840
ttgatcgttg tcgattcagt tgcagacgcc ttaaaagccg aaatgttgaa gcatcaagct     900
gttgaattgt ccgctgcaca aggtcaacaa ttgttaccat tgttattgcc taaagttgat     960
gaacaaggta gaggttctgt ttcaagagat tgggtcggta gagacgccgc taagattgca    1020
gccgctatag gtttgcaagt tccagaacaa actagattgt tgttgttgga aacagcagcc    1080
gatcacccct ttgcaatcac agaaatgatg atgccagtttt tgcctatggt cagagtagct    1140
aatgtagacc aagctattgc attagccgtt aaattggaag gtggttgtca tcacaccgct    1200
gcaatgcatt ccagaaattt agatcacttg gacagaatgg ctaacgcaat ggatacttct    1260
atcttcgtta agaacggtcc atgcttagct ggtttgggtt cggtggtga aggttggacc     1320 actatgacaa tcacaacccc taccggtgaa ggtgtcacct cagctagaac tttcgtaaga    1380
ttaagaagat gcgttatggt cgatcatttg agaattgttt ag                        1422

<210> SEQ ID NO 18
<211> LENGTH: 473
<212> TYPE: PRT
<213> ORGANISM: Pseudomonas M1

<400> SEQUENCE: 18

Met Asp Ile Asn Pro Lys Glu Ile Glu Gln Val Val Lys Ala Val Leu
1               5                   10                  15

Ala Ser Ile Gly Ala Thr Ser Thr Ala Ala Val Ala Ser Pro Gly Ala
            20                  25                  30

Thr Cys Ala Pro Gly Val Phe Val Glu Leu Asp Ala Ala Val Ala Ala
```

```
            35                  40                  45
Ala Ala Gln Ala Gln Lys Ala Leu Arg Ser Val Ala Met Arg Asp Arg
 50                  55                  60
Ala Ile Ala Ala Ile Arg Ala Ala Gly Glu Arg His Ala Gln Glu Leu
 65                  70                  75                  80
Ala Glu Leu Ala Val Glu Glu Thr Gly Met Gly Arg Val Ala Asp Lys
                 85                  90                  95
Thr Ala Lys Asn Ile Ala Gln Ala Arg His Thr Pro Gly Ser Glu Cys
            100                 105                 110
Leu Gln Ala Gln Val Leu Ser Gly Asp Arg Gly Leu Thr Leu Ile Glu
        115                 120                 125
Asn Ala Ala Trp Gly Val Ile Ala Ser Val Thr Pro Ser Thr Asn Pro
    130                 135                 140
Ala Ala Thr Val Ile Asn Asn Ala Ile Ser Met Ile Ala Ala Gly Asn
145                 150                 155                 160
Ser Val Val Phe Ala Pro His Pro Ala Ala Lys Arg Val Ser Gln Arg
                165                 170                 175
Thr Val Ser Leu Leu Asn Glu Ala Met Val Glu Ala Gly Ala Pro Ala
            180                 185                 190
Asn Leu Ile Thr Thr Val Gln Arg Pro Asp Ile Glu Thr Ala Gln Arg
        195                 200                 205
Leu Phe Arg Tyr Pro Gly Ile Gly Leu Leu Val Val Thr Gly Gly Glu
    210                 215                 220
Ala Val Val Glu Ala Ala Arg Lys His Thr Asp Lys Arg Leu Ile Ala
225                 230                 235                 240
Ala Gly Ala Gly Asn Pro Pro Val Val Val Asp Glu Thr Ala Asp Leu
                245                 250                 255
Ala Arg Ala Ala Arg Asp Ile Val Phe Gly Ala Ser Phe Asp Asn Asn
            260                 265                 270
Ile Ile Cys Ala Asp Glu Lys Val Leu Ile Val Val Asp Ser Val Ala
        275                 280                 285
Asp Ala Leu Lys Ala Glu Met Leu Lys His Gln Ala Val Glu Leu Ser
    290                 295                 300
Ala Ala Gln Gly Gln Gln Leu Leu Pro Leu Leu Leu Pro Lys Val Asp
305                 310                 315                 320
Glu Gln Gly Arg Gly Ser Val Ser Arg Asp Trp Val Gly Arg Asp Ala
                325                 330                 335
Ala Lys Ile Ala Ala Ala Ile Gly Leu Gln Val Pro Glu Gln Thr Arg
            340                 345                 350
Leu Leu Leu Leu Glu Thr Ala Ala Asp His Pro Phe Ala Ile Thr Glu
        355                 360                 365
Met Met Met Pro Val Leu Pro Met Val Arg Val Ala Asn Val Asp Gln
    370                 375                 380
Ala Ile Ala Leu Ala Val Lys Leu Glu Gly Gly Cys His His Thr Ala
385                 390                 395                 400
Ala Met His Ser Arg Asn Leu Asp His Leu Asp Arg Met Ala Asn Ala
                405                 410                 415
Met Asp Thr Ser Ile Phe Val Lys Asn Gly Pro Cys Leu Ala Gly Leu
            420                 425                 430
Gly Phe Gly Gly Glu Gly Trp Thr Thr Met Thr Ile Thr Thr Pro Thr
        435                 440                 445
Gly Glu Gly Val Thr Ser Ala Arg Thr Phe Val Arg Leu Arg Arg Cys
    450                 455                 460
```

Val Met Val Asp His Leu Arg Ile Val
465                 470

<210> SEQ ID NO 19
<211> LENGTH: 1437
<212> TYPE: DNA
<213> ORGANISM: Morganella morganii

<400> SEQUENCE: 19

```
atggatcaaa aggaaatcga aaatgtagtc aaagccgtat tagcctcaat gtccgcaggt     60
actcaaccag ccgccgcctc cgccgcacca caacaagctg cagcctccca aaataacggt    120
tttggtgtat tcgaaagttt ggatgacgct gttttagctg caaagaagc acaaaaatcc    180
ttgaagactg ttgaaatgag aaatttatgt attggtgcta tcagaagagc cgctaccgaa    240
catgcaagag aattggctgt tttagcagtc gaagaaactg gtatgggtag agttgaagat    300
aaattggcta gaacttagc ccaagctaac ggtactccag gtgtagaatg cttgagacct    360
gaagttttaa caggtgatca tggtttgacc ttaatagaaa atgcagcctg gggtgtcatc    420
gcttctgtaa ctccatcaac aaaccctgct gcaacagcca tcaataacgc tatctctatg    480
attgctggtg taattcagt cattttttgca ccacaccctg ccgctaaaaa ggtttctcaa    540
agaacaatca ccatcttgaa tgaagctatt gttgcagccg gtggtccaaa taacttgtta    600
gtcactgtag ccaaacctga tatcgaaaca gctcaaagat tgttcaagta tccaggtata    660
ggtttgttag ttgtcactgg tggtgacgct gtagttgaat ccgcaagaaa gcatacaaac    720
aagagattga tagctgcagg tgctggtaac ccacctgtcg tagttgatga acagcagac    780
atcgaaagag ccgctaaagc cattgttcac ggtgctagtt ttgataacaa catcatctgt    840
gctgacgaaa agttttgat cgcagtcgat tgcattgccg acaagttaat cacagaaatg    900
caaagaaacc atgcagtttt gttgaccaga gaacaatctg aaaaattaat tcctgtattg    960
ttgaagaacg ttgatgaaac cggtcacggt actgtctcaa gagattgggt tggtagagac   1020
gcagccaaaa tagctgcagc catcggtatg actgttccag cagatacaag attgttaatt   1080
gccgaaaccg actgtaagca tcctttgct gtcactgaat tgatgatgcc agtattgcct   1140
atcataagag taaaggatgt tgaccaagca atagatttgg ccgttaagtt agaaggtggt   1200
tgtcatcaca ctgctgcaat gcactccaac aacatcagta acttgaacag aatggcaaac   1260
gccatcgata catctatctt cgttaagaac ggtccatgca tagctggttt gggtttaggt   1320
ggtgaaggtt ggactacaat gaccatcacc actcctactg gtgaaggtgt tacatgtgca   1380
agaacctttg tcagattaag aagatgcact atggttgatt cattcagaat tgtctag      1437
```

<210> SEQ ID NO 20
<211> LENGTH: 478
<212> TYPE: PRT
<213> ORGANISM: Morganella morganii

<400> SEQUENCE: 20

Met Asp Gln Lys Glu Ile Glu Asn Val Val Lys Ala Val Leu Ala Ser
1               5                   10                  15

Met Ser Ala Gly Thr Gln Pro Ala Ala Ala Ser Ala Ala Pro Gln Gln
            20                  25                  30

Ala Ala Ala Ser Gln Asn Asn Gly Phe Gly Val Phe Glu Ser Leu Asp
        35                  40                  45

Asp Ala Val Leu Ala Ala Lys Glu Ala Gln Lys Ser Leu Lys Thr Val
    50                  55                  60

```
Glu Met Arg Asn Leu Cys Ile Gly Ala Ile Arg Arg Ala Ala Thr Glu
 65                  70                  75                  80

His Ala Arg Glu Leu Ala Val Leu Ala Val Glu Thr Gly Met Gly
                 85                  90                  95

Arg Val Glu Asp Lys Leu Ala Lys Asn Leu Ala Gln Ala Asn Gly Thr
                100                 105                 110

Pro Gly Val Glu Cys Leu Arg Pro Glu Val Leu Thr Gly Asp His Gly
                115                 120                 125

Leu Thr Leu Ile Glu Asn Ala Ala Trp Gly Val Ile Ala Ser Val Thr
130                 135                 140

Pro Ser Thr Asn Pro Ala Ala Thr Ala Ile Asn Asn Ala Ile Ser Met
145                 150                 155                 160

Ile Ala Gly Gly Asn Ser Val Ile Phe Ala Pro His Pro Ala Ala Lys
                165                 170                 175

Lys Val Ser Gln Arg Thr Ile Thr Ile Leu Asn Glu Ala Ile Val Ala
                180                 185                 190

Ala Gly Gly Pro Asn Asn Leu Leu Val Thr Val Ala Lys Pro Asp Ile
                195                 200                 205

Glu Thr Ala Gln Arg Leu Phe Lys Tyr Pro Gly Ile Gly Leu Leu Val
210                 215                 220

Val Thr Gly Gly Asp Ala Val Val Glu Ser Ala Arg Lys His Thr Asn
225                 230                 235                 240

Lys Arg Leu Ile Ala Ala Gly Ala Gly Asn Pro Pro Val Val Val Asp
                245                 250                 255

Glu Thr Ala Asp Ile Glu Arg Ala Ala Lys Ala Ile Val His Gly Ala
                260                 265                 270

Ser Phe Asp Asn Asn Ile Ile Cys Ala Asp Glu Lys Val Leu Ile Ala
                275                 280                 285

Val Asp Cys Ile Ala Asp Lys Leu Ile Thr Glu Met Gln Arg Asn His
290                 295                 300

Ala Val Leu Leu Thr Arg Glu Gln Ser Glu Lys Leu Ile Pro Val Leu
305                 310                 315                 320

Leu Lys Asn Val Asp Glu Thr Gly His Gly Thr Val Ser Arg Asp Trp
                325                 330                 335

Val Gly Arg Asp Ala Ala Lys Ile Ala Ala Ile Gly Met Thr Val
                340                 345                 350

Pro Ala Asp Thr Arg Leu Leu Ile Ala Glu Thr Asp Cys Lys His Pro
                355                 360                 365

Phe Ala Val Thr Glu Leu Met Met Pro Val Leu Pro Ile Ile Arg Val
                370                 375                 380

Lys Asp Val Asp Gln Ala Ile Asp Leu Ala Val Lys Leu Glu Gly Gly
385                 390                 395                 400

Cys His His Thr Ala Ala Met His Ser Asn Asn Ile Ser Asn Leu Asn
                405                 410                 415

Arg Met Ala Asn Ala Ile Asp Thr Ser Ile Phe Val Lys Asn Gly Pro
                420                 425                 430

Cys Ile Ala Gly Leu Gly Leu Gly Gly Glu Gly Trp Thr Thr Met Thr
                435                 440                 445

Ile Thr Thr Pro Thr Gly Glu Gly Val Thr Cys Ala Arg Thr Phe Val
                450                 455                 460

Arg Leu Arg Arg Cys Thr Met Val Asp Ser Phe Arg Ile Val
465                 470                 475
```

<210> SEQ ID NO 21
<211> LENGTH: 1410
<212> TYPE: DNA
<213> ORGANISM: Calditrix abyssii

<400> SEQUENCE: 21

| | | | | | |
|---|---|---|---|---|---|
| atgcatttag | acgacaaaca | atcgcacaa | atagtagaaa | ccgtattatc | aagattagaa | 60 |
| agaaacgaaa | gtagaacagg | tagaagtaga | cacccacaag | gtgtctttga | aaccttggat | 120 |
| gaagctgtag | aagctgcaag | acaagcacaa | aagaaaatta | gaaaattgga | attgagagct | 180 |
| aagatcatcc | aagcaatcag | acaagccggt | gttaaacatg | caagagaatt | ggcagaaatg | 240 |
| gccgttcaag | aaactggtat | gggtagagtc | gaagataaga | tagcaaagaa | catctctcaa | 300 |
| gccgaaaaga | ccccaggtat | tgaagattta | caacctttgg | ctttatcagg | tgaccacggt | 360 |
| ttgactttaa | tcgaaaatgc | cgcttggggt | gttattgcct | ctgtcacacc | atcaaccaac | 420 |
| cctggtgcta | ctgttatcaa | taactctatc | tcaatgattg | cagccggtaa | tgctgttgtc | 480 |
| tatgcaccac | atcctgctgc | aaaaaaggtc | tcccaaagag | ccattgaaat | attgaacaaa | 540 |
| gctattgaag | ccgctggtgg | tccagcaaca | ttgttaacta | cagtcgccga | acctagtatc | 600 |
| gaaaccgctc | aaaagttatt | cgtatatcca | ggtattgatt | tgttagtagt | tactggtggt | 660 |
| gaagctgtcg | taaaagcagc | cagaaaggtt | acagacaaaa | gattaatggc | tgcaggtgca | 720 |
| ggtaatccac | ctgttgtcgt | agatgaaaca | gctgacattg | caaaagccgc | tagagatata | 780 |
| gtctggggtg | cttctttcga | taataacatc | gtatgtgcag | acgaaaaaga | aatcattgcc | 840 |
| gttgatgcca | ttgctgacag | attgaaggaa | gaaatgaaaa | agcaccaagc | agttgaatta | 900 |
| actccacaac | aaggtgaaga | attggctcaa | atcatcttag | aagattatcc | aggtcctaat | 960 |
| gcaagaataa | acgaaagtg | ggttggtaaa | gacgcctaca | agttcgctag | agaaataggt | 1020 |
| ttgaacgtat | caaaggaaac | aagattgttg | ttcgttgaag | ctgataagga | ccatcctttc | 1080 |
| gcacaattgg | aattaatgat | gccagttatc | cctttgatca | gagcagccga | tgccgacaaa | 1140 |
| gctatcgatt | tggctattga | attagaacac | ggttatagac | atacagctgc | aatgcattcc | 1200 |
| agacacattg | atcatatgga | cagaatggct | aacgaaatca | acaccagtat | cttcgttaaa | 1260 |
| aacggtccat | gtttggcagg | tttaggtttc | ggtggtgaag | gttggacttc | catgacaatt | 1320 |
| accactccta | ccggtgaagg | tgtaacttcc | gctagaagtt | ttgttagatt | gagaagatgc | 1380 |
| gttgtcgtag | atcatttcag | aattgtttag | | | | 1410 |

<210> SEQ ID NO 22
<211> LENGTH: 469
<212> TYPE: PRT
<213> ORGANISM: Calditrix abyssii

<400> SEQUENCE: 22

Met His Leu Asp Asp Lys Gln Ile Ala Gln Ile Val Glu Thr Val Leu
1               5                   10                  15

Ser Arg Leu Glu Arg Asn Glu Ser Arg Thr Gly Arg Ser Arg His Pro
            20                  25                  30

Gln Gly Val Phe Glu Thr Leu Asp Glu Ala Val Glu Ala Ala Arg Gln
        35                  40                  45

Ala Gln Lys Lys Ile Arg Lys Leu Glu Leu Arg Ala Lys Ile Ile Gln
    50                  55                  60

Ala Ile Arg Gln Ala Gly Val Lys His Ala Arg Glu Leu Ala Glu Met
65                  70                  75                  80

Ala Val Gln Glu Thr Gly Met Gly Arg Val Glu Asp Lys Ile Ala Lys
            85                  90                  95

Asn Ile Ser Gln Ala Glu Lys Thr Pro Gly Ile Glu Asp Leu Gln Pro
        100                 105                 110

Leu Ala Leu Ser Gly Asp His Gly Leu Thr Leu Ile Glu Asn Ala Ala
    115                 120                 125

Trp Gly Val Ile Ala Ser Val Thr Pro Ser Thr Asn Pro Gly Ala Thr
130                 135                 140

Val Ile Asn Asn Ser Ile Ser Met Ile Ala Ala Gly Asn Ala Val Val
145                 150                 155                 160

Tyr Ala Pro His Pro Ala Ala Lys Lys Val Ser Gln Arg Ala Ile Glu
                165                 170                 175

Ile Leu Asn Lys Ala Ile Glu Ala Ala Gly Gly Pro Ala Thr Leu Leu
            180                 185                 190

Thr Thr Val Ala Glu Pro Ser Ile Glu Thr Ala Gln Lys Leu Phe Val
        195                 200                 205

Tyr Pro Gly Ile Asp Leu Leu Val Val Thr Gly Gly Glu Ala Val Val
    210                 215                 220

Lys Ala Ala Arg Lys Val Thr Asp Lys Arg Leu Met Ala Ala Gly Ala
225                 230                 235                 240

Gly Asn Pro Pro Val Val Asp Glu Thr Ala Asp Ile Ala Lys Ala
                245                 250                 255

Ala Arg Asp Ile Val Trp Gly Ala Ser Phe Asp Asn Asn Ile Val Cys
            260                 265                 270

Ala Asp Glu Lys Glu Ile Ile Ala Val Asp Ala Ile Ala Asp Arg Leu
        275                 280                 285

Lys Glu Glu Met Lys Lys His Gln Ala Val Glu Leu Thr Pro Gln Gln
    290                 295                 300

Gly Glu Glu Leu Ala Gln Ile Ile Leu Glu Asp Tyr Pro Gly Pro Asn
305                 310                 315                 320

Ala Arg Ile Asn Arg Lys Trp Val Gly Lys Asp Ala Tyr Lys Phe Ala
                325                 330                 335

Arg Glu Ile Gly Leu Asn Val Ser Lys Glu Thr Arg Leu Leu Phe Val
            340                 345                 350

Glu Ala Asp Lys Asp His Pro Phe Ala Gln Leu Glu Leu Met Met Pro
        355                 360                 365

Val Ile Pro Leu Ile Arg Ala Ala Asp Ala Asp Lys Ala Ile Asp Leu
    370                 375                 380

Ala Ile Glu Leu Glu His Gly Tyr Arg His Thr Ala Ala Met His Ser
385                 390                 395                 400

Arg His Ile Asp His Met Asp Arg Met Ala Asn Glu Ile Asn Thr Ser
                405                 410                 415

Ile Phe Val Lys Asn Gly Pro Cys Leu Ala Gly Leu Gly Phe Gly Gly
            420                 425                 430

Glu Gly Trp Thr Ser Met Thr Ile Thr Thr Pro Thr Gly Glu Gly Val
        435                 440                 445

Thr Ser Ala Arg Ser Phe Val Arg Leu Arg Arg Cys Val Val Val Asp
    450                 455                 460

His Phe Arg Ile Val
465

<210> SEQ ID NO 23
<211> LENGTH: 1398
<212> TYPE: DNA

<213> ORGANISM: Marinobacter aquaeoli

<400> SEQUENCE: 23

| | | |
|---|---|---|
| atgcaaacag acgcccaaca aatagaaagt atcgttagaa gagtcataga acaattacac | 60 |
| agtccacaaa gagatggtga agttatggt gtctttagaa ccttggatga cgcagtagcc | 120 |
| ggtgctcaag gtgcttataa aaagataaga accatggctc aaagagaagc aattatagct | 180 |
| gcaatcagaa gaactggtag tgaaaatgtt caagcattgt ctgaattagc cgtccaagaa | 240 |
| acaggtttcg gtagagtaga agataagatc agaaagcata gattggtttt agacaaaact | 300 |
| cctggtatcg aagctattgt tccaatggca gtcacaggtg atcacggttt gtctttaatt | 360 |
| gaaaatgctc catgggtgt aatagcatcc gttacccta gtactaaccc atctgctact | 420 |
| atcttgaaca acgcaatctc aatgatcgcc gctggtaatt cagttgtctt ttccccacat | 480 |
| cctgcagcca gagctgtctc ccaaagaaca atccaattga tcaacagagc ctctgtttca | 540 |
| gctggtggtc ctgcaaactt agtcacctgt gtagaagaac caacaattga agctgcaacc | 600 |
| agattgtttt cattccctgg tatacaattg ttaaccatca ctggtggtga aggtgtagtt | 660 |
| aatgccgcta gaaagttac tgataagaga ttaatcgcag ccggtccagg taacccacct | 720 |
| gtcgtagttg atgaaacagc tgacattgaa agagctgcaa tttcaatagt tcaaggtgca | 780 |
| tccttcgata caacatcat atgtgttgac gaaaggaaa taatcgccgt cgaatccatt | 840 |
| gctactgaat tgaagacagc tatgtgcaga catggtgccg ctgaaataaa tgcagatcaa | 900 |
| gcagacgccg tcgctagatt ggtattagct ggttacccag gtcctaaccc acaccctaaa | 960 |
| ccagaatggg ttggtagaga tgctgaaaag attgcagccg ctgcaggttt tagtgtacct | 1020 |
| gcaggtacta gattgttagt tacagaaacc gaaagagatc atgcattcgc cactacagaa | 1080 |
| atgatgttgc cagttatctc tttaataaga gctagagatg cagaccaagc cattgattgg | 1140 |
| gcagttgaat tggaagccgg taatagacat acagccgcta tgcactcaag aaatatcgac | 1200 |
| aacttgtcca gaatgggttt agaaataaac tgttctttgt tcgttaaaaa cggtccttgc | 1260 |
| ttggccggtt taggtgctgg tggtgaaggt tggacaagta tgaccatatc tactccaaca | 1320 |
| ggtgaaggtg taaccaacgc tagtactttc gttagaaaga aagatgcac aatggttgat | 1380 |
| tctttcagaa ttgtctag | 1398 |

<210> SEQ ID NO 24
<211> LENGTH: 465
<212> TYPE: PRT
<213> ORGANISM: Marinobacter aquaeoli

<400> SEQUENCE: 24

Met Gln Thr Asp Ala Gln Gln Ile Glu Ser Ile Val Arg Arg Val Ile
1               5                   10                  15

Glu Gln Leu His Ser Pro Gln Arg Asp Gly Glu Ser Tyr Gly Val Phe
            20                  25                  30

Arg Thr Leu Asp Asp Ala Val Ala Gly Ala Gln Gly Ala Tyr Lys Lys
        35                  40                  45

Ile Arg Thr Met Ala Gln Arg Glu Ala Ile Ile Ala Ala Ile Arg Arg
    50                  55                  60

Thr Gly Ser Glu Asn Val Gln Ala Leu Ser Glu Leu Ala Val Gln Glu
65                  70                  75                  80

Thr Gly Phe Gly Arg Val Glu Asp Lys Ile Arg Lys His Arg Leu Val
                85                  90                  95

Leu Asp Lys Thr Pro Gly Ile Glu Ala Ile Val Pro Met Ala Val Thr

```
            100                 105                 110
Gly Asp His Gly Leu Ser Leu Ile Glu Asn Ala Pro Trp Gly Val Ile
            115                 120                 125

Ala Ser Val Thr Pro Ser Thr Asn Pro Ser Ala Thr Ile Leu Asn Asn
130                 135                 140

Ala Ile Ser Met Ile Ala Ala Gly Asn Ser Val Val Phe Ser Pro His
145                 150                 155                 160

Pro Ala Ala Arg Ala Val Ser Gln Arg Thr Ile Gln Leu Ile Asn Arg
                165                 170                 175

Ala Ser Val Ser Ala Gly Gly Pro Ala Asn Leu Val Thr Cys Val Glu
                180                 185                 190

Glu Pro Thr Ile Glu Ala Ala Thr Arg Leu Phe Ser Phe Pro Gly Ile
                195                 200                 205

Gln Leu Leu Thr Ile Thr Gly Gly Glu Gly Val Asn Ala Ala Arg
            210                 215                 220

Lys Val Thr Asp Lys Arg Leu Ile Ala Ala Gly Pro Gly Asn Pro Pro
225                 230                 235                 240

Val Val Val Asp Glu Thr Ala Asp Ile Glu Arg Ala Ala Ile Ser Ile
                245                 250                 255

Val Gln Gly Ala Ser Phe Asp Asn Asn Ile Ile Cys Val Asp Glu Lys
                260                 265                 270

Glu Ile Ile Ala Val Glu Ser Ile Ala Thr Glu Leu Lys Thr Ala Met
                275                 280                 285

Cys Arg His Gly Ala Ala Glu Ile Asn Ala Asp Gln Ala Asp Ala Val
                290                 295                 300

Ala Arg Leu Val Leu Ala Gly Tyr Pro Gly Pro Asn Pro His Pro Lys
305                 310                 315                 320

Pro Glu Trp Val Gly Arg Asp Ala Glu Lys Ile Ala Ala Ala Gly
                325                 330                 335

Phe Ser Val Pro Ala Gly Thr Arg Leu Leu Val Thr Glu Thr Glu Arg
                340                 345                 350

Asp His Ala Phe Ala Thr Thr Glu Met Met Leu Pro Val Ile Ser Leu
                355                 360                 365

Ile Arg Ala Arg Asp Ala Asp Gln Ala Ile Asp Trp Ala Val Glu Leu
                370                 375                 380

Glu Ala Gly Asn Arg His Thr Ala Ala Met His Ser Arg Asn Ile Asp
385                 390                 395                 400

Asn Leu Ser Arg Met Gly Leu Glu Ile Asn Cys Ser Leu Phe Val Lys
                405                 410                 415

Asn Gly Pro Cys Leu Ala Gly Leu Gly Ala Gly Glu Gly Trp Thr
                420                 425                 430

Ser Met Thr Ile Ser Thr Pro Thr Gly Glu Gly Val Thr Asn Ala Ser
                435                 440                 445

Thr Phe Val Arg Lys Arg Arg Cys Thr Met Val Asp Ser Phe Arg Ile
                450                 455                 460

Val
465

<210> SEQ ID NO 25
<211> LENGTH: 1434
<212> TYPE: DNA
<213> ORGANISM: Shewanella benthica

<400> SEQUENCE: 25
```

-continued

| | |
|---|---|
| atggatcaaa aacaaatcga agaaatcgta aaatcaatcg tattacaatt aaatgacaac | 60 |
| ccaggtatag cctcctcagc caacaccttg aatcaaaaca cattaaccga acagggtgat | 120 |
| tatggtgtct ttgaaacttt ggacggtgct gtagctgcag ccactgctgc acaaaagcaa | 180 |
| attagaacag ttgcaatgag agatgaaatc atcacagcca tcagaagaat gaccaaaaag | 240 |
| catgccagag aattatcaga aatggctgtt gaagaaacag gtttcggtag agtcgaagat | 300 |
| aagataaaaa agcacatctt ggtcgctcaa agaactcctg gtacagaaat tttatcccca | 360 |
| caagcagtat ccggtgatag tggtttctct ttgatggaaa atgctccatg gggtgtcatc | 420 |
| gcatcagtaa ccccttccac taacccaact tgtacagtta taaacaacgc tatatcaatg | 480 |
| atagccgctg gtaatgcagt tgtctttgcc ccacatcctg cagccaaaaa ggtttcccaa | 540 |
| tacactatcc aattagtaaa caaggcttct gaatcagttg gtggtcctgc atacatatgc | 600 |
| actacagtag ccaaaccatc tttggaaaat gctcaagcat tattcgttta ccctggtatt | 660 |
| agattgttag tagttactgg tggtgatgct gtcgtagaag ctgcaagagc agttacagac | 720 |
| aaaagattga tcgccgctgg tccaggtaac ccacctgttg tcgtagatga aaccgctgac | 780 |
| atagaaagag cagccataag tatcgtagaa ggtgcttctt tcgataataa catagtttgt | 840 |
| gcaacagaaa aggaaatcat tgctgtcgat tcaatcgcag acgaattaaa agctgcaatg | 900 |
| tgcagaaatg gtgcccattt gttaactgct gatcaagccg aagctgttgc aagagttgtc | 960 |
| ttgaaaggtt atcctggtga caagccatca cctaacccaa aatgggttgg tagagatgct | 1020 |
| tccaagttag ccgctgcagc cggtatagac gtcccagcag aaacaagatt gttaatcttt | 1080 |
| gaagccgata atctcacgt tttcgctgta gttgaacaaa tgatgcctat tttgccatta | 1140 |
| atcagagctg caaatgccga tcaagctatt gactgggctg ttgaattgga aaataagaac | 1200 |
| agacatacag ccgctatcca cagtaagaac atcgatgttt tgaccagaat ggcttacgaa | 1260 |
| atggactgtt ctttgttagc aaagaacggt cctgccatcg cagccattgg tgcaggtggt | 1320 |
| gaaggttgga ccactatgac cattagtacc ccaactggtg aaggtgttac taacgctttg | 1380 |
| acattcacca gaaagagaag atgcactgca gttgattctt tcagaattgt ctag | 1434 |

<210> SEQ ID NO 26
<211> LENGTH: 477
<212> TYPE: PRT
<213> ORGANISM: Shewanella benthica

<400> SEQUENCE: 26

Met Asp Gln Lys Gln Ile Glu Glu Ile Val Lys Ser Ile Val Leu Gln
1               5                   10                  15

Leu Asn Asp Asn Pro Gly Ile Ala Ser Ser Ala Asn Thr Leu Asn Gln
            20                  25                  30

Asn Thr Leu Thr Glu Gln Gly Asp Tyr Gly Val Phe Glu Thr Leu Asp
        35                  40                  45

Gly Ala Val Ala Ala Ala Thr Ala Ala Gln Lys Gln Ile Arg Thr Val
    50                  55                  60

Ala Met Arg Asp Glu Ile Ile Thr Ala Ile Arg Arg Met Thr Lys Lys
65                  70                  75                  80

His Ala Arg Glu Leu Ser Glu Met Ala Val Glu Glu Thr Gly Phe Gly
                85                  90                  95

Arg Val Glu Asp Lys Ile Lys Lys His Ile Leu Val Ala Gln Arg Thr
            100                 105                 110

Pro Gly Thr Glu Ile Leu Ser Pro Gln Ala Val Ser Gly Asp Ser Gly
        115                 120                 125

```
Phe Ser Leu Met Glu Asn Ala Pro Trp Gly Val Ile Ala Ser Val Thr
    130                 135                 140

Pro Ser Thr Asn Pro Thr Cys Thr Val Ile Asn Asn Ala Ile Ser Met
145                 150                 155                 160
Ile Ala Ala Gly Asn Ala Val Val Phe Ala Pro His Pro Ala Ala Lys
                165                 170                 175
Lys Val Ser Gln Tyr Thr Ile Gln Leu Val Asn Lys Ala Ser Glu Ser
            180                 185                 190
Val Gly Gly Pro Ala Tyr Ile Cys Thr Thr Val Ala Lys Pro Ser Leu
        195                 200                 205
Glu Asn Ala Gln Ala Leu Phe Val Tyr Pro Gly Ile Arg Leu Leu Val
    210                 215                 220
Val Thr Gly Gly Asp Ala Val Val Glu Ala Ala Arg Ala Val Thr Asp
225                 230                 235                 240

Lys Arg Leu Ile Ala Ala Gly Pro Gly Asn Pro Pro Val Val Val Asp
                245                 250                 255
Glu Thr Ala Asp Ile Glu Arg Ala Ala Ile Ser Ile Val Glu Gly Ala
            260                 265                 270

Ser Phe Asp Asn Asn Ile Val Cys Ala Thr Glu Lys Glu Ile Ile Ala
        275                 280                 285

Val Asp Ser Ile Ala Asp Glu Leu Lys Ala Ala Met Cys Arg Asn Gly
    290                 295                 300

Ala His Leu Leu Thr Ala Asp Gln Ala Glu Ala Val Ala Arg Val Val
305                 310                 315                 320
Leu Lys Gly Tyr Pro Gly Asp Lys Pro Ser Pro Asn Pro Lys Trp Val
                325                 330                 335

Gly Arg Asp Ala Ser Lys Leu Ala Ala Ala Ala Gly Ile Asp Val Pro
            340                 345                 350

Ala Glu Thr Arg Leu Leu Ile Phe Glu Ala Asp Lys Ser His Val Phe
        355                 360                 365

Ala Val Val Glu Gln Met Met Pro Ile Leu Pro Leu Ile Arg Ala Ala
    370                 375                 380

Asn Ala Asp Gln Ala Ile Asp Trp Ala Val Glu Leu Glu Asn Lys Asn
385                 390                 395                 400
Arg His Thr Ala Ala Ile His Ser Lys Asn Ile Asp Val Leu Thr Arg
                405                 410                 415

Met Ala Tyr Glu Met Asp Cys Ser Leu Leu Ala Lys Asn Gly Pro Ala
            420                 425                 430

Ile Ala Ala Ile Gly Ala Gly Gly Glu Gly Trp Thr Thr Met Thr Ile
        435                 440                 445

Ser Thr Pro Thr Gly Glu Gly Val Thr Asn Ala Leu Thr Phe Thr Arg
    450                 455                 460

Lys Arg Arg Cys Thr Ala Val Asp Ser Phe Arg Ile Val
465                 470                 475
```

<210> SEQ ID NO 27
<211> LENGTH: 1428
<212> TYPE: DNA
<213> ORGANISM: Bacillus vireti

<400> SEQUENCE: 27

```
atgcaaatca acgaaaccga cataaagaaa atggtagaac aagtattaaa acaattaggt      60
caaacagaag ctgctggtgc cccaatcgct ccacaaaatg atgtttcttt aggtgacggt     120
```

-continued

```
gtatttgcaa ctgttgatga agctgcagcc gctgcaagag ttgcttggga aaaattgaga     180
aagttgcctt tagcatcaag aagacaaatg attgacaata tgagagaagt ttcctgtgcc     240
caagctaacg aattggcaca attagccgtt gatgaaacag gtttaggtag agtcgaagac     300
aaagtagcta agattttgtt agccgctaat aaaacaccag gtgttgaaga tttggtctct     360
acctcatatt ccggtgatga cggtttgact ttagtcgaat acgctcctat cggtgtattc     420
ggttcaatta ctccatccac aaaccctgca gccactgtta taaataacag tatttcttta     480
atcgctgcag gtaatacagt tgtctataac ccacatccta gtgctaagag agtttctttg     540
aagactttga agttgttaaa tcaagccatt gtcgccgctg gtggtccaga aaatgctttg     600
acaagtgttg cagcccctaa cttagaaacc tctgcacaag ttatgaatca cccaaaagtc     660
aacgccttag tagttacagg tggtggtcct gtcgtaaagg ctgcaatggc tgtaggtaaa     720
aaggttatcg ccgctggtcc aggtaatcca cctgttgtcg tagatgaaac agcaattata     780
tcacaagcag ccgctcatat tgttcaaggt gcttcctttg ataataacgt tttgtgtacc     840
gcagaaaaag aagtcttcgt tgttgataag gcagccaatg ctttaaaagc agaaatggtt     900
aagaacggtg ctatagaatt gaaaggtttt caattcgaaa aattgttaga aaaggtatta     960
gttaaaaaga atgataaatt ttacccaaac agagatttca ttggcaagga cgctagtgtt    1020
atattgcaag ctgcaggtat ccaagtctct ccaaacgtaa aattgatcat agcagaaact    1080
acaaaggatc acccttttggt tatgactgaa atgttgatgc caatcttacc tattgtcaga    1140
gtaccagatg tagacaaagc tattgaatta gccgttatag ctgaaaaggg taatagacat    1200
accgcaataa tgcactcaca aaacatcacc aacttgacta agatggcaca agaaatacaa    1260
gccactatct ttgtaaagaa cggtccatca gttgctggtt tgggttttga atccgaaggt    1320
ttcaccactt taacaattgc cggtcctacc ggtgaaggtt tgacttctgc aaaaacattt    1380
accagacaaa gaagatgcgt tttggtcgat ggtttcagaa taatctag                 1428
```

<210> SEQ ID NO 28
<211> LENGTH: 475
<212> TYPE: PRT
<213> ORGANISM: Bacillus vireti

<400> SEQUENCE: 28

```
Met Gln Ile Asn Glu Thr Asp Ile Lys Lys Met Val Glu Gln Val Leu
1               5                   10                  15

Lys Gln Leu Gly Gln Thr Glu Ala Ala Gly Ala Pro Ile Ala Pro Gln
                20                  25                  30

Asn Asp Val Ser Leu Gly Asp Gly Val Phe Ala Thr Val Asp Glu Ala
            35                  40                  45

Ala Ala Ala Ala Arg Val Ala Trp Glu Lys Leu Arg Lys Leu Pro Leu
        50                  55                  60

Ala Ser Arg Arg Gln Met Ile Asp Asn Met Arg Glu Val Ser Cys Ala
65                  70                  75                  80

Gln Ala Asn Glu Leu Ala Gln Leu Ala Val Asp Glu Thr Gly Leu Gly
                85                  90                  95

Arg Val Glu Asp Lys Val Ala Lys Ile Leu Leu Ala Ala Asn Lys Thr
            100                 105                 110

Pro Gly Val Glu Asp Leu Val Ser Thr Ser Tyr Ser Gly Asp Asp Gly
        115                 120                 125

Leu Thr Leu Val Glu Tyr Ala Pro Ile Gly Val Phe Gly Ser Ile Thr
    130                 135                 140
```

```
Pro Ser Thr Asn Pro Ala Ala Thr Val Ile Asn Asn Ser Ile Ser Leu
145                 150                 155                 160

Ile Ala Ala Gly Asn Thr Val Val Tyr Asn Pro His Pro Ser Ala Lys
            165                 170                 175

Arg Val Ser Leu Lys Thr Leu Lys Leu Leu Asn Gln Ala Ile Val Ala
            180                 185                 190

Ala Gly Gly Pro Glu Asn Ala Leu Thr Ser Val Ala Ala Pro Asn Leu
        195                 200                 205

Glu Thr Ser Ala Gln Val Met Asn His Pro Lys Val Asn Ala Leu Val
    210                 215                 220

Val Thr Gly Gly Gly Pro Val Val Lys Ala Ala Met Ala Val Gly Lys
225                 230                 235                 240

Lys Val Ile Ala Ala Gly Pro Gly Asn Pro Pro Val Val Val Asp Glu
                245                 250                 255

Thr Ala Ile Ile Ser Gln Ala Ala His Ile Val Gln Gly Ala Ser
                260                 265                 270

Phe Asp Asn Asn Val Leu Cys Thr Ala Glu Lys Glu Val Phe Val Val
        275                 280                 285

Asp Lys Ala Ala Asn Ala Leu Lys Ala Glu Met Val Lys Asn Gly Ala
290                 295                 300

Ile Glu Leu Lys Gly Phe Gln Phe Glu Lys Leu Leu Glu Lys Val Leu
305                 310                 315                 320

Val Lys Lys Asn Asp Lys Phe Tyr Pro Asn Arg Asp Phe Ile Gly Lys
                325                 330                 335

Asp Ala Ser Val Ile Leu Gln Ala Gly Ile Gln Val Ser Pro Asn
                340                 345                 350

Val Lys Leu Ile Ile Ala Glu Thr Thr Lys Asp His Pro Leu Val Met
            355                 360                 365

Thr Glu Met Leu Met Pro Ile Leu Pro Ile Val Arg Val Pro Asp Val
    370                 375                 380

Asp Lys Ala Ile Glu Leu Ala Val Ile Ala Glu Lys Gly Asn Arg His
385                 390                 395                 400

Thr Ala Ile Met His Ser Gln Asn Ile Thr Asn Leu Thr Lys Met Ala
                405                 410                 415

Gln Glu Ile Gln Ala Thr Ile Phe Val Lys Asn Gly Pro Ser Val Ala
                420                 425                 430

Gly Leu Gly Phe Glu Ser Glu Gly Phe Thr Thr Leu Thr Ile Ala Gly
            435                 440                 445

Pro Thr Gly Glu Gly Leu Thr Ser Ala Lys Thr Phe Thr Arg Gln Arg
    450                 455                 460

Arg Cys Val Leu Val Asp Gly Phe Arg Ile Ile
465                 470                 475

<210> SEQ ID NO 29
<211> LENGTH: 1458
<212> TYPE: DNA
<213> ORGANISM: Streptococcus massiliensis

<400> SEQUENCE: 29
atgggtttat cagaaatcga acaattagtc aagcaaatct tatcagaaga catattagaa      60
agtcaagaat ccgcacaata cagtcaatcc ttggttggta caaggaaat ccaaggtgat     120 atcttagaag gcaaggaaac agaatctggt gtcttttcaa ccgtagatca agcagttcaa     180
gctgcaaaga tagcccaaaa gaaatacttc gacacttcta tcgaaagaag aaaaaagatt     240
```

-continued

```
atcgccgcta taagatcaag attgttacca gaagttgaag aaatagctaa aagagcattg    300
gaagaaaccg gtatgggtaa cttccaagat aagatagcta agaacagatt ggccttagaa    360
gctactccag gtgtcgaaga tttgatgtat gcaaccagag ccttaactgg tgacaatggt    420
ttgactttat atgaaatgtg tccttacggt gttatcggtg caattgcccc atcaacaaac    480
cctactgaaa caatcatcaa taactccatc agtatgttgg cagccggtaa cacaatttac    540
ttcgctccac atcctggtgc aagagaaact acaatctggt tgatcagaaa gataaacaag    600
atagctaaag atgcatccgg tatagacaac ttgatcgtca ccatagaaaa cccaagtata    660
caagctgcac aagaaatgat ggtacaccca gatattgcta tattagttgt cactggtggt    720
cctggtgtag ttgctcaagc aatgaaatct ggtaaaaagg ttattggtgc cggtgctggt    780
aatccacctg caatcgtcga tgaaactgcc aacattgaaa aggctggtca agatatagtt    840
gacggtgcct catttgacaa taacattcct tgtactgctg aaaagaatat aatcgtcgta    900
tcttcagttg ctgaatactt gatcttcaac atgcaaaagg caggtgcctt ctacgtcaaa    960
gatatcgaag acatcaaaaa gttagaaaac ttgtgcttga cagaaaaggg taccactaac   1020
aaaaagtatg ttggtaagtc tgctgaaaaa atcttgaccg atgcaggtgt tacctatact   1080
ggtcatccaa gattagtaat tgttgaaggt tacccagata tgccttttgc tgttgaagaa   1140
atgttgatgc cagttgtccc tttaattaga gtccctgatt tcgacactgc cttggaagta   1200
gctttggaat tagaacatgg ttacaaacac acagctacca ttcactccca aaatgtaagt   1260
agattaaaca aggccgctag agctatggaa acatctatct tcgttaagaa cggtccatca   1320
ttcgcaggtt tgggtttaag aggtgaaggt ccaacaaccct ttactattgc tactcctaca   1380
ggtgaaggta ctacaaccgc aagatccttt gccagaataa gaagatgcgt tttaagtgat   1440
gcattcatga tcagatag                                                 1458
```

<210> SEQ ID NO 30
<211> LENGTH: 485
<212> TYPE: PRT
<213> ORGANISM: Streptococcus massiliensis

<400> SEQUENCE: 30

```
Met Gly Leu Ser Glu Ile Glu Gln Leu Val Lys Gln Ile Leu Ser Glu
 1               5                  10                  15

Asp Ile Leu Glu Ser Gln Glu Ser Ala Gln Tyr Ser Gln Ser Leu Val
            20                  25                  30

Gly Thr Lys Glu Ile Gln Gly Asp Ile Leu Glu Gly Lys Glu Thr Glu
        35                  40                  45

Ser Gly Val Phe Ser Thr Val Asp Gln Ala Val Gln Ala Ala Lys Ile
    50                  55                  60

Ala Gln Lys Lys Tyr Phe Asp Thr Ser Ile Glu Arg Arg Lys Lys Ile
65                  70                  75                  80

Ile Ala Ala Ile Arg Ser Arg Leu Leu Pro Glu Val Glu Glu Ile Ala
                85                  90                  95

Lys Arg Ala Leu Glu Glu Thr Gly Met Gly Asn Phe Gln Asp Lys Ile
            100                 105                 110

Ala Lys Asn Arg Leu Ala Leu Glu Ala Thr Pro Gly Val Glu Asp Leu
        115                 120                 125

Met Tyr Ala Thr Arg Ala Leu Thr Gly Asp Asn Gly Leu Thr Leu Tyr
    130                 135                 140

Glu Met Cys Pro Tyr Gly Val Ile Gly Ala Ile Ala Pro Ser Thr Asn
145                 150                 155                 160
```

Pro Thr Glu Thr Ile Ile Asn Ser Ile Ser Met Leu Ala Ala Gly
            165                 170                 175

Asn Thr Ile Tyr Phe Ala Pro His Pro Gly Ala Arg Glu Thr Thr Ile
            180                 185                 190

Trp Leu Ile Arg Lys Ile Asn Lys Ile Ala Lys Asp Ala Ser Gly Ile
            195                 200                 205

Asp Asn Leu Ile Val Thr Ile Glu Asn Pro Ser Ile Gln Ala Ala Gln
210                 215                 220

Glu Met Met Val His Pro Asp Ile Ala Ile Leu Val Val Thr Gly Gly
225                 230                 235                 240

Pro Gly Val Val Ala Gln Ala Met Lys Ser Gly Lys Lys Val Ile Gly
            245                 250                 255

Ala Gly Ala Gly Asn Pro Pro Ala Ile Val Asp Glu Thr Ala Asn Ile
            260                 265                 270

Glu Lys Ala Gly Gln Asp Ile Val Asp Gly Ala Ser Phe Asp Asn Asn
            275                 280                 285

Ile Pro Cys Thr Ala Glu Lys Asn Ile Ile Val Val Ser Ser Val Ala
290                 295                 300

Glu Tyr Leu Ile Phe Asn Met Gln Lys Ala Gly Ala Phe Tyr Val Lys
305                 310                 315                 320

Asp Ile Glu Asp Ile Lys Lys Leu Glu Asn Leu Cys Leu Thr Glu Lys
            325                 330                 335

Gly Thr Thr Asn Lys Lys Tyr Val Gly Lys Ser Ala Glu Lys Ile Leu
            340                 345                 350

Thr Asp Ala Gly Val Thr Tyr Thr Gly His Pro Arg Leu Val Ile Val
            355                 360                 365

Glu Gly Tyr Pro Asp Met Pro Phe Ala Val Glu Glu Met Leu Met Pro
370                 375                 380

Val Val Pro Leu Ile Arg Val Pro Asp Phe Asp Thr Ala Leu Glu Val
385                 390                 395                 400

Ala Leu Glu Leu Glu His Gly Tyr Lys His Thr Ala Thr Ile His Ser
            405                 410                 415

Gln Asn Val Ser Arg Leu Asn Lys Ala Ala Arg Ala Met Glu Thr Ser
            420                 425                 430

Ile Phe Val Lys Asn Gly Pro Ser Phe Ala Gly Leu Gly Leu Arg Gly
            435                 440                 445

Glu Gly Pro Thr Thr Phe Thr Ile Ala Thr Pro Thr Gly Glu Gly Thr
            450                 455                 460

Thr Thr Ala Arg Ser Phe Ala Arg Ile Arg Arg Cys Val Leu Ser Asp
465                 470                 475                 480

Ala Phe Met Ile Arg
            485

<210> SEQ ID NO 31
<211> LENGTH: 1446
<212> TYPE: DNA
<213> ORGANISM: Desulfospira joergensenii

<400> SEQUENCE: 31
atggctgacg tattggaaaa agacatagaa gctatcgtaa cagaagtatt aaagaagatg      60
acattgccaa cctcctctcc taacggttct tcacctcaag aaactttgtt agattctgac     120
ggtgattggg gtgtctttcc aggtttagat caagctgtag ctgcagcctc agctgcacaa     180
aaaagaatac caacaatagc tgttagagaa caagttgtca gaatggtcag aagagccgct     240

```
agagcaaatg ccagaagatt agccgaaatg gctgttgatg aaaccggtat gggtagagtc    300
gaagacaagg taaaaagaa tttgttagtt gccaacagaa caccaggtcc tgaaattttg    360
tctcctgcag ccgctactgg tgatgctggt ttaacattgt ttgaaaatgc cccatggggt    420
gttattgctt ctgtcactcc ttcaacaaac ccagcagcca caatcttcaa taacaccatt    480
tccatggtct ctggtggtaa tactgtagtt tatgcagttc atccaggtgc caagagaact    540
acattagaaa cagttaaggt cgtaaacaag gcagtctacg aagaattggg tataaacaac    600
ataatcactt gtgttaagga accttctatc gaaaccgctc aaaagttatt cacttatcca    660
ggtatcaact tgttagttgt tactggtggt gaagcagtag ttgatgctgc aaaaaagata    720
actgacaaga gattgatcgc cgctggtgct ggtaacccac ctgtcgttgt tgatgacact    780
gcagatttgg ccagagcagc ccaatctatc tacgatggtg cttcattcga caacaacatc    840
gtttgttgcg atgaaaagga aatcatagct ttagacacag ttgcagataa attgaaggac    900
gaattgaaga attgcggtgc tgttgaaatt tccttggacc aagctgatgc aatagccaga    960
aaggttttgt tggattaccc ctggttcaaat ccaagaccta acccaaagtg ggttggtaga   1020
gatgctgcag ttttggcttc tgccgctggt atatcagtac cagaaacatg tagattgtta   1080
atcgttgatg caggtaccga cactggttac accttgcca aaatggaaca aatgatgcct   1140
ttaataccaa tcttgagagc aagagatttc aatcaagcat ggaatgggc attgttattg   1200
gaaaacgatt gcagacattc cgctggtttg cacagtaaga atattgacaa catggataca   1260
atggctaaag cagtcaatac ctcattattc gtaaagaacg gtcctcacat tgccggtttg   1320
ggtgctggtg gtgaaggttg gacctccatg actataagta caccaaccgg tgaaggtgta   1380
tccaatgcaa gaactttcgt tagattgaga agatgtacat tggttggtag tttcagaatt   1440
gcttag                                                              1446
```

<210> SEQ ID NO 32
<211> LENGTH: 481
<212> TYPE: PRT
<213> ORGANISM: Desulfospira joergensenii

<400> SEQUENCE: 32

Met Ala Asp Val Leu Glu Lys Asp Ile Glu Ala Ile Val Thr Glu Val
1               5                   10                  15

Leu Lys Lys Met Thr Leu Pro Thr Ser Ser Pro Asn Gly Ser Ser Pro
            20                  25                  30

Gln Glu Thr Leu Leu Asp Ser Asp Gly Asp Trp Gly Val Phe Pro Gly
        35                  40                  45

Leu Asp Gln Ala Val Ala Ala Ser Ala Ala Gln Lys Arg Ile Pro
    50                  55                  60

Thr Ile Ala Val Arg Glu Gln Val Val Arg Met Val Arg Arg Ala Ala
65                  70                  75                  80

Arg Ala Asn Ala Arg Arg Leu Ala Glu Met Ala Val Asp Glu Thr Gly
                85                  90                  95

Met Gly Arg Val Glu Asp Lys Val Lys Lys Asn Leu Leu Val Ala Asn
            100                 105                 110

Arg Thr Pro Gly Pro Glu Ile Leu Ser Pro Ala Ala Thr Gly Asp
        115                 120                 125

Ala Gly Leu Thr Leu Phe Glu Asn Ala Pro Trp Gly Val Ile Ala Ser
    130                 135                 140

Val Thr Pro Ser Thr Asn Pro Ala Ala Thr Ile Phe Asn Asn Thr Ile

```
            145                 150                 155                 160
Ser Met Val Ser Gly Gly Asn Thr Val Val Tyr Ala Val His Pro Gly
                    165                 170                 175

Ala Lys Arg Thr Thr Leu Glu Thr Val Lys Val Asn Lys Ala Val
                180                 185                 190

Tyr Glu Glu Leu Gly Ile Asn Asn Ile Ile Thr Cys Val Lys Glu Pro
            195                 200                 205

Ser Ile Glu Thr Ala Gln Lys Leu Phe Thr Tyr Pro Gly Ile Asn Leu
    210                 215                 220

Leu Val Val Thr Gly Gly Glu Ala Val Val Asp Ala Ala Lys Lys Ile
225                 230                 235                 240

Thr Asp Lys Arg Leu Ile Ala Ala Gly Ala Gly Asn Pro Pro Val Val
                245                 250                 255

Val Asp Asp Thr Ala Asp Leu Ala Arg Ala Ala Gln Ser Ile Tyr Asp
            260                 265                 270

Gly Ala Ser Phe Asp Asn Asn Ile Val Cys Cys Asp Glu Lys Glu Ile
        275                 280                 285

Ile Ala Leu Asp Thr Val Ala Asp Lys Leu Lys Asp Glu Leu Lys Asn
290                 295                 300

Cys Gly Ala Val Glu Ile Ser Leu Asp Gln Ala Asp Ala Ile Ala Arg
305                 310                 315                 320

Lys Val Leu Leu Asp Tyr Pro Gly Ser Asn Pro Arg Pro Asn Pro Lys
                325                 330                 335

Trp Val Gly Arg Asp Ala Ala Val Leu Ala Ser Ala Ala Gly Ile Ser
            340                 345                 350

Val Pro Glu Thr Cys Arg Leu Leu Ile Val Asp Ala Gly Thr Asp Thr
        355                 360                 365

Gly Tyr Thr Phe Ala Lys Met Glu Gln Met Met Pro Leu Ile Pro Ile
    370                 375                 380

Leu Arg Ala Arg Asp Phe Asn Gln Ala Leu Glu Trp Ala Leu Leu Leu
385                 390                 395                 400

Glu Asn Asp Cys Arg His Ser Ala Gly Leu His Ser Lys Asn Ile Asp
                405                 410                 415

Asn Met Asp Thr Met Ala Lys Ala Val Asn Thr Ser Leu Phe Val Lys
            420                 425                 430

Asn Gly Pro His Ile Ala Gly Leu Gly Ala Gly Gly Glu Gly Trp Thr
        435                 440                 445

Ser Met Thr Ile Ser Thr Pro Thr Gly Glu Gly Val Ser Asn Ala Arg
    450                 455                 460

Thr Phe Val Arg Leu Arg Arg Cys Thr Leu Val Gly Ser Phe Arg Ile
465                 470                 475                 480

Ala

<210> SEQ ID NO 33
<211> LENGTH: 1455
<212> TYPE: DNA
<213> ORGANISM: Bilophila wadsworthia

<400> SEQUENCE: 33
atggacgtta gacaacaaga tgtagaaaga atcgtagtcg aagtattaaa gaaaatgatg      60
agtgaccaac caacagccgc agcaaccaca gttgtcgctg catccggttg tgattgcggt     120
gactttggtt tgttcgatag attagaagac gctgtccaag ccgctgaagc agcccaaaag     180
aaaattagta cagtagcaat gagagataag ataatcgctg caataagaaa ggctggtttg     240
```

```
gaaaatgcca aagcatttgc agaaattgca cataacgaaa ccggtatggg tagagtctct    300
gataagatcg ctaagaacat cttggtatgc gaaagaactc ctggtacaga atgcttatcc    360
ccaatggcaa ttagtggtga catgggtttg actttaatag aaaatgcacc atggggtgta    420
atcgcctctg ttaccccttc aactaaccca accgctactg ttataaataa cgccatctcc    480
atgattgctg gtggtaatag tgttatcttt gctccacatc ctaacgctaa gagagcatct    540
caaactgcaa ttcaagtatt gaacaaggct atcatcgaag caacaggtgt tgccaacttg    600
ttagtcgctg taaagaacc taccattgaa gttgcacaag aattattctc acacccaaga    660
ataaagttgt tagtagttac tggtggtgaa gccgtcgtag cccaagctag aaaagttgct    720
acaatgagat tgattgccgc tggtgcaggt aatccacctg ttgtcgtaga tgaaacagcc    780
aacattgcta gagcagccag atctatatat gatggtgcct cattcgacaa taacatcatc    840
tgtgctgacg aaaaggaaat catcgcagtt gattctatag ccgaccaatt aaaagctgaa    900
atgaaggcaa ttggtgccgt tgaaatatca ttggaacaag cagatgccgt cgctagagtt    960
gtcttaagaa attaccctca agttgaaggt ggcaaggctc aaatcctaa cccaaaatgg   1020 gtcggtagag atgctgcatt gatagcaaag gccgctggta tcgatgttcc agactcctgc   1080
agattgttga tcgttgatgt caagagagac ataaaccatg tctttgctag agtagaacaa   1140
ttgatgcctg taattccatt gttaagagca gccaacgttg atgaagctat cgaatgggca   1200
ttgattttag aaagaggttt gtctcatacc gctggtatgc actcaagaaa tattgataac   1260
atggacaaga tggcaagagc catgaacact tcattattcg ttaagaacgg tcctcacttg   1320
gctgcattag gtgctggtgg tgaaggttgg actacaatga caatttccac accaaccggt   1380
gaaggtgtta cctgtgctag aagttttgtc agattgagaa gatgttgcgt agttgataat   1440
ttcagaatag tttag                                                   1455
```

<210> SEQ ID NO 34
<211> LENGTH: 484
<212> TYPE: PRT
<213> ORGANISM: Bilophila wadsworthia

<400> SEQUENCE: 34

```
Met Asp Val Arg Gln Gln Asp Val Glu Arg Ile Val Val Glu Val Leu
1               5                   10                  15

Lys Lys Met Met Ser Asp Gln Pro Thr Ala Ala Ala Thr Thr Val Val
            20                  25                  30

Ala Ala Ser Gly Cys Asp Cys Gly Asp Phe Gly Leu Phe Asp Arg Leu
        35                  40                  45

Glu Asp Ala Val Gln Ala Ala Glu Ala Ala Gln Lys Lys Ile Ser Thr
    50                  55                  60

Val Ala Met Arg Asp Lys Ile Ile Ala Ile Arg Lys Ala Gly Leu
65                  70                  75                  80

Glu Asn Ala Lys Ala Phe Ala Glu Ile Ala His Asn Glu Thr Gly Met
                85                  90                  95

Gly Arg Val Ser Asp Lys Ile Ala Lys Asn Ile Leu Val Cys Glu Arg
            100                 105                 110

Thr Pro Gly Thr Glu Cys Leu Ser Pro Met Ala Ile Ser Gly Asp Met
        115                 120                 125

Gly Leu Thr Leu Ile Glu Asn Ala Pro Trp Gly Val Ile Ala Ser Val
    130                 135                 140

Thr Pro Ser Thr Asn Pro Thr Ala Thr Val Ile Asn Asn Ala Ile Ser
```

Met Ile Ala Gly Gly Asn Ser Val Ile Phe Ala Pro His Pro Asn Ala
145                 150                 155                 160

Lys Arg Ala Ser Gln Thr Ala Ile Gln Val Leu Asn Lys Ala Ile Ile
                165                 170                 175

Glu Ala Thr Gly Val Ala Asn Leu Leu Val Ala Val Lys Glu Pro Thr
            180                 185                 190

Ile Glu Val Ala Gln Glu Leu Phe Ser His Pro Arg Ile Lys Leu Leu
        195                 200                 205

Val Val Thr Gly Gly Glu Ala Val Val Ala Gln Ala Arg Lys Val Ala
210                 215                 220                 225 (wait)

Val Val Thr Gly Gly Glu Ala Val Val Ala Gln Ala Arg Lys Val Ala
225                 230                 235                 240

Thr Met Arg Leu Ile Ala Ala Gly Ala Gly Asn Pro Pro Val Val Val
                245                 250                 255

Asp Glu Thr Ala Asn Ile Ala Arg Ala Ala Arg Ser Ile Tyr Asp Gly
            260                 265                 270

Ala Ser Phe Asp Asn Asn Ile Ile Cys Ala Asp Glu Lys Glu Ile Ile
        275                 280                 285

Ala Val Asp Ser Ile Ala Asp Gln Leu Lys Ala Glu Met Lys Ala Ile
    290                 295                 300

Gly Ala Val Glu Ile Ser Leu Glu Gln Ala Asp Ala Val Ala Arg Val
305                 310                 315                 320

Val Leu Arg Asn Tyr Pro Gln Val Glu Gly Gly Lys Ala Pro Asn Pro
                325                 330                 335

Asn Pro Lys Trp Val Gly Arg Asp Ala Ala Leu Ile Ala Lys Ala Ala
            340                 345                 350

Gly Ile Asp Val Pro Asp Ser Cys Arg Leu Leu Ile Val Asp Val Lys
        355                 360                 365

Arg Asp Ile Asn His Val Phe Ala Arg Val Glu Gln Leu Met Pro Val
    370                 375                 380

Ile Pro Leu Leu Arg Ala Ala Asn Val Asp Glu Ala Ile Glu Trp Ala
385                 390                 395                 400

Leu Ile Leu Glu Arg Gly Leu Ser His Thr Ala Gly Met His Ser Arg
                405                 410                 415

Asn Ile Asp Asn Met Asp Lys Met Ala Arg Ala Met Asn Thr Ser Leu
            420                 425                 430

Phe Val Lys Asn Gly Pro His Leu Ala Ala Leu Gly Ala Gly Gly Glu
        435                 440                 445

Gly Trp Thr Thr Met Thr Ile Ser Thr Pro Thr Gly Glu Gly Val Thr
    450                 455                 460

Cys Ala Arg Ser Phe Val Arg Leu Arg Arg Cys Cys Val Val Asp Asn
465                 470                 475                 480

Phe Arg Ile Val

<210> SEQ ID NO 35
<211> LENGTH: 1419
<212> TYPE: DNA
<213> ORGANISM: Ilyobacter polytropus

<400> SEQUENCE: 35
atgaacttgg atgctaacaa cttgaacaac atagtctcct taataatgaa agaattggac        60
aaaaataaca acatagatga cactggtcaa ggttgtggtg gtgaagaagg caagaacggt       120
attttctctt ctatggacac tgctgtttct aaagccaagg aagctcaagt aacattgttc       180
gcctctaaat tggaattaag agaaagaatc atcaaggcta tcagagaaga tgttagagaa       240

```
gctgcagccg aattggcaga atcgccgtt gaagaaaccg gtatgggtag agtcgatgac    300
aagactttga agcattacgt cactgtagat aaaacaccag gtgttgaaga cttgagagca    360
tttgcctata gtggtgataa cggtttaact gtaatggaat tgtctcctta cggtgttatt    420
ggttctataa caccatcaac caatccttcc gaaacaattg tttgcaacgc tatcggtatg    480
attgctgcag gtaattcagt tgtctttgcc ccacaccctg gtgctaaaaa gacatcctta    540
agagcagttg aaattttgaa caaagctgtc gcaagagccg gtggtccaaa caacttggta    600
gttacaatct tcgaaccttc aatcgaaaac accaacaaga tggtcaagaa cccagatata    660
aagatggtcg tagctaccgg tggtcctggt gttgtcaagt ccgttatgtc cagtggtaaa    720
aaggctatag gtgctggtgc aggtaatcca cctgttttgg tcgatgaaac tgcagacatc    780
gaaaaagccg ctaaggatat agttaacggt tgtagtttcg acaacaactt accatgcatt    840
accgaaaaag aagtagttgc cgtagattct atcactgact acttgatctt cgaaatgcaa    900
aagaatggtg catacttggt tcaagattca aagacaataa aaaagttgtg tgaaatggtc    960
atcaatgacg gttcaccaaa cagagcttat gtaggtaaaa acgcatccta catcttgaag   1020
gatttaggta ttgatgttgg tgacgaaata aaggtcatca ttgtagaaac tgatgcaggt   1080
catcctttgg ccgtattaga aatgttgatg ccagttttgc ctatagtaag agttaaggat   1140
gctttggaag gtataaaggt ttgcaaaaag ttagaagacg gtttgagaca tacagcaatg   1200
atacactcta agaacatcga tatcttaacc aagtacgcca gagacatgga aactacaatc   1260
ttggttaaaa acggtccatc ttattcaggt attggtgtcg gtggtgaagg ttacaccact   1320
tttaccattg ctggtcctac tggtgaaggt ttaacatccg ctaaaagttt cgcaagaaat   1380
agaagatgtg cattagttgg tggtttgtct attaagtag                          1419
```

<210> SEQ ID NO 36
<211> LENGTH: 472
<212> TYPE: PRT
<213> ORGANISM: Ilyobacter polytropus

<400> SEQUENCE: 36

```
Met Asn Leu Asp Ala Asn Asn Leu Asn Asn Ile Val Ser Leu Ile Met
1               5                   10                  15

Lys Glu Leu Asp Lys Asn Asn Asn Ile Asp Asp Thr Gly Gln Gly Cys
            20                  25                  30

Gly Gly Glu Glu Gly Lys Asn Gly Ile Phe Ser Ser Met Asp Thr Ala
        35                  40                  45

Val Ser Lys Ala Lys Glu Ala Gln Val Thr Leu Phe Ala Ser Lys Leu
    50                  55                  60

Glu Leu Arg Glu Arg Ile Ile Lys Ala Ile Arg Glu Asp Val Arg Glu
65                  70                  75                  80

Ala Ala Ala Glu Leu Ala Glu Ile Ala Val Glu Glu Thr Gly Met Gly
                85                  90                  95

Arg Val Asp Asp Lys Thr Leu Lys His Tyr Val Thr Val Asp Lys Thr
            100                 105                 110

Pro Gly Val Glu Asp Leu Arg Ala Phe Ala Tyr Ser Gly Asp Asn Gly
        115                 120                 125

Leu Thr Val Met Glu Leu Ser Pro Tyr Gly Val Ile Gly Ser Ile Thr
    130                 135                 140

Pro Ser Thr Asn Pro Ser Glu Thr Ile Val Cys Asn Ala Ile Gly Met
145                 150                 155                 160
```

Ile Ala Ala Gly Asn Ser Val Val Phe Ala Pro His Pro Gly Ala Lys
            165                 170                 175

Lys Thr Ser Leu Arg Ala Val Glu Ile Leu Asn Lys Ala Val Ala Arg
        180                 185                 190

Ala Gly Gly Pro Asn Asn Leu Val Val Thr Ile Phe Glu Pro Ser Ile
        195                 200                 205

Glu Asn Thr Asn Lys Met Val Lys Asn Pro Asp Ile Lys Met Val Val
210                 215                 220

Ala Thr Gly Gly Pro Gly Val Val Lys Ser Val Met Ser Ser Gly Lys
225                 230                 235                 240

Lys Ala Ile Gly Ala Gly Ala Gly Asn Pro Pro Val Leu Val Asp Glu
            245                 250                 255

Thr Ala Asp Ile Glu Lys Ala Ala Lys Asp Ile Val Asn Gly Cys Ser
        260                 265                 270

Phe Asp Asn Asn Leu Pro Cys Ile Thr Glu Lys Glu Val Val Ala Val
        275                 280                 285

Asp Ser Ile Thr Asp Tyr Leu Ile Phe Glu Met Gln Lys Asn Gly Ala
        290                 295                 300

Tyr Leu Val Gln Asp Ser Lys Thr Ile Lys Lys Leu Cys Glu Met Val
305                 310                 315                 320

Ile Asn Asp Gly Ser Pro Asn Arg Ala Tyr Val Gly Lys Asn Ala Ser
            325                 330                 335

Tyr Ile Leu Lys Asp Leu Gly Ile Asp Val Gly Asp Glu Ile Lys Val
        340                 345                 350

Ile Ile Val Glu Thr Asp Ala Gly His Pro Leu Ala Val Leu Glu Met
        355                 360                 365

Leu Met Pro Val Leu Pro Ile Val Arg Val Lys Asp Ala Leu Glu Gly
370                 375                 380

Ile Lys Val Cys Lys Lys Leu Glu Asp Gly Leu Arg His Thr Ala Met
385                 390                 395                 400

Ile His Ser Lys Asn Ile Asp Ile Leu Thr Lys Tyr Ala Arg Asp Met
            405                 410                 415

Glu Thr Thr Ile Leu Val Lys Asn Gly Pro Ser Tyr Ser Gly Ile Gly
        420                 425                 430

Val Gly Gly Glu Gly Tyr Thr Thr Phe Thr Ile Ala Gly Pro Thr Gly
        435                 440                 445

Glu Gly Leu Thr Ser Ala Lys Ser Phe Ala Arg Asn Arg Arg Cys Ala
450                 455                 460

Leu Val Gly Gly Leu Ser Ile Lys
465                 470

<210> SEQ ID NO 37
<211> LENGTH: 825
<212> TYPE: PRT
<213> ORGANISM: Bifidobacterium animalis

<400> SEQUENCE: 37

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Leu Ala His Ile Asn Arg
 65                  70                  75                  80

Leu Ile Ala Asp His Gln Gln Asn Thr Val Phe Ile Met Gly Pro Gly
             85                  90                  95

His Gly Gly Pro Ala Gly Thr Ala Gln Ser Tyr Ile Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
            165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
            245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
        275                 280                 285

Pro Phe Tyr Pro Met Leu Ile Phe Arg Thr Pro Lys Gly Trp Thr Cys
290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
            325                 330                 335

Leu Lys Gly Trp Met Glu Ser Tyr Lys Pro Glu Glu Leu Phe Asn Ala
            340                 345                 350

Asp Gly Ser Ile Lys Glu Asp Val Thr Ala Phe Met Pro Lys Gly Glu
        355                 360                 365

Leu Arg Ile Gly Ala Asn Pro Asn Ala Asn Gly Gly Arg Ile Arg Glu
370                 375                 380

Asp Leu Lys Leu Pro Glu Leu Asp Gln Tyr Glu Ile Thr Gly Val Lys
385                 390                 395                 400

Glu Tyr Gly His Gly Trp Gly Gln Val Glu Ala Pro Arg Ser Leu Gly
            405                 410                 415

Ala Tyr Cys Arg Asp Ile Ile Lys Asn Asn Pro Asp Ser Phe Arg Val
            420                 425                 430

Phe Gly Pro Asp Glu Thr Ala Ser Asn Arg Leu Asn Ala Thr Tyr Glu
        435                 440                 445

Val Thr Lys Lys Gln Trp Asp Asn Gly Tyr Leu Ser Ala Leu Val Asp
450                 455                 460

Glu Asn Met Ala Val Thr Gly Gln Val Val Glu Gln Leu Ser Glu His
465                 470                 475                 480

| | | | | | | | | | | | |
|---|---|---|---|---|---|---|---|---|---|---|---|
|Gln|Cys|Glu|Gly|Phe|Leu|Glu|Ala|Tyr|Leu|Leu|Thr|Gly|Arg|His|Gly|
| | | | |485| | | |490| | | |495| | | |

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
            515                 520                 525

Arg Lys Pro Ile Ser Ser Val Asn Leu Leu Val Ser Ser His Val Trp
            530                 535                 540

Arg Gln Asp His Asn Gly Phe Ser His Gln Asp Pro Gly Val Thr Ser
545                 550                 555                 560

Val Leu Leu Asn Lys Thr Phe Asn Asn Asp His Val Thr Asn Ile Tyr
            565                 570                 575

Phe Ala Thr Asp Ala Asn Met Leu Leu Ala Ile Ala Glu Lys Cys Phe
            580                 585                 590

Lys Ser Thr Asn Lys Ile Asn Ala Ile Phe Ala Gly Lys Gln Pro Ala
            595                 600                 605

Ala Thr Trp Ile Thr Leu Asp Glu Val Arg Ala Glu Leu Glu Ala Gly
            610                 615                 620

Ala Ala Glu Trp Lys Trp Ala Ser Asn Ala Lys Ser Asn Asp Glu Val
625                 630                 635                 640

Gln Val Val Leu Ala Ala Gly Asp Val Pro Thr Gln Glu Ile Met
            645                 650                 655

Ala Ala Ser Asp Ala Leu Asn Lys Met Gly Ile Lys Phe Lys Val Val
            660                 665                 670

Asn Val Val Asp Leu Ile Lys Leu Gln Ser Ser Lys Glu Asn Asp Glu
            675                 680                 685

Ala Met Ser Asp Glu Asp Phe Ala Asp Leu Phe Thr Ala Asp Lys Pro
690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Thr Val Val Gly Tyr Lys Glu
            725                 730                 735

Gln Gly Ser Thr Thr Thr Pro Phe Asp Met Val Arg Val Asn Asp Met
            740                 745                 750

Asp Arg Tyr Ala Leu Gln Ala Lys Ala Leu Glu Leu Ile Asp Ala Asp
            755                 760                 765

Lys Tyr Ala Asp Lys Ile Asn Glu Leu Asn Glu Phe Arg Lys Thr Ala
            770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Ser Met Leu Ser Ala
            805                 810                 815

Thr Ala Ala Thr Ala Gly Asp Asn Glu
            820                 825

<210> SEQ ID NO 38
<211> LENGTH: 2478
<212> TYPE: DNA
<213> ORGANISM: Schizosaccharomyces_pombe

<400> SEQUENCE: 38
atggctactc aaaacgatat ccctaactcg actcccgagg atttagcgaa acaagttgaa      60
attgccgaaa acaccccga tcctcctgct atgccctcgc gtcttcctga ctctttaaaa     120
accctcgaag ctaaaatcga cacttcaaag attaccgacg aagaggttgc caatgtccat     180

```
cgttttcaac gtgcatgtga ttacctcgca gcttccctga ttttcctttc caacggtctc      240
tacaccggcg gtgacctaga ggaaaaagat atcaaaacta gactgctagg ccattggggt      300
acttgtcccg gcttgagcat cgtttactct cactgtaatc gtatcattaa taaatatgat      360
ctcaacatgc tctttgtcgt aggccctggc catggtgctc ctgccatttt atcggctctt      420
ttccttgaag attctttggg cccctttttac cctcgatacc aatttaccaa ggaaggcttg      480 aacaaccttta ttaacaccctt ctcccttccc ggtggttttc cttctcatgt caacgccgag      540
gtccctggtg ccattcacga gggcggtgaa ttgggttatg cgttgtccgt cagttacggt      600
gcagttcttg atcgtcccga cctgattgta acttgcgttg tcggtgatgg tgaggcagag      660
accggcccca ctgccacttc ttggcatgct cataaattct tggatcctgc tgaatcgggt      720
gctgtgattc ctgttttgga acttaatggt tacaagattt ccgagcgtac catttacggt      780
tgcatggatg atagtgagct tctctctttg tttagcggtt ttggctatga agttgccatt      840
gtaaacgata cccccgacca aaacagggtt atggctgcaa ctatggattg ggccgttgaa      900
cgcattcatg acatccaaca tcgcgctcgt gttaacagag aagaaatcaa acccagatgg      960
cccatgatta tccttcgtac ccctaagggt aaaggatgtc ccaagtattt gaatggcaaa     1020 ttttttagaag gtaccttccg tgctcaccaa gttcctttga aattggctcg caccgatacc     1080
aaccagcgca atcttctaaa ggattggctg aacagctaca actgccaaga cttcttagac     1140
gaacatggac ttcctactaa gggcatcacc gagcatcttc cgcctcgtga aagcgcatg      1200 ggtcagcgtc atgagacata caattcttat ctacctttga aggtacctga ttggaaaaaa     1260
tacggtgtca agaagggaga accactagt gccacttcgg tcgttggtca atatcttgat     1320
gaactcctcg taaccaacga ttcaacccctt agaatttttct cacccgatga gttggaaagt     1380
aataaattag atggcgcttt gaagcactca tatcgtacca tgcaaactga tccagagctc     1440
atggcaaagc gtggtcgcgt taccgaagtc cttttcagagc acctttgcca aggtttcatg     1500
cagggttata ctttaactgg acgtaccgcg attttcccct catatgaagc ctttatgact     1560
attgttgtta gtatgcttgt tcagtactcc aaattttttga agatgggctt ggagaccgga     1620
tggcatggaa aatttggtag cttgaactat gttacttcca gtacttgggc aagacaagag     1680
cataacggtt tctcccatca atcacccagg tttatcacca ctatgctctc tctgaaacct     1740
ggtgttagcc gcgtatactt cccaccggat gccaattgct tcttagcaac cgtcgcccga     1800
tgcatgaagt ctgagaatac tatcaacctt atggtttcta gtaaaaatcc acaaccagcc     1860
tacctatctg ttgaagaggc cgaacatcat tgcaaggccg gtgctagtgt ttggaagttt     1920
gctagtacag ataatggcga aaatcctgat gttgttattg ccggcgtcgg aaatgagatt     1980
atgtttgaag tagttaaagc cgcagagatg cttcaaaatg acattcctga gctccgagtg     2040
cgtgtcatta acgtcactga cttgatggta cttttcgagct tacatcccca tggtatgaat     2100
cctgcggaat ttgattcttt gtttaccaaa gatcgccatg ttcatttcaa ctatcacggt     2160
tatgtgatgg acttgaaggc tctcttgttt gatcgcatac aaggtacacg ggtcactatg     2220
gagggctatc gagaggaagg tactactacc actccttta atatgatgat gtgtaacaat     2280
acctctcgtt atcatgttgc aagaatggct ttgcaacatg ctttacacaa tcctaccgtg     2340
gccgttaatt gtaacatgtt gtgtgccaaa tatgcttgga agctcgaaga gattgaaaat     2400
tatattatgg aaaacaagga tgatcctcct gaaatttatg ctgctcctgt ctttaaaaat     2460
aagacttcca cattatag                                                   2478
```

<210> SEQ ID NO 39
<211> LENGTH: 825
<212> TYPE: PRT
<213> ORGANISM: Schizosaccharomyces_pombe

<400> SEQUENCE: 39

Met Ala Thr Gln Asn Asp Ile Pro Asn Ser Thr Pro Glu Asp Leu Ala
1               5                   10                  15

Lys Gln Val Glu Ile Ala Glu Lys His Pro Asp Pro Pro Ala Met Pro
            20                  25                  30

Ser Arg Leu Pro Asp Ser Leu Lys Thr Leu Glu Ala Lys Ile Asp Thr
        35                  40                  45

Ser Lys Ile Thr Asp Glu Glu Val Ala Asn Val His Arg Phe Gln Arg
50                  55                  60

Ala Cys Asp Tyr Leu Ala Ala Ser Leu Ile Phe Leu Ser Asn Gly Leu
65                  70                  75                  80

Tyr Thr Gly Gly Asp Leu Glu Glu Lys Asp Ile Lys Thr Arg Leu Leu
                85                  90                  95

Gly His Trp Gly Thr Cys Pro Gly Leu Ser Ile Val Tyr Ser His Cys
            100                 105                 110

Asn Arg Ile Ile Asn Lys Tyr Asp Leu Asn Met Leu Phe Val Val Gly
        115                 120                 125

Pro Gly His Gly Ala Pro Ala Ile Leu Ser Ala Leu Phe Leu Glu Asp
130                 135                 140

Ser Leu Gly Pro Phe Tyr Pro Arg Tyr Gln Phe Thr Lys Glu Gly Leu
145                 150                 155                 160

Asn Asn Leu Ile Asn Thr Phe Ser Leu Pro Gly Gly Phe Pro Ser His
                165                 170                 175

Val Asn Ala Glu Val Pro Gly Ala Ile His Glu Gly Gly Glu Leu Gly
            180                 185                 190

Tyr Ala Leu Ser Val Ser Tyr Gly Ala Val Leu Asp Arg Pro Asp Leu
        195                 200                 205

Ile Val Thr Cys Val Val Gly Asp Gly Glu Ala Glu Thr Gly Pro Thr
210                 215                 220

Ala Thr Ser Trp His Ala His Lys Phe Leu Asp Pro Ala Glu Ser Gly
225                 230                 235                 240

Ala Val Ile Pro Val Leu Glu Leu Asn Gly Tyr Lys Ile Ser Glu Arg
                245                 250                 255

Thr Ile Tyr Gly Cys Met Asp Asp Ser Glu Leu Leu Ser Leu Phe Ser
            260                 265                 270

Gly Phe Gly Tyr Glu Val Ala Ile Val Asn Asp Thr Pro Asp Gln Asn
        275                 280                 285

Arg Val Met Ala Ala Thr Met Asp Trp Ala Val Glu Arg Ile His Asp
290                 295                 300

Ile Gln His Arg Ala Arg Val Asn Arg Glu Glu Ile Lys Pro Arg Trp
305                 310                 315                 320

Pro Met Ile Ile Leu Arg Thr Pro Lys Gly Lys Gly Cys Pro Lys Tyr
                325                 330                 335

Leu Asn Gly Lys Phe Leu Glu Gly Thr Phe Arg Ala His Gln Val Pro
            340                 345                 350

Leu Lys Leu Ala Arg Thr Asp Thr Asn Gln Arg Asn Leu Leu Lys Asp
        355                 360                 365

Trp Leu Asn Ser Tyr Asn Cys Gln Asp Phe Leu Asp Glu His Gly Leu
370                 375                 380

```
Pro Thr Lys Gly Ile Thr Glu His Leu Pro Pro Arg Glu Lys Arg Met
385                 390                 395                 400

Gly Gln Arg His Glu Thr Tyr Asn Ser Tyr Leu Pro Leu Lys Val Pro
                405                 410                 415

Asp Trp Lys Lys Tyr Gly Val Lys Lys Gly Glu Thr Thr Ser Ala Thr
            420                 425                 430

Ser Val Val Gly Gln Tyr Leu Asp Glu Leu Leu Val Thr Asn Asp Ser
        435                 440                 445

Thr Leu Arg Ile Phe Ser Pro Asp Glu Leu Glu Ser Asn Lys Leu Asp
    450                 455                 460

Gly Ala Leu Lys His Ser Tyr Arg Thr Met Gln Thr Asp Pro Glu Leu
465                 470                 475                 480

Met Ala Lys Arg Gly Arg Val Thr Glu Val Leu Ser Glu His Leu Cys
                485                 490                 495

Gln Gly Phe Met Gln Gly Tyr Thr Leu Thr Gly Arg Thr Ala Ile Phe
                500                 505                 510

Pro Ser Tyr Glu Ala Phe Met Thr Ile Val Val Ser Met Leu Val Gln
            515                 520                 525

Tyr Ser Lys Phe Leu Lys Met Gly Leu Glu Thr Gly Trp His Gly Lys
        530                 535                 540

Phe Gly Ser Leu Asn Tyr Val Thr Ser Thr Trp Ala Arg Gln Glu
545                 550                 555                 560

His Asn Gly Phe Ser His Gln Ser Pro Arg Phe Ile Thr Thr Met Leu
                565                 570                 575

Ser Leu Lys Pro Gly Val Ser Arg Val Tyr Phe Pro Pro Asp Ala Asn
                580                 585                 590

Cys Phe Leu Ala Thr Val Ala Arg Cys Met Lys Ser Glu Asn Thr Ile
            595                 600                 605

Asn Leu Met Val Ser Ser Lys Asn Pro Gln Pro Ala Tyr Leu Ser Val
        610                 615                 620

Glu Glu Ala Glu His His Cys Lys Ala Gly Ala Ser Val Trp Lys Phe
625                 630                 635                 640

Ala Ser Thr Asp Asn Gly Glu Asn Pro Asp Val Val Ile Ala Gly Val
                645                 650                 655

Gly Asn Glu Ile Met Phe Glu Val Val Lys Ala Ala Glu Met Leu Gln
                660                 665                 670

Asn Asp Ile Pro Glu Leu Arg Val Arg Val Ile Asn Val Thr Asp Leu
            675                 680                 685

Met Val Leu Ser Ser Leu His Pro His Gly Met Asn Pro Ala Glu Phe
        690                 695                 700

Asp Ser Leu Phe Thr Lys Asp Arg His Val His Phe Asn Tyr His Gly
705                 710                 715                 720

Tyr Val Met Asp Leu Lys Ala Leu Leu Phe Asp Arg Ile Gln Gly Thr
                725                 730                 735

Arg Val Thr Met Glu Gly Tyr Arg Glu Gly Thr Thr Thr Pro
                740                 745                 750

Phe Asn Met Met Met Cys Asn Asn Thr Ser Arg Tyr His Val Ala Arg
            755                 760                 765

Met Ala Leu Gln His Ala Leu His Asn Pro Thr Val Ala Val Asn Cys
        770                 775                 780

Asn Met Leu Cys Ala Lys Tyr Ala Trp Lys Leu Glu Glu Ile Glu Asn
785                 790                 795                 800
```

Tyr Ile Met Glu Asn Lys Asp Asp Pro Pro Glu Ile Tyr Ala Ala Pro
           805                 810                 815

Val Phe Lys Asn Lys Thr Ser Thr Leu
           820                 825

<210> SEQ ID NO 40
<211> LENGTH: 2343
<212> TYPE: DNA
<213> ORGANISM: Aspergillus_niger

<400> SEQUENCE: 40

| | | | | | |
|---|---|---|---|---|---|
| atgcctggtg | aagtcataga | aagacctaac | cctgctccta | agccatccca | cgttcctgat | 60 |
| ttggtagaaa | agttgattat | ccctgcccaa | aagactaagt | tggaaaagtc | agattgtgac | 120 |
| gctttacata | aatatagaag | agctgcagcc | tacattgctg | caggtcactg | ggtacttgc | 180 |
| ccaggtttga | tcttagttta | ctctcatttg | aactacttaa | ttaaaaagca | aaacttggat | 240 |
| atgttatatg | ttgtcggtcc | aggtcacggt | gccctggtt | tgttagcttc | attgtggtta | 300 |
| gaaggttcct | tgggtaaatt | ctacccacaa | tacacaaagg | ataaggaagg | tttgcataat | 360 |
| ttgatatcaa | ccttctctac | ttcagcaggt | ttaccatccc | atataaacgc | agaaactcct | 420 |
| ggtgccatcc | acgaaggtgg | tgaattgggt | tatgccttat | ccgttagttt | tggtgctgtc | 480 |
| atggacaatc | cagatttgat | tgttacatgt | gtagttggtg | acggtgaagc | tgaaaccggt | 540 |
| cctaccgcta | cttcatggca | cgctattaaa | tatatcgatc | cagccgaatc | cggtgctgtt | 600 |
| ttgcctatat | tgcatgtcaa | cggttttaaa | atctcagaaa | gaaccatatt | cggttgtatg | 660 |
| gacaacagag | aaatagtttg | cttgtttact | ggttatggtt | accaagttag | aattgtcgaa | 720 |
| gatttggaag | atatcgacaa | cgatttgcat | tctgcaatgt | catgggccgt | cgaagaaatt | 780 |
| agaaacatac | aaaaagccgc | tagaagtggt | aaaccaatta | tgaaaccaca | atggcctatg | 840 |
| atagttttga | gaacaccaaa | gggttggtct | ggtcctaaag | aattacatgg | tcaattcatt | 900 |
| gaaggttcct | tccatagtca | ccaagttcca | ttgcctaatg | ctaaaaagga | tgacgaagaa | 960 |
| ttgcaagcat | tacaaaagtg | gttgtcttca | tacaagccag | atgaattgtt | tactgaatct | 1020 |
| ggtgacgtta | tcgatgaaat | attgtccata | atcccaagtg | atgacaaaaa | gttgggtatg | 1080 |
| agacctgaag | catacaaaac | tcatttgcca | cctgacttac | cagattggag | acaattttgt | 1140 |
| gttaaaaagg | gtgaccaatt | cagtgctatg | aaggcaattg | gttctttat | agatcaagta | 1200 |
| ttcgttaaaa | atccacacac | agttagattg | ttttcacctg | atgaattaga | atctaacaag | 1260 |
| ttgtcagcag | ccttatccca | taccggtaga | aacttccaat | gggatgaatt | ttctaacgct | 1320 |
| aaaggtggta | gagtaatcga | agttttgtct | gaacacttat | gccaaggttt | tatgcaaggt | 1380 |
| tatacattga | ccggtagaac | aggtattttt | ccatcttacg | aatcattctt | aggtatcatt | 1440 |
| cataccatga | tggtacaata | tgccaaattc | gctaagatgg | caaaagaaac | tgcctggcat | 1500 |
| cacgatgttt | ccagtataaa | ttacatcgaa | acttctacat | gggctagaca | agaacataat | 1560 |
| ggttttagtc | accaaaaccc | atctttcatt | ggtgcagtct | tgaaattaaa | gccttatgct | 1620 |
| gcaagagtat | acttgccacc | tgatgctaac | acattttga | ctacattgca | tcactgtttg | 1680 |
| aagagtaaga | attacataaa | cttaatggtt | ggttctaagc | aaccaacacc | tgtttactta | 1740 |
| agtccagaag | aagctgaatc | tcattgtaga | gcaggtgcct | caattttaa | gttctgctcc | 1800 |
| accgacggtg | gtttgagacc | tgatgtcgta | ttagttggta | tcggtgtcga | agtaatgttt | 1860 |
| gaagtcataa | aagccgctgc | aatcttgaga | gaaagatgcc | agaattaag | agtaagagtt | 1920 |
| gtcaacgtta | ctgatttgtt | catattagaa | aacgaaggtg | ctcatcctca | cgcattgaag | 1980 |

```
catgaagcat tcgacaattt gtttactgaa gatagatcta tccatttcaa ctaccacggt   2040
tacgttaacg aattgcaagg tttgttattc ggtagaccaa gattagacag agctacaatt   2100
aagggttata agaagaagg ttcaaccact acacctttcg atatgatgtt ggtcaacgaa    2160
gtatccagat accatgtcgc aaaggccgct gtaactggtg gtgccagatt caatgaaaag   2220
gttaagttga gacatcaaga attgtgttca gaatttgatc acaacatcgc tgaaactaga   2280
aagtacataa tgaacaacca tcaagaccca gaagatacat acaatatgcc ttccttcaac   2340
tag                                                                2343
```

<210> SEQ ID NO 41
<211> LENGTH: 815
<212> TYPE: PRT
<213> ORGANISM: Aspergillus_niger

<400> SEQUENCE: 41

```
Met Pro Ser Asp Ser Asn Asp Gln Ser Ile Ser Ala Tyr Gly Ala Ala
1               5                   10                  15

Arg Ser Thr Val Lys Gly Gln Asn Leu Asp Pro Glu Glu Val Arg Lys
            20                  25                  30

Met Asp Ala Tyr Phe Arg Ala Ser Met Tyr Leu Cys Leu Gly Met Leu
        35                  40                  45

Tyr Leu Arg Glu Asn Val Leu Leu Lys Gln Pro Leu Lys Val Glu His
    50                  55                  60

Leu Lys Ala Arg Leu Leu Gly His Trp Gly Ser Asp Ala Gly Gln Ser
65                  70                  75                  80

Phe Thr Trp Ile His Met Asn Arg Leu Ile Lys Lys Tyr Asp Leu Asp
                85                  90                  95

Val Leu Phe Ile Ser Gly Pro Gly His Gly Ala Pro Gly Ile Leu Ser
            100                 105                 110

Gln Ser Tyr Leu Glu Gly Val Tyr Ser Glu Val Tyr Pro Asp Lys Ser
        115                 120                 125

Glu Asp Glu Arg Gly Met Gln Arg Phe Phe Lys Gln Phe Ser Phe Pro
    130                 135                 140

Gly Gly Ile Gly Ser His Ala Thr Pro Glu Thr Pro Gly Ser Leu His
145                 150                 155                 160

Glu Gly Gly Glu Leu Gly Tyr Ser Ile Ser His Ala Phe Gly Thr Val
                165                 170                 175

Phe Asp His Pro Asn Leu Ile Thr Leu Thr Met Val Gly Asp Gly Glu
            180                 185                 190

Ala Glu Thr Gly Pro Leu Ala Thr Ser Trp His Ser Thr Lys Tyr Leu
        195                 200                 205

Asn Pro Cys Thr Asp Gly Ala Val Leu Pro Val Leu His Leu Asn Gly
    210                 215                 220

Tyr Lys Ile Asn Asn Pro Thr Leu Leu Ala Arg Ile Ser His Asp Glu
225                 230                 235                 240

Leu Ser Ala Leu Met Lys Gly Tyr Gly Trp Thr Pro Tyr Phe Val Glu
                245                 250                 255

Gly Ser Asp Arg Glu Thr Met His Gln Ala Met Ala Ala Thr Leu Glu
            260                 265                 270

His Cys Val Leu Glu Ile Arg Lys Phe Gln Lys Lys Ala Arg Glu Ser
        275                 280                 285

Lys Glu Pro Phe Arg Pro His Trp Pro Met Ile Ile Leu Arg Ser Pro
    290                 295                 300
```

-continued

Lys Gly Trp Ser Ala Pro Arg Glu Val Asp Gly Lys Leu Leu Glu Gly
305                 310                 315                 320

Phe Trp Arg Ala His Gln Ile Pro Ile Thr Asp Val Leu Thr Asn Pro
            325                 330                 335

Ser His Leu Gln Leu Leu Glu Ser Trp Met Lys Ser Tyr Lys Pro Glu
            340                 345                 350

Glu Leu Phe Thr His Asp Gly Arg Leu Ile Ser Glu Leu Lys Ala Leu
            355                 360                 365

Ala Pro Thr Gly Asn Ser Arg Met Ser Ala Asn Pro Val Gly Asn Gly
370                 375                 380

Gly Leu Leu Arg Arg Pro Leu Asp Leu Pro Asp Phe Arg Lys Tyr Ala
385                 390                 395                 400

Leu Thr Ser Ile Asp Pro Gly Ala Thr Ile Arg Gly Ser Met Val Asn
            405                 410                 415

Met Ser His Tyr Leu Arg Asp Val Val Ala Phe Asn Gln Thr Asn Phe
            420                 425                 430

Arg Val Phe Gly Pro Asp Glu Thr Glu Ser Asn Lys Leu Ser Glu Ile
            435                 440                 445

Tyr Lys Ala Gly Lys Lys Val Trp Leu Ala Glu Tyr Phe Pro Glu Asp
450                 455                 460

Asn Asn Gly Gly Asn Leu Ser Met Ala Gly Arg Val Met Glu Met Leu
465                 470                 475                 480

Ser Glu His Thr Cys Glu Gly Trp Leu Glu Gly Tyr Val Leu Ser Gly
            485                 490                 495

Arg His Gly Leu Leu Asn Ser Tyr Glu Pro Phe Ile His Ile Ile Asp
            500                 505                 510

Ser Met Val Asn Gln His Cys Lys Trp Ile Glu Lys Cys Leu Glu Val
            515                 520                 525

Glu Trp Arg Ala Lys Val Ala Ser Leu Asn Ile Leu Leu Thr Ala Thr
530                 535                 540

Val Trp Arg Gln Asp His Asn Gly Phe Thr His Gln Asp Pro Gly Phe
545                 550                 555                 560

Leu Asp Val Val Ala Asn Lys Ser Pro Glu Val Val Arg Ile Tyr Leu
            565                 570                 575

Pro Pro Asp Gly Asn Ser Leu Leu Ser Val Met Asp His Cys Phe Arg
            580                 585                 590

Ser Ala Asn Tyr Val Asn Val Ile Val Ala Asp Lys Gln Asp His Ile
            595                 600                 605

Gln Phe Met Asp Met Asp Ala Ala Ile Ala His Cys Thr Lys Gly Val
            610                 615                 620

Gly Ile Trp Asp Trp Ala Ser Asn Asp Gln Gly Ala Glu Pro Asp Val
625                 630                 635                 640

Val Met Ala Ala Cys Gly Asp Val Pro Thr His Glu Ala Leu Ala Ala
            645                 650                 655

Thr Ala Leu Leu Arg Glu His Leu Pro Gln Leu Lys Val Arg Phe Val
            660                 665                 670

Asn Val Val Asp Leu Phe Lys Leu Met Ser Lys Ile His His Pro His
            675                 680                 685

Gly Met Ser Asp Arg Glu Trp Lys Ala Ile Phe Thr Ala Asp Arg Pro
            690                 695                 700

Ile Val Phe Asn Phe His Ser Tyr Pro Trp Leu Ile His Arg Leu Thr
705                 710                 715                 720

```
Tyr Lys Arg Pro Gly Gln Glu Asn Ile His Val Arg Gly Tyr Lys Glu
                725                 730                 735

Lys Gly Asn Ile Asp Thr Pro Phe Glu Leu Ala Val Arg Asn Gln Thr
            740                 745                 750

Asp Arg Tyr Ser Leu Ala Val Asp Ala Ile Asp His Ala Arg Gly Leu
        755                 760                 765

Gly Asn Thr Ala Ser Gly Val Arg Glu Lys Phe Leu Asn Met Gln Leu
    770                 775                 780

Leu Ala Lys Gln Lys Ala Tyr Asp Asp Gly Ile Asp Pro Asp Tyr Ile
785                 790                 795                 800

Arg Asn Trp Thr Trp Gln Tyr Pro Arg Lys Lys Gly Glu Gly Val
                805                 810                 815

<210> SEQ ID NO 42
<211> LENGTH: 2448
<212> TYPE: DNA
<213> ORGANISM: Acidithiobacillus_ferrooxidans

<400> SEQUENCE: 42
```

| | | |
|---|---|---|
| atgaccacag aacacgatgc tgcctgcgaa ggtgaaagta tatccgctta cggtacagcc | 60 |
| agagccacag tcgaagatca accattaaat actgatgact tgagaaaaat cgatgcctat | 120 |
| tggagagctt ctttgtactt atgtttgggc atgttgtatt tgagagataa cccattgtta | 180 |
| agagacccat taaagcctga acatataaag cctagattgt taggtcactg gggttctgat | 240 |
| gctggtcaat gcttcacata catccatttc aacagattaa ttaacaaata tgacttgaat | 300 |
| gccatataca tctccggtcc aggtcacggt gctcctgcaa tattatctca agcatatttg | 360 |
| gaaggtacat attccgaaac ctacccagat aaaagtcaag acatcgctgg tatgagaaga | 420 |
| ttttcaagc aattttcttt ccctggtggt attggttcac atgctacccc agaaactcct | 480 |
| ggttctatac acgaaggtgg tgaattgggt tattccgtaa gtcatgcctt tggtactgtt | 540 |
| tacgataatc cagacttaat tgctttggtc atggttggtg acggtgaagc tgaaactggt | 600 |
| cctttagcaa catcttggca ttcaaataag ttcttgaacc caatcacaga tggtgctgta | 660 |
| ttgcctgttt tgcatttgaa cggttacaag attaataacc caaccatttt ggctagaata | 720 |
| actcacgaag aattagaagc attgtttata ggttacggtt acactccata cttcgtcgaa | 780 |
| ggttccgatc ctgccagtat gcatcaagct atggctgcaa caatggaaag atgtgtattg | 840 |
| aaaattagag aatttcaaga taaggccaga cacactggta cagctttcag accaagatgg | 900 |
| cctatgatta tattgagatc cccaaaaggt tggactgctc ctagaaaggt tgatggtcat | 960 |
| tatttggaag ttttttggag agcacatcaa attccaatac ctgacgttgt ctcaaatcca | 1020 |
| gcacatttgc aattgttaga tcttggatg agatcataca gacctgaaga attatttgat | 1080 |
| gcacaaggta gattgattcc agaattacat gaattggccc ctaaaggtaa agaagaatg | 1140 |
| tccgcaaatc cagttgccaa cggtggtttg ttaagaagac cattagatat gcctgacttt | 1200 |
| agagttttca gtattgctgt ccaagatgca ggtggtacaa gagcagacaa tgttccaacc | 1260 |
| ttaggtcatt tcttgagaga aatcactaga agaaacatgc aaaactttag aattttcggt | 1320 |
| cctgatgaaa cccaatctaa caaattagat gctatctatg acgtcactca aaaagtatgg | 1380 |
| ttgggtgcat actttccaga agatgccgac ggtggtgcct agctttgtc cggtagagtt | 1440 |
| atggaaatgt tgagtgaaca tacattagaa ggttggttgg aaggttattt gttatctggt | 1500 |
| agacatggtt tgattaattc atacgaagcc tttatccata tcatagattc tatgttcaac | 1560 |
| caacacgcta atggttaga aaagtgtaac gaattgccat ggagagcaaa agtagcctca | 1620 |

| | | |
|---|---|---|
| ttaaatttgt tgatcacagg tttggtttgg agacaagatc ataacggttt tacccaccaa | 1680 |
| gatccaggtt tcttagacgt agttgctaat aagtcaccta acgtcgtaag aatatatttg | 1740 |
| ccacctgatg caaattgttt gttatccgtc accgaccatt gcttgagaag tgtaaactac | 1800 |
| atcaacgtta tcgtcgctga taagcaaact catttgcaat acttggatat ggacgccgct | 1860 |
| atggctcact gtgcaaaggg tgccggtatt tgggaatggg catctaatga tatgggtgaa | 1920 |
| gaaccagacg ttgtcatggc ctcttgcggt gacgttccta ctatggaatc attagcagcc | 1980 |
| acagcattgt tgagacaaca tttgccagat atcaagatca gattcgttaa cgtagttgac | 2040 |
| ttattcaagt tggtcccaca caccgaacat cctcacggta tgactgatag agaatttgaa | 2100 |
| gcattgttta cttcttctaa gccagttatt tttaatttcc attcatatcc ttggttaatc | 2160 |
| cacagattga cctacagaag accagcacaa catcacatac atgttagagg ttacaaggaa | 2220 |
| aagggtaaca tcgatactcc tttagaattg gctataagaa accaaacaga cagattttct | 2280 |
| ttggctattg atgcaataga cagaatccca agattctgtg atacaggttc aggtgttaga | 2340 |
| gaaattttgt tgaatttgca attcgcatgc aagaaccatg cctatgaata cggtgtcgat | 2400 |
| ccacaagaaa taacagactg gcaatggcca ttcagagata cccctttaa | 2448 |

<210> SEQ ID NO 43
<211> LENGTH: 815
<212> TYPE: PRT
<213> ORGANISM: Acidithiobacillus_ferrooxidans

<400> SEQUENCE: 43

Met Thr Thr Glu His Asp Ala Ala Cys Glu Gly Glu Ser Ile Ser Ala
1               5                   10                  15

Tyr Gly Thr Ala Arg Ala Thr Val Glu Asp Gln Pro Leu Asn Thr Asp
            20                  25                  30

Asp Leu Arg Lys Ile Asp Ala Tyr Trp Arg Ala Ser Leu Tyr Leu Cys
        35                  40                  45

Leu Gly Met Leu Tyr Leu Arg Asp Asn Pro Leu Leu Arg Asp Pro Leu
    50                  55                  60

Lys Pro Glu His Ile Lys Pro Arg Leu Leu Gly His Trp Gly Ser Asp
65                  70                  75                  80

Ala Gly Gln Cys Phe Thr Tyr Ile His Phe Asn Arg Leu Ile Asn Lys
                85                  90                  95

Tyr Asp Leu Asn Ala Ile Tyr Ile Ser Gly Pro Gly His Gly Ala Pro
            100                 105                 110

Ala Ile Leu Ser Gln Ala Tyr Leu Glu Gly Thr Tyr Ser Glu Thr Tyr
        115                 120                 125

Pro Asp Lys Ser Gln Asp Ile Ala Gly Met Arg Arg Phe Phe Lys Gln
    130                 135                 140

Phe Ser Phe Pro Gly Gly Ile Gly Ser His Ala Thr Pro Glu Thr Pro
145                 150                 155                 160

Gly Ser Ile His Glu Gly Gly Glu Leu Gly Tyr Ser Val Ser His Ala
                165                 170                 175

Phe Gly Thr Val Tyr Asp Asn Pro Asp Leu Ile Ala Leu Val Met Val
            180                 185                 190

Gly Asp Gly Glu Ala Glu Thr Gly Pro Leu Ala Thr Ser Trp His Ser
        195                 200                 205

Asn Lys Phe Leu Asn Pro Ile Thr Asp Gly Ala Val Leu Pro Val Leu
    210                 215                 220

-continued

His Leu Asn Gly Tyr Lys Ile Asn Asn Pro Thr Ile Leu Ala Arg Ile
225                 230                 235                 240

Thr His Glu Glu Leu Glu Ala Leu Phe Ile Gly Tyr Gly Tyr Thr Pro
            245                 250                 255

Tyr Phe Val Glu Gly Ser Asp Pro Ala Ser Met His Gln Ala Met Ala
        260                 265                 270

Ala Thr Met Glu Arg Cys Val Leu Lys Ile Arg Glu Phe Gln Asp Lys
    275                 280                 285

Ala Arg His Thr Gly Thr Ala Phe Arg Pro Arg Trp Pro Met Ile Ile
290                 295                 300

Leu Arg Ser Pro Lys Gly Trp Thr Ala Pro Arg Lys Val Asp Gly His
305                 310                 315                 320

Tyr Leu Glu Gly Phe Trp Arg Ala His Gln Ile Pro Ile Pro Asp Val
            325                 330                 335

Val Ser Asn Pro Ala His Leu Gln Leu Leu Glu Ser Trp Met Arg Ser
        340                 345                 350

Tyr Arg Pro Glu Glu Leu Phe Asp Ala Gln Gly Arg Leu Ile Pro Glu
    355                 360                 365

Leu His Glu Leu Ala Pro Lys Gly Lys Arg Arg Met Ser Ala Asn Pro
370                 375                 380

Val Ala Asn Gly Gly Leu Leu Arg Arg Pro Leu Asp Met Pro Asp Phe
385                 390                 395                 400

Arg Val Phe Ser Ile Ala Val Gln Asp Ala Gly Gly Thr Arg Ala Asp
            405                 410                 415

Asn Val Pro Thr Leu Gly His Phe Leu Arg Glu Ile Thr Arg Arg Asn
        420                 425                 430

Met Gln Asn Phe Arg Ile Phe Gly Pro Asp Glu Thr Gln Ser Asn Lys
    435                 440                 445

Leu Asp Ala Ile Tyr Asp Val Thr Gln Lys Val Trp Leu Gly Ala Tyr
450                 455                 460

Phe Pro Glu Asp Ala Asp Gly Gly Ala Leu Ala Leu Ser Gly Arg Val
465                 470                 475                 480

Met Glu Met Leu Ser Glu His Thr Leu Glu Gly Trp Leu Glu Gly Tyr
            485                 490                 495

Leu Leu Ser Gly Arg His Gly Leu Ile Asn Ser Tyr Glu Ala Phe Ile
        500                 505                 510

His Ile Ile Asp Ser Met Phe Asn Gln His Ala Lys Trp Leu Glu Lys
    515                 520                 525

Cys Asn Glu Leu Pro Trp Arg Ala Lys Val Ala Ser Leu Asn Leu Leu
530                 535                 540

Ile Thr Gly Leu Val Trp Arg Gln Asp His Asn Gly Phe Thr His Gln
545                 550                 555                 560

Asp Pro Gly Phe Leu Asp Val Val Ala Asn Lys Ser Pro Asn Val Val
            565                 570                 575

Arg Ile Tyr Leu Pro Pro Asp Ala Asn Cys Leu Leu Ser Val Thr Asp
        580                 585                 590

His Cys Leu Arg Ser Val Asn Tyr Ile Asn Val Ile Ala Asp Lys
    595                 600                 605

Gln Thr His Leu Gln Tyr Leu Asp Met Asp Ala Ala Met Ala His Cys
610                 615                 620

Ala Lys Gly Ala Gly Ile Trp Glu Trp Ala Ser Asn Asp Met Gly Glu
625                 630                 635                 640

Glu Pro Asp Val Val Met Ala Ser Cys Gly Asp Val Pro Thr Met Glu

|   |   |   |   |   | 645 |   |   |   |   | 650 |   |   |   |   | 655 |   |
|---|---|---|---|---|---|---|---|---|---|---|---|---|---|---|---|---|

Ser Leu Ala Ala Thr Ala Leu Leu Arg Gln His Leu Pro Asp Ile Lys
                660                 665                 670

Ile Arg Phe Val Asn Val Val Asp Leu Phe Lys Leu Val Pro His Thr
            675                 680                 685

Glu His Pro His Gly Met Thr Asp Arg Glu Phe Glu Ala Leu Phe Thr
        690                 695                 700

Ser Ser Lys Pro Val Ile Phe Asn Phe His Ser Tyr Pro Trp Leu Ile
705                 710                 715                 720

His Arg Leu Thr Tyr Arg Arg Pro Ala Gln His His Ile His Val Arg
                725                 730                 735

Gly Tyr Lys Glu Lys Gly Asn Ile Asp Thr Pro Leu Glu Leu Ala Ile
            740                 745                 750

Arg Asn Gln Thr Asp Arg Phe Ser Leu Ala Ile Asp Ala Ile Asp Arg
        755                 760                 765

Ile Pro Arg Phe Cys Asp Thr Gly Ser Gly Val Arg Glu Ile Leu Leu
770                 775                 780

Asn Leu Gln Phe Ala Cys Lys Asn His Ala Tyr Glu Tyr Gly Val Asp
785                 790                 795                 800

Pro Gln Glu Ile Thr Asp Trp Gln Trp Pro Phe Arg Asp Thr Pro
                805                 810                 815

<210> SEQ ID NO 44
<211> LENGTH: 2475
<212> TYPE: DNA
<213> ORGANISM: Bifidobacterium_asteroids

<400> SEQUENCE: 44

| | | | | |
|---|---|---|---|---|
| atgacaaatc | ctgtaatagg | tactccttgg | gcaaagttag | aaacaccaat agccgaagaa | 60 |
| accatagaag | ccgtagataa | atactggaga | gctgcaaact | atttgtccat aggtcaaatc | 120 |
| tacttgagaa | gtaatccatt | aatgaaggaa | cctttacaa | gagaagatgt caagcataga | 180 |
| ttagtaggtc | actggggtac | tacaccaggt | ttgaacttct | tgttgggtca tatcaacaga | 240 |
| ttgatcgctg | atcaccaaca | aaacactgtt | attatcatgg | gtccaggtca tggtggtcct | 300 |
| gcaggtacct | cccaaagtta | tttggatggt | acttactcag | aatactaccc aaagatcaca | 360 |
| aacgacgaag | ctggtttgca | aaagtttttc | agacaatttt | cctatccagg tggtatacct | 420 |
| agtcatttcg | ctccagaaac | tcctggttcc | atccacgaag | tggtgaatt gggttatgca | 480 |
| ttatcccatg | cttacggtgc | aatcatgaat | aacccaagtt | tgtttgttcc ttgtattgtc | 540 |
| ggtgacggtg | aagcagaaac | cggtccatta | gccactggtt | ggcaatctaa caaattggtt | 600 |
| aatccaagaa | ccgatggtat | tgtcttgcct | atcttgcatt | tgaatggtta caagattgct | 660 |
| aatccaacta | tcttgtctag | aatctcagat | gaagaattac | acgaatactt caagggtatg | 720 |
| ggttacgaac | ttttgaatt | tgttgctggt | ttcgatgacg | aagatcattt gtcaatacac | 780 |
| agaagatttg | cagatttgtt | agaaacagtc | ttcgacaaga | tctgcaacat caaggctaga | 840 |
| gcagaaactg | atgacatgac | aagaccatgt | taccctatga | tcattttag aacaccaaaa | 900 |
| ggttggacct | gccctaagtt | catagatggt | aaaaagactg | aaggttcttg gagagcacat | 960 |
| caagttccat | tgacttcagc | aagagacaca | gaagcccact | tccaaatctt gaaaaattgg | 1020 |
| ttagcttctt | acaagcctga | agaattgttc | gatgaaaagg | gtgcattaag accagaagtt | 1080 |
| acatcattca | tgcctaaggg | tgacttaaga | attggtgaaa | tccaaacgc taatggtggt | 1140 |
| agattgttga | agccattgga | attacctgat | atccatgact | acgaaataga tgttaaaaag | 1200 |

```
catggtcacg gttggggtgc caccgaagct actagagtat tgggttatta cacaagagat    1260
gttttagcta agaatccaac cgattttaga attttcggtc ctgacgaaac tgcatctaac    1320
agattagccg ctgcatatga agtaacaaat aagcaatggg atgcagacta cttgtccgaa    1380
ttaacagatg aacatatggc ccacaccggt caagttatcg aacaattaag tgaacatcaa    1440
atggaaggtt tcttggaagg ttatttgtta actggtagac acggtatttg gtcttcatac    1500
gaatctttcg ttcatgtcat agattcaatg atcaatcaac acgctaaatg gttggaagca    1560
actgttagag aaataccatg gagaaagcct atcgctggtt tgaacttgtt agtaacatct    1620
catgtttgga gacaagatca taatggtttt tcacaccaag acccaggttt cgttgatata    1680
ttgttgaaca aaaacttcaa caacgatcat gttgtcaaca tctatttccc tgccgacgct    1740
aacatgttgt tgaacgttgg tgaaagatgt tacaaatcca caactgcat caatgcaatt     1800 tttgccggta acaaccagc cgctacctat caaagtgtcg atgaagcagc cgctgaattg     1860
gaaaaaggtg cagccagatg ggattgggct tctaatgcaa aggacgccga agatgctgac    1920
gttgttattg ctactgctgg tgacatacca actcaagaag cattggctgc tgatgacatg    1980
ttgcaaaaat tgggtgtaaa ggttcaattc gttaacgtcg tagatttgtt gaagatccaa    2040
gacgctgaag aaaacgatca agcattgtct gacgaagagt ttactgaatt attctcaaag    2100
gataagccag tcttgtttgc attccatgcc tatcctggtt caatctatag attgatacat    2160
ggtagaccaa accacgataa ttttttccgta catggttatg aagaacaagg tagtaccact    2220 acaccttcg atatggtcag agtaaataac atggacagat ggtgtttagc cgcttctgcc    2280
ttgcaattag ttgatgctaa taagtacact gatcaaatag acaagtggac aaagtttaga    2340
gatgaagcct ttcaattcgc tgttgataaa ggttatgatc atccagacta caccgattgg    2400
gtatggcctg atgctaacag agcaggtcaa gaaactattt ctgccacagc agccaccgct    2460
ggtgacaatg aataa    2475
```

<210> SEQ ID NO 45
<211> LENGTH: 824
<212> TYPE: PRT
<213> ORGANISM: Bifidobacterium_asteroids

<400> SEQUENCE: 45

Met Thr Asn Pro Val Ile Gly Thr Pro Trp Ala Lys Leu Glu Thr Pro
1               5                   10                  15

Ile Ala Glu Glu Thr Ile Glu Ala Val Asp Lys Tyr Trp Arg Ala Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Leu Gly His Ile Asn Arg
65                  70                  75                  80

Leu Ile Ala Asp His Gln Gln Asn Thr Val Ile Ile Met Gly Pro Gly
                85                  90                  95

His Gly Gly Pro Ala Gly Thr Ser Gln Ser Tyr Leu Asp Gly Thr Tyr
            100                 105                 110

Ser Glu Tyr Tyr Pro Lys Ile Thr Asn Asp Glu Ala Gly Leu Gln Lys
        115                 120                 125

Phe Phe Arg Gln Phe Ser Tyr Pro Gly Gly Ile Pro Ser His Phe Ala
    130                 135                 140

```
Pro Glu Thr Pro Gly Ser Ile His Glu Gly Gly Leu Gly Tyr Ala
145                 150                 155                 160

Leu Ser His Ala Tyr Gly Ala Ile Met Asn Asn Pro Ser Leu Phe Val
            165                 170                 175

Pro Cys Ile Val Gly Asp Gly Glu Ala Glu Thr Gly Pro Leu Ala Thr
        180                 185                 190

Gly Trp Gln Ser Asn Lys Leu Val Asn Pro Arg Thr Asp Gly Ile Val
    195                 200                 205

Leu Pro Ile Leu His Leu Asn Gly Tyr Lys Ile Ala Asn Pro Thr Ile
210                 215                 220

Leu Ser Arg Ile Ser Asp Glu Glu Leu His Glu Tyr Phe Lys Gly Met
225                 230                 235                 240

Gly Tyr Glu Pro Phe Glu Phe Val Ala Gly Phe Asp Asp Glu Asp His
                245                 250                 255

Leu Ser Ile His Arg Arg Phe Ala Asp Leu Leu Glu Thr Val Phe Asp
            260                 265                 270

Lys Ile Cys Asn Ile Lys Ala Arg Ala Glu Thr Asp Asp Met Thr Arg
        275                 280                 285

Pro Cys Tyr Pro Met Ile Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Thr Ser Ala Arg Asp Thr Glu Ala His Phe Gln Ile
                325                 330                 335

Leu Lys Asn Trp Leu Ala Ser Tyr Lys Pro Glu Glu Leu Phe Asp Glu
            340                 345                 350

Lys Gly Ala Leu Arg Pro Glu Val Thr Ser Phe Met Pro Lys Gly Asp
        355                 360                 365

Leu Arg Ile Gly Glu Asn Pro Asn Ala Asn Gly Gly Arg Leu Leu Lys
370                 375                 380

Pro Leu Glu Leu Pro Asp Ile His Asp Tyr Glu Ile Asp Val Lys Lys
385                 390                 395                 400

His Gly His Gly Trp Gly Ala Thr Glu Ala Thr Arg Val Leu Gly Tyr
                405                 410                 415

Tyr Thr Arg Asp Val Leu Ala Lys Asn Pro Thr Asp Phe Arg Ile Phe
            420                 425                 430

Gly Pro Asp Glu Thr Ala Ser Asn Arg Leu Ala Ala Ala Tyr Glu Val
        435                 440                 445

Thr Asn Lys Gln Trp Asp Ala Asp Tyr Leu Ser Glu Leu Thr Asp Glu
    450                 455                 460

His Met Ala His Thr Gly Gln Val Ile Glu Gln Leu Ser Glu His Gln
465                 470                 475                 480

Met Glu Gly Phe Leu Glu Gly Tyr Leu Leu Thr Gly Arg His Gly Ile
                485                 490                 495

Trp Ser Ser Tyr Glu Ser Phe Val His Val Ile Asp Ser Met Ile Asn
            500                 505                 510

Gln His Ala Lys Trp Leu Glu Ala Thr Val Arg Glu Ile Pro Trp Arg
        515                 520                 525

Lys Pro Ile Ala Gly Leu Asn Leu Leu Val Thr Ser His Val Trp Arg
    530                 535                 540

Gln Asp His Asn Gly Phe Ser His Gln Asp Pro Gly Phe Val Asp Ile
545                 550                 555                 560
```

```
Leu Leu Asn Lys Asn Phe Asn Asn Asp His Val Val Asn Ile Tyr Phe
            565                 570                 575
Pro Ala Asp Ala Asn Met Leu Leu Asn Val Gly Glu Arg Cys Tyr Lys
            580                 585                 590
Ser Thr Asn Cys Ile Asn Ala Ile Phe Ala Gly Lys Gln Pro Ala Ala
            595                 600                 605
Thr Tyr Gln Ser Val Asp Glu Ala Ala Ala Glu Leu Glu Lys Gly Ala
            610                 615                 620
Ala Arg Trp Asp Trp Ala Ser Asn Ala Lys Asp Ala Glu Asp Ala Asp
625                 630                 635                 640
Val Val Ile Ala Thr Ala Gly Asp Ile Pro Thr Gln Glu Ala Leu Ala
            645                 650                 655
Ala Asp Asp Met Leu Gln Lys Leu Gly Val Lys Val Gln Phe Val Asn
            660                 665                 670
Val Val Asp Leu Leu Lys Ile Gln Asp Ala Glu Glu Asn Asp Gln Ala
            675                 680                 685
Leu Ser Asp Glu Glu Phe Thr Glu Leu Phe Ser Lys Asp Lys Pro Val
            690                 695                 700
Leu Phe Ala Phe His Ala Tyr Pro Gly Ser Ile Tyr Arg Leu Ile His
705                 710                 715                 720
Gly Arg Pro Asn His Asp Asn Phe Ser Val His Gly Tyr Glu Glu Gln
            725                 730                 735
Gly Ser Thr Thr Thr Pro Phe Asp Met Val Arg Val Asn Asn Met Asp
            740                 745                 750
Arg Trp Cys Leu Ala Ala Ser Ala Leu Gln Leu Val Asp Ala Asn Lys
            755                 760                 765
Tyr Thr Asp Gln Ile Asp Lys Trp Thr Lys Phe Arg Asp Glu Ala Phe
            770                 775                 780
Gln Phe Ala Val Asp Lys Gly Tyr Asp His Pro Asp Tyr Thr Asp Trp
785                 790                 795                 800
Val Trp Pro Asp Ala Asn Arg Ala Gly Gln Glu Thr Ile Ser Ala Thr
            805                 810                 815
Ala Ala Thr Ala Gly Asp Asn Glu
            820
```

<210> SEQ ID NO 46
<211> LENGTH: 2478
<212> TYPE: DNA
<213> ORGANISM: Bifidobacterium_catenulatum

<400> SEQUENCE: 46

```
atgacctccc ctgtaattgg taccccatgg aagaagttaa acgctcctgt aagtgaagaa      60
gctattgaag tgtcgataa gtattggggt gctgcaaact acttgtccat cggtcaaata     120
tatttgagaa gtaaccccatt gatgaaagaa cctttcacta gagaagatgt aaagcataga     180
ttggttggtc actggggtac tacaccaggt ttgaactttt taatcggtca tatcaacaga     240
ttgatcgctg atcacaagca aaacaccgtt attatcatgg gtccaggtca tggtggtcct     300
gcaggtactg cccaatctta tttggatggt acctacactg aaacattccc taaaataact     360
aaggacgaag caggtttgca aaagtttttc agacaatttt cctacccagg tggtattcct     420
agtcattatg ctccagaaac acctggttca atacacgaag tggtgaatt gggttacgca     480
ttatcccatg cttatggtgc agttatgaat aacccaagtt gtttgttcc tgcaattgtc     540
ggtgacggtg aagccgaaac tggtccatta gcaacagcct gggattacga caacatcatt     600
```

| | | |
|---|---|---|
| aatccaagaa ctgatggtat cgttttgcct atattgcact taaacggtta caagatcgct | 660 |
| aacccaacaa tcttgtctag aatctcagat gaagaattgc atgaattttt ccacggtatg | 720 |
| ggttatgaac cttacgaatt tgttgctaga ttcgataatg aagaccattt gtctattcac | 780 |
| agaagatttg cagaattgtt cgaaactgtc ttcgacgaaa tctgtgatat caaagccgct | 840 |
| gcacataccg atgacatgac tagaccattc taccctatga taatctttag aaccccaaaa | 900 |
| ggttggactt gccctaagtt cattgatggt aaaaagacag aaggttcctg agaagtcat | 960 |
| caagtaccat tggcttccgc aagagatacc gaagctcact ttgaagtttt gactaactgg | 1020 |
| ttggaatctt acaaccctga gaattgttc gatgaaaacg gtgctgtaaa accagaagtt | 1080 |
| acagcttttta tgcctaccgg tgaattaaga atcggtgcta atccaaacgc aaatggtggt | 1140 |
| gttattagag aagaattgaa tttgcctgcc ttagaagatt acgaagtaaa agaagttgct | 1200 |
| gaatatggtc atggttgggg tcaattggaa gctactagaa gattaggtgt ttacacaaga | 1260 |
| gacattttta agaacaaccc agattctttt agaatattcg gtcctgatga aactgcatca | 1320 |
| aacagattgc aagccgctta cgacgtcaca aataagaaat gggatgcagg ttatttgtct | 1380 |
| tcacaagtag atgaccatat ggccgtcaca ggtcaagtaa ccgaacaatt gtctgaacac | 1440 |
| caaatggaag gtttcttgga agcttacttg ttaactggta gacatggtat ctggtccagt | 1500 |
| tatgaatcta ttgtccatgt aaacgattca atgttgaatc aacacgcaaa atggttcgca | 1560 |
| gccacagtta gagaaattcc atggagaaag cctatctctt caatgaattt gttagtttcc | 1620 |
| agtcatgtct ggagacaaga ccaaacaggt ttttctcacc aagatccagg tgtcacctcc | 1680 |
| gtattgttga gtagatgttt caacaacgat aacgttatag gtatatactt tgctgtcgat | 1740 |
| tccgacatgt tgttagccgg tgctgataaa tgctatcaaa gtagaaaggt catgaatgcc | 1800 |
| ggtatagtag gtagagctcc agctgcaacc tggttgatct taggtgaagc aagagccgaa | 1860 |
| ttggaaaaag gtgccgctga atgggaatgg gcctctactg ctaagtcaaa tgacgaagct | 1920 |
| caaattgtat tagcttcagc aggtgacgtt cctgcacaag aaatcatggc agccgctgac | 1980 |
| aagttgaacg aattgggtat taagtttaaa gttgtcaacg tagttgatttt ggttaagttg | 2040 |
| caatctacaa aggaaaatga ccaagctata tcagatgcag acttcgccga cttgtttacc | 2100 |
| gaagataagc cagtcttatt cgcttatcat tcttacgcat cagacgttag aggtttgatc | 2160 |
| tacgatagac caaatcatga tgactttaac gttcacggta atcaagaaca aggttctacc | 2220 |
| actacacctt acgacatggt tagagtcaac aacatcgatt catacgaatt ggttgccgaa | 2280 |
| gctttaagaa tgatagatgc cgacaagtac gctgatgaaa tcaacgaatt ggaagctttt | 2340 |
| agacaagaag catttcaatt cgccgttgat aatggttatg atcatccaga ctacactgat | 2400 |
| tgggtctatt ctggtgtcaa cacaaccaag caaggtgcag tctcagccac agcagcaacc | 2460 |
| gcaggtgaca acgaataa | 2478 |

<210> SEQ ID NO 47
<211> LENGTH: 825
<212> TYPE: PRT
<213> ORGANISM: Bifidobacterium_catenulatum

<400> SEQUENCE: 47

Met Thr Ser Pro Val Ile Gly Thr Pro Trp Lys Lys Leu Asn Ala Pro
1               5                   10                  15

Val Ser Glu Glu Ala Ile Glu Gly Val Asp Lys Tyr Trp Gly Ala Ala
            20                  25                  30

Asn Tyr Leu Ser Ile Gly Gln Ile Tyr Leu Arg Ser Asn Pro Leu Met

-continued

```
                35                  40                  45
Lys Glu Pro Phe Thr Arg Glu Asp Val Lys His Arg Leu Val Gly His
            50                  55                  60
Trp Gly Thr Thr Pro Gly Leu Asn Phe Leu Ile Gly His Ile Asn Arg
 65                  70                  75                  80
Leu Ile Ala Asp His Lys Gln Asn Thr Val Ile Met Gly Pro Gly
                85                  90                  95
His Gly Gly Pro Ala Gly Thr Ala Gln Ser Tyr Leu Asp Gly Thr Tyr
            100                 105                 110
Thr Glu Thr Phe Pro Lys Ile Thr Lys Asp Glu Ala Gly Leu Gln Lys
            115                 120                 125
Phe Phe Arg Gln Phe Ser Tyr Pro Gly Gly Ile Pro Ser His Tyr Ala
            130                 135                 140
Pro Glu Thr Pro Gly Ser Ile His Glu Gly Gly Glu Leu Gly Tyr Ala
145                 150                 155                 160
Leu Ser His Ala Tyr Gly Ala Val Met Asn Asn Pro Ser Leu Phe Val
                165                 170                 175
Pro Ala Ile Val Gly Asp Gly Glu Ala Glu Thr Gly Pro Leu Ala Thr
            180                 185                 190
Ala Trp Asp Tyr Asp Asn Ile Ile Asn Pro Arg Thr Asp Gly Ile Val
            195                 200                 205
Leu Pro Ile Leu His Leu Asn Gly Tyr Lys Ile Ala Asn Pro Thr Ile
            210                 215                 220
Leu Ser Arg Ile Ser Asp Glu Glu Leu His Glu Phe Phe His Gly Met
225                 230                 235                 240
Gly Tyr Glu Pro Tyr Glu Phe Val Ala Arg Phe Asp Asn Glu Asp His
                245                 250                 255
Leu Ser Ile His Arg Arg Phe Ala Glu Leu Phe Glu Thr Val Phe Asp
            260                 265                 270
Glu Ile Cys Asp Ile Lys Ala Ala Ala His Thr Asp Asp Met Thr Arg
            275                 280                 285
Pro Phe Tyr Pro Met Ile Ile Phe Arg Thr Pro Lys Gly Trp Thr Cys
            290                 295                 300
Pro Lys Phe Ile Asp Gly Lys Lys Thr Glu Gly Ser Trp Arg Ser His
305                 310                 315                 320
Gln Val Pro Leu Ala Ser Ala Arg Asp Thr Glu Ala His Phe Glu Val
                325                 330                 335
Leu Thr Asn Trp Leu Glu Ser Tyr Asn Pro Glu Glu Leu Phe Asp Glu
            340                 345                 350
Asn Gly Ala Val Lys Pro Glu Val Thr Ala Phe Met Pro Thr Gly Glu
            355                 360                 365
Leu Arg Ile Gly Ala Asn Pro Asn Ala Asn Gly Gly Val Ile Arg Glu
            370                 375                 380
Glu Leu Asn Leu Pro Ala Leu Glu Asp Tyr Glu Val Lys Glu Val Ala
385                 390                 395                 400
Glu Tyr Gly His Gly Trp Gly Gln Leu Glu Ala Thr Arg Arg Leu Gly
                405                 410                 415
Val Tyr Thr Arg Asp Ile Phe Lys Asn Asn Pro Asp Ser Phe Arg Ile
            420                 425                 430
Phe Gly Pro Asp Glu Thr Ala Ser Asn Arg Leu Gln Ala Ala Tyr Asp
            435                 440                 445
Val Thr Asn Lys Lys Trp Asp Ala Gly Tyr Leu Ser Ser Gln Val Asp
            450                 455                 460
```

Asp His Met Ala Val Thr Gly Gln Val Thr Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Ile Val His Val Asn Asp Ser Met Leu
            500                 505                 510

Asn Gln His Ala Lys Trp Phe Ala Ala Thr Val Arg Glu Ile Pro Trp
        515                 520                 525

Arg Lys Pro Ile Ser Ser Met Asn Leu Leu Val Ser Ser His Val Trp
530                 535                 540

Arg Gln Asp Gln Thr Gly Phe Ser His Gln Asp Pro Gly Val Thr Ser
545                 550                 555                 560

Val Leu Leu Ser Arg Cys Phe Asn Asn Asp Asn Val Ile Gly Ile Tyr
                565                 570                 575

Phe Ala Val Asp Ser Asp Met Leu Leu Ala Gly Ala Asp Lys Cys Tyr
            580                 585                 590

Gln Ser Arg Lys Val Met Asn Ala Gly Ile Val Gly Arg Ala Pro Ala
        595                 600                 605

Ala Thr Trp Leu Ile Leu Gly Glu Ala Arg Ala Glu Leu Glu Lys Gly
610                 615                 620

Ala Ala Glu Trp Glu Trp Ala Ser Thr Ala Lys Ser Asn Asp Glu Ala
625                 630                 635                 640

Gln Ile Val Leu Ala Ser Ala Gly Asp Val Pro Ala Gln Glu Ile Met
                645                 650                 655

Ala Ala Ala Asp Lys Leu Asn Glu Leu Gly Ile Lys Phe Lys Val Val
            660                 665                 670

Asn Val Val Asp Leu Val Lys Leu Gln Ser Thr Lys Glu Asn Asp Gln
        675                 680                 685

Ala Ile Ser Asp Ala Asp Phe Ala Asp Leu Phe Thr Glu Asp Lys Pro
690                 695                 700

Val Leu Phe Ala Tyr His Ser Tyr Ala Ser Asp Val Arg Gly Leu Ile
705                 710                 715                 720

Tyr Asp Arg Pro Asn His Asp Asp Phe Asn Val His Gly Asn Gln Glu
                725                 730                 735

Gln Gly Ser Thr Thr Thr Pro Tyr Asp Met Val Arg Val Asn Asn Ile
            740                 745                 750

Asp Ser Tyr Glu Leu Val Ala Glu Ala Leu Arg Met Ile Asp Ala Asp
        755                 760                 765

Lys Tyr Ala Asp Glu Ile Asn Glu Leu Glu Ala Phe Arg Gln Glu Ala
770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Thr Lys Gln Gly Ala Val Ser Ala
                805                 810                 815

Thr Ala Ala Thr Ala Gly Asp Asn Glu
            820                 825

<210> SEQ ID NO 48
<211> LENGTH: 2376
<212> TYPE: DNA
<213> ORGANISM: Clostridium_butyricum

<400> SEQUENCE: 48
atgacaaaca tcaactattc ctcagaatca tacttaaaga aggtagacgc ttattggaga      60

```
gccacaaact acatttcagt cggtcaattg tatttgaagg gtaacccatt gttaagagaa    120
ccattaaagc ctgaacatgt taaaaatgct gttttggtc actggggtac tatagctggt      180
caaaacttca tctacgcaca tttgaataga gttatcaaca aatacgattt gtccatgttg    240
tacattagtg gtccaggtca cggtggtcaa gtcatggtat ctaactcata tttggatggt    300
tcctatagtg aagtttaccc tgaaattact caagacttgg aaggtttatc caagttgtac   360
aagcaatttt ctttctcagg tggtatcggt tctcatgcta caccacaagc acctggttca    420
attcacgaag gtggtgaatt aggttattct ttggttcatg gttttggtgc catcttagat    480
aatccagact tgattgctac cgttgtcgta ggtgacggtg aagccgaaac tggtccttta   540
gctacatctt ggcaattgaa taagtttata aacccagtta cagatggtgt tgtcttacct   600
atcttgtatt tgaatggttt caaaatctca aacccaacaa ttatggctaa gatgaccgat   660
gaagaattac aaaagtactt cgaaggtttg ggttgggacc caattttcgt cgagggtaat  720
gaacctgaag taatgcatca attgatggca gaaaagatgg atgaagccat agaaaagatt    780
ttgacaatca aaaagcacgc attggaagaa aatgatatgt ctagaccaaa gtggcctgtt   840
attttaaaca gaaccccaaa aggttggact ggtcctaagg aattggatgg taaaccaatt    900
gaaggttcct ttagagccca tcaagttcca ataccttccg atagtaagca catggaatgt    960
gctgatgact tgtcaaaatg gatgaatacc tatggtcctg aagaattatt cactgaagat  1020
ggtaaattgg ttgaagaaat cgcagaaatc atcccaaagg gtgacagaag aatgtcatgc   1080
aatcctgcca ctaacggtgg taaaataatg aagggtttga gattgccaga ttatagagaa   1140
tacgcaatcg acaataagga aaagggtaaa aacgttgccc aagatatgtt gatattgggt    1200
aaatacgtca gagatgtaat gaagttaaac gacaaggaaa gaaactttag agtcttctct   1260
ccagatgaag ctgcatcaaa cagattgtac gctatgttcg aagaaacaaa gagacaatgg  1320
gttggtgaaa ttgatgaacc atacgacgaa ttttttagcac ctgatggtag aattttagac  1380
tccatgttga gtgaacatat agctgaaggt gcattggaag cctatttgtt aacaggtaga   1440
catggtttta tccactctta cgaatcattc ttaagagtag ttgattcaat gatcacccaa   1500
catttcaagt ggttgaacca atgtgaagat attccatgga gagctgacat cccttccttg   1560
aatttgatta atacttctca tatctggcaa caagatcata acggttatac acaccaagac  1620
ccaggcatgt taggtcattt ggctgataaa aattctggtt taattcacga atacttgcct   1680
gttgatgcaa acacattgtt agtcaccttc gacaagtgca ttagatctat aaatcaagtt    1740
aacgtcatga cagcctcaaa acatccaaga caacaatggt tcaccatcga agaagctgaa   1800
tatttggtaa ataagggttt gggtatcgtt gattgggcat ctactgacaa aaacggtgaa   1860
acagatattg tatttgcaat ggccggtgac acccccaactt tagaaggttt ggccgctgtt   1920
caattgttac atgattattt gcctgacttg aagattagat tcgttaacat cgtcgatttg   1980
ttgaaattgc aatccccaga agtttacgaa catggtatca gtgatgaaga gtttaatatg   2040
atcttcacca aggacaaacc tatcatttttt ggtttccacg gttacgaaaa cttagtcgat   2100
actttgtttt tcaagagaga caaccataac gtatctgttc acggttacag agataaaggt   2160
gaaataacta caggttttga catgagagtc atgaacgaat tagatagatt caacttggta   2220
aaggacgcta tctataattt gccacaattg ggtaacaaag gtgcacatat catccaagaa   2280
atgaacgaaa agttggaaat ccatactaag ttcgttcacg aaaacggtat cgatttgcct   2340
gaaattgcta actggcaatg gaagggtttg aaataa                              2376
```

<210> SEQ ID NO 49
<211> LENGTH: 791
<212> TYPE: PRT
<213> ORGANISM: Clostridium_butyricum

<400> SEQUENCE: 49

```
Met Thr Asn Ile Asn Tyr Ser Ser Glu Ser Tyr Leu Lys Lys Val Asp
1               5                   10                  15

Ala Tyr Trp Arg Ala Thr Asn Tyr Ile Ser Val Gly Gln Leu Tyr Leu
            20                  25                  30

Lys Gly Asn Pro Leu Leu Arg Glu Pro Leu Lys Pro Glu His Val Lys
        35                  40                  45

Asn Ala Val Phe Gly His Trp Gly Thr Ile Ala Gly Gln Asn Phe Ile
    50                  55                  60

Tyr Ala His Leu Asn Arg Val Ile Asn Lys Tyr Asp Leu Ser Met Leu
65                  70                  75                  80

Tyr Ile Ser Gly Pro Gly His Gly Gly Gln Val Met Val Ser Asn Ser
                85                  90                  95

Tyr Leu Asp Gly Ser Tyr Ser Glu Val Tyr Pro Glu Ile Thr Gln Asp
            100                 105                 110

Leu Glu Gly Leu Ser Lys Leu Tyr Lys Gln Phe Ser Phe Ser Gly Gly
        115                 120                 125

Ile Gly Ser His Ala Thr Pro Gln Ala Pro Gly Ser Ile His Glu Gly
    130                 135                 140

Gly Glu Leu Gly Tyr Ser Leu Val His Gly Phe Gly Ala Ile Leu Asp
145                 150                 155                 160

Asn Pro Asp Leu Ile Ala Thr Val Val Val Gly Asp Gly Glu Ala Glu
                165                 170                 175

Thr Gly Pro Leu Ala Thr Ser Trp Gln Leu Asn Lys Phe Ile Asn Pro
            180                 185                 190

Val Thr Asp Gly Val Val Leu Pro Ile Leu Tyr Leu Asn Gly Phe Lys
        195                 200                 205

Ile Ser Asn Pro Thr Ile Met Ala Lys Met Thr Asp Glu Glu Leu Gln
    210                 215                 220

Lys Tyr Phe Glu Gly Leu Gly Trp Asp Pro Ile Phe Val Glu Gly Asn
225                 230                 235                 240

Glu Pro Glu Val Met His Gln Leu Met Ala Glu Lys Met Asp Glu Ala
                245                 250                 255

Ile Glu Lys Ile Leu Thr Ile Lys Lys His Ala Leu Glu Glu Asn Asp
            260                 265                 270

Met Ser Arg Pro Lys Trp Pro Val Ile Leu Asn Arg Thr Pro Lys Gly
        275                 280                 285

Trp Thr Gly Pro Lys Glu Leu Asp Gly Lys Pro Ile Glu Gly Ser Phe
    290                 295                 300

Arg Ala His Gln Val Pro Ile Pro Phe Asp Ser Lys His Met Glu Cys
305                 310                 315                 320

Ala Asp Asp Phe Val Lys Trp Met Asn Thr Tyr Gly Pro Glu Glu Leu
                325                 330                 335

Phe Thr Glu Asp Gly Lys Leu Val Glu Glu Ile Ala Glu Ile Ile Pro
            340                 345                 350

Lys Gly Asp Arg Arg Met Ser Cys Asn Pro Ala Thr Asn Gly Gly Lys
        355                 360                 365

Ile Met Lys Gly Leu Arg Leu Pro Asp Tyr Arg Glu Tyr Ala Ile Asp
    370                 375                 380
```

-continued

```
Asn Lys Glu Lys Gly Lys Asn Val Ala Gln Asp Met Leu Ile Leu Gly
385                 390                 395                 400

Lys Tyr Val Arg Asp Val Met Lys Leu Asn Asp Lys Glu Arg Asn Phe
            405                 410                 415

Arg Val Phe Ser Pro Asp Glu Ala Ala Ser Asn Arg Leu Tyr Ala Met
                420                 425                 430

Phe Glu Glu Thr Lys Arg Gln Trp Val Gly Glu Ile Asp Glu Pro Tyr
        435                 440                 445

Asp Glu Phe Leu Ala Pro Asp Gly Arg Ile Leu Asp Ser Met Leu Ser
    450                 455                 460

Glu His Ile Ala Glu Gly Ala Leu Glu Ala Tyr Leu Leu Thr Gly Arg
465                 470                 475                 480

His Gly Phe Ile His Ser Tyr Glu Ser Phe Leu Arg Val Val Asp Ser
                485                 490                 495

Met Ile Thr Gln His Phe Lys Trp Leu Asn Gln Cys Glu Asp Ile Pro
            500                 505                 510

Trp Arg Ala Asp Ile Pro Ser Leu Asn Leu Ile Asn Thr Ser His Ile
        515                 520                 525

Trp Gln Gln Asp His Asn Gly Tyr Thr His Gln Asp Pro Gly Met Leu
    530                 535                 540

Gly His Leu Ala Asp Lys Asn Ser Gly Leu Ile His Glu Tyr Leu Pro
545                 550                 555                 560

Val Asp Ala Asn Thr Leu Leu Val Thr Phe Asp Lys Cys Ile Arg Ser
                565                 570                 575

Ile Asn Gln Val Asn Val Met Thr Ala Ser Lys His Pro Arg Gln Gln
            580                 585                 590

Trp Phe Thr Ile Glu Glu Ala Glu Tyr Leu Val Asn Lys Gly Leu Gly
        595                 600                 605

Ile Val Asp Trp Ala Ser Thr Asp Lys Asn Gly Glu Thr Asp Ile Val
    610                 615                 620

Phe Ala Met Ala Gly Asp Thr Pro Thr Leu Glu Gly Leu Ala Ala Val
625                 630                 635                 640

Gln Leu Leu His Asp Tyr Leu Pro Asp Leu Lys Ile Arg Phe Val Asn
                645                 650                 655

Ile Val Asp Leu Leu Lys Leu Gln Ser Pro Glu Val Tyr Glu His Gly
            660                 665                 670

Ile Ser Asp Glu Glu Phe Asn Met Ile Phe Thr Lys Asp Lys Pro Ile
        675                 680                 685

Ile Phe Gly Phe His Gly Tyr Glu Asn Leu Val Asp Thr Leu Phe Phe
    690                 695                 700

Lys Arg Asp Asn His Asn Val Ser Val His Gly Tyr Arg Asp Lys Gly
705                 710                 715                 720

Glu Ile Thr Thr Gly Phe Asp Met Arg Val Met Asn Glu Leu Asp Arg
                725                 730                 735

Phe Asn Leu Val Lys Asp Ala Ile Tyr Asn Leu Pro Gln Leu Gly Asn
            740                 745                 750

Lys Gly Ala His Ile Ile Gln Glu Met Asn Gly Lys Leu Glu Ile His
        755                 760                 765

Thr Lys Phe Val His Glu Asn Gly Ile Asp Leu Pro Glu Ile Ala Asn
    770                 775                 780

Trp Gln Trp Lys Gly Leu Lys
785                 790
```

<210> SEQ ID NO 50
<211> LENGTH: 2505
<212> TYPE: DNA
<213> ORGANISM: Cryptococcus_neoformans

<400> SEQUENCE: 50

| | | | | | |
|---|---|---|---|---|---|
| atggcagaag | aaacctcatc | attaacatca | ttcggtcaag | caagatccac | tgtcaaagac | 60 |
| caaccattaa | ctgtagaaga | attaaaaaaa | attgatgcct | atatgagagc | ttctttgtac | 120 |
| ttatgtttgg | gcatgttgta | tttgagacaa | aacccattgt | tgaaggaacc | tttgaagaaa | 180 |
| gaacatttga | aggccagatt | gttaggtcac | tggggttccg | atgctggtca | aatctttact | 240 |
| tacatccata | tgaacagatt | gattaagaaa | tacgatttgg | acgctttgtt | cgttagtggt | 300 |
| ccaggtcacg | gtgcacctgc | cgtcttatcc | caaagttatt | ggaaggtgt | atataccgaa | 360 |
| gtttacccaa | atattactga | agatgtcgag | ggtatgagaa | gattttttcaa | gcaattttcc | 420 |
| ttccctggtg | gtgttggtag | tcatgcaaca | ccagaaaccc | ctggttcttt | acacgaaggt | 480 |
| ggtgaattgg | gttactctat | tcacatgct | tttggtacga | tcttcgataa | cccaaactta | 540 |
| atcactttga | caatggttgg | tgacggtgaa | tcagaaaccg | gtcctttagc | tgcatcctgg | 600 |
| catagtacaa | agttcttgaa | cccaatcacc | gatggtgctg | tattgcctgt | tttgcatttg | 660 |
| aatggttaca | agatcaataa | cccaacagtt | ttagctagaa | tatcccacga | agaaatcgaa | 720 |
| gcattgttta | ttggttatgg | ttggaaacct | tacttcgttg | aaggttctga | tttgacctca | 780 |
| atgcatcaag | caatggccgc | tactttagaa | aaggccgttt | tggaaattaa | agcataccaa | 840 |
| aagcaagcca | gagattctgg | taaagccttt | agaccaagat | ggcctatgat | tatattaaga | 900 |
| tctccaaagg | gttggactgc | acctagaaac | gtttcaggtc | atcacttgga | aggttattgg | 960 |
| agagcccatc | aaattccatt | agccgatgtt | gcttccaata | gtgaacactt | gaaattgtta | 1020 |
| gaagactgga | tgagatctta | caagccagaa | gaattattca | cagaagatgg | taaattgata | 1080 |
| cctgaattaa | aggcattgcc | acctgcaggt | caagccagaa | tgtctgccaa | tccagtctca | 1140 |
| aacggtggtt | tagtaagaaa | agcattaaac | ttgcctgatt | tcaaggacta | cgctattaag | 1200 |
| gatatagcac | caggtgttac | tttagccccct | tctatgtcaa | atatggcttt | gttcgtcaga | 1260 |
| gatgtaatta | aaaagaatca | aacaaacttc | agattattcg | gtccagacga | aaccgaatca | 1320 |
| aacaaattgg | cagccgttta | tgaagctggt | aaaaaggtct | ggatgggtga | atacttacca | 1380 |
| gaagataccg | acggtggtaa | tttggctcat | gcaggtagag | ttatggaaat | tttgtccgaa | 1440 |
| cacactgtcg | aaggttggtt | agaaggttat | gtattgtctg | gtagacatgg | tttgttaaac | 1500 |
| tcatacgaac | cttttattca | tatcatcgat | agtatggtta | ccaacactg | taagtggata | 1560 |
| gaaaagtgct | tagaagtcga | atggagagtt | aaagtctctt | cattgaacat | cttgttgacc | 1620 |
| gcaactgttt | ggagacaaga | tcataatggt | tttactcacc | aagatccagg | tttcttagac | 1680 |
| gttgtcgcta | taagtctcc | tgaagtagtt | agaatatatt | tgccacctga | tggtaattgt | 1740 |
| ttgttatccg | taatgaacca | ttgcttcgac | agtaaaaatt | acgttaacgt | cgtagttgct | 1800 |
| gataagcaag | accatttgca | atacttggat | atggaagctg | cagtagctca | ctgtacaaaa | 1860 |
| ggtttaggta | tttgggaatg | gcatgcgtt | ggtgacccaa | atgaaaaccc | tgacttagta | 1920 |
| atggcatgtt | gcggtgacgt | tccaactatg | gaatctttgg | ccgctacagc | tttgttgaag | 1980 |
| gaatatttgc | ctgaattgaa | gatcagattc | gttaacgtcg | ttgatttgtt | taaattgata | 2040 |
| tcacatgtcg | atcatccaca | cggtttgacc | gacagacaat | gggtatccta | cttcactgaa | 2100 |
| gacacaccaa | tcatctttaa | tttccatagt | taccccttggt | taatacacag | attgacatac | 2160 |

```
aagagaccag gttcacaaaa catccatgtt agaggttaca aggaaaaggg taacatagat    2220
actcctttag aattggcaat cagaaatgaa acagacagat actctttagc tatggatgca    2280
atagacagat tgccacattt gaaaaataag ggttcaatgg ctagagaaaa attgtacgat    2340
gcacaaatta aggccagaga ctgggctttt gaacacggta tagatccaga agacgttaga    2400
aaatggaagt ggccatacgg tcctaaaact gaaggtattg cctctaagtt gggtttcggt    2460
ggtgaaaata agcaacaagt tgcttccgtc ggtacaagtg aataa                    2505
```

<210> SEQ ID NO 51
<211> LENGTH: 834
<212> TYPE: PRT
<213> ORGANISM: Cryptococcus_neoformans

<400> SEQUENCE: 51

```
Met Ala Glu Glu Thr Ser Ser Leu Thr Ser Phe Gly Gln Ala Arg Ser
1               5                   10                  15

Thr Val Lys Asp Gln Pro Leu Thr Val Glu Glu Leu Lys Lys Ile Asp
            20                  25                  30

Ala Tyr Met Arg Ala Ser Leu Tyr Leu Cys Leu Gly Met Leu Tyr Leu
        35                  40                  45

Arg Gln Asn Pro Leu Leu Lys Glu Pro Leu Lys Lys Glu His Leu Lys
    50                  55                  60

Ala Arg Leu Leu Gly His Trp Gly Ser Asp Ala Gly Gln Ile Phe Thr
65                  70                  75                  80

Tyr Ile His Met Asn Arg Leu Ile Lys Lys Tyr Asp Leu Asp Ala Leu
                85                  90                  95

Phe Val Ser Gly Pro Gly His Gly Ala Pro Ala Val Leu Ser Gln Ser
            100                 105                 110

Tyr Leu Glu Gly Val Tyr Thr Glu Val Tyr Pro Asn Ile Thr Glu Asp
        115                 120                 125

Val Glu Gly Met Arg Arg Phe Phe Lys Gln Phe Ser Phe Pro Gly Gly
    130                 135                 140

Val Gly Ser His Ala Thr Pro Glu Thr Pro Gly Ser Leu His Glu Gly
145                 150                 155                 160

Gly Glu Leu Gly Tyr Ser Ile Ser His Ala Phe Gly Thr Val Phe Asp
                165                 170                 175

Asn Pro Asn Leu Ile Thr Leu Thr Met Val Gly Asp Gly Glu Ser Glu
            180                 185                 190

Thr Gly Pro Leu Ala Ala Ser Trp His Ser Thr Lys Phe Leu Asn Pro
        195                 200                 205

Ile Thr Asp Gly Ala Val Leu Pro Val Leu His Leu Asn Gly Tyr Lys
    210                 215                 220

Ile Asn Asn Pro Thr Val Leu Ala Arg Ile Ser His Glu Glu Ile Glu
225                 230                 235                 240

Ala Leu Phe Ile Gly Tyr Gly Trp Lys Pro Tyr Phe Val Glu Gly Ser
                245                 250                 255

Asp Leu Thr Ser Met His Gln Ala Met Ala Ala Thr Leu Glu Lys Ala
            260                 265                 270

Val Leu Glu Ile Lys Ala Tyr Gln Lys Gln Ala Arg Asp Ser Gly Lys
        275                 280                 285

Ala Phe Arg Pro Arg Trp Pro Met Ile Ile Leu Arg Ser Pro Lys Gly
    290                 295                 300

Trp Thr Ala Pro Arg Asn Val Ser Gly His His Leu Glu Gly Tyr Trp
```

```
            305                 310                 315                 320
Arg Ala His Gln Ile Pro Leu Ala Asp Val Ala Ser Asn Ser Glu His
                325                 330                 335
Leu Lys Leu Leu Glu Asp Trp Met Arg Ser Tyr Lys Pro Glu Glu Leu
                340                 345                 350
Phe Thr Glu Asp Gly Lys Leu Ile Pro Glu Leu Lys Ala Leu Pro Pro
                355                 360                 365
Ala Gly Gln Ala Arg Met Ser Ala Asn Pro Val Ser Asn Gly Gly Leu
                370                 375                 380
Val Arg Lys Ala Leu Asn Leu Pro Asp Phe Lys Asp Tyr Ala Ile Lys
385                 390                 395                 400
Asp Ile Ala Pro Gly Val Thr Leu Ala Pro Ser Met Ser Asn Met Ala
                405                 410                 415
Leu Phe Val Arg Asp Val Ile Lys Lys Asn Gln Thr Asn Phe Arg Leu
                420                 425                 430
Phe Gly Pro Asp Glu Thr Glu Ser Asn Lys Leu Ala Ala Val Tyr Glu
                435                 440                 445
Ala Gly Lys Lys Val Trp Met Gly Glu Tyr Leu Pro Glu Asp Thr Asp
                450                 455                 460
Gly Gly Asn Leu Ala His Ala Gly Arg Val Met Glu Ile Leu Ser Glu
465                 470                 475                 480
His Thr Val Glu Gly Trp Leu Glu Gly Tyr Val Leu Ser Gly Arg His
                485                 490                 495
Gly Leu Leu Asn Ser Tyr Glu Pro Phe Ile His Ile Ile Asp Ser Met
                500                 505                 510
Val Asn Gln His Cys Lys Trp Ile Glu Lys Cys Leu Glu Val Glu Trp
                515                 520                 525
Arg Val Lys Val Ser Ser Leu Asn Ile Leu Leu Thr Ala Thr Val Trp
                530                 535                 540
Arg Gln Asp His Asn Gly Phe Thr His Gln Asp Pro Gly Phe Leu Asp
545                 550                 555                 560
Val Val Ala Asn Lys Ser Pro Glu Val Val Arg Ile Tyr Leu Pro Pro
                565                 570                 575
Asp Gly Asn Cys Leu Leu Ser Val Met Asn His Cys Phe Asp Ser Lys
                580                 585                 590
Asn Tyr Val Asn Val Val Ala Asp Lys Gln Asp His Leu Gln Tyr
                595                 600                 605
Leu Asp Met Glu Ala Ala Val Ala His Cys Thr Lys Gly Leu Gly Ile
                610                 615                 620
Trp Glu Trp Ala Cys Val Gly Asp Pro Asn Glu Asn Pro Asp Leu Val
625                 630                 635                 640
Met Ala Cys Cys Gly Asp Val Pro Thr Met Glu Ser Leu Ala Ala Thr
                645                 650                 655
Ala Leu Leu Lys Glu Tyr Leu Pro Glu Leu Lys Ile Arg Phe Val Asn
                660                 665                 670
Val Val Asp Leu Phe Lys Leu Ile Ser His Val Asp His Pro His Gly
                675                 680                 685
Leu Thr Asp Arg Gln Trp Val Ser Tyr Phe Thr Glu Asp Thr Pro Ile
                690                 695                 700
Ile Phe Asn Phe His Ser Tyr Pro Trp Leu Ile His Arg Leu Thr Tyr
705                 710                 715                 720
Lys Arg Pro Gly Ser Gln Asn Ile His Val Arg Gly Tyr Lys Glu Lys
                725                 730                 735
```

```
Gly Asn Ile Asp Thr Pro Leu Glu Leu Ala Ile Arg Asn Glu Thr Asp
                740                 745                 750

Arg Tyr Ser Leu Ala Met Asp Ala Ile Asp Arg Leu Pro His Leu Lys
        755                 760                 765

Asn Lys Gly Ser Met Ala Arg Glu Lys Leu Tyr Asp Ala Gln Ile Lys
    770                 775                 780

Ala Arg Asp Trp Ala Phe Glu His Gly Ile Asp Pro Glu Asp Val Arg
785                 790                 795                 800

Lys Trp Lys Trp Pro Tyr Gly Pro Lys Thr Glu Gly Ile Ala Ser Lys
                805                 810                 815

Leu Gly Phe Gly Gly Glu Asn Lys Gln Gln Val Ala Ser Val Gly Thr
            820                 825                 830

Ser Glu

<210> SEQ ID NO 52
<211> LENGTH: 2409
<212> TYPE: DNA
<213> ORGANISM: Cyanothece

<400> SEQUENCE: 52
```

| | | | | | |
|---|---|---|---|---|---|
| atggttgcca | cacctgaaag | acctacatta | gaacaaaccc | cattatccgc | agaagaatta | 60 |
| agacaaatac | aagcatactg | gagagcatgt | aactatttgg | ctgttggtat | gatatatttg | 120 |
| agagataacc | cattgttgaa | agacccttg | actgaagatc | atgttaagaa | tagattgttg | 180 |
| ggtcactggg | gttcttcacc | aggtttgtct | tttatatata | tccatttgaa | cagattaatt | 240 |
| aaaaagtatg | gtttagatgt | tatatacatg | gccggtccag | gtcacggtgc | tcctggtatt | 300 |
| ttgggtccag | tctacttaga | aggtacttat | tccgaaacat | accctgacaa | aagtgaagat | 360 |
| gaagagggta | tgaaaaagtt | tttcaagcaa | ttttctttcc | caggtggtat | tggttcacat | 420 |
| tgtaccccag | aaactcctgg | ttctatacac | gaaggtggtg | aattgggtta | ttccttaagt | 480 |
| catgcttacg | gtgctgcatt | ggacaatcct | gatttgattg | ttgccgctgt | tgtcggtgac | 540 |
| ggtgaagcag | aaacaggtcc | attggccacc | gcttggcatt | ctaataagtt | tattaaccct | 600 |
| attagagatg | gtgctgtttt | gccaatcttg | catttgaatg | gttataagat | tgcaaaccca | 660 |
| actatcttag | ccagaatttc | ccacgaagaa | ttggaatatt | tgtttaaagg | ttacggttac | 720 |
| aagccttact | tgttgaagg | tagtgatcca | gaagtcatgc | atcaaaagat | ggcagccaca | 780 |
| ttagaaaccg | caatagccga | aatcaagcac | attaacaag | aagctagaac | atcaggtgtc | 840 |
| gcaaaaagac | aatatggcc | tatgatcgta | ttgagatctc | ctaagggttg | gactggtcca | 900 |
| gcttcagttg | acggtaaaaa | gacagaagat | ttctggagat | ctcatcaagt | ccctttatca | 960 |
| ggcatgcatg | taatccagc | acacattaaa | gtattggaag | actggttaaa | gtcctatacc | 1020 |
| cctgaagaat | tgttcgatga | aaacggtact | ttaattcctg | aattgaagga | attagctcca | 1080 |
| actggtcatc | acagaatgtc | agcaaatcca | catgccaacg | tggtttgtt | aagaaaagac | 1140 |
| ttgaagatgc | ctgatttcag | aaattacggt | gtagaagttg | ctaaaccagg | tactgtcgaa | 1200 |
| gttggtaaca | cagcattgtt | gggtaacttt | ttaagagatg | ttatggccaa | caacatgaca | 1260 |
| aacttcagag | tcttcggtcc | tgatgaaacc | gcctctaata | gattgaacgc | tatctatgaa | 1320 |
| atctctaaga | aagtttggat | gggtgaaata | ttaccagaag | atgcagacgg | tactgaaatc | 1380 |
| actacagatg | gtagagttat | ggaaatgtta | tcagaacata | cattgcaagg | ttggttagaa | 1440 |
| ggttatttgt | taacaggtag | acatggtttc | tttcacacct | acgaagcatt | tgcacatgta | 1500 |

```
gttgactcta tgtttaatca acacgctaaa tggttggata tttgtaagaa cgaagtccca    1560
tggagagcat cagtatccag tttaaacatc ttgttatctt caacagtttg gagacaagat    1620
cataacggtt tctcccacca agacccaggt tatgttgatt tggtcaccaa taagagtgct    1680
gacgtcgtaa gagtctactt tccacctgat gcaaattgtt tgttatccgt agccaaccat    1740
tgcttgaaaa gtacagacta cgttaacgtc atcgtatctg ataagcaaat ccatttgcaa    1800
tacttaaaca tggaccaagc cattaaacac tgcaccaagg gtattggtat atgggattgg    1860
gcttctaatg atgactgtgg tactgaacca gaccatcctg atgtaataat ggcatcatgc    1920
ggtgacgttg ctaccaaaga agcattggct gcaactgcca tattaagaga gaatttcct    1980 gacttgaaag ttagattcat caacgttgtc gatttgttta agttacaatc cgaaatagaa    2040
catccacacg gtttgagtga tagagacttc gataatttgt ttactaagga taagcctatc    2100
attttcaatt tccatggtta cccatggttg attcacaaat taacctacag aagaactaac    2160
catcacaact acatgttag aggttacaag gaaaagggta acatcaacac acctttggaa    2220
ttagctatta ataaccaaat cgacagattc aatttggtta ttgatgttat aaacagagta    2280
ccaaaattag gttctgccgc tgcatacgtt tacgaaagaa tgaagaacgc aatcatagaa    2340
catagagcct atgcttacga acacggtatc gataagcctg aaattaataa ctggaagtgg    2400
ccacattaa                                                            2409
```

<210> SEQ ID NO 53
<211> LENGTH: 802
<212> TYPE: PRT
<213> ORGANISM: Cyanothece

<400> SEQUENCE: 53

```
Met Val Ala Thr Pro Glu Arg Pro Thr Leu Glu Gln Thr Pro Leu Ser
1               5                   10                  15

Ala Glu Glu Leu Arg Gln Ile Gln Ala Tyr Trp Arg Ala Cys Asn Tyr
            20                  25                  30

Leu Ala Val Gly Met Ile Tyr Leu Arg Asp Asn Pro Leu Leu Lys Asp
        35                  40                  45

Pro Leu Thr Glu Asp His Val Lys Asn Arg Leu Leu Gly His Trp Gly
    50                  55                  60

Ser Ser Pro Gly Leu Ser Phe Ile Tyr Ile His Leu Asn Arg Leu Ile
65                  70                  75                  80

Lys Lys Tyr Gly Leu Asp Val Ile Tyr Met Ala Gly Pro Gly His Gly
                85                  90                  95

Ala Pro Gly Ile Leu Gly Pro Val Tyr Leu Glu Gly Thr Tyr Ser Glu
            100                 105                 110

Thr Tyr Pro Asp Lys Ser Glu Asp Glu Glu Gly Met Lys Lys Phe Phe
        115                 120                 125

Lys Gln Phe Ser Phe Pro Gly Gly Ile Gly Ser His Cys Thr Pro Glu
    130                 135                 140

Thr Pro Gly Ser Ile His Glu Gly Gly Glu Leu Gly Tyr Ser Leu Ser
145                 150                 155                 160

His Ala Tyr Gly Ala Ala Leu Asp Asn Pro Asp Leu Ile Val Ala Ala
                165                 170                 175

Val Val Gly Asp Gly Glu Ala Glu Thr Gly Pro Leu Ala Thr Ala Trp
            180                 185                 190

His Ser Asn Lys Phe Ile Asn Pro Ile Arg Asp Gly Ala Val Leu Pro
        195                 200                 205
```

```
Ile Leu His Leu Asn Gly Tyr Lys Ile Ala Asn Pro Thr Ile Leu Ala
210                 215                 220

Arg Ile Ser His Glu Glu Leu Glu Tyr Leu Phe Lys Gly Tyr Gly Tyr
225                 230                 235                 240

Lys Pro Tyr Phe Val Glu Gly Ser Asp Pro Glu Val Met His Gln Lys
                245                 250                 255

Met Ala Ala Thr Leu Glu Thr Ala Ile Ala Glu Ile Lys His Ile Gln
            260                 265                 270

Gln Glu Ala Arg Thr Ser Gly Val Ala Lys Arg Pro Ile Trp Pro Met
        275                 280                 285

Ile Val Leu Arg Ser Pro Lys Gly Trp Thr Gly Pro Ala Ser Val Asp
290                 295                 300

Gly Lys Lys Thr Glu Asp Phe Trp Arg Ser His Gln Val Pro Leu Ser
305                 310                 315                 320

Gly Met His Gly Asn Pro Ala His Ile Lys Val Leu Glu Asp Trp Leu
                325                 330                 335

Lys Ser Tyr Thr Pro Glu Glu Leu Phe Asp Glu Asn Gly Thr Leu Ile
            340                 345                 350

Pro Glu Leu Lys Glu Leu Ala Pro Thr Gly His His Arg Met Ser Ala
        355                 360                 365

Asn Pro His Ala Asn Gly Gly Leu Leu Arg Lys Asp Leu Lys Met Pro
370                 375                 380

Asp Phe Arg Asn Tyr Gly Val Glu Val Ala Lys Pro Gly Thr Val Glu
385                 390                 395                 400

Val Gly Asn Thr Ala Leu Leu Gly Asn Phe Leu Arg Asp Val Met Ala
                405                 410                 415

Asn Asn Met Thr Asn Phe Arg Val Phe Gly Pro Asp Glu Thr Ala Ser
            420                 425                 430

Asn Arg Leu Asn Ala Ile Tyr Glu Ile Ser Lys Lys Val Trp Met Gly
        435                 440                 445

Glu Ile Leu Pro Glu Asp Ala Asp Gly Thr Glu Ile Thr Thr Asp Gly
450                 455                 460

Arg Val Met Glu Met Leu Ser Glu His Thr Leu Gln Gly Trp Leu Glu
465                 470                 475                 480

Gly Tyr Leu Leu Thr Gly Arg His Gly Phe Phe His Thr Tyr Glu Ala
                485                 490                 495

Phe Ala His Val Val Asp Ser Met Phe Asn Gln His Ala Lys Trp Leu
            500                 505                 510

Asp Ile Cys Lys Asn Glu Val Pro Trp Arg Ala Ser Val Ser Ser Leu
        515                 520                 525

Asn Ile Leu Leu Ser Ser Thr Val Trp Arg Gln Asp His Asn Gly Phe
530                 535                 540

Ser His Gln Asp Pro Gly Tyr Val Asp Leu Val Thr Asn Lys Ser Ala
545                 550                 555                 560

Asp Val Val Arg Val Tyr Phe Pro Pro Asp Ala Asn Cys Leu Leu Ser
                565                 570                 575

Val Ala Asn His Cys Leu Lys Ser Thr Asp Tyr Val Asn Val Ile Val
            580                 585                 590

Ser Asp Lys Gln Ile His Leu Gln Tyr Leu Asn Met Asp Gln Ala Ile
        595                 600                 605

Lys His Cys Thr Lys Gly Ile Gly Ile Trp Asp Trp Ala Ser Asn Asp
610                 615                 620

Asp Cys Gly Thr Glu Pro Asp His Pro Asp Val Ile Met Ala Ser Cys
```

```
                625                 630                 635                 640
        Gly Asp Val Ala Thr Lys Glu Ala Leu Ala Ala Thr Ala Ile Leu Arg
                            645                 650                 655
        Glu Glu Phe Pro Asp Leu Lys Val Arg Phe Ile Asn Val Val Asp Leu
                        660                 665                 670
        Phe Lys Leu Gln Ser Glu Ile Glu His Pro His Gly Leu Ser Asp Arg
                    675                 680                 685
        Asp Phe Asp Asn Leu Phe Thr Lys Asp Lys Pro Ile Ile Phe Asn Phe
                690                 695                 700
        His Gly Tyr Pro Trp Leu Ile His Lys Leu Thr Tyr Arg Arg Thr Asn
        705                 710                 715                 720
        His His Asn Leu His Val Arg Gly Tyr Lys Glu Lys Gly Asn Ile Asn
                            725                 730                 735
        Thr Pro Leu Glu Leu Ala Ile Asn Asn Gln Ile Asp Arg Phe Asn Leu
                        740                 745                 750
        Val Ile Asp Val Ile Asn Arg Val Pro Lys Leu Gly Ser Ala Ala Ala
                    755                 760                 765
        Tyr Val Tyr Glu Arg Met Lys Asn Ala Ile Ile Glu His Arg Ala Tyr
                770                 775                 780
        Ala Tyr Glu His Gly Ile Asp Lys Pro Glu Ile Asn Asn Trp Lys Trp
        785                 790                 795                 800
        Pro His

<210> SEQ ID NO 54
<211> LENGTH: 2367
<212> TYPE: DNA
<213> ORGANISM: Eremococcus_coleocola

<400> SEQUENCE: 54
atgactgtag actataactc aaaagaatac ttaacattgg tcgataaatg gtggagagca      60
gcaaactact tgtccgttgg tcaaatgttc ttgagagata acccattgtt gcaagaagaa     120
gttactgcag accatgtcaa attgaatcct atcggtcact ggggtacaat tggtggtcaa     180
aacttcttgt atgctcattt gaatagaatt ataaacaagt acaatgttaa catgttttac     240
attgaaggtc aggtcacggg tggtcaagtc atggtaacta ttcctacttt ggatggtagt     300
tatactgaaa gatacccaga gtttactcaa gacatcgctg gtatgaagaa attgtttaaa     360
acctttcctt tccctggtgg tattggttca catgctgcac cagaaactcc tggttccatg     420
cacgaaggtg tgaattggg ttatgcttta agtcatgcaa caggtgccat attggataac     480
ccagacgtta tcgccgctac agttgtcggt gacggtgaag cagaaaccgg tcctttggca     540
gccggttggt tttccaatgt attcataaac ccagttagtg atggtgctgt cttacctatc     600
ttgtacttaa atggtggtaa aattgctaac ccaaccatct tggcaagaaa gtcaaacgaa     660
gatttgacta gtactttga gggtatgggt tggaaacctt acatcgtcga aggtactgat     720
ccagaacaag tacatcctat tatggctaag gtattggatg aagttatcga agaaattcaa     780
gcaatacaag ccgaagctag aaagggtaaa gctgaagatg caaaaatgcc acattggcct     840
atgattttat atagaacccc aaaaggttgg actggtcctg aagaagttga aggtaaaact     900
attcaaggtt cttttagagc acatcaagtc ccaatacctg tatcaggtag aaacatggaa     960
gatatcgact tgttaatcaa ctggttgaag tcttacggtc agaagaatt attcacagaa    1020
aacggtgaat ggttgatga attaaaggaa tttgccccaa agggtgacca tagaatggct    1080
atgaatcctt tgactaatgg tggtaaccca aaacctttaa atatgccaaa ctggaaggat    1140
```

```
tatgctttgg aaataggtac acctggttct aaagatgcac aagacatgat cgaatttggt    1200
ggtttcgcca gagatatagt taaggaaaac ccagaaaact ttagaatttt cggtcctgat    1260
gaaacaaagt ctaacagatt gaacaaggtt ttcgaagtca ccaatagaca atggttagaa    1320
ccaatttcag aaaagttcga tgaaaacatg tctgcttcag gtagagttat agactctcaa    1380
ttgtcagaac atcaaaacca aggtttcttg gaagcatatg tcttaacagg tagacacggt    1440
ttctttgctt cttacgaatc tttctttaga acagttgatt ccatgataac ccaacatttc    1500
aagtggataa gaaaatctgc caagcactca tggagaaagc catatcaaag tttgaatttg    1560
atctccgcta gtacagtttt tcaacaagat cataacggtt acacccacca agacccaggt    1620
ttgttaactc atattggtga aaaacacggt gaatatatga gagcttactt acctgcagat    1680
accaattctt tgttagccgt tatggacaag gctttagat ccgaaaacgt cattaactac     1740
gtagttactt ctaagcatcc aagacctcaa tttttcacag ccgatgaagc tgaagaattg    1800
gtaaacgaag gtttgaaagt tatagattgg gcttctacag ttaaggataa cgaagaacca    1860
gacgtcgtaa tcgctgcagc cggtaccgaa cctaatttcg aagctatcgc tgcaatttca    1920
tatttggtaa aagcatttcc agaattaaag atcagattcg ttaacgttgt cgatttgttt    1980
agattgagat ctccagaaat cgaccctaga ggtttgtcag atgacgaatt tgatgcaatc    2040
ttcaccaaag acaagccagt tttctttgcc tttcattcct acgaaggcat gttgaaggat    2100
attttcttta ctagacataa ccacaactta tacgcacacg gttacagaga aaatggtgaa    2160
ataactacac ctttcgatat gagagtcttg aacgaattag acagatttca tttgtcagca    2220
cacgtagccg atgtagttta tggtgacaag gcaagagact acgtcgccga aatgaagggt    2280
aaagtacaag aacatagaga ttacgttgaa gaatacggtg ctgacatgcc agaagttgaa    2340
gattggaaat gggaagacat taagtaa                                         2367
```

<210> SEQ ID NO 55
<211> LENGTH: 788
<212> TYPE: PRT
<213> ORGANISM: Eremococcus_coleocola

<400> SEQUENCE: 55

```
Met Thr Val Asp Tyr Asn Ser Lys Glu Tyr Leu Thr Leu Val Asp Lys
1               5                   10                  15

Trp Trp Arg Ala Ala Asn Tyr Leu Ser Val Gly Gln Met Phe Leu Arg
            20                  25                  30

Asp Asn Pro Leu Leu Gln Glu Glu Val Thr Ala Asp His Val Lys Leu
        35                  40                  45

Asn Pro Ile Gly His Trp Gly Thr Ile Gly Gly Gln Asn Phe Leu Tyr
    50                  55                  60

Ala His Leu Asn Arg Ile Ile Asn Lys Tyr Asn Val Asn Met Phe Tyr
65                  70                  75                  80

Ile Glu Gly Pro Gly His Gly Gly Gln Val Met Val Thr Asn Ser Tyr
                85                  90                  95

Leu Asp Gly Ser Tyr Thr Glu Arg Tyr Pro Glu Phe Thr Gln Asp Ile
            100                 105                 110

Ala Gly Met Lys Lys Leu Phe Lys Thr Phe Ser Phe Pro Gly Gly Ile
        115                 120                 125

Gly Ser His Ala Ala Pro Glu Thr Pro Gly Ser Met His Glu Gly Gly
    130                 135                 140

Glu Leu Gly Tyr Ala Leu Ser His Ala Thr Gly Ala Ile Leu Asp Asn
```

-continued

```
        145                 150                 155                 160
Pro Asp Val Ile Ala Ala Thr Val Val Gly Asp Gly Glu Ala Glu Thr
                    165                 170                 175
Gly Pro Leu Ala Ala Gly Trp Phe Ser Asn Val Phe Ile Asn Pro Val
                    180                 185                 190
Ser Asp Gly Ala Val Leu Pro Ile Leu Tyr Leu Asn Gly Gly Lys Ile
                    195                 200                 205
Ala Asn Pro Thr Ile Leu Ala Arg Lys Ser Asn Glu Asp Leu Thr Lys
                    210                 215                 220
Tyr Phe Glu Gly Met Gly Trp Lys Pro Tyr Ile Val Glu Gly Thr Asp
225                 230                 235                 240
Pro Glu Gln Val His Pro Ile Met Ala Lys Val Leu Asp Glu Val Ile
                    245                 250                 255
Glu Glu Ile Gln Ala Ile Gln Ala Glu Ala Arg Lys Gly Lys Ala Glu
                    260                 265                 270
Asp Ala Lys Met Pro His Trp Pro Met Ile Leu Tyr Arg Thr Pro Lys
                    275                 280                 285
Gly Trp Thr Gly Pro Glu Glu Val Glu Gly Lys Thr Ile Gln Gly Ser
                    290                 295                 300
Phe Arg Ala His Gln Val Pro Ile Pro Val Ser Gly Arg Asn Met Glu
305                 310                 315                 320
Asp Ile Asp Leu Leu Ile Asn Trp Leu Lys Ser Tyr Gly Pro Glu Glu
                    325                 330                 335
Leu Phe Thr Glu Asn Gly Glu Leu Val Asp Glu Leu Lys Glu Phe Ala
                    340                 345                 350
Pro Lys Gly Asp His Arg Met Ala Met Asn Pro Leu Thr Asn Gly Gly
                    355                 360                 365
Asn Pro Lys Pro Leu Asn Met Pro Asn Trp Lys Asp Tyr Ala Leu Glu
                    370                 375                 380
Ile Gly Thr Pro Gly Ser Lys Asp Ala Gln Asp Met Ile Glu Phe Gly
385                 390                 395                 400
Gly Phe Ala Arg Asp Ile Val Lys Glu Asn Pro Glu Asn Phe Arg Ile
                    405                 410                 415
Phe Gly Pro Asp Glu Thr Lys Ser Asn Arg Leu Asn Lys Val Phe Glu
                    420                 425                 430
Val Thr Asn Arg Gln Trp Leu Glu Pro Ile Ser Glu Lys Phe Asp Glu
                    435                 440                 445
Asn Met Ser Ala Ser Gly Arg Val Ile Asp Ser Gln Leu Ser Glu His
450                 455                 460
Gln Asn Gln Gly Phe Leu Glu Ala Tyr Val Leu Thr Gly Arg His Gly
465                 470                 475                 480
Phe Phe Ala Ser Tyr Glu Ser Phe Phe Arg Thr Val Asp Ser Met Ile
                    485                 490                 495
Thr Gln His Phe Lys Trp Ile Arg Lys Ser Ala Lys His Ser Trp Arg
                    500                 505                 510
Lys Pro Tyr Gln Ser Leu Asn Leu Ile Ser Ala Ser Thr Val Phe Gln
                    515                 520                 525
Gln Asp His Asn Gly Tyr Thr His Gln Asp Pro Gly Leu Leu Thr His
                    530                 535                 540
Ile Gly Glu Lys His Gly Glu Tyr Met Arg Ala Tyr Leu Pro Ala Asp
545                 550                 555                 560
Thr Asn Ser Leu Leu Ala Val Met Asp Lys Ala Phe Arg Ser Glu Asn
                    565                 570                 575
```

```
Val Ile Asn Tyr Val Val Thr Ser Lys His Pro Arg Pro Gln Phe Phe
            580                 585                 590

Thr Ala Asp Glu Ala Glu Leu Val Asn Glu Gly Leu Lys Val Ile
    595                 600                 605

Asp Trp Ala Ser Thr Val Lys Asp Asn Glu Glu Pro Asp Val Val Ile
610                 615                 620

Ala Ala Ala Gly Thr Glu Pro Asn Phe Glu Ala Ile Ala Ala Ile Ser
625                 630                 635                 640

Tyr Leu Val Lys Ala Phe Pro Glu Leu Lys Ile Arg Phe Val Asn Val
            645                 650                 655

Val Asp Leu Phe Arg Leu Arg Ser Pro Glu Ile Asp Pro Arg Gly Leu
            660                 665                 670

Ser Asp Asp Glu Phe Asp Ala Ile Phe Thr Lys Asp Lys Pro Val Phe
            675                 680                 685

Phe Ala Phe His Ser Tyr Glu Gly Met Leu Lys Asp Ile Phe Phe Thr
            690                 695                 700

Arg His Asn His Asn Leu Tyr Ala His Gly Tyr Arg Glu Asn Gly Glu
705                 710                 715                 720

Ile Thr Thr Pro Phe Asp Met Arg Val Leu Asn Glu Leu Asp Arg Phe
                725                 730                 735

His Leu Ser Ala His Val Ala Asp Val Val Tyr Gly Asp Lys Ala Arg
            740                 745                 750

Asp Tyr Val Ala Glu Met Lys Gly Lys Val Gln Glu His Arg Asp Tyr
            755                 760                 765

Val Glu Glu Tyr Gly Ala Asp Met Pro Glu Val Glu Asp Trp Lys Trp
770                 775                 780

Glu Asp Ile Lys
785

<210> SEQ ID NO 56
<211> LENGTH: 2479
<212> TYPE: DNA
<213> ORGANISM: Gardnerella_vaginalis

<400> SEQUENCE: 56
atgacctccc ctgtaatcgg taccccatgg aaaaagttaa atgccccagt atcagaagca      60
gccatagaag gtgtagacaa gtattggaga gttgctaact atttgtccat tggtcaaata     120
tacttgagaa gtaatccatt aatgaaggaa ccttttacaa gagaagatgt caagcataga     180
ttagtaggtc actggggtac tacaccaggt ttgaacttct taatcggtca tatcaacaga     240
ttcattgcag aacaccaaca aaacaccgtt attatcatgg gtccaggtca tggtggtcct     300
gccggtactg ctcaatccta tttggatggt acctacactg aatattaccc aaaaattacc     360
aaggacgaag ctggtttgca aaagtttttc agacaattct cttatccagg tggtatacct     420
tcacattttg ctccagaaac tcctggttca atccacgaag tggtgaatt gggttatgca     480 ttatctcatg catacggtgc cgttatgaat aacccatcat tgtttgttcc tgcaattgtc     540
ggtgacggtg aagccgaaac cggtccattg gctactggtt ggcaatcaaa caagttagtc     600
aatccaagaa ctgatggtat cgtattgcct atattgcatt tgaatggtta caagattgct     660
aatccaacaa tattgtccag aatcagtgat gaagaattac atgaattttt ccacggtatg     720
ggttatgaac cttacgaatt tgttgcaggt tcgatgacg aagaccatat gtctatacac     780
agaagatttg ccgatatgtt cgaaactatc ttcgacgaaa tctgtgatat caaagccgaa     840
```

```
gctcaaacca atgatgttac tagaccattc taccctatga tcatttttag aacaccaaag    900
ggttggacct gccctaagtt cattgatggt aaaaagacag aaggttcctg agagcccat    960 caagttccat tggcaagtgc cagagatacc gaagctcact ttgaagtctt gaagaactgg  1020
ttgaagtctt acaagcctga agaattattc aatgaagacg gttccattaa agaagatgtt  1080
ttgagtttta tgccacaggg tgaattaaga attggtcaaa atcctaacgc taatggtggt  1140
agaataagag aagatttgaa attgccaaat ttggatgact acgaagtaaa ggaagttaag  1200
gaatttggtc atggttgggg tcaattggaa gccactagaa gattaggtgt ttacacaaga  1260
gacgtcatca agaataaccc agattccttt agaattttcg gtcctgatga aactgctagt  1320
aacagattgc aagctgcata cgaagtaaca aataagcaat gggacgctgg ttacttgtcc  1380
gaattagttg atgaacatat ggcagtaaca ggtcaagtta ccgaacaatt gagtgaacac  1440
caaatggaag gtttcttaga agcatatttg ttaacaggta gacatggtat ctggtcttca  1500
tacgaatctt ttgtccatgt aatcgattca atgttgaatc aacacgcaaa gtggttagaa  1560
gccactgtta gagaaattcc atggagaaaa cctatatcca gtatgaactt gttagtctct  1620
tcacatgtat ggagacaaga ccataatggt ttctctcacc aagatccagg tgtcacctca  1680
gtattgttga acaaaacttt caataacgac catgtaatcg gtatctattt ccctgttgat  1740
tctaacatgt tgttagctgt tggtgaaaag gtctacaagt caacaaacat gatcaacgct  1800
atcttcgcag gtaaacaacc agccgctact tggttgacat tagatgaagc aagagaagaa  1860
ttggaaaaag gtgcagccga atggaagtgg gcctctaatg ctaaaaataa cgacgaagta  1920
caagttgtct tggctggtat tggtgacgtt cctcaacaag aattaatggc tgcagccgac  1980
aaattgaaca gttaggtgt taagtttaaa gtagttaaca tcgtcgattt gttgaaattg  2040
caatctgcaa aggaaaataa cgaagccttg actgacgaag agtttactga attgtttact  2100
gctgataagc cagtcttgtt agcttatcat tcttacgcac acgatgtaag aggtttaatt  2160
ttcgacagac caaaccatga taacttcaac gttcacggtt acaaggaaca aggttcaacc  2220
actacacctt acgatatggt tagagtcaat gatatggaca gatatgaatt gacagctgaa  2280
gcattaagaa tggtcgatgc tgacaagtac gcagacgaaa ttaaaaagtt ggaagatttc  2340
agattagaag cctttcaatt cgctgttgat aaaggttatg atcatccaga ctacacagac  2400
tgggtatggc caggtgttaa aaccgataag cctggtgcag ttacagccac cgctgcaact  2460
gctggtgaca atgaataat                                               2479
```

<210> SEQ ID NO 57
<211> LENGTH: 825
<212> TYPE: PRT
<213> ORGANISM: Gardnerella_vaginalis

<400> SEQUENCE: 57

Met Thr Ser Pro Val Ile Gly Thr Pro Trp Lys Lys Leu Asn Ala Pro
1               5                   10                  15

Val Ser Glu Ala Ala Ile Glu Gly Val Asp Lys Tyr Trp Arg Val Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80

```
Phe Ile Ala Glu His Gln Gln Asn Thr Val Ile Met Gly Pro Gly
                 85                  90                  95
His Gly Gly Pro Ala Gly Thr Ala Gln Ser Tyr Leu Asp Gly Thr Tyr
            100                 105                 110
Thr Glu Tyr Tyr Pro Lys Ile Thr Lys Asp Glu Ala Gly Leu Gln Lys
        115                 120                 125
Phe Phe Arg Gln Phe Ser Tyr Pro Gly Gly Ile Pro Ser His Phe Ala
130                 135                 140
Pro Glu Thr Pro Gly Ser Ile His Glu Gly Gly Glu Leu Gly Tyr Ala
145                 150                 155                 160
Leu Ser His Ala Tyr Gly Ala Val Met Asn Asn Pro Ser Leu Phe Val
                165                 170                 175
Pro Ala Ile Val Gly Asp Gly Glu Ala Glu Thr Gly Pro Leu Ala Thr
            180                 185                 190
Gly Trp Gln Ser Asn Lys Leu Val Asn Pro Arg Thr Asp Gly Ile Val
        195                 200                 205
Leu Pro Ile Leu His Leu Asn Gly Tyr Lys Ile Ala Asn Pro Thr Ile
    210                 215                 220
Leu Ser Arg Ile Ser Asp Glu Glu Leu His Glu Phe His Gly Met
225                 230                 235                 240
Gly Tyr Glu Pro Tyr Glu Phe Val Ala Gly Phe Asp Asp Glu His
                245                 250                 255
Met Ser Ile His Arg Arg Phe Ala Asp Met Phe Glu Thr Ile Phe Asp
            260                 265                 270
Glu Ile Cys Asp Ile Lys Ala Glu Ala Gln Thr Asn Asp Val Thr Arg
        275                 280                 285
Pro Phe Tyr Pro Met Ile Ile Phe Arg Thr Pro Lys Gly Trp Thr Cys
290                 295                 300
Pro Lys Phe Ile Asp Gly Lys Lys Thr Glu Gly Ser Trp Arg Ala His
305                 310                 315                 320
Gln Val Pro Leu Ala Ser Ala Arg Asp Thr Glu Ala His Phe Glu Val
                325                 330                 335
Leu Lys Asn Trp Leu Lys Ser Tyr Lys Pro Glu Glu Leu Phe Asn Glu
            340                 345                 350
Asp Gly Ser Ile Lys Glu Asp Val Leu Ser Phe Met Pro Gln Gly Glu
        355                 360                 365
Leu Arg Ile Gly Gln Asn Pro Asn Ala Asn Gly Gly Arg Ile Arg Glu
    370                 375                 380
Asp Leu Lys Leu Pro Asn Leu Asp Asp Tyr Glu Val Lys Glu Val Lys
385                 390                 395                 400
Glu Phe Gly His Gly Trp Gly Gln Leu Glu Ala Thr Arg Arg Leu Gly
                405                 410                 415
Val Tyr Thr Arg Asp Val Ile Lys Asn Asn Pro Asp Ser Phe Arg Ile
            420                 425                 430
Phe Gly Pro Asp Glu Thr Ala Ser Asn Arg Leu Gln Ala Ala Tyr Glu
        435                 440                 445
Val Thr Asn Lys Gln Trp Asp Ala Gly Tyr Leu Ser Glu Leu Val Asp
    450                 455                 460
Glu His Met Ala Val Thr Gly Gln Val Thr Glu Gln Leu Ser Glu His
465                 470                 475                 480
Gln Met Glu Gly Phe Leu Glu Ala Tyr Leu Leu Thr Gly Arg His Gly
                485                 490                 495
Ile Trp Ser Ser Tyr Glu Ser Phe Val His Val Ile Asp Ser Met Leu
```

```
                500             505             510
Asn Gln His Ala Lys Trp Leu Glu Ala Thr Val Arg Glu Ile Pro Trp
            515                 520             525
Arg Lys Pro Ile Ser Ser Met Asn Leu Leu Val Ser Ser His Val Trp
        530                 535             540
Arg Gln Asp His Asn Gly Phe Ser His Gln Asp Pro Gly Val Thr Ser
545             550                 555             560
Val Leu Leu Asn Lys Thr Phe Asn Asn Asp His Val Ile Gly Ile Tyr
            565                 570             575
Phe Pro Val Asp Ser Asn Met Leu Leu Ala Val Gly Glu Lys Val Tyr
        580                 585             590
Lys Ser Thr Asn Met Ile Asn Ala Ile Phe Ala Gly Lys Gln Pro Ala
            595                 600             605
Ala Thr Trp Leu Thr Leu Asp Glu Ala Arg Glu Leu Glu Lys Gly
        610                 615             620
Ala Ala Glu Trp Lys Trp Ala Ser Asn Ala Lys Asn Asn Asp Glu Val
625             630                 635             640
Gln Val Val Leu Ala Gly Ile Gly Asp Val Pro Gln Gln Glu Leu Met
            645                 650             655
Ala Ala Ala Asp Lys Leu Asn Lys Leu Gly Val Lys Phe Lys Val Val
            660                 665             670
Asn Ile Val Asp Leu Leu Lys Leu Gln Ser Ala Lys Glu Asn Asn Glu
        675                 680             685
Ala Leu Thr Asp Glu Glu Phe Thr Glu Leu Phe Thr Ala Asp Lys Pro
        690                 695             700
Val Leu Leu Ala Tyr His Ser Tyr Ala His Asp Val Arg Gly Leu Ile
705             710                 715             720
Phe Asp Arg Pro Asn His Asp Asn Phe Asn Val His Gly Tyr Lys Glu
            725                 730             735
Gln Gly Ser Thr Thr Thr Pro Tyr Asp Met Val Arg Val Asn Asp Met
            740                 745             750
Asp Arg Tyr Glu Leu Thr Ala Glu Ala Leu Arg Met Val Asp Ala Asp
        755                 760             765
Lys Tyr Ala Asp Glu Ile Lys Lys Leu Glu Asp Phe Arg Leu Glu Ala
        770                 775             780
Phe Gln Phe Ala Val Asp Lys Gly Tyr Asp His Pro Asp Tyr Thr Asp
785             790                 795             800
Trp Val Trp Pro Gly Val Lys Thr Asp Lys Pro Gly Ala Val Thr Ala
            805                 810             815
Thr Ala Ala Thr Ala Gly Asp Asn Glu
            820                 825

<210> SEQ ID NO 58
<211> LENGTH: 2517
<212> TYPE: DNA
<213> ORGANISM: Glaciibacter_superstes

<400> SEQUENCE: 58
atgacagact ccgctacagc cccagttcct gacagaagag ccaccgcttt cgcacataga    60
gacccagcag aattagacga tggtacattg gctgcattag atgcctggtg gagaactgct   120
aactatttgt ctgttggtca aatatacttg ttggataacc cattgttaag acaacctttg   180
gaaagagaac aattaaagcc aagattgtta ggtcattggg gtactacacc tggttttgaat  240 ttcttgtacg ctcacttgaa cagagttatc agagaaagag atttgtctac tatcttcatt   300
```

```
accggtccag gtcatggtgg tcctggtatg gtcgcaaatg cctatttgga tggtacttat    360
tccgaattat acccacacgt agcaagaagt gaagacggta ttagagaatt gtttagacaa    420
ttttcattcc caggtggtat tccttctcat gcttcaccag aaacacctgg ttccatacac    480
gaaggtggtg aattgggtta tgccttaagt catgcttacg gtgccgcttt tgataatcca    540
ggtttgttag ttgcagccgt tgtcggtgac ggtgaagccg aaactggtcc tttagctaca    600
tcctggcata gtaacaagtt cttagatcca ttagctgacg tgtagttttt gcctatcttg    660
cacttaaatg gttacaaaat cgcaaaccca acagttttgg ctagaatacc agaacatgaa    720
ttgttatcct tgatgagagg ttatggtcac accccatact tagttagtgg tggttttgat    780
ggtgaagacc ctgctgcagt acatagaaga ttcgctaaga ccttggatac tgttttgaac    840
caaatcgcag aaatcaaagc tcagccgct gcaggtacat ggaaggtag accagcatgg    900
cctatgatta tattaagaac cccaaaaggt tggacttgtc ctgaagaaat tgatggtttg    960
ccagctgaaa actcttggag atcacatcaa gtaccattag cttctgcaag atatactcct   1020
gaacacttgg gtgttttaga cggttggttg agatcataca gaccagaaga attatttgat   1080
gccgctggtg caccaatgcc tgttgccaca gctttggcac cagatggtga attaagaatg   1140
tctgctaatc ctgtcgcaaa cggtggtatt ttgaagagag atttggtatt accagatttc   1200
agagactatg ctgttgacgt cccagtacct ggtgcaacag tcaatgaagc caccagagta   1260
ttgggtcaat ggttagctga tgttattaga gcaaacccag acacttttag aatattcggt   1320
cctgatgaaa ccgcttccaa tagattgggt gcagttttag aagtcactga taaacaatgg   1380
aacgctgaat acttgccaac agacgaacat ttggctagaa gaggtagagt tattgaaatg   1440
ttgagtgaac accaatgcca aggttggtta aaggttatt tgttaaccgg tagacatggt   1500
ttgtttaata cttacgaagc attcgtacat atcgttggtt ctatgttcaa ccaacacgct   1560
aaatggttga aggtttcaaa agaaatccca tggagaagac ctattgcatc cttaaactac   1620
ttgttgactt ctcatgtttg gagacaagat cataacggtt tatctcacca agatccaggt   1680
tttattgacc acgtcgtaaa taagaaagct gatgttgtca gagtttatt gcctttcgac   1740
gccaacacct tgttgtctgc ttacgatcat tgtttgagat cagttgatta cgtaaacgta   1800
gttgtcgcag gtaaacaacc aacttttaac tggttgtcca tggatagagc catcgctcat   1860
atgaccagag gtttaggtat tttcgaatgg gctggaactg aagttgaagg tgaagaacca   1920
gatgttgttt ggcttgtgc tggtgacgta cctacattgg aagttttagc agccgcttct   1980
attttgagac aagctatacc agatttgaag gttagagtcg taaacgttgt tgatttgatg   2040
agattagtct ctgaaggtga acatcctcac ggcatgtcag atagagaata tgacgccgtt   2100
tttactaaag atagaccagt catattcgct tatcatggtt acccttggtt gatccacaga   2160
ttaacatata gaagaaacgg tcatgctaac ttgcacgtta gaggttacaa agaagaaggt   2220
accactacaa ccccattcga tatggtcatg ttgaacgata tcgacagata ccatttggta   2280
gttgatgtcg tagacagagt tcctggttta ggtgaaagat atgctggttt gagacaaaga   2340
atgttagatg ccagagtaag agctagagca tatacaagag aacatggtga agatataccA   2400
gaagttgcag actggacttg gacagccggt cctgaaagac aagctagaga gtcaatacc   2460
ggtgttggtc aagtcaatac tggtgctgct gctactggtg gtgacaatga atcataa      2517
```

<210> SEQ ID NO 59
<211> LENGTH: 838
<212> TYPE: PRT

<213> ORGANISM: Glaciibacter_superstes

<400> SEQUENCE: 59

| | | | | | | | | | | | | | | |
|---|---|---|---|---|---|---|---|---|---|---|---|---|---|---|
| Met | Thr | Asp | Ser | Ala | Thr | Ala | Pro | Val | Pro | Asp | Arg | Arg | Ala | Thr | Ala |
| 1 | | | | 5 | | | | | 10 | | | | | 15 | |
| Phe | Ala | His | Arg | Asp | Pro | Ala | Glu | Leu | Asp | Asp | Gly | Thr | Leu | Ala | Ala |
| | | | 20 | | | | | 25 | | | | | 30 | | |
| Leu | Asp | Ala | Trp | Trp | Arg | Thr | Ala | Asn | Tyr | Leu | Ser | Val | Gly | Gln | Ile |
| | | 35 | | | | | 40 | | | | | 45 | | | |
| Tyr | Leu | Leu | Asp | Asn | Pro | Leu | Leu | Arg | Gln | Pro | Leu | Glu | Arg | Glu | Gln |
| | 50 | | | | | 55 | | | | | 60 | | | | |
| Leu | Lys | Pro | Arg | Leu | Leu | Gly | His | Trp | Gly | Thr | Thr | Pro | Gly | Leu | Asn |
| 65 | | | | | 70 | | | | | 75 | | | | | 80 |
| Phe | Leu | Tyr | Ala | His | Leu | Asn | Arg | Val | Ile | Arg | Glu | Arg | Asp | Leu | Ser |
| | | | | 85 | | | | | 90 | | | | | 95 | |
| Thr | Ile | Phe | Ile | Thr | Gly | Pro | Gly | His | Gly | Gly | Pro | Gly | Met | Val | Ala |
| | | | | 100 | | | | | 105 | | | | | 110 | |
| Asn | Ala | Tyr | Leu | Asp | Gly | Thr | Tyr | Ser | Glu | Leu | Tyr | Pro | His | Val | Ala |
| | | | 115 | | | | | 120 | | | | | 125 | | |
| Arg | Ser | Glu | Asp | Gly | Ile | Arg | Glu | Leu | Phe | Arg | Gln | Phe | Ser | Phe | Pro |
| | 130 | | | | | 135 | | | | | 140 | | | | |
| Gly | Gly | Ile | Pro | Ser | His | Ala | Ser | Pro | Glu | Thr | Pro | Gly | Ser | Ile | His |
| 145 | | | | | 150 | | | | | 155 | | | | | 160 |
| Glu | Gly | Gly | Glu | Leu | Gly | Tyr | Ala | Leu | Ser | His | Ala | Tyr | Gly | Ala | Ala |
| | | | | 165 | | | | | 170 | | | | | 175 | |
| Phe | Asp | Asn | Pro | Gly | Leu | Leu | Val | Ala | Ala | Val | Val | Gly | Asp | Gly | Glu |
| | | | 180 | | | | | 185 | | | | | 190 | | |
| Ala | Glu | Thr | Gly | Pro | Leu | Ala | Thr | Ser | Trp | His | Ser | Asn | Lys | Phe | Leu |
| | | 195 | | | | | 200 | | | | | 205 | | | |
| Asp | Pro | Leu | Ala | Asp | Gly | Val | Val | Leu | Pro | Ile | Leu | His | Leu | Asn | Gly |
| | 210 | | | | | 215 | | | | | 220 | | | | |
| Tyr | Lys | Ile | Ala | Asn | Pro | Thr | Val | Leu | Ala | Arg | Ile | Pro | Glu | His | Glu |
| 225 | | | | | 230 | | | | | 235 | | | | | 240 |
| Leu | Leu | Ser | Leu | Met | Arg | Gly | Tyr | Gly | His | Thr | Pro | Tyr | Leu | Val | Ser |
| | | | | 245 | | | | | 250 | | | | | 255 | |
| Gly | Gly | Phe | Asp | Gly | Glu | Asp | Pro | Ala | Ala | Val | His | Arg | Arg | Phe | Ala |
| | | | 260 | | | | | 265 | | | | | 270 | | |
| Lys | Thr | Leu | Asp | Thr | Val | Leu | Asn | Gln | Ile | Ala | Glu | Ile | Lys | Ala | Ser |
| | | 275 | | | | | 280 | | | | | 285 | | | |
| Ala | Ala | Ala | Gly | Thr | Leu | Glu | Gly | Arg | Pro | Ala | Trp | Pro | Met | Ile | Ile |
| | 290 | | | | | 295 | | | | | 300 | | | | |
| Leu | Arg | Thr | Pro | Lys | Gly | Trp | Thr | Cys | Pro | Glu | Glu | Ile | Asp | Gly | Leu |
| 305 | | | | | 310 | | | | | 315 | | | | | 320 |
| Pro | Ala | Glu | Asn | Ser | Trp | Arg | Ser | His | Gln | Val | Pro | Leu | Ala | Ser | Ala |
| | | | | 325 | | | | | 330 | | | | | 335 | |
| Arg | Asp | Thr | Pro | Glu | His | Leu | Gly | Val | Leu | Asp | Gly | Trp | Leu | Arg | Ser |
| | | | 340 | | | | | 345 | | | | | 350 | | |
| Tyr | Arg | Pro | Glu | Glu | Leu | Phe | Asp | Ala | Ala | Gly | Ala | Pro | Met | Pro | Val |
| | | 355 | | | | | 360 | | | | | 365 | | | |
| Ala | Thr | Ala | Leu | Ala | Pro | Asp | Gly | Glu | Leu | Arg | Met | Ser | Ala | Asn | Pro |
| | 370 | | | | | 375 | | | | | 380 | | | | |
| Val | Ala | Asn | Gly | Gly | Ile | Leu | Lys | Arg | Asp | Leu | Val | Leu | Pro | Asp | Phe |
| 385 | | | | | 390 | | | | | 395 | | | | | 400 |

```
Arg Asp Tyr Ala Val Asp Val Pro Val Pro Gly Ala Thr Val Asn Glu
            405                 410                 415

Ala Thr Arg Val Leu Gly Gln Trp Leu Ala Asp Val Ile Arg Ala Asn
        420                 425                 430

Pro Asp Thr Phe Arg Ile Phe Gly Pro Asp Glu Thr Ala Ser Asn Arg
        435                 440                 445

Leu Gly Ala Val Leu Glu Val Thr Asp Lys Gln Trp Asn Ala Glu Tyr
    450                 455                 460

Leu Pro Thr Asp Glu His Leu Ala Arg Arg Gly Arg Val Ile Glu Met
465                 470                 475                 480

Leu Ser Glu His Gln Cys Gln Gly Trp Leu Glu Gly Tyr Leu Leu Thr
                485                 490                 495

Gly Arg His Gly Leu Phe Asn Thr Tyr Glu Ala Phe Val His Ile Val
                500                 505                 510

Gly Ser Met Phe Asn Gln His Ala Lys Trp Leu Lys Val Ser Lys Glu
            515                 520                 525

Ile Pro Trp Arg Arg Pro Ile Ala Ser Leu Asn Tyr Leu Leu Thr Ser
    530                 535                 540

His Val Trp Arg Gln Asp His Asn Gly Leu Ser His Gln Asp Pro Gly
545                 550                 555                 560

Phe Ile Asp His Val Val Asn Lys Lys Ala Asp Val Val Arg Val Tyr
                565                 570                 575

Leu Pro Phe Asp Ala Asn Thr Leu Leu Ser Ala Tyr Asp His Cys Leu
            580                 585                 590

Arg Ser Val Asp Tyr Val Asn Val Val Ala Gly Lys Gln Pro Thr
            595                 600                 605

Phe Asn Trp Leu Ser Met Asp Arg Ala Ile Ala His Met Thr Arg Gly
    610                 615                 620

Leu Gly Ile Phe Glu Trp Ala Gly Thr Glu Val Glu Gly Glu Glu Pro
625                 630                 635                 640

Asp Val Val Leu Ala Cys Ala Gly Asp Val Pro Thr Leu Glu Val Leu
                645                 650                 655

Ala Ala Ala Ser Ile Leu Arg Gln Ala Ile Pro Asp Leu Lys Val Arg
            660                 665                 670

Val Val Asn Val Val Asp Leu Met Arg Leu Val Ser Glu Gly Glu His
            675                 680                 685

Pro His Gly Met Ser Asp Arg Glu Tyr Asp Ala Val Phe Thr Lys Asp
    690                 695                 700

Arg Pro Val Ile Phe Ala Tyr His Gly Tyr Pro Trp Leu Ile His Arg
705                 710                 715                 720

Leu Thr Tyr Arg Arg Asn Gly His Ala Asn Leu His Val Arg Gly Tyr
                725                 730                 735

Lys Glu Glu Gly Thr Thr Thr Pro Phe Asp Met Val Met Leu Asn
            740                 745                 750

Asp Ile Asp Arg Tyr His Leu Val Val Asp Val Asp Arg Val Pro
    755                 760                 765

Gly Leu Gly Glu Arg Tyr Ala Gly Leu Arg Gln Arg Met Leu Asp Ala
    770                 775                 780

Arg Val Arg Ala Arg Ala Tyr Thr Arg Glu His Gly Glu Asp Ile Pro
785                 790                 795                 800

Glu Val Ala Asp Trp Thr Trp Thr Ala Gly Pro Glu Arg Gln Ala Arg
                805                 810                 815

Glu Val Asn Thr Gly Val Gly Gln Val Asn Thr Gly Ala Ala Ala Thr
```

```
                   820            825            830
Gly Gly Asp Asn Glu Ser
        835

<210> SEQ ID NO 60
<211> LENGTH: 2379
<212> TYPE: DNA
<213> ORGANISM: Kingella_kingae

<400> SEQUENCE: 60
atgactaata agacacaatt tgacacccct gaatacttgg gtaaagtcga tgcttggtgg     60
agagccgcta actacatttc cgtcgctcaa atgtatttga aggataaccc attgttgaag    120
acacctttag tagcaaacga cgttaaagcc catccaattg gtcattgggg tactgttcct    180
ggtcaaaact tcatctatgc tcatttgaat agagcaatca acaagtatga tgttgacatg    240
ttctacatag aaggtccagg tcacggtggt caagtcatgg tatctaattc atacttagat    300
ggttcttaca ctgaaatcta cccagatatt acacaagaca ccgcaggttt gaaaaagtta    360
tgcaagatat tttcttttcc tggtggtatc gcctcacatg ctgcaccaga aacacctggt    420
tctattcacg aaggtggtga attgggttat gctttatcac atgcctttgg tgctgttttg    480
gataatccaa acgttatagc cgctgcagtc atcggtgacg gtgaagcaga aacaggtcct    540
ttgtgcgccg ttggtttggt aataccttc ataaatccag taaacgatgg tgctgtttta    600
cctatcttgt acttaaatgg tggtaaaata cataacccaa caatattggc aagaaaaacc    660
gatgaagaat taaagcaata cttcaacggt atgggttggg aacctatctt cgttgatgtc    720
aataacgttg acaactacca tgaaattatg tcccaaaaag tcgatgaagc tgtagaacac    780
atcttgagta tttggcaaac tgcaagaaca caaaaggcag aagatgccac tatgccacat    840
tggcctgttt tggttgctag aataccaaaa ggttggaccg tcctaagac ttggcacggt    900
gaaccaattg aaggtggttt tagagcacat caagttccaa tacctgcatc ttcacacgat    960
atggaaacag ctggtgaatt ggaaaagtgg ttaagatctt atagacctga agaattgttc   1020
gatgacaatg ttgtttctt agacaagtgg agagacattt ccccaaaagg tgcaaagaga   1080
atgagtgttc atcctatcac taatggtggt attaacccaa aagcattggt catgcctgat   1140
tggacacaac acgccttaga aattggtgtc ccaggttctc aagatgctca agacatggta   1200
gaatgcggta gattaatggc cgatgttgtc actgctaacc aaacaacttt agaattttc   1260
ggtcctgacg aaaccaagtc aaacagattg aaccaagtct tccaagtaac taagagacaa   1320
tggttaggta gaagagatga agcatatgac gaatggattg caccagttgg tagagtcata   1380
gattcccaat tgagtgaaca tcaagctgaa ggtttcttgg aaggttatgt tttaacaggt   1440
agacacggtt tctttgcttc ttacgaatca tttttcagag tagttgattc catgatcact   1500
caacatttca gtggttgag aaagtgtaag acacacgccg cttggagaaa tgattatcca   1560
tccttgaact tagtcgctac cagtactgta ttccaacaag atcataacgg ttacactcac   1620
caagaccctg gtttgttaac acatttggcc gaaaagaaac cagaatttgt aagagaatat   1680
ttgcctgctg attcaaacac cttaatggca gttatgtccg aagccttaac ttctagagat   1740
agaattaatt tgatcgtttc cagtaagcat ttgagaccaa attttttcaa cgctgaagaa   1800
gcaaaagaat tggttagaga aggttacaag gtcatagatt gggcttccac ctgtcatgat   1860
ggtgaaccag acgtcgtaat cgcagccgct ggtactgaac taatatgga agcattggca   1920
gccattagta tcttgcataa gcaattccca gaattaaaga ttagattcat aaacgttgtc   1980
```

-continued

```
gatatattga aattgagaca cccatctata gaccctagag gtttgtcaga tgaacaattt    2040
gacgctttat tcactcaaga aaagccagta gttttctgtt tccatggtta tgaaggtatg    2100
attagagatt tgttttccc tagagcaaat cataacgtta gaatccacgg ttacagagaa    2160
aatggtgaca ttactacacc atttgacatg agagttttat cagaaatgga tagattccat    2220
gtagccaaag acgctgcaca agctgtttat ggtgacaagg cctctgaatt tgctaaaaag    2280
atgggtgaaa cagtcgcttt ccatagatca tacatcagag aacacggtac cgatattcca    2340
gaagttgccg aatggaaatg caacctttg gctaagtaa                            2379
```

<210> SEQ ID NO 61
<211> LENGTH: 792
<212> TYPE: PRT
<213> ORGANISM: Kingella_kingae

<400> SEQUENCE: 61

```
Met Thr Asn Lys Thr Gln Phe Asp Thr Pro Glu Tyr Leu Gly Lys Val
1               5                   10                  15

Asp Ala Trp Trp Arg Ala Ala Asn Tyr Ile Ser Val Ala Gln Met Tyr
            20                  25                  30

Leu Lys Asp Asn Pro Leu Leu Lys Thr Pro Leu Val Ala Asn Asp Val
        35                  40                  45

Lys Ala His Pro Ile Gly His Trp Gly Thr Val Pro Gly Gln Asn Phe
    50                  55                  60

Ile Tyr Ala His Leu Asn Arg Ala Ile Asn Lys Tyr Asp Val Asp Met
65                  70                  75                  80

Phe Tyr Ile Glu Gly Pro Gly His Gly Gly Gln Val Met Val Ser Asn
                85                  90                  95

Ser Tyr Leu Asp Gly Ser Tyr Thr Glu Ile Tyr Pro Asp Ile Thr Gln
            100                 105                 110

Asp Thr Ala Gly Leu Lys Lys Leu Cys Lys Ile Phe Ser Phe Pro Gly
        115                 120                 125

Gly Ile Ala Ser His Ala Ala Pro Glu Thr Pro Gly Ser Ile His Glu
    130                 135                 140

Gly Gly Glu Leu Gly Tyr Ala Leu Ser His Ala Phe Gly Ala Val Leu
145                 150                 155                 160

Asp Asn Pro Asn Val Ile Ala Ala Val Ile Gly Asp Gly Glu Ala
                165                 170                 175

Glu Thr Gly Pro Leu Cys Ala Gly Trp Phe Gly Asn Thr Phe Ile Asn
            180                 185                 190

Pro Val Asn Asp Gly Ala Val Leu Pro Ile Leu Tyr Leu Asn Gly Gly
        195                 200                 205

Lys Ile His Asn Pro Thr Ile Leu Ala Arg Lys Thr Asp Glu Glu Leu
    210                 215                 220

Lys Gln Tyr Phe Asn Gly Met Gly Trp Glu Pro Ile Phe Val Asp Val
225                 230                 235                 240

Asn Asn Val Asp Asn Tyr His Glu Ile Met Ser Gln Lys Val Asp Glu
                245                 250                 255

Ala Val Glu His Ile Leu Ser Ile Trp Gln Thr Ala Arg Thr Gln Lys
            260                 265                 270

Ala Glu Asp Ala Thr Met Pro His Trp Pro Val Leu Val Ala Arg Ile
        275                 280                 285

Pro Lys Gly Trp Thr Gly Pro Lys Thr Trp His Gly Glu Pro Ile Glu
    290                 295                 300
```

```
Gly Gly Phe Arg Ala His Gln Val Pro Ile Pro Ala Ser Ser His Asp
305                 310                 315                 320

Met Glu Thr Ala Gly Glu Leu Glu Lys Trp Leu Arg Ser Tyr Arg Pro
                325                 330                 335

Glu Glu Leu Phe Asp Asp Asn Gly Cys Phe Leu Asp Lys Trp Arg Asp
                340                 345                 350

Ile Ser Pro Lys Gly Ala Lys Arg Met Ser Val His Pro Ile Thr Asn
                355                 360                 365

Gly Gly Ile Asn Pro Lys Ala Leu Val Met Pro Asp Trp Thr Gln His
370                 375                 380

Ala Leu Glu Ile Gly Val Pro Gly Ser Gln Asp Ala Gln Asp Met Val
385                 390                 395                 400

Glu Cys Gly Arg Leu Met Ala Asp Val Val Thr Ala Asn Pro Asn Asn
                405                 410                 415

Phe Arg Ile Phe Gly Pro Asp Glu Thr Lys Ser Asn Arg Leu Asn Gln
                420                 425                 430

Val Phe Gln Val Thr Lys Arg Gln Trp Leu Gly Arg Arg Asp Glu Ala
                435                 440                 445

Tyr Asp Glu Trp Ile Ala Pro Val Gly Arg Val Ile Asp Ser Gln Leu
450                 455                 460

Ser Glu His Gln Ala Glu Gly Phe Leu Glu Gly Tyr Val Leu Thr Gly
465                 470                 475                 480

Arg His Gly Phe Phe Ala Ser Tyr Glu Ser Phe Phe Arg Val Val Asp
                485                 490                 495

Ser Met Ile Thr Gln His Phe Lys Trp Leu Arg Lys Cys Lys Thr His
                500                 505                 510

Ala Ala Trp Arg Asn Asp Tyr Pro Ser Leu Asn Leu Val Ala Thr Ser
                515                 520                 525

Thr Val Phe Gln Gln Asp His Asn Gly Tyr Thr His Gln Asp Pro Gly
                530                 535                 540

Leu Leu Thr His Leu Ala Glu Lys Lys Pro Glu Phe Val Arg Glu Tyr
545                 550                 555                 560

Leu Pro Ala Asp Ser Asn Thr Leu Met Ala Val Met Ser Glu Ala Leu
                565                 570                 575

Thr Ser Arg Asp Arg Ile Asn Leu Ile Val Ser Ser Lys His Leu Arg
                580                 585                 590

Pro Gln Phe Phe Asn Ala Glu Glu Ala Lys Glu Leu Val Arg Glu Gly
                595                 600                 605

Tyr Lys Val Ile Asp Trp Ala Ser Thr Cys His Asp Gly Glu Pro Asp
                610                 615                 620

Val Val Ile Ala Ala Gly Thr Glu Pro Asn Met Glu Ala Leu Ala
625                 630                 635                 640

Ala Ile Ser Ile Leu His Lys Gln Phe Pro Glu Leu Lys Ile Arg Phe
                645                 650                 655

Ile Asn Val Val Asp Ile Leu Lys Leu Arg His Pro Ser Ile Asp Pro
                660                 665                 670

Arg Gly Leu Ser Asp Glu Gln Phe Asp Ala Leu Phe Thr Gln Glu Lys
                675                 680                 685

Pro Val Val Phe Cys Phe His Gly Tyr Glu Gly Met Ile Arg Asp Leu
                690                 695                 700

Phe Phe Pro Arg Ala Asn His Asn Val Arg Ile His Gly Tyr Arg Glu
705                 710                 715                 720

Asn Gly Asp Ile Thr Thr Pro Phe Asp Met Arg Val Leu Ser Glu Met
```

|  |  | 725 |  |  |  | 730 |  |  |  | 735 |  |
|---|---|---|---|---|---|---|---|---|---|---|---|

Asp Arg Phe His Val Ala Lys Asp Ala Ala Gln Ala Val Tyr Gly Asp
           740                      745                   750

Lys Ala Ser Glu Phe Ala Lys Lys Met Gly Glu Thr Val Ala Phe His
      755                   760                   765

Arg Ser Tyr Ile Arg Glu His Gly Thr Asp Ile Pro Glu Val Ala Glu
  770                    775                   780

Trp Lys Trp Gln Pro Leu Ala Lys
785                790

<210> SEQ ID NO 62
<211> LENGTH: 2367
<212> TYPE: DNA
<213> ORGANISM: Lactobacillus plantarum

<400> SEQUENCE: 62

| | | | | |
|---|---|---|---|---|
| atgacaacag | attactcatc | ccctgcatac | ttacaaaagg tagacaaata | ctggagagcc | 60 |
| gctaactact | tatccgtcgg | tcaattatat | ttgaaggaca | acccattgtt gcaaagacct | 120 |
| ttaaaagcat | ctgatgtaaa | ggttcatcca | ataggtcact | ggggtactat cgctggtcaa | 180 |
| aacttcatct | atgcacattt | gaatagagtc | attaacaaat | acggtttgaa gatgttctac | 240 |
| gtagaaggtc | ctggtcacgg | tggtcaagtc | atggtatcta | attcatactt ggacggtaca | 300 |
| tataccgata | tctatccaga | ataacccaa | gatgttgagg | gtatgcaaaa attgtttaaa | 360 |
| caattttctt | ccctggtgg | tgtcgcttca | catgctgcac | cagaaacacc tggttccatt | 420 |
| cacgaaggtg | gtgaattggg | ttattccata | agtcatggtg | ttggtgcaat cttagataat | 480 |
| ccagacgaaa | ttgccgctgt | tgtcgtaggt | gacggtgaat | cagaaactgg tcctttggct | 540 |
| acatcttggc | aatcaaccaa | gtttatcaat | ccaattaacg | atggtgcagt tttacctata | 600 |
| ttgaatttga | atggtttta | aatctctaat | ccaactattt | tcggtagaac atcagatgct | 660 |
| aagattaaag | aatacttcga | atcaatgaac | tgggaaccta | tcttcgtaga aggtgacgac | 720 |
| ccagaaaagg | ttcatcctgc | cttggctaaa | gcaatggatg | aagcagttga aaagattaaa | 780 |
| gccatccaaa | aacacgctag | agaaaataac | gatgctactt | taccagtctg gcctatgata | 840 |
| gtttttagag | caccaaaagg | ttggacaggt | cctaagtcct | gggatggtga caaaatcgaa | 900 |
| ggttcttta | gagcacatca | aattccaata | cctgttgatc | aaaatgacat ggaacacgcc | 960 |
| gatgctttgg | ttgattggtt | agaatcctat | caaccaaagg | aattgtttaa cgaagatggt | 1020 |
| agtttaaagg | atgacataaa | ggaaataata | ccaacaggtg | actctagaat ggcagccaat | 1080 |
| cctataacca | acggtggtgt | cgatccaaaa | gcattgaatt | tgcctaactt cagagattat | 1140 |
| gcagtagaca | cttctaagga | aggtgccaat | gttaaacaag | atatgatcgt ctggtcagat | 1200 |
| tacttgagag | acgttattaa | aaagaatcca | gacaacttca | gattgttcgg tcctgatgaa | 1260 |
| acaatgtcta | acagattgta | cggtgttttt | gaaactacaa | acagacaatg gatggaagac | 1320 |
| attcatccag | attccgacca | atacgaagca | cctgccggta | gagtattgga tgcccaatta | 1380 |
| agtgaacatc | aagctgaagg | ttggttggaa | ggttatgttt | taacaggtag acacggtttg | 1440 |
| tttgcatctt | acgaagcctt | cttgagagtt | gtcgattcaa | tgttaccca acatttcaag | 1500 |
| tggttgagaa | aggctaacga | attagattgg | agaaagaaat | acccatcctt aaacatcata | 1560 |
| gctgcaagta | ctgttttcca | acaagaccat | aatggttaca | cccaccaaga tcctggtgca | 1620 |
| ttgactcatt | tggccgaaaa | gaaaccagaa | tacattagaa | aatacttgcc tgctgacgca | 1680 |
| aatacccttgt | tagctgtagg | tgacgttatt | tttagatcac | aagaaaagat caactacgta | 1740 |

```
gttacttcta aacacccaag acaacaatgg ttctcaattg aagaagccaa acaattggtc   1800
gataatggtt taggtataat cgactgggct tccactgatc aaggtagtga accagatatc   1860
gtttttgccg ctgcaggtac tgaacctaca ttggaaacct tagccgctat tcaattgtta   1920
catgattctt tcccagaaat gaagatcaga ttcgttaacg tcgtagacat cttgaagtta   1980
agatccccag aaaaagatcc tagaggtttg agtgatgcag aatttgacca ttacttcaca   2040
aaggataagc cagttgtctt tgccttccac ggttacgaag atttggttag agatattttc   2100
tttgatagac ataaccacaa cttatacgtt catggttaca gagaaaacgg tgacataacc   2160
actccatttg atgttagagt catgaaccaa atggatagat tcgacttggc caagtctgct   2220
attgcagccc aacctgctat ggaaaatact ggtgctgcat ttgttcaatc aatggataac   2280
atgttagcta aacataacgc atacattaga gacgcaggta cagatttgcc agaagttaac   2340
gattggcaat ggaaaggttt aaagtaa                                       2367
```

<210> SEQ ID NO 63
<211> LENGTH: 788
<212> TYPE: PRT
<213> ORGANISM: Lactobacillus plantarum

<400> SEQUENCE: 63

```
Met Thr Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
            20                  25                  30

Asp Asn Pro Leu Leu Gln Arg Pro Leu Lys Ala Ser Asp Val Lys Val
        35                  40                  45

His Pro Ile Gly His Trp Gly Thr Ile Ala Gly Gln Asn Phe Ile Tyr
    50                  55                  60

Ala His Leu Asn Arg Val Ile Asn Lys Tyr Gly Leu Lys Met Phe Tyr
65                  70                  75                  80

Val Glu Gly Pro Gly His Gly Gly Gln Val Met Val Ser Asn Ser Tyr
                85                  90                  95

Leu Asp Gly Thr Tyr Thr Asp Ile Tyr Pro Glu Ile Thr Gln Asp Val
            100                 105                 110

Glu Gly Met Gln Lys Leu Phe Lys Gln Phe Ser Phe Pro Gly Gly Val
        115                 120                 125

Ala Ser His Ala Ala Pro Glu Thr Pro Gly Ser Ile His Glu Gly Gly
    130                 135                 140

Glu Leu Gly Tyr Ser Ile Ser His Gly Val Gly Ala Ile Leu Asp Asn
145                 150                 155                 160

Pro Asp Glu Ile Ala Ala Val Val Val Gly Asp Gly Glu Ser Glu Thr
                165                 170                 175

Gly Pro Leu Ala Thr Ser Trp Gln Ser Thr Lys Phe Ile Asn Pro Ile
            180                 185                 190

Asn Asp Gly Ala Val Leu Pro Ile Leu Asn Leu Asn Gly Phe Lys Ile
        195                 200                 205

Ser Asn Pro Thr Ile Phe Gly Arg Thr Ser Asp Ala Lys Ile Lys Glu
    210                 215                 220

Tyr Phe Glu Ser Met Asn Trp Glu Pro Ile Phe Val Glu Gly Asp Asp
225                 230                 235                 240

Pro Glu Lys Val His Pro Ala Leu Ala Lys Ala Met Asp Glu Ala Val
                245                 250                 255
```

```
Glu Lys Ile Lys Ala Ile Gln Lys His Ala Arg Glu Asn Asn Asp Ala
            260                 265                 270

Thr Leu Pro Val Trp Pro Met Ile Val Phe Arg Ala Pro Lys Gly Trp
        275                 280                 285

Thr Gly Pro Lys Ser Trp Asp Gly Asp Lys Ile Glu Gly Ser Phe Arg
    290                 295                 300

Ala His Gln Ile Pro Ile Pro Val Asp Gln Asn Asp Met Glu His Ala
305                 310                 315                 320

Asp Ala Leu Val Asp Trp Leu Glu Ser Tyr Gln Pro Lys Glu Leu Phe
                325                 330                 335

Asn Glu Asp Gly Ser Leu Lys Asp Ile Lys Glu Ile Ile Pro Thr
            340                 345                 350

Gly Asp Ser Arg Met Ala Ala Asn Pro Ile Thr Asn Gly Gly Val Asp
        355                 360                 365

Pro Lys Ala Leu Asn Leu Pro Asn Phe Arg Asp Tyr Ala Val Asp Thr
    370                 375                 380

Ser Lys Glu Gly Ala Asn Val Lys Gln Asp Met Ile Val Trp Ser Asp
385                 390                 395                 400

Tyr Leu Arg Asp Val Ile Lys Lys Asn Pro Asp Asn Phe Arg Leu Phe
                405                 410                 415

Gly Pro Asp Glu Thr Met Ser Asn Arg Leu Tyr Gly Val Phe Glu Thr
            420                 425                 430

Thr Asn Arg Gln Trp Met Glu Asp Ile His Pro Asp Ser Asp Gln Tyr
        435                 440                 445

Glu Ala Pro Ala Gly Arg Val Leu Asp Ala Gln Leu Ser Glu His Gln
    450                 455                 460

Ala Glu Gly Trp Leu Glu Gly Tyr Val Leu Thr Gly Arg His Gly Leu
465                 470                 475                 480

Phe Ala Ser Tyr Glu Ala Phe Leu Arg Val Val Asp Ser Met Leu Thr
                485                 490                 495

Gln His Phe Lys Trp Leu Arg Lys Ala Asn Glu Leu Asp Trp Arg Lys
            500                 505                 510

Lys Tyr Pro Ser Leu Asn Ile Ile Ala Ala Ser Thr Val Phe Gln Gln
        515                 520                 525

Asp His Asn Gly Tyr Thr His Gln Asp Pro Gly Ala Leu Thr His Leu
    530                 535                 540

Ala Glu Lys Lys Pro Glu Tyr Ile Arg Glu Tyr Leu Pro Ala Asp Ala
545                 550                 555                 560

Asn Thr Leu Leu Ala Val Gly Asp Val Ile Phe Arg Ser Gln Glu Lys
                565                 570                 575

Ile Asn Tyr Val Val Thr Ser Lys His Pro Arg Gln Gln Trp Phe Ser
            580                 585                 590

Ile Glu Glu Ala Lys Gln Leu Val Asp Asn Gly Leu Gly Ile Ile Asp
        595                 600                 605

Trp Ala Ser Thr Asp Gln Gly Ser Glu Pro Asp Ile Val Phe Ala Ala
    610                 615                 620

Ala Gly Thr Glu Pro Thr Leu Glu Thr Leu Ala Ala Ile Gln Leu Leu
625                 630                 635                 640

His Asp Ser Phe Pro Glu Met Lys Ile Arg Phe Val Asn Val Val Asp
                645                 650                 655

Ile Leu Lys Leu Arg Ser Pro Glu Lys Asp Pro Arg Gly Leu Ser Asp
            660                 665                 670

Ala Glu Phe Asp His Tyr Phe Thr Lys Asp Lys Pro Val Val Phe Ala
```

```
                    675                 680                 685
    Phe His Gly Tyr Glu Asp Leu Val Arg Asp Ile Phe Phe Asp Arg His
                690                 695                 700

Asn His Asn Leu Tyr Val His Gly Tyr Arg Glu Asn Gly Asp Ile Thr
    705                 710                 715                 720

Thr Pro Phe Asp Val Arg Val Met Asn Gln Met Asp Arg Phe Asp Leu
                    725                 730                 735

Ala Lys Ser Ala Ile Ala Ala Gln Pro Ala Met Glu Asn Thr Gly Ala
                740                 745                 750

Ala Phe Val Gln Ser Met Asp Asn Met Leu Ala Lys His Asn Ala Tyr
                755                 760                 765

Ile Arg Asp Ala Gly Thr Asp Leu Pro Glu Val Asn Asp Trp Gln Trp
    770                 775                 780

Lys Gly Leu Lys
    785

<210> SEQ ID NO 64
<211> LENGTH: 2454
<212> TYPE: DNA
<213> ORGANISM: Leuconostoc_citreum

<400> SEQUENCE: 64
atggcagact tcgactcaaa ggaatactta gaattggtag acaaatggtg gagagcaaca      60
aactacttat ccgctggtat gatttttctg aaaagtaatc cattattttc tgttacaaac     120
acccctattc aagctgaaga tgttaaagtc aagccaattg gtcattgggg tactatatct     180
ggtcaaacat tcttgtatgc ccacgctaac agattgatta caaatacga tttgaatatg     240 ttttacatag gtggtccagg tcatggtggt caagtaatgg ttactaacgc atacttagat     300
ggtgaatata ccgaagacta ccctgaaatt actcaagatt tggaaggcat gtctagattg     360
tttaaaagat tttctttccc aggtggtatc ggttcacata tgacagctca aacccctggt     420
tctttgcacg aaggtggtga attgggttat tccttaagtc atgccttcgg tgctgtttta     480
gataatccag accaaattgc atttgccgtt gtcggtgacg gtgaagcaga aaccggtcct     540
tccatgactt cttggcactc tacaaaattc ttgaatgcaa agaacgatgg tgccgtctta     600
ccaatcttgg acttaaatgg tttcaaaatc tctaacccta caattttctc tagaatgtcc     660
gatgaagaaa tcactaagtt tttcgaaggt ttgggttact caccaagatt cattgaaaac     720
gatgacatcc atgattatgc tgcataccac gaattggccg ctaaagtttt agatcaagct     780
atcgaagaca ttcaagctat acaaaaagat gcaagagaaa acggtaaata cgaagacggt     840
acaattccag catggcctgt cattatagcc agattgccaa agggttgggg tggtcctact     900
catgatgaag acgtaaccc aatcgaaaat tctttagag cacatcaagt accattgcct     960
ttagcacaaa ataagttgga actttgtct caattcgaag attggatgaa ctcttacaag    1020
cctgaagaat tgtttaatgc agatggttcc ttgaaagacg aattaaaggc tatagcacca    1080
aaaggtgaca agagaatgag tgcaaatcct atcgccaacg tggtagaag aagaggtgaa    1140 gaagctactg atttgacatt accagactgg agacaattca caaacgatat aaccaacgaa    1200
aacagaggtc atgaattgcc taaggttact caaaacatgg atatgactac attgtctaac    1260
tatttggaag aagtcgctaa gttaaaccca acatcattca gagtatttgg tcctgatgaa    1320
actatgtcaa acagattgtg gtccttgttt aataccacta cagacaatg gatgaagaa    1380 gtaaaagaac caaatgatca atacgttggt cctgaaggta gaatcattga cagtcaatta    1440
```

```
tctgaacatc aagccgaagg ttggttggaa ggttacactt tgacaggtag agtaggtata    1500
ttcgcttcat acgaatcctt tttgagagta gttgacacta tggttactca acatttcaag    1560
tggttgagac acgcttctga acaagcatgg agaaacgatt acccatcctt gaacttaatt    1620
gccaccagta ctgctttcca acaagatcat aatggttaca cacaccaaga cccaggcatg    1680
ttgacccatt tggctgaaaa gaaatctaac ttcattagag aatatttgcc tgcagatggt    1740
aactccttgt tagccgttca agacagagct tttagtgaaa gacacaaggt caatttgata    1800
atcgcatcta agcaaccaag acaacaatgg ttcacagcag atgaagccga cgaattggct    1860
aacgaaggtt tgaagatcat cgattgggct tcaacagcac catccggtga cgttgacatt    1920
acctttgcat cttcaggtac agaacctacc atagaaactt tggcagcctt gtggttaatc    1980
aatcaagcat ttccagaggt taagtttaga tacgtcaacg tcgtagaatt gttgagattg    2040
caaaagaaat ctgaatctca tatgaacgat gaaagagaat tatccgacgc cgagtttaat    2100 aagttttcc aagctgataa gcctgttatc ttcggttttc atgcttacga agacttaatc    2160
gaatcatttt tctttgaaag aaaattcaag ggtgacgtct atgtacacgg ttacagagaa    2220
gatggtgaca ttacaaccac ttacgatatg agagtttact ctaaattgga cagatttcat    2280
caagcaaagg aagctgcaga aatcttaagt gccaattcta ctattgatca agccgctgca    2340
gacacattca tcgaaaagat ggatgccacc ttggctaagc attttgaagt tactagaaat    2400
gaaggtagag atattgaaga gtttactgac tggaactggt cagctttaaa ataa          2454

<210> SEQ ID NO 65
<211> LENGTH: 817
<212> TYPE: PRT
<213> ORGANISM: Leuconostoc_citreum

<400> SEQUENCE: 65

Met Ala Asp Phe Asp Ser Lys Glu Tyr Leu Glu Leu Val Asp Lys Trp
1               5                   10                  15

Trp Arg Ala Thr Asn Tyr Leu Ser Ala Gly Met Ile Phe Leu Lys Ser
            20                  25                  30

Asn Pro Leu Phe Ser Val Thr Asn Thr Pro Ile Gln Ala Glu Asp Val
        35                  40                  45

Lys Val Lys Pro Ile Gly His Trp Gly Thr Ile Ser Gly Gln Thr Phe
    50                  55                  60

Leu Tyr Ala His Ala Asn Arg Leu Ile Asn Lys Tyr Asp Leu Asn Met
65                  70                  75                  80

Phe Tyr Ile Gly Gly Pro Gly His Gly Gly Gln Val Met Val Thr Asn
                85                  90                  95

Ala Tyr Leu Asp Gly Glu Tyr Thr Glu Asp Tyr Pro Glu Ile Thr Gln
            100                 105                 110

Asp Leu Glu Gly Met Ser Arg Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Ser Leu Ser His Ala Phe Gly Ala Val Leu
145                 150                 155                 160

Asp Asn Pro Asp Gln Ile Ala Phe Ala Val Val Gly Asp Gly Glu Ala
                165                 170                 175

Glu Thr Gly Pro Ser Met Thr Ser Trp His Ser Thr Lys Phe Leu Asn
            180                 185                 190

Ala Lys Asn Asp Gly Ala Val Leu Pro Ile Leu Asp Leu Asn Gly Phe
```

```
            195                 200                 205
Lys Ile Ser Asn Pro Thr Ile Phe Ser Arg Met Ser Asp Glu Glu Ile
            210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Ala Tyr His Glu Leu Ala Ala Lys Val
                245                 250                 255

Leu Asp Gln Ala Ile Glu Asp Ile Gln Ala Ile Gln Lys Asp Ala Arg
                260                 265                 270

Glu Asn Gly Lys Tyr Glu Asp Gly Thr Ile Pro Ala Trp Pro Val Ile
                275                 280                 285

Ile Ala Arg Leu Pro Lys Gly Trp Gly Gly Pro Thr His Asp Glu Asp
        290                 295                 300

Gly Asn Pro Ile Glu Asn Ser Phe Arg Ala His Gln Val Pro Leu Pro
305                 310                 315                 320

Leu Ala Gln Asn Lys Leu Glu Thr Leu Ser Gln Phe Glu Asp Trp Met
                325                 330                 335

Asn Ser Tyr Lys Pro Glu Glu Leu Phe Asn Ala Asp Gly Ser Leu Lys
                340                 345                 350

Asp Glu Leu Lys Ala Ile Ala Pro Lys Gly Asp Lys Arg Met Ser Ala
                355                 360                 365

Asn Pro Ile Ala Asn Gly Gly Arg Arg Arg Gly Glu Glu Ala Thr Asp
370                 375                 380

Leu Thr Leu Pro Asp Trp Arg Gln Phe Thr Asn Asp Ile Thr Asn Glu
385                 390                 395                 400

Asn Arg Gly His Glu Leu Pro Lys Val Thr Gln Asn Met Asp Met Thr
                405                 410                 415

Thr Leu Ser Asn Tyr Leu Glu Glu Val Ala Lys Leu Asn Pro Thr Ser
                420                 425                 430

Phe Arg Val Phe Gly Pro Asp Glu Thr Met Ser Asn Arg Leu Trp Ser
        435                 440                 445

Leu Phe Asn Thr Thr Asn Arg Gln Trp Met Glu Glu Val Lys Glu Pro
450                 455                 460

Asn Asp Gln Tyr Val Gly Pro Glu Gly Arg Ile Ile Asp Ser Gln Leu
465                 470                 475                 480

Ser Glu His Gln Ala Glu Gly Trp Leu Glu Gly Tyr Thr Leu Thr Gly
                485                 490                 495

Arg Val Gly Ile Phe Ala Ser Tyr Glu Ser Phe Leu Arg Val Val Asp
                500                 505                 510

Thr Met Val Thr Gln His Phe Lys Trp Leu Arg His Ala Ser Glu Gln
                515                 520                 525

Ala Trp Arg Asn Asp Tyr Pro Ser Leu Asn Leu Ile Ala Thr Ser Thr
        530                 535                 540

Ala Phe Gln Gln Asp His Asn Gly Tyr Thr His Gln Asp Pro Gly Met
545                 550                 555                 560

Leu Thr His Leu Ala Glu Lys Lys Ser Asn Phe Ile Arg Glu Tyr Leu
                565                 570                 575

Pro Ala Asp Gly Asn Ser Leu Leu Ala Val Gln Asp Arg Ala Phe Ser
                580                 585                 590

Glu Arg His Lys Val Asn Leu Ile Ile Ala Ser Lys Gln Pro Arg Gln
                595                 600                 605

Gln Trp Phe Thr Ala Asp Glu Ala Asp Glu Leu Ala Asn Glu Gly Leu
        610                 615                 620
```

Lys Ile Ile Asp Trp Ala Ser Thr Ala Pro Ser Gly Asp Val Asp Ile
625                 630                 635                 640

Thr Phe Ala Ser Ser Gly Thr Glu Pro Thr Ile Glu Thr Leu Ala Ala
            645                 650                 655

Leu Trp Leu Ile Asn Gln Ala Phe Pro Glu Val Lys Phe Arg Tyr Val
        660                 665                 670

Asn Val Val Glu Leu Leu Arg Leu Gln Lys Lys Ser Glu Ser His Met
    675                 680                 685

Asn Asp Glu Arg Glu Leu Ser Asp Ala Glu Phe Asn Lys Phe Phe Gln
690                 695                 700

Ala Asp Lys Pro Val Ile Phe Gly Phe His Ala Tyr Glu Asp Leu Ile
705                 710                 715                 720

Glu Ser Phe Phe Glu Arg Lys Phe Lys Gly Asp Val Tyr Val His
                725                 730                 735

Gly Tyr Arg Glu Asp Gly Asp Ile Thr Thr Thr Tyr Asp Met Arg Val
            740                 745                 750

Tyr Ser Lys Leu Asp Arg Phe His Gln Ala Lys Glu Ala Ala Glu Ile
        755                 760                 765

Leu Ser Ala Asn Ser Thr Ile Asp Gln Ala Ala Ala Asp Thr Phe Ile
    770                 775                 780

Glu Lys Met Asp Ala Thr Leu Ala Lys His Phe Glu Val Thr Arg Asn
785                 790                 795                 800

Glu Gly Arg Asp Ile Glu Glu Phe Thr Asp Trp Asn Trp Ser Ala Leu
            805                 810                 815

Lys

<210> SEQ ID NO 66
<211> LENGTH: 2475
<212> TYPE: DNA
<213> ORGANISM: Metascardovia_criceti

<400> SEQUENCE: 66

```
atgacatccc cagttattgg taccccatgg agaaagttgg acgccccctgt atccgaagaa      60 gcattagaag gtgtagacaa gtattggaga gcttccaact atttgagtat aggtcaaatc     120
tacttgagat caaacccatt gatgaaggaa ccttcacaa gagaagatgt caagcataga     180
ttagtaggtc actggggtac tacaccaggt ttgaactttt taataggtca tatcaacaga     240
ttgatcgcag atcacggtca aaacactgtt attatcatgg gtccaggtca tggtggtcct     300
gctggtacat cccaaagtta tttgacggt acctactctg aatacttccc agaaatcaca     360
aaggatgaag caggtttgca aaagttttc agacaattct cttacccagg tggtatccct     420
tcacattttg caccagaaac ccctggttca attcacgaag tggtgaatt gggttatgct     480 ttatctcatg cctacggtgc tgttatgaat aacccatcat tatttgtacc tgctattgtt     540
ggtgacggtg aagctgaaac aggtccatta gcaaccggtt ggcaatctaa caaattggtt     600
aatccaagaa ccgatggtat agtcttgcct atcttgcatt gaacggtta taagattgcc     660 aatccaacta tattggctag aatctctgat gaagaattgc atgaattttt ccacggtatg     720
ggttatgaac ttacgaatt tgttgctggt ttcgatgacg aagacgcaat gtcaattcac     780
agaagatttg ctgatttgtt cgaaacagtt ttcgacgaaa tctgtgatat caaggctacc     840
gcacaaacta cgatgttga cagaccattc taccctatga tcattttag aactccaaag     900 ggttggacat gccctaagtt cattgatggt aaaaagacag aaggttcttg gagatcacat     960
```

```
caagtaccat tggcctccgc tagagatacc gaagaacact ttgaagtttt gaaaaattgg    1020
ttggaaagtt acaagcctga agaattattc actgaagatg gtgccgtcag accagaagta    1080
acagctttta tgcctgaggg tgaattgaga ataggtgaaa atccaaacgc caatggtggt    1140
agaatcagag aagaattgga cttacctgct ttggaagatt acgaagtaac tgaagttaaa    1200
gaatttggtc atggttgggg tcaattggaa gcaaccagaa agttgggtga atacactaga    1260
gacataatca agagaaaccc agattccttt agaattttcg gtcctgatga aaccgctagt    1320
aatagattgc aagctgcata tgaagtcact aacaaacaat gggacaatgg ttacttgtct    1380
gaattagttg atgaacatat ggcagttact ggtcaagtca cagaacaatt atcagaacac    1440
caaatggaag gtttcttgga agcttatttg ttaacaggta gacatggtat ttggtcttca    1500
tacgaatcct tcgtccatgt aatcgatagt atgttgaacc aacacgctaa atggttagaa    1560
gcaactgtta gagaaatccc atggagaaag cctatttcca gtatgaactt gttagtatct    1620
tcacatgttt ggagacaaga tcataatggt ttttcccacc aagacccagg tgttatcgat    1680
atattgttga acaaaaactt caacaacgac cacgttgtcg gtatctattt ccctgtagat    1740
tctaacatgt tgttagccgt ttccgaaaag gcttacaaga gtacaaacat gatcaacgca    1800
ataatcgccg gtaaacaacc agccgctaca tggttgacct tagatgaagc aagagaagaa    1860
ttagccaaag gtgcagccga atggaagtgg gcttctaacg cagaaggtga cgacgttgat    1920
attgtattgg cttcagttgg tgacgtccct actcaagaat tgatggctgc agccgacaaa    1980
ttaaagggtt acggtataaa atacaagttc gttaacgtag ttgatttgtt atctatccaa    2040
aacgcatcag aaaatgacca agccttgtct gatgaagagt ttactgaatt gtttactgca    2100
gataaaccag tcttgatggc ctatcatgca tacgccagag aagtaagatc cttaatttgg    2160
gacagaccaa atcatgataa cttcaatgtt cacggttatg aagaacaagg tagtaccact    2220
acaccttttg acatggttag agtcaacaac atagatagat acgaattgac tgctgaagca    2280
ttaagagccg ttgatgctga caaattcgct gacgaaatag aaaagttgga agcttttaga    2340
actgaagcat tcaattcgc cgttgataat ggttatgatc atccagacta cacagattgg    2400
gtctggtctg tgtccaaac tgaaaagcca ggtgctgtat ctgccactgc tgccactgcc    2460
ggtgacaacg aataa                                                   2475
```

<210> SEQ ID NO 67
<211> LENGTH: 824
<212> TYPE: PRT
<213> ORGANISM: Metascardovia_criceti

<400> SEQUENCE: 67

Met Thr Ser Pro Val Ile Gly Thr Pro Trp Arg Lys Leu Asp Ala Pro
1               5                   10                  15

Val Ser Glu Glu Ala Leu Glu Gly Val Asp Lys Tyr Trp Arg Ala Ser
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80

Leu Ile Ala Asp His Gly Gln Asn Thr Val Ile Ile Met Gly Pro Gly
                85                  90                  95

His Gly Gly Pro Ala Gly Thr Ser Gln Ser Tyr Leu Asp Gly Thr Tyr

```
                100                 105                 110
Ser Glu Tyr Phe Pro Glu Ile Thr Lys Asp Glu Ala Gly Leu Gln Lys
            115                 120                 125
Phe Phe Arg Gln Phe Ser Tyr Pro Gly Gly Ile Pro Ser His Phe Ala
            130                 135                 140
Pro Glu Thr Pro Gly Ser Ile His Glu Gly Gly Glu Leu Gly Tyr Ala
145                 150                 155                 160
Leu Ser His Ala Tyr Gly Ala Val Met Asn Asn Pro Ser Leu Phe Val
                165                 170                 175
Pro Ala Ile Val Gly Asp Gly Glu Ala Glu Thr Gly Pro Leu Ala Thr
            180                 185                 190
Gly Trp Gln Ser Asn Lys Leu Val Asn Pro Arg Thr Asp Gly Ile Val
            195                 200                 205
Leu Pro Ile Leu His Leu Asn Gly Tyr Lys Ile Ala Asn Pro Thr Ile
            210                 215                 220
Leu Ala Arg Ile Ser Asp Glu Leu His Glu Phe Phe His Gly Met
225                 230                 235                 240
Gly Tyr Glu Pro Tyr Glu Phe Val Ala Gly Phe Asp Asp Glu Asp Ala
                245                 250                 255
Met Ser Ile His Arg Arg Phe Ala Asp Leu Phe Glu Thr Val Phe Asp
                260                 265                 270
Glu Ile Cys Asp Ile Lys Ala Thr Ala Gln Thr Asn Asp Val Asp Arg
            275                 280                 285
Pro Phe Tyr Pro Met Ile Ile Phe Arg Thr Pro Lys Gly Trp Thr Cys
            290                 295                 300
Pro Lys Phe Ile Asp Gly Lys Lys Thr Glu Gly Ser Trp Arg Ser His
305                 310                 315                 320
Gln Val Pro Leu Ala Ser Ala Arg Asp Thr Glu His Phe Glu Val
                325                 330                 335
Leu Lys Asn Trp Leu Glu Ser Tyr Lys Pro Glu Glu Leu Phe Thr Glu
            340                 345                 350
Asp Gly Ala Val Arg Pro Glu Val Thr Ala Phe Met Pro Glu Gly Glu
            355                 360                 365
Leu Arg Ile Gly Glu Asn Pro Asn Ala Asn Gly Gly Arg Ile Arg Glu
            370                 375                 380
Glu Leu Asp Leu Pro Ala Leu Glu Asp Tyr Glu Val Thr Glu Val Lys
385                 390                 395                 400
Glu Phe Gly His Gly Trp Gly Gln Leu Glu Ala Thr Arg Lys Leu Gly
                405                 410                 415
Glu Tyr Thr Arg Asp Ile Ile Lys Arg Asn Pro Asp Ser Phe Arg Ile
                420                 425                 430
Phe Gly Pro Asp Glu Thr Ala Ser Asn Arg Leu Gln Ala Ala Tyr Glu
            435                 440                 445
Val Thr Asn Lys Gln Trp Asp Asn Gly Tyr Leu Ser Glu Leu Val Asp
            450                 455                 460
Glu His Met Ala Val Thr Gly Gln Val Thr Glu Gln Leu Ser Glu His
465                 470                 475                 480
Gln Met Glu Gly Phe Leu Glu Ala Tyr Leu Leu Thr Gly Arg His Gly
                485                 490                 495
Ile Trp Ser Ser Tyr Glu Ser Phe Val His Val Ile Asp Ser Met Leu
                500                 505                 510
Asn Gln His Ala Lys Trp Leu Glu Ala Thr Val Arg Glu Ile Pro Trp
            515                 520                 525
```

```
Arg Lys Pro Ile Ser Ser Met Asn Leu Leu Val Ser Ser His Val Trp
    530                 535                 540

Arg Gln Asp His Asn Gly Phe Ser His Gln Asp Pro Gly Val Ile Asp
545                 550                 555                 560

Ile Leu Leu Asn Lys Asn Phe Asn Asn Asp His Val Val Gly Ile Tyr
                565                 570                 575

Phe Pro Val Asp Ser Asn Met Leu Leu Ala Val Ser Glu Lys Ala Tyr
            580                 585                 590

Lys Ser Thr Asn Met Ile Asn Ala Ile Ile Ala Gly Lys Gln Pro Ala
        595                 600                 605

Ala Thr Trp Leu Thr Leu Asp Glu Ala Arg Glu Glu Leu Ala Lys Gly
    610                 615                 620

Ala Ala Glu Trp Lys Trp Ala Ser Asn Ala Glu Gly Asp Asp Val Asp
625                 630                 635                 640

Ile Val Leu Ala Ser Val Gly Asp Val Pro Thr Gln Glu Leu Met Ala
                645                 650                 655

Ala Ala Asp Lys Leu Lys Gly Tyr Gly Ile Lys Tyr Lys Phe Val Asn
            660                 665                 670

Val Val Asp Leu Leu Ser Ile Gln Asn Ala Ser Glu Asn Asp Gln Ala
        675                 680                 685

Leu Ser Asp Glu Glu Phe Thr Glu Leu Phe Thr Ala Asp Lys Pro Val
    690                 695                 700

Leu Met Ala Tyr His Ala Tyr Ala Arg Glu Val Arg Ser Leu Ile Trp
705                 710                 715                 720

Asp Arg Pro Asn His Asp Asn Phe Asn Val His Gly Tyr Glu Glu Gln
                725                 730                 735

Gly Ser Thr Thr Thr Pro Phe Asp Met Val Arg Val Asn Asn Ile Asp
            740                 745                 750

Arg Tyr Glu Leu Thr Ala Glu Ala Leu Arg Ala Val Asp Ala Asp Lys
        755                 760                 765

Phe Ala Asp Glu Ile Glu Lys Leu Glu Ala Phe Arg Thr Glu Ala Phe
    770                 775                 780

Gln Phe Ala Val Asp Asn Gly Tyr Asp His Pro Asp Tyr Thr Asp Trp
785                 790                 795                 800

Val Trp Ser Gly Val Gln Thr Glu Lys Pro Gly Ala Val Ser Ala Thr
                805                 810                 815

Ala Ala Thr Ala Gly Asp Asn Glu
            820

<210> SEQ ID NO 68
<211> LENGTH: 2385
<212> TYPE: DNA
<213> ORGANISM: Oenococcus oeni

<400> SEQUENCE: 68
atgactatca actacgattc aaaagactac ttaaaatacg tcgatgctta ctggagagcc      60
gctaactact tatccgtcgg tcaattgttc ttgagaaaca acccattgtt gaaggatgaa     120
ttacaatcta aggacgtcaa aatcaagcca attggtcatt ggggtactgt agctcctcaa     180
aactttatct atgcacactt gaatagagcc attttgaaat atgatttgaa tatgttctac     240
attgaaggta gtggtcatgg tggtcaagtt atggtctcta actcatactt ggatggttct     300
tataccgaaa cttacccaaa agttacacaa gatattcagg gtatgcaaag attgtttaaa     360
caattttcat tccctggtgg tatagcttcc catgctgcac cagaaacccc tggttctatc     420
```

```
cacgaaggtg gtgaattggg ttattccatt agtcatggtg ttggtgcaat attagataat   480
ccagacgtca ttgccgctgt agaaataggt gacggtgaat ctgaaacagg tcctttggca   540
gcctcttggt tctcagataa attcataaac ccaatccatg acggtgctgt tttacctatc   600
gtccaaatta atggttttaa gatctcaaac ccaacaatat tgtccagaat gagtgataga   660
gacttaacca actactacca tggtatgggt tgggaacctt tgtttgttga aactgatggt   720
tccgacaact tcaaagttca cgcagaaatg gcagatgccg ttgataaagc catcgaaaag   780
attaaagcta tccaaaagaa tgcaagaaac aacaacgatg acagtttgcc aatatggcct   840
atgatcgttt taagagcacc aaaaggttgg acaggtccta aaaaggattt ggacggtaac   900
ccaatcgaaa attcttttag agcacatcaa gtaccaattc ctgttgatgc aaaccatttg   960
gaacacaagg atatgttgat cgactggatg aagagttaca agcctgaaga attgttcaac  1020
gaagatggtt ctttaaagga atcgtaaag gttaaccaac caaaaggtca agaagaatg  1080
gctatgaacc ctataacaaa tggtggtatc aagccaagaa ccttgaacat gcctgatatg  1140
gaaagatttg cattccctaa aaattctttg aagaacaata gaaacctgg tatggatttg  1200
caagttgtct ccacttttat agctgaaatt attaagaaaa atccaatcaa tttcagacaa  1260
ttcggtcctg atgaaactat gtcaaacaga ttgtgggatg agtttaaagt aacaaacaga  1320
caatggatgc aagccgttca tgaaccaaat gatcaataca tggctcacag tggtagaatt  1380
ttggatgccc aattatctga acatcaagct gaaggttgga tggaaggtta tgttttgaca  1440
ggtagacacg cctttttcgc ttcatacgaa gcctttacta gaatcatcga ttccatgttg  1500
acacaatact acaagtggtt gagaaaggcc gttgaacaag attggagaca tgactatcca  1560
agtttaaacg tcattaatgc atctcacgcc ttccaacaag atcataatgg ttacacccac  1620
caagacccag gcatgttaac tcatatggct gaaaagggtc acgaatttgt taacgaattt  1680
ttgcctgctg atgcaaactc attgttagca gtcatgaata agtctttgca agtaagaaac  1740
aagattaata tcatcgtcgc atcaaagcat ccaagaactc aatggtttac aatagatgaa  1800
gccaaggaat tggtagacaa cggtttaggt attataccat gggcttccaa tgatgacggt  1860
gttgaacctg atgtagtttt tgctgcaggt ggtacagaag ctaccatgga atctttggcc  1920
gctatttcat tgttacatga atccttccca gaattaaagt ttagattcat taacgttatt  1980
gatttgttaa agttgagaaa gaaaggtgac aatgatgact atagaggttt gtcagatttg  2040
gaatttgacc attacttcac tagagaaaaa ccagtcgttt tctctttcca cggtttcgaa  2100
tctttggcta gagatttgtt ttatgacaga cataaccaca atgtcatttt tcatggttac  2160
agagaaaacg gtgacataac tacacctttt gacatgagag tattgaatca tttggataga  2220
ttccacttag ctaaagacgc aattaacgcc accaagtatg ctgatgttgc aggtcaattt  2280
gaccaaagaa tggatgacat gttagccaaa catactgctt acatttgtga tcaaggtacc  2340
gacttgccag aagttacttc ttggcaatgg caagatatta agtaa            2385
```

<210> SEQ ID NO 69
<211> LENGTH: 794
<212> TYPE: PRT
<213> ORGANISM: Oenococcus oeni

<400> SEQUENCE: 69

Met Thr Ile Asn Tyr Asp Ser Lys Asp Tyr Leu Lys Tyr Val Asp Ala
1               5                   10                  15

Tyr Trp Arg Ala Ala Asn Tyr Leu Ser Val Gly Gln Leu Phe Leu Arg

-continued

```
                20                  25                  30
Asn Asn Pro Leu Leu Lys Asp Glu Leu Gln Ser Lys Asp Val Lys Ile
            35                  40                  45
Lys Pro Ile Gly His Trp Gly Thr Val Ala Pro Gln Asn Phe Ile Tyr
 50                  55                  60
Ala His Leu Asn Arg Ala Ile Leu Lys Tyr Asp Leu Asn Met Phe Tyr
 65                  70                  75                  80
Ile Glu Gly Ser Gly His Gly Gly Gln Val Met Val Ser Asn Ser Tyr
                85                  90                  95
Leu Asp Gly Ser Tyr Thr Glu Thr Tyr Pro Lys Val Thr Gln Asp Ile
            100                 105                 110
Gln Gly Met Gln Arg Leu Phe Lys Gln Phe Ser Phe Pro Gly Gly Ile
            115                 120                 125
Ala Ser His Ala Ala Pro Glu Thr Pro Gly Ser Ile His Glu Gly Gly
            130                 135                 140
Glu Leu Gly Tyr Ser Ile Ser His Gly Val Gly Ala Ile Leu Asp Asn
145                 150                 155                 160
Pro Asp Val Ile Ala Ala Val Glu Ile Gly Asp Gly Glu Ser Glu Thr
                165                 170                 175
Gly Pro Leu Ala Ala Ser Trp Phe Ser Asp Lys Phe Ile Asn Pro Ile
            180                 185                 190
His Asp Gly Ala Val Leu Pro Ile Val Gln Ile Asn Gly Phe Lys Ile
            195                 200                 205
Ser Asn Pro Thr Ile Leu Ser Arg Met Ser Asp Arg Asp Leu Thr Asn
            210                 215                 220
Tyr Tyr His Gly Met Gly Trp Glu Pro Leu Phe Val Glu Thr Asp Gly
225                 230                 235                 240
Ser Asp Asn Phe Lys Val His Ala Glu Met Ala Asp Ala Val Asp Lys
                245                 250                 255
Ala Ile Glu Lys Ile Lys Ala Ile Gln Lys Asn Ala Arg Asn Asn Asn
            260                 265                 270
Asp Asp Ser Leu Pro Ile Trp Pro Met Ile Val Leu Arg Ala Pro Lys
            275                 280                 285
Gly Trp Thr Gly Pro Lys Lys Asp Leu Asp Gly Asn Pro Ile Glu Asn
            290                 295                 300
Ser Phe Arg Ala His Gln Val Pro Ile Pro Val Asp Ala Asn His Leu
305                 310                 315                 320
Glu His Lys Asp Met Leu Ile Asp Trp Met Lys Ser Tyr Lys Pro Glu
                325                 330                 335
Glu Leu Phe Asn Glu Asp Gly Ser Leu Lys Glu Ile Val Lys Val Asn
            340                 345                 350
Gln Pro Lys Gly Gln Arg Arg Met Ala Met Asn Pro Ile Thr Asn Gly
            355                 360                 365
Gly Ile Lys Pro Arg Thr Leu Asn Met Pro Asp Met Glu Arg Phe Ala
            370                 375                 380
Phe Pro Lys Asn Ser Leu Lys Asn Lys Lys Pro Gly Met Asp Leu
385                 390                 395                 400
Gln Val Val Ser Thr Phe Ile Ala Glu Ile Ile Lys Lys Asn Pro Ile
            405                 410                 415
Asn Phe Arg Gln Phe Gly Pro Asp Glu Thr Met Ser Asn Arg Leu Trp
            420                 425                 430
Asp Glu Phe Lys Val Thr Asn Arg Gln Trp Met Gln Ala Val His Glu
            435                 440                 445
```

Pro Asn Asp Gln Tyr Met Ala His Ser Gly Arg Ile Leu Asp Ala Gln
         450                 455                 460

Leu Ser Glu His Gln Ala Glu Gly Trp Met Glu Gly Tyr Val Leu Thr
465                 470                 475                 480

Gly Arg His Ala Phe Phe Ala Ser Tyr Glu Ala Phe Thr Arg Ile Ile
                485                 490                 495

Asp Ser Met Leu Thr Gln Tyr Tyr Lys Trp Leu Arg Lys Ala Val Glu
                500                 505                 510

Gln Asp Trp Arg His Asp Tyr Pro Ser Leu Asn Val Ile Asn Ala Ser
            515                 520                 525

His Ala Phe Gln Gln Asp His Asn Gly Tyr Thr His Gln Asp Pro Gly
        530                 535                 540

Met Leu Thr His Met Ala Glu Lys Gly His Glu Phe Val Asn Glu Phe
545                 550                 555                 560

Leu Pro Ala Asp Ala Asn Ser Leu Leu Ala Val Met Asn Lys Ser Leu
                565                 570                 575

Gln Val Arg Asn Lys Ile Asn Ile Ile Val Ala Ser Lys His Pro Arg
                580                 585                 590

Thr Gln Trp Phe Thr Ile Asp Glu Ala Lys Glu Leu Val Asp Asn Gly
            595                 600                 605

Leu Gly Ile Ile Pro Trp Ala Ser Asn Asp Asp Gly Val Glu Pro Asp
        610                 615                 620

Val Val Phe Ala Ala Gly Gly Thr Glu Ala Thr Met Glu Ser Leu Ala
625                 630                 635                 640

Ala Ile Ser Leu Leu His Glu Ser Phe Pro Glu Leu Lys Phe Arg Phe
                645                 650                 655

Ile Asn Val Ile Asp Leu Leu Lys Leu Arg Lys Lys Gly Asp Asn Asp
                660                 665                 670

Asp Tyr Arg Gly Leu Ser Asp Leu Glu Phe Asp His Tyr Phe Thr Arg
            675                 680                 685

Glu Lys Pro Val Val Phe Ser Phe His Gly Phe Glu Ser Leu Ala Arg
690                 695                 700

Asp Leu Phe Tyr Asp Arg His Asn His Asn Val Ile Phe His Gly Tyr
705                 710                 715                 720

Arg Glu Asn Gly Asp Ile Thr Thr Pro Phe Asp Met Arg Val Leu Asn
                725                 730                 735

His Leu Asp Arg Phe His Leu Ala Lys Asp Ala Ile Asn Ala Thr Lys
            740                 745                 750

Tyr Ala Asp Val Ala Gly Gln Phe Asp Gln Arg Met Asp Asp Met Leu
        755                 760                 765

Ala Lys His Thr Ala Tyr Ile Cys Asp Gln Gly Thr Asp Leu Pro Glu
770                 775                 780

Val Thr Ser Trp Gln Trp Gln Asp Ile Lys
785                 790

<210> SEQ ID NO 70
<211> LENGTH: 2598
<212> TYPE: DNA
<213> ORGANISM: Rhodosporidium toruloides

<400> SEQUENCE: 70
atggctgaca acgccgacgc tccaccacct ccaatagtcc cttcacaata cgctcaacat        60
ccagacgctc cattatcctc attaccagtt caattggacc cttctcaata tacagctaaa       120

-continued

```
tacccagcaa agcatttgga tgccattgtc gctaattgga gattgtcctg ttatttgggt      180
gctagtcaaa ttttcttgca atctaacgca atcttgtcaa gaaaattgac taaggatgac      240
gtaaaaccaa gaagagcaca tacaaatttg gctggtgaca tccaaggtgg tttgtcttta      300
gcctacgttc acacccaagc attgatcaga gaaaaggtg acgaagaagg tgctgaacca       360
aagatgattt tcgtcactgg tccaggtcat ggtgcccctg ctatattgtc tccattgtac      420
atcgaaggtg ctatctcaaa gttctaccca caatacccct tgaacgaaca aggtttagaa      480
aagttcgtta agtacttctc ctggccaggt ggtttcccta gtcatgtcaa cgctgaaaca      540
ccaggttgca tacacgaagg tggtgaattg ggttatgcct taggtgtagc ttacggttcc      600
gttatggaca gacctgaaca aatcagtgtt gtcgtagttg gtgacggtga atctgaaact      660
ggtccaactg caacagcctg gcattcacac aaatggttag atcctgcaga atccggtgcc      720
gttttgccaa tcttgcatgt caacggtttt aagatctctg aaagaactat cccaggtaca      780
atggataacg ttgaattgtc tttgttgtac tcaggttacg gttaccaagt cagattcgta      840
gaatacaaag ctcaaggtga agcacatatg ggtggtaatg atcctgctga cagagttttg      900
cacgaagaca tggctgcaag tttagattgg gcatatggtg aaataagaaa aatccaaaag      960
gccgctagat ctggtggtaa accaattgat aagccaagat ggcctatgat aatcttgaga     1020
tcacctaagg gttggacagg tccatcttca gaacatggta acaattgtt gaacaacttt      1080
gcctctcacc aagttccatt gcctgatgct aaaactgatg acgaagctaa cgcatatttg     1140
gaaagatggt tgaagagtta cgaagctgat aagttgttcg acttctctga agataactta     1200
aagagaggta caatcttcga ccaattgttg tacgaagcat tgcctaagga tatggaaaga     1260
agattaggtt tcgttaagga aacttacaac ggttacaagc cattggaatt agatgactgg     1320
aaaaagtacg gttttaaaaa gggtgaagac gtatcatgta tgaaagccat cgctggttac     1380
ttaacagatg ttattaaaag aaaccctaag gagtttagaa ttttcagtcc agacgaattg     1440
gctttaaata agttggatgg tgttttctct gtcactgaaa gaaacatgca atgggaccca     1500
gaaactgctc ataagggtgg tagagttaca gaaatgttgt ctgaacactc attgcaagca     1560
tggttacaag gttataccctt aactggtaga catggtgttt ttccatctta cgaagcattc     1620
ttgggtattg tcgccacaat gaccgtacaa tataccaagt ttatgaagat ggcattggaa     1680
actaattgga gaggtcctac cgcctcttta acttacatcg aaacttcaac atggaccaga     1740
caagaacata atggttactc ccaccaaaac ccaggtttcg taagtactgt tttgtccta      1800
cctagtcaat tagctagagt ttactttcca tcagatgcaa atacatccgt aagtgttatc     1860
gcccattgtt tgagatccaa aaattacata aacttaatag ttggtacaaa ggctccaacc     1920
cctgtctact tgtctgtaga agaagcagaa agacattgca ttgcaggtgc ctctgtttgg     1980
gaaaattatt cagttgataa gggtgtcgat ccagacgtcg tattggtagg catcggttac     2040
gaattaacag aagaagttat ccatgcagcc gctttgttga gaaggatttt tggtactgaa     2100
ttgagagtca gagttgtcaa cgtagttgat ttgttagtat tagctcctaa gggtgaccat     2160
ccacacgcct tggatgaagc tggttttaat tcattattcc cacctggtgt tcctatcatt     2220
tttaactacc atggttacgc aggtcaatta gcctccttgt tattcgatag aaaacactcc     2280
gttggtagaa gtagaatgag aatcttcgct tactcagaac aaggtactac aaccactcca     2340
tttgcaatga tgtgttgcaa taacactgat agattcaatt tggctgctga agcattggaa     2400
atggtcacat tgaatttgac aacccaacat aacattaccg tgaagaaaaa gagacacaga     2460
gtaggttcag tcgtagctag agcacatgaa agaatgtcct tctacaagca caaaaaggtt     2520
```

```
gtcatgatga gatacgctgc agaaacccaa aaggatcatc cagaaattgg tgaagttgca    2580
actttggccg aacaataa                                                  2598
```

<210> SEQ ID NO 71
<211> LENGTH: 865
<212> TYPE: PRT
<213> ORGANISM: Rhodosporidium toruloides

<400> SEQUENCE: 71

```
Met Ala Asp Asn Ala Asp Ala Pro Pro Pro Ile Val Pro Ser Gln
1               5                   10                  15

Tyr Ala Gln His Pro Asp Ala Pro Leu Ser Ser Leu Pro Val Gln Leu
            20                  25                  30

Asp Pro Ser Gln Tyr Thr Ala Lys Tyr Pro Ala Lys His Leu Asp Ala
        35                  40                  45

Ile Val Ala Asn Trp Arg Leu Ser Cys Tyr Leu Gly Ala Ser Gln Ile
    50                  55                  60

Phe Leu Gln Ser Asn Ala Ile Leu Ser Arg Lys Leu Thr Lys Asp Asp
65                  70                  75                  80

Val Lys Pro Arg Arg Ala His Thr Asn Leu Ala Gly Asp Ile Gln Gly
                85                  90                  95

Gly Leu Ser Leu Ala Tyr Val His Thr Gln Ala Leu Ile Arg Arg Lys
            100                 105                 110

Gly Asp Glu Glu Gly Ala Glu Pro Lys Met Ile Phe Val Thr Gly Pro
        115                 120                 125

Gly His Gly Ala Pro Ala Ile Leu Ser Pro Leu Tyr Ile Glu Gly Ala
    130                 135                 140

Ile Ser Lys Phe Tyr Pro Gln Tyr Pro Leu Asn Glu Gln Gly Leu Glu
145                 150                 155                 160

Lys Phe Val Lys Tyr Phe Ser Trp Pro Gly Gly Phe Pro Ser His Val
                165                 170                 175

Asn Ala Glu Thr Pro Gly Cys Ile His Glu Gly Gly Glu Leu Gly Tyr
            180                 185                 190

Ala Leu Gly Val Ala Tyr Gly Ser Val Met Asp Arg Pro Glu Gln Ile
        195                 200                 205

Ser Val Val Val Gly Asp Gly Glu Ser Glu Thr Gly Pro Thr Ala
    210                 215                 220

Thr Ala Trp His Ser His Lys Trp Leu Asp Pro Ala Glu Ser Gly Ala
225                 230                 235                 240

Val Leu Pro Ile Leu His Val Asn Gly Phe Lys Ile Ser Glu Arg Thr
                245                 250                 255

Ile Pro Gly Thr Met Asp Asn Val Glu Leu Ser Leu Leu Tyr Ser Gly
            260                 265                 270

Tyr Gly Tyr Gln Val Arg Phe Val Glu Tyr Lys Ala Gln Gly Glu Ala
        275                 280                 285

His Met Gly Gly Asn Asp Pro Ala Asp Arg Val Leu His Glu Asp Met
    290                 295                 300

Ala Ala Ser Leu Asp Trp Ala Tyr Gly Glu Ile Arg Lys Ile Gln Lys
305                 310                 315                 320

Ala Ala Arg Ser Gly Gly Lys Pro Ile Asp Lys Pro Arg Trp Pro Met
                325                 330                 335

Ile Ile Leu Arg Ser Pro Lys Gly Trp Thr Gly Pro Ser Ser Glu His
            340                 345                 350
```

```
Gly Lys Gln Leu Leu Asn Asn Phe Ala Ser His Gln Val Pro Leu Pro
            355                 360                 365

Asp Ala Lys Thr Asp Asp Glu Ala Asn Ala Tyr Leu Glu Arg Trp Leu
        370                 375                 380

Lys Ser Tyr Glu Ala Asp Lys Leu Phe Asp Phe Ser Glu Asp Asn Leu
385                 390                 395                 400

Lys Arg Gly Thr Ile Phe Asp Gln Leu Leu Tyr Glu Ala Leu Pro Lys
                405                 410                 415

Asp Met Glu Arg Arg Leu Gly Phe Val Lys Glu Thr Tyr Asn Gly Tyr
            420                 425                 430

Lys Pro Leu Glu Leu Asp Asp Trp Lys Lys Tyr Gly Phe Lys Lys Gly
        435                 440                 445

Glu Asp Val Ser Cys Met Lys Ala Ile Ala Gly Tyr Leu Thr Asp Val
    450                 455                 460

Ile Lys Arg Asn Pro Lys Glu Phe Arg Ile Phe Ser Pro Asp Glu Leu
465                 470                 475                 480

Ala Leu Asn Lys Leu Asp Gly Val Phe Ser Val Thr Glu Arg Asn Met
                485                 490                 495

Gln Trp Asp Pro Glu Thr Ala His Lys Gly Arg Val Thr Glu Met
            500                 505                 510

Leu Ser Glu His Ser Leu Gln Ala Trp Leu Gln Gly Tyr Thr Leu Thr
        515                 520                 525

Gly Arg His Gly Val Phe Pro Ser Tyr Glu Ala Phe Leu Gly Ile Val
    530                 535                 540

Ala Thr Met Thr Val Gln Tyr Thr Lys Phe Met Lys Met Ala Leu Glu
545                 550                 555                 560

Thr Asn Trp Arg Gly Pro Thr Ala Ser Leu Thr Tyr Ile Glu Thr Ser
                565                 570                 575

Thr Trp Thr Arg Gln Glu His Asn Gly Tyr Ser His Gln Asn Pro Gly
            580                 585                 590

Phe Val Ser Thr Val Leu Ser Leu Pro Ser Gln Leu Ala Arg Val Tyr
        595                 600                 605

Phe Pro Ser Asp Ala Asn Thr Ser Val Ser Val Ile Ala His Cys Leu
    610                 615                 620

Arg Ser Lys Asn Tyr Ile Asn Leu Ile Val Gly Thr Lys Ala Pro Thr
625                 630                 635                 640

Pro Val Tyr Leu Ser Val Glu Glu Ala Glu Arg His Cys Ile Ala Gly
                645                 650                 655

Ala Ser Val Trp Glu Asn Tyr Ser Val Asp Lys Gly Val Asp Pro Asp
            660                 665                 670

Val Val Leu Val Gly Ile Gly Tyr Glu Leu Thr Glu Glu Val Ile His
        675                 680                 685

Ala Ala Ala Leu Leu Arg Lys Asp Phe Gly Thr Glu Leu Arg Val Arg
    690                 695                 700

Val Val Asn Val Val Asp Leu Leu Val Leu Ala Pro Lys Gly Asp His
705                 710                 715                 720

Pro His Ala Leu Asp Glu Ala Gly Phe Asn Ser Leu Phe Pro Pro Gly
                725                 730                 735

Val Pro Ile Ile Phe Asn Tyr His Gly Tyr Ala Gly Gln Leu Ala Ser
            740                 745                 750

Leu Leu Phe Asp Arg Lys His Ser Val Gly Arg Ser Arg Met Arg Ile
        755                 760                 765

Phe Ala Tyr Ser Glu Gln Gly Thr Thr Thr Thr Pro Phe Ala Met Met
```

```
              770             775             780
Cys Cys Asn Asn Thr Asp Arg Phe Asn Leu Ala Ala Glu Ala Leu Glu
785                 790             795                 800

Met Val Thr Leu Asn Leu Thr Thr Gln His Asn Ile Thr Gly Glu Glu
                805             810             815

Lys Arg His Arg Val Gly Ser Val Val Ala Arg Ala His Glu Arg Met
            820             825             830

Ser Phe Tyr Lys His Lys Lys Val Val Met Met Arg Tyr Ala Ala Glu
            835             840             845

Thr Gln Lys Asp His Pro Glu Ile Gly Glu Val Ala Thr Leu Ala Glu
        850             855             860

Gln
865

<210> SEQ ID NO 72
<211> LENGTH: 2478
<212> TYPE: DNA
<213> ORGANISM: Scardovia inopinata

<400> SEQUENCE: 72
atgacatctc ctgtaattgg tacccatgg aagaagttgg atagacctgt aaccgacgaa      60
gcattggaag tgttgataa gtattggaga gctgcaaact atatgtccat cggtcaaata     120
tatttgagaa gtaatccatt aatgaaggaa ccttttacaa gagaagatgt aaagcataga     180
ttggttggtc actggggtac tacaccaggt ttgaactttt tattcggtca tatcaacaga     240
ttgatcgcag atcaccaaca aaacactgtt ttcattatgg gtccaggtca tggtggtcct     300
gctggtactt ctcaatctta tttggatggt acctacactg aatactaccc aaagataaca     360
aacgacgaag ctggtttgca aaagttttc agacaatttt cctacccagg tggtatccct     420
agtcattacg caccagaaac tcctggttca attcacgaag tggtgaatt gggttatgct     480 ttatctcatg cctacggtgc tatcatgaat aacccatcat tgtttgtagc cgctattgtt     540
ggtgacggtg aagctgaaac tggtccttta gcaacaggtt ggcaatctaa caagttggtc     600
aatccaagaa cagatggtat cgtattgcct atattgcatt tgaatggtta caagattgcc     660
aatccaacca tattggctag aatctctgac gaagaattac acgatttctt tagaggtatg     720
ggttataatc cttacgaatt tgttgcaggt ttcgatgacg aagaccatat gtctattcac     780
agaagattcg ctgatttgtt agaaactgta ttcgacgaaa tctgtgatat caaagctact     840
gcacaaacaa atgatgttga cagaccattc taccctatga tcatattcag accccaaaa      900 ggttggactt gccctaagtt tattgatggt aaaaagaccg aaggttcctg agagcacat      960 caagtcccat tggccagtgc tagagatact gaagaacact tccaagtatt gaagaattgg    1020
ttagaatctt acaagcctga agaattgttc gatgaaaagg gtacattgag accagaagtt    1080
accgagttta tgcctaaggg tgacttgaga attggtgcta atccaaacgc aaatggtggt    1140
agaatcagag aagatttgaa attgcctgtt ttggatgact acaaagtcaa ggaagtagaa    1200
gaatttggtc atggtggggg tcaattggaa gcaactagaa gattaggtgt ttacacaaga    1260
gacatcatta gttaaacccc agattccttt tgaatattcg gtcctgatga aactgctagt    1320
aatagattgc aagcagccta tgaagttaca acaaacaat gggacaatgg ttacttgtct    1380
tcattagtcg atgaacatat ggctgtcacc ggtcaagtaa ctgaacaatt atcagaacac    1440
caaatggaag gttttattga aggttacgtt ttgacaggta gacatggtat atggtccagt    1500
tacgaatctt tcgttcatgt catcgattca atgttgaatc aacacgctaa gtggttagaa    1560
```

```
gcaactgtta gagaaattcc atggagaaag cctatatctt cagttaactt gttagtctcc    1620
agtcatgtat ggagacaaga ccataatggt ttttctcacc aagatccagg tgttgtctca    1680
gttttgttga acaaaacttt taataacgac catgtcattg gtatctattt cgcaaccgat    1740
gccaatatgt tgttagccat tggtgaaaaa gcatataaat ctactaacaa gataaatgct    1800
ataatcgcag gtaaacaacc agctgcaacc tggttgtcat tagatgaagc aagagccgaa    1860
ttaactaaag gtgccgctga atggaagtgg gcctccaccg ctaaaaataa cgacgaaact    1920
gaaatagttt tagcaagtgt tggtgacgtc ccaactcaag aaataatggc agccgctgac    1980
aaattgaagg gttacggtat taagtttaaa gtagttaacg tcgtagattt gttatcttta    2040
caaaacccaa aggaaaacaa cgaagcattg tcagacgaag agtttactga attattcacc    2100
gccgataagc ctgtattgat ggcatatcat tcctacgcca gagaagttaa gggtttgttg    2160
ttcgatagac caaacaacgc taacttcaat attcacggtt atcaagaaca aggttcaacc    2220
actacacctt tcgatatggt tagagttaac gatatcgaca gatacgaatt gacagctgaa    2280
gcattgagaa tgttagatgc cgacaagtac gctgatgaca ttaaaaagtt agaagatttc    2340
agacaagaag cattccaata tgccgttgat aacggtcatg atcacccaga ctacacagat    2400
tgggtttggt ctggtgtcaa aaccgataag cctggtgcag ttacagccac cgcagccact    2460
gctggtgaca atgaataa                                                  2478

<210> SEQ ID NO 73
<211> LENGTH: 825
<212> TYPE: PRT
<213> ORGANISM: Scardovia inopinata

<400> SEQUENCE: 73

Met Thr Ser Pro Val Ile Gly Thr Pro Trp Lys Lys Leu Asp Arg Pro
1               5                   10                  15

Val Thr Asp Glu Ala Leu Glu Gly Val Asp Lys Tyr Trp Arg Ala Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Phe Gly His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ser Gln Ser Tyr Leu Asp Gly Thr Tyr
            100                 105                 110

Thr Glu Tyr Tyr Pro Lys Ile Thr Asn Asp Glu Ala Gly Leu Gln Lys
        115                 120                 125

Phe Phe Arg Gln Phe Ser Tyr Pro Gly Gly Ile Pro Ser His Tyr Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asn Asn Pro Ser Leu Phe Val
                165                 170                 175

Ala Ala Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205
```

```
Leu Pro Ile Leu His Leu Asn Gly Tyr Lys Ile Ala Asn Pro Thr Ile
    210                 215                 220
Leu Ala Arg Ile Ser Asp Glu Glu Leu His Asp Phe Phe Arg Gly Met
225                 230                 235                 240
Gly Tyr Asn Pro Tyr Glu Phe Val Ala Gly Phe Asp Asp Glu Asp His
                245                 250                 255
Met Ser Ile His Arg Arg Phe Ala Asp Leu Leu Glu Thr Val Phe Asp
            260                 265                 270
Glu Ile Cys Asp Ile Lys Ala Thr Ala Gln Thr Asn Asp Val Asp Arg
        275                 280                 285
Pro Phe Tyr Pro Met Ile Ile Phe Arg Thr Pro Lys Gly Trp Thr Cys
    290                 295                 300
Pro Lys Phe Ile Asp Gly Lys Lys Thr Glu Gly Ser Trp Arg Ala His
305                 310                 315                 320
Gln Val Pro Leu Ala Ser Ala Arg Asp Thr Glu Glu His Phe Gln Val
                325                 330                 335
Leu Lys Asn Trp Leu Glu Ser Tyr Lys Pro Glu Glu Leu Phe Asp Glu
            340                 345                 350
Lys Gly Thr Leu Arg Pro Glu Val Thr Glu Phe Met Pro Lys Gly Asp
        355                 360                 365
Leu Arg Ile Gly Ala Asn Pro Asn Ala Asn Gly Gly Arg Ile Arg Glu
    370                 375                 380
Asp Leu Lys Leu Pro Val Leu Asp Asp Tyr Lys Val Lys Glu Val Glu
385                 390                 395                 400
Glu Phe Gly His Gly Trp Gly Gln Leu Glu Ala Thr Arg Arg Leu Gly
                405                 410                 415
Val Tyr Thr Arg Asp Ile Ile Lys Leu Asn Pro Asp Ser Phe Arg Ile
            420                 425                 430
Phe Gly Pro Asp Glu Thr Ala Ser Asn Arg Leu Gln Ala Ala Tyr Glu
        435                 440                 445
Val Thr Asn Lys Gln Trp Asp Asn Gly Tyr Leu Ser Ser Leu Val Asp
    450                 455                 460
Glu His Met Ala Val Thr Gly Gln Val Thr Glu Gln Leu Ser Glu His
465                 470                 475                 480
Gln Met Glu Gly Phe Ile Glu Gly Tyr Val Leu Thr Gly Arg His Gly
                485                 490                 495
Ile Trp Ser Ser Tyr Glu Ser Phe Val His Val Ile Asp Ser Met Leu
            500                 505                 510
Asn Gln His Ala Lys Trp Leu Glu Ala Thr Val Arg Glu Ile Pro Trp
        515                 520                 525
Arg Lys Pro Ile Ser Ser Val Asn Leu Leu Val Ser Ser His Val Trp
    530                 535                 540
Arg Gln Asp His Asn Gly Phe Ser His Gln Asp Pro Gly Val Val Ser
545                 550                 555                 560
Val Leu Leu Asn Lys Thr Phe Asn Asn Asp His Val Ile Gly Ile Tyr
                565                 570                 575
Phe Ala Thr Asp Ala Asn Met Leu Leu Ala Ile Gly Glu Lys Ala Tyr
            580                 585                 590
Lys Ser Thr Asn Lys Ile Asn Ala Ile Ile Ala Gly Lys Gln Pro Ala
        595                 600                 605
Ala Thr Trp Leu Ser Leu Asp Glu Ala Arg Ala Glu Leu Thr Lys Gly
    610                 615                 620
```

| | | | | | | | | | | | |
|---|---|---|---|---|---|---|---|---|---|---|---|
| Ala | Ala | Glu | Trp | Lys | Trp | Ala | Ser | Thr | Ala | Lys | Asn Asn Asp Glu Thr |
| 625 | | | | 630 | | | | 635 | | | 640 |
| Glu | Ile | Val | Leu | Ala | Ser | Val | Gly | Asp | Val | Pro | Thr Gln Glu Ile Met |
| | | | 645 | | | | | 650 | | | 655 |
| Ala | Ala | Ala | Asp | Lys | Leu | Lys | Gly | Tyr | Gly | Ile | Lys Phe Lys Val Val |
| | | 660 | | | | | 665 | | | | 670 |
| Asn | Val | Val | Asp | Leu | Leu | Ser | Leu | Gln | Asn | Pro | Lys Glu Asn Asn Glu |
| | 675 | | | | | 680 | | | | | 685 |
| Ala | Leu | Ser | Asp | Glu | Glu | Phe | Thr | Glu | Leu | Phe | Thr Ala Asp Lys Pro |
| 690 | | | | | 695 | | | | | 700 | |
| Val | Leu | Met | Ala | Tyr | His | Ser | Tyr | Ala | Arg | Glu | Val Lys Gly Leu Leu |
| 705 | | | | 710 | | | | 715 | | | 720 |
| Phe | Asp | Arg | Pro | Asn | Asn | Ala | Asn | Phe | Asn | Ile | His Gly Tyr Gln Glu |
| | | | 725 | | | | | 730 | | | 735 |
| Gln | Gly | Ser | Thr | Thr | Thr | Pro | Phe | Asp | Met | Val | Arg Val Asn Asp Ile |
| | | | 740 | | | | 745 | | | | 750 |
| Asp | Arg | Tyr | Glu | Leu | Thr | Ala | Glu | Ala | Leu | Arg | Met Leu Asp Ala Asp |
| | | 755 | | | | | 760 | | | | 765 |
| Lys | Tyr | Ala | Asp | Asp | Ile | Lys | Lys | Leu | Glu | Asp | Phe Arg Gln Glu Ala |
| 770 | | | | | | 775 | | | | 780 | |
| Phe | Gln | Tyr | Ala | Val | Asp | Asn | Gly | His | Asp | His | Pro Asp Tyr Thr Asp |
| 785 | | | | 790 | | | | 795 | | | 800 |
| Trp | Val | Trp | Ser | Gly | Val | Lys | Thr | Asp | Lys | Pro | Gly Ala Val Thr Ala |
| | | | 805 | | | | | 810 | | | 815 |
| Thr | Ala | Thr | Ala | Gly | Asp | Asn | Glu | | | | |
| | 820 | | | | | 825 | | | | | |

<210> SEQ ID NO 74
<211> LENGTH: 2469
<212> TYPE: DNA
<213> ORGANISM: Schizosaccharomyces japonicus

<400> SEQUENCE: 74

```
atgaagttcg aagccaccaa agaatttatg aacgaatcca gaacagaagc cgcaaaagcc    60
gacccatcac cattacaatc ccacttacca gctactttgg atacattgca agttcatttg   120
ttgaaagact atgtacctga agatgacttg gttacattaa agaatttcca agagtatgt   180
aactacatcg ctgcagccat gattttcttg tgcgataacg ttttgttaga aaacaaatta   240
acatctgacc atattaagcc aagattgtta ggtcattggg gtacttgtcc tgccttggct   300
ttagcatact cccattgcaa cagaatcatc agtaagtaca atttggatat gttatttgtt   360
actggtccag gtcacggtgc ccctgctatt ttggctgcat tatacatcga aggttcttta   420
caagcatatt acccacaata cggtcataac atgcaaggtt tgcacagatt gatcaccaaa   480
ttttctgtca ctggtggttt cccatcacat gtcaatgccg aagtacctgg tgctatacac   540
gaaggtggtg aattgggtta tgcattatct gtatcatacg gtgccgtttt ggatagacca   600
aatttgattg ttgcctgtgt tgtcggtgac ggtgaagctg aaaccggtcc tactgccgct   660
tcttggcatt gccacaaatt catagatcca gcagaatcag gtgccgtcat acctatcttg   720
aatttgaatg gttttaagat ctcagaaaga acagtatatg ttgtatggga tagaagagaa   780
ttgtctgctt tgttttctgg tttcggttac aagtagtttt tcgtagatta cagaactgct   840
gatgacgtta atagagatat ggcagccgct atggactggt gtgttgaaat catacatgaa   900
atacaagatg cagccagagc aggtacacca ataatcaaac caagatggcc tatgattata   960
```

-continued

```
ttgcacaccc caaagggttg gggttgccct aaaactttgc atggtaaacc attagaaggt    1020
acttttagag cacatcaagt tcctttgaaa aatgctaaga ctgatgcaga agaattgggt    1080
caattagaaa actggttgaa gtcttaccat atagaagatt tcatcgacaa gtcaaacggt    1140
ttgccattaa agggtttgat tgaacactta ccacctagag taaaaagaat gggtcaaaag    1200
actgatgcta ataacgactt ccaaccatta tgtgttcctg attggaacga cttttctatc    1260
gatagaggta ttttggaatc tgctacctca attgttggta aatacttgga tagagtctta    1320
caagcaaacc caaagacttt gagattattt tcccctgatg aattagccag taacaaattg    1380
gacggtgttt tagaacattc aaacagaaca ttgcaaaccg atgccatatc cgcttggagt    1440
agaggtagag taacagaagt tttgtctgaa catatgtgcc aaggtttcat gcaaggttat    1500
accttaactg gtagaaccgc tattttttcca tcctacgaag cattcttgcc tatcataact    1560
tctatgacag ttcaatacac caagttcttg aagatggcat tagaaactaa gtggcatggt    1620 agtcggtt ccttaaacta cgtaactaca agtacatggg ctagacaaga acataatggt    1680
ttttctcacc aatcaccaag attcataacc actatgttgt cctttaagcc tacattaacc    1740
agagtttatt tcccacctga tacaaactgt ttcttgtcta ctatcgcaca ttgcttatct    1800
tcagacaatg gtgttaactt gatggtctcc agtaaaaatc caggtccttc ctggttaagt    1860
agagaagaag ctgaagaaca ttgtgtcgca ggtgcctctg tatggaagtt cgcatcaact    1920
gatggtggtt tagatccaga cgtcgtatta gttggtatcg gtaacgaaat catgttcgaa    1980
gtcatagctg cagcctctat cttggctcat gatttgccaa aattgagaat tagagttgtc    2040
aacatcacag atttgatgat cttagccgac aatcatccac actccatgag tgaaatcgag    2100
tttaatgctt tattcactcc taacagacat gtccacttca attatcatgg ttacgtaatg    2160
gatttgcaat ctttgttatt ttcaagaatc gacgcatcta gagtttcaat ggaaggttat    2220
tgtgaagaag gtacaaccac tacaccattc aatatgatga ttgcaaacag aacttctaga    2280
taccatgttg ccatggctgc agtcgctggt gcaacatgta accctgaagt tgctatgaat    2340
tgccacaaat tgatatcaaa ctacaagcat agattgactc aaattaaaca ctatatatac    2400
gaaaacggtg ttgatccaga aggtactttt gatatccctg acaatttgac aaagggtcaa    2460
gtcatttaa                                                           2469
```

<210> SEQ ID NO 75
<211> LENGTH: 822
<212> TYPE: PRT
<213> ORGANISM: Schizosaccharomyces japonicus

<400> SEQUENCE: 75

```
Met Lys Phe Glu Ala Thr Lys Glu Phe Met Asn Glu Ser Arg Thr Glu
1               5                   10                  15

Ala Ala Lys Ala Asp Pro Ser Pro Leu Gln Ser His Leu Pro Ala Thr
            20                  25                  30

Leu Asp Thr Leu Gln Val His Leu Leu Lys Asp Tyr Val Pro Glu Asp
        35                  40                  45

Asp Leu Val Thr Leu Lys Asn Phe Gln Arg Val Cys Asn Tyr Ile Ala
    50                  55                  60

Ala Ala Met Ile Phe Leu Cys Asp Asn Val Leu Glu Asn Lys Leu
65                  70                  75                  80

Thr Ser Asp His Ile Lys Pro Arg Leu Leu Gly His Trp Gly Thr Cys
                85                  90                  95

Pro Ala Leu Ala Leu Ala Tyr Ser His Cys Asn Arg Ile Ile Ser Lys
```

-continued

```
                100                 105                 110
Tyr Asn Leu Asp Met Leu Phe Val Thr Gly Pro Gly His Gly Ala Pro
            115                 120                 125
Ala Ile Leu Ala Ala Leu Tyr Ile Glu Gly Ser Leu Gln Ala Tyr Tyr
        130                 135                 140
Pro Gln Tyr Gly His Asn Met Gln Gly Leu His Arg Leu Ile Thr Lys
145                 150                 155                 160
Phe Ser Val Thr Gly Gly Phe Pro Ser His Val Asn Ala Glu Val Pro
                165                 170                 175
Gly Ala Ile His Glu Gly Gly Glu Leu Gly Tyr Ala Leu Ser Val Ser
            180                 185                 190
Tyr Gly Ala Val Leu Asp Arg Pro Asn Leu Ile Val Ala Cys Val Val
        195                 200                 205
Gly Asp Gly Glu Ala Glu Thr Gly Pro Thr Ala Ala Ser Trp His Cys
210                 215                 220
His Lys Phe Ile Asp Pro Ala Glu Ser Gly Ala Val Ile Pro Ile Leu
225                 230                 235                 240
Asn Leu Asn Gly Phe Lys Ile Ser Glu Arg Thr Val Tyr Gly Cys Met
                245                 250                 255
Asp Arg Arg Glu Leu Ser Ala Leu Phe Ser Gly Phe Gly Tyr Gln Val
            260                 265                 270
Val Phe Val Asp Tyr Arg Thr Ala Asp Asp Val Asn Arg Asp Met Ala
        275                 280                 285
Ala Ala Met Asp Trp Cys Val Glu Ile His Glu Ile Gln Asp Ala
        290                 295                 300
Ala Arg Ala Gly Thr Pro Ile Ile Lys Pro Arg Trp Pro Met Ile Ile
305                 310                 315                 320
Leu His Thr Pro Lys Gly Trp Gly Cys Pro Lys Thr Leu His Gly Lys
                325                 330                 335
Pro Leu Glu Gly Thr Phe Arg Ala His Gln Val Pro Leu Lys Asn Ala
            340                 345                 350
Lys Thr Asp Ala Glu Glu Leu Gly Gln Leu Glu Asn Trp Leu Lys Ser
        355                 360                 365
Tyr His Ile Glu Asp Phe Ile Asp Lys Ser Asn Gly Leu Pro Leu Lys
        370                 375                 380
Gly Leu Ile Glu His Leu Pro Pro Arg Val Lys Arg Met Gly Gln Lys
385                 390                 395                 400
Thr Asp Ala Asn Asn Asp Phe Gln Pro Leu Cys Val Pro Asp Trp Asn
                405                 410                 415
Asp Phe Ser Ile Asp Arg Gly Ile Leu Glu Ser Ala Thr Ser Ile Val
            420                 425                 430
Gly Lys Tyr Leu Asp Arg Val Leu Gln Ala Asn Pro Lys Thr Leu Arg
        435                 440                 445
Leu Phe Ser Pro Asp Glu Leu Ala Ser Asn Lys Leu Asp Gly Val Leu
        450                 455                 460
Glu His Ser Asn Arg Thr Leu Gln Thr Asp Ala Ile Ser Ala Trp Ser
465                 470                 475                 480
Arg Gly Arg Val Thr Glu Val Leu Ser Glu His Met Cys Gln Gly Phe
                485                 490                 495
Met Gln Gly Tyr Thr Leu Thr Gly Arg Thr Ala Ile Phe Pro Ser Tyr
            500                 505                 510
Glu Ala Phe Leu Pro Ile Ile Thr Ser Met Thr Val Gln Tyr Thr Lys
        515                 520                 525
```

Phe Leu Lys Met Ala Leu Glu Thr Lys Trp His Gly Arg Val Gly Ser
            530                 535                 540

Leu Asn Tyr Val Thr Thr Ser Thr Trp Ala Arg Gln Glu His Asn Gly
545                 550                 555                 560

Phe Ser His Gln Ser Pro Arg Phe Ile Thr Thr Met Leu Ser Phe Lys
                565                 570                 575

Pro Thr Leu Thr Arg Val Tyr Phe Pro Pro Asp Thr Asn Cys Phe Leu
            580                 585                 590

Ser Thr Ile Ala His Cys Leu Ser Ser Asp Asn Gly Val Asn Leu Met
            595                 600                 605

Val Ser Ser Lys Asn Pro Gly Pro Ser Trp Leu Ser Arg Glu Glu Ala
        610                 615                 620

Glu Glu His Cys Val Ala Gly Ala Ser Val Trp Lys Phe Ala Ser Thr
625                 630                 635                 640

Asp Gly Gly Leu Asp Pro Asp Val Val Leu Val Gly Ile Gly Asn Glu
                645                 650                 655

Ile Met Phe Glu Val Ile Ala Ala Ser Ile Leu Ala His Asp Leu
                660                 665                 670

Pro Lys Leu Arg Ile Arg Val Val Asn Ile Thr Asp Leu Met Ile Leu
            675                 680                 685

Ala Asp Asn His Pro His Ser Met Ser Glu Ile Glu Phe Asn Ala Leu
690                 695                 700

Phe Thr Pro Asn Arg His Val His Phe Asn Tyr His Gly Tyr Val Met
705                 710                 715                 720

Asp Leu Gln Ser Leu Leu Phe Ser Arg Ile Asp Ala Ser Arg Val Ser
                725                 730                 735

Met Glu Gly Tyr Cys Glu Glu Gly Thr Thr Thr Pro Phe Asn Met
            740                 745                 750

Met Ile Ala Asn Arg Thr Ser Arg Tyr His Val Ala Met Ala Ala Val
            755                 760                 765

Ala Gly Ala Thr Cys Asn Pro Glu Val Ala Met Asn Cys His Lys Leu
        770                 775                 780

Ile Ser Asn Tyr Lys His Arg Leu Thr Gln Ile Lys His Tyr Ile Tyr
785                 790                 795                 800

Glu Asn Gly Val Asp Pro Glu Gly Thr Phe Asp Ile Pro Asp Asn Leu
                805                 810                 815

Thr Lys Gly Gln Val Ile
            820

<210> SEQ ID NO 76
<211> LENGTH: 2430
<212> TYPE: DNA
<213> ORGANISM: Trichoder mareesei

<400> SEQUENCE: 76
atgccaggtg aagtcataga ccaaccaaac cctcctccat taacatccca cttgccagat      60
accatagaag aattagcagt aaagcctagt aaagctccat tgtctaattt ggatttggtt     120
tctttgagag aatttcaaag agctgcatgt tatatagctt ccgcaatgat cttcttaaag     180
gataacgtat tgttggacag agaattgaga tttgaagatg ttaagcctag attgttaggt     240
cattggggta cttgcccagg tttgatattg atctggtcac acttaaattt gttaattaga     300
gattcttcac aagacatgtt gttcgttata ggtcctggtc atggtgcacc agccgcttta     360 gcctgttttgt ggttagaagg ttcttttggaa agattttacc ctgataagta cagaacagac     420

-continued

```
aaggaaggtt tgcataattt gataacaaaa ttttctgttc caaccggttt cccttctcat    480
ataaacccag aaactcctgg ttgtatccac gaaggtggtg aattgggtta tgccttagct    540
gtctcatttg gtgctgtaat ggataagcct gacttgatag ttccatgcgt tgtcggtgac    600
ggtgaagcag aaacaggtcc aaccgcagcc gcttggcatt caatcaaata cttagatcct    660
gctgaatccg gtgcagttat cccaattttg cacgtcaacg gttttaagat atctgaaaga    720
actatcttcg gttgtatgga taacacagaa ttggttttgt tattctctgg ttatggttac    780
gaagtttgca tcgtcgaaaa tttggatgct attgacactg aattgcatac agccttattt    840
tgggctttga gtgaaattaa aagaatacaa ggtgcagcca gatctggtaa ccctattacc    900
aagccaagat ggcctatgat tatattgaga actcctaaag gttggaccgg tccaagaact    960
gttgatgaca gatcattga aggttctttc catgcacacc aagtaccagt tacaaaagcc   1020
aataaggatg aaggtcattt gagaattta caagattggt tgaagagtta cgacgttaga   1080
ggtttgttac cagatggtaa accttctggt gacttttttgg acattttacc acctgatcct   1140
cataaaagat taggtcaatc taagttggct tacgactgtc atcaaccatt ggatttgcct   1200
gactggagac cacactcagt tgataaattt gaagaagcct ccagtatgca caatccggt    1260 aaattcttgg atgtagttgc tagacaaaac atgaagactt ttagaatttt ctctccagat   1320
gaattagaat caaataagtt atccgcagta ttggatcatt cttcaagaaa cttccaatgg   1380
gaccaatatt ctagagcaca aggtggtaga gttatagaaa tcttgtccga acactgttgc   1440
caaggtttct tgcaaggtta cttttgaca ggtagaactg ctattttttcc ttcttacgaa   1500 tcattcttag gtatcatcca tacaatgatg atacaatact ccaaattcag taagatatct   1560
agaaaattgc catggagagg tgacttgtct tctattaatt acatcgaaac ctctacttgg   1620
gcaagacaag aacataatgg ttttttcacac caaaacccat ccttcatagg tgctgtcttg   1680
aatttgaaag cagaaatcgc cagagtatac ttgccacctg atgcaaactg tttcttgtct   1740
actttgcatc actgcttgca atccaaaaat tacgtcaact tgatgatagg tagtaagcaa   1800 ccaaccctg tatacttgtc tgctgaagat gcacaaagac attgtgaaga cggtgccagt   1860
atatggagat gggcttctac ccatgatggt gaacaccctg acgtcgtatt agttggtatc   1920
ggtgtcgaag taactttga agtcattaaa gctgcacaat tgttatctag attagctcca   1980
aatttgagag ttagagttgt caacgtcaca gatttgttag tattacctca tgaaagtcat   2040
cacccacacg ctttggactc taaagcattt gaagatatgt tcacattgga caagccagtc   2100
tgcttcaatt atcattcata cgctaccgaa ttacaaggtt tgttatttgg tagacctgca   2160
ttgcacagaa tgtcagttga aggttataaa gaagaaggtt ccactacaac cccattcgat   2220
atgatgttgt taaacactgt ttcaagattc catgttgcct ccagagcttt gaaggccgct   2280
gcagcccaaa acgatgaagt caaggaaaac ttaagtgcat tgttagccaa ggtagatgac   2340
gaaatgaagt ctgttaagga ttacatcgaa caatggggta agttgacccc agatgacatc   2400
tatgaattgg atttcttgaa gaaagactaa                                    2430
```

<210> SEQ ID NO 77
<211> LENGTH: 809
<212> TYPE: PRT
<213> ORGANISM: Trichoder mareesei

<400> SEQUENCE: 77

Met Pro Gly Glu Val Ile Asp Gln Pro Asn Pro Pro Leu Thr Ser
1               5                   10                  15

-continued

His Leu Pro Asp Thr Ile Glu Glu Leu Ala Val Lys Pro Ser Lys Ala
    20                  25                  30

Pro Leu Ser Asn Leu Asp Leu Val Ser Leu Arg Glu Phe Gln Arg Ala
            35                  40                  45

Ala Cys Tyr Ile Ala Ser Ala Met Ile Phe Leu Lys Asp Asn Val Leu
50                  55                  60

Leu Asp Arg Glu Leu Arg Phe Glu Asp Val Lys Pro Arg Leu Leu Gly
65                  70                  75                  80

His Trp Gly Thr Cys Pro Gly Leu Ile Leu Ile Trp Ser His Leu Asn
                85                  90                  95

Leu Leu Ile Arg Asp Ser Ser Gln Asp Met Leu Phe Val Ile Gly Pro
            100                 105                 110

Gly His Gly Ala Pro Ala Ala Leu Ala Cys Leu Trp Leu Glu Gly Ser
        115                 120                 125

Leu Glu Arg Phe Tyr Pro Asp Lys Tyr Arg Thr Asp Lys Glu Gly Leu
130                 135                 140

His Asn Leu Ile Thr Lys Phe Ser Val Pro Thr Gly Phe Pro Ser His
145                 150                 155                 160

Ile Asn Pro Glu Thr Pro Gly Cys Ile His Glu Gly Gly Glu Leu Gly
                165                 170                 175

Tyr Ala Leu Ala Val Ser Phe Gly Ala Val Met Asp Lys Pro Asp Leu
            180                 185                 190

Ile Val Pro Cys Val Val Gly Asp Gly Glu Ala Glu Thr Gly Pro Thr
        195                 200                 205

Ala Ala Ala Trp His Ser Ile Lys Tyr Leu Asp Pro Ala Glu Ser Gly
        210                 215                 220

Ala Val Ile Pro Ile Leu His Val Asn Gly Phe Lys Ile Ser Glu Arg
225                 230                 235                 240

Thr Ile Phe Gly Cys Met Asp Asn Thr Glu Leu Val Leu Leu Phe Ser
                245                 250                 255

Gly Tyr Gly Tyr Glu Val Cys Ile Val Glu Asn Leu Asp Ala Ile Asp
            260                 265                 270

Thr Glu Leu His Thr Ala Leu Phe Trp Ala Leu Ser Glu Ile Lys Arg
        275                 280                 285

Ile Gln Gly Ala Ala Arg Ser Gly Asn Pro Ile Thr Lys Pro Arg Trp
290                 295                 300

Pro Met Ile Ile Leu Arg Thr Pro Lys Gly Trp Thr Gly Pro Arg Thr
305                 310                 315                 320

Val Asp Asp Lys Ile Ile Glu Gly Ser Phe His Ala His Gln Val Pro
                325                 330                 335

Val Thr Lys Ala Asn Lys Asp Glu Gly His Leu Arg Ile Leu Gln Asp
            340                 345                 350

Trp Leu Lys Ser Tyr Asp Val Arg Gly Leu Leu Pro Asp Gly Lys Pro
        355                 360                 365

Ser Gly Asp Phe Leu Asp Ile Leu Pro Pro Asp Pro His Lys Arg Leu
        370                 375                 380

Gly Gln Ser Lys Leu Ala Tyr Asp Cys His Gln Pro Leu Asp Leu Pro
385                 390                 395                 400

Asp Trp Arg Pro His Ser Val Asp Lys Phe Glu Glu Ala Ser Ser Met
                405                 410                 415

Gln Gln Ser Gly Lys Phe Leu Asp Val Val Ala Arg Gln Asn Met Lys
            420                 425                 430

```
Thr Phe Arg Ile Phe Ser Pro Asp Glu Leu Glu Ser Asn Lys Leu Ser
            435                 440                 445

Ala Val Leu Asp His Ser Ser Arg Asn Phe Gln Trp Asp Gln Tyr Ser
450                 455                 460

Arg Ala Gln Gly Gly Arg Val Ile Glu Ile Leu Ser Glu His Cys Cys
465                 470                 475                 480

Gln Gly Phe Leu Gln Gly Tyr Thr Leu Thr Gly Arg Thr Ala Ile Phe
                485                 490                 495

Pro Ser Tyr Glu Ser Phe Leu Gly Ile Ile His Thr Met Met Ile Gln
            500                 505                 510

Tyr Ser Lys Phe Ser Lys Ile Ser Arg Lys Leu Pro Trp Arg Gly Asp
            515                 520                 525

Leu Ser Ser Ile Asn Tyr Ile Glu Thr Ser Thr Trp Ala Arg Gln Glu
530                 535                 540

His Asn Gly Phe Ser His Gln Asn Pro Ser Phe Ile Gly Ala Val Leu
545                 550                 555                 560

Asn Leu Lys Ala Glu Ile Ala Arg Val Tyr Leu Pro Pro Asp Ala Asn
                565                 570                 575

Cys Phe Leu Ser Thr Leu His His Cys Leu Gln Ser Lys Asn Tyr Val
                580                 585                 590

Asn Leu Met Ile Gly Ser Lys Gln Pro Thr Pro Val Tyr Leu Ser Ala
            595                 600                 605

Glu Asp Ala Gln Arg His Cys Glu Asp Gly Ala Ser Ile Trp Arg Trp
            610                 615                 620

Ala Ser Thr His Asp Gly Glu His Pro Asp Val Val Leu Val Gly Ile
625                 630                 635                 640

Gly Val Glu Val Thr Phe Glu Val Ile Lys Ala Ala Gln Leu Leu Ser
                645                 650                 655

Arg Leu Ala Pro Asn Leu Arg Val Arg Val Asn Val Thr Asp Leu
            660                 665                 670

Leu Val Leu Pro His Glu Ser His His Pro His Ala Leu Asp Ser Lys
            675                 680                 685

Ala Phe Glu Asp Met Phe Thr Leu Asp Lys Pro Val Cys Phe Asn Tyr
690                 695                 700

His Ser Tyr Ala Thr Glu Leu Gln Gly Leu Leu Phe Gly Arg Pro Ala
705                 710                 715                 720

Leu His Arg Met Ser Val Glu Gly Tyr Lys Glu Gly Ser Thr Thr
                725                 730                 735

Thr Pro Phe Asp Met Met Leu Val Asn Thr Val Ser Arg Phe His Val
            740                 745                 750

Ala Ser Arg Ala Leu Lys Ala Ala Ala Gln Asn Asp Glu Val Lys
            755                 760                 765

Glu Asn Leu Ser Ala Leu Leu Ala Lys Val Asp Asp Glu Met Lys Ser
770                 775                 780

Val Lys Asp Tyr Ile Glu Gln Trp Gly Lys Val Asp Pro Asp Asp Ile
785                 790                 795                 800

Tyr Glu Leu Asp Phe Leu Lys Lys Asp
                805
```